US007713966B2

(12) United States Patent
Gege et al.

(10) Patent No.: US 7,713,966 B2
(45) Date of Patent: May 11, 2010

(54) HETEROBICYCLIC METALLOPROTEASE INHIBITORS

(75) Inventors: Christian Gege, Ehingen (DE); Matthias Schneider, Dossenheim (DE); Carine Chevrier, Ramonchamp (FR); Hongbo Deng, Southborough, MA (US); Irving Sucholeiki, Winchester, MA (US); Brian M. Gallagher, Jr., Merrimac, MA (US); Michael Bosies, Weinheim (DE); Christoph Steeneck, Dossenheim (DE); Xinyuan Wu, Newton, MA (US); Matthias Hochgürtel, Schriesheim (DE); Bert Nolte, Aachen (DE); Arthur Taveras, Southborough, MA (US)

(73) Assignee: Alantos Pharmaceuticals Holding, Inc., Thousand Oaks, CA (US)

( * ) Notice: Subject to any disclaimer, the term of this patent is extended or adjusted under 35 U.S.C. 154(b) by 0 days.

(21) Appl. No.: 11/986,626

(22) Filed: Nov. 20, 2007

(65) Prior Publication Data

US 2008/0261968 A1 Oct. 23, 2008

Related U.S. Application Data

(60) Provisional application No. 60/860,195, filed on Nov. 20, 2006.

(51) Int. Cl.

| | |
|---|---|
| *A61K 31/535* | (2006.01) |
| *C07D 265/12* | (2006.01) |
| *C07D 413/00* | (2006.01) |
| *A01N 43/00* | (2006.01) |
| *A01N 43/46* | (2006.01) |
| *A61K 31/553* | (2006.01) |
| *A61K 31/554* | (2006.01) |
| *A61K 31/55* | (2006.01) |
| *A61K 31/54* | (2006.01) |
| *C07D 498/00* | (2006.01) |
| *C07D 291/08* | (2006.01) |
| *C07D 281/02* | (2006.01) |
| *C07D 267/02* | (2006.01) |
| *C07D 223/16* | (2006.01) |
| *C07D 513/00* | (2006.01) |

(52) U.S. Cl. ...................... 514/230.5; 544/92; 544/119; 544/48; 544/61; 544/62; 544/183; 544/184; 544/220; 540/552; 540/594; 514/211.09; 514/217.01; 514/222.8; 514/224.2; 514/243; 514/246

(58) Field of Classification Search ............. 514/230.5; 544/92, 119

See application file for complete search history.

(56) References Cited

U.S. PATENT DOCUMENTS

| | | | | |
|---|---|---|---|---|
| 2002/0016460 | A1 | 2/2002 | Snow et al. | |
| 2008/0176870 | A1 * | 7/2008 | Nolte et al. | 514/259.31 |

FOREIGN PATENT DOCUMENTS

| | | |
|---|---|---|
| DE | 27 46 750 | 4/1979 |
| EP | 1 500 652 | 1/2005 |
| EP | 1 544 200 | 6/2005 |
| WO | WO 02/14319 | 2/2002 |
| WO | WO 2005/105760 | 11/2005 |

OTHER PUBLICATIONS

Abstract:: Joshi, et al., Indian J of Chemistry, "Synthesis of some new 4-quinazolinone-2-carboxylic acid esters, -2-carboxamides, -2-carbohydrazides and their tosyl derivatives having potential biological activity" 26B(6) 602-602 (1987).

Abstract::XP-002473571: 3H-1,2,3-Triazolo[4,5-djpyrimidine-5-carboxamide, 3-[(2-chlorophenyl)methyl]-N-(2,3-dihydro-1,4-benzodiozin-6-yl)-4,7-dihydro-7-oxo-.

Abstract:: XP-002473572: 3H-1,2,3-Triazolo[4,5-djpyrimidine-5-carboxamide, N-1,b-benzodiozol-5yl-3-[(3- chloropheny)methyl]-4,7-dihydro-7-oxo-.

Abstract:: XP-002473573: Benzo[b]thiophene-3-carboxylic acid, 2-[[(1,4-dihydro-4-oxo-2-quinazolininy1)thioxomethyl]amino]-4,5,6,7-tetrahydro-, ethyl ester.

Abstract:: XP-002473574: 2-Quinazolinecarbothioamide, N-1,3-benzodioxo1-5-y1-1,4-dihydro-4-oxo-.

Abstract:: XP-002473575: 2-Quinazolinecarbothioamide, N-(2,3-dihydro-1,4-benzodioxin-6-y1)-1,4-dihydro-4-oxo.

Abstract:: XP-002473576: 2-Quinazolinecarbothioamide, N-(2,3-dihydro-1,3-dihydro-1,3-dioxo-1H-isoindo1-5-y1)-1,4-dihyd ro-4-oxo-.

Abstract:: XP-002473577: 2-Quinazolinecarbothioamide, N-(6-acetyl-1,3-benzodioxo1-5-y1)-1,4dihydro-4-oxo.

Abstract:: XP-002473578: 2-Quinazolinecarbothioamide, 1,4-dihydro-4-oxo-N-(6,7,8,9-tetrahydro-6-oxo-8-thioxo-1H-purin-2-yl)-.

Abstract:: XP-002473579: 2-Quinazolinecarbothioamide, 1,4-dihydro-4-oxo-N-(6,7,8,9-tetrahydro-68-dioxo-1H-purin-2-y1).

* cited by examiner

*Primary Examiner*—James O Wilson
*Assistant Examiner*—Erich A Leeser
(74) *Attorney, Agent, or Firm*—Elsa D. Lemoine

(57) ABSTRACT

The present invention relates generally to azabicyclic containing pharmaceutical agents, and in particular, to azabicyclic metalloprotease inhibiting compounds. More particularly, the present invention provides a new class of azabicyclic MMP-3, MMP-8 and/or MMP-13 inhibiting compounds, which exhibit an increased potency and selectivity in relation to currently known MMP-13, MMP-8 and MMP-3 inhibitors.

12 Claims, No Drawings

HETEROBICYCLIC METALLOPROTEASE INHIBITORS

This application claims the benefit of U.S. Provisional Application No. 60/860,195, filed Nov. 20, 2006, which is hereby incorporated by reference.

FIELD OF THE INVENTION

The present invention relates generally to amide containing azabicyclic metalloprotease inhibiting compounds, and more particularly to azabicyclic amide MMP-13, MMP-8, MMP-3 and MMP-2 inhibiting compounds.

BACKGROUND OF THE INVENTION

Matrix metalloproteinases (MMPs) and aggrecanases (ADAMTS=a disintegrin and metalloproteinase with thrombospondin motif) are a family of structurally related zinc-containing enzymes that have been reported to mediate the breakdown of connective tissue in normal physiological processes such as embryonic development, reproduction, and tissue remodelling. Over-expression of MMPs and aggrecanases or an imbalance between extracellular matrix synthesis and degradation has been suggested as factors in inflammatory, malignant and degenerative disease processes. MMPs and aggrecanases are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis.

The ADAMTSs are a group of proteases that are encoded in 19 ADAMTS genes in humans. The ADAMTSs are extracellular, multidomain enzymes whose functions include collagen processing, cleavage of the matrix proteoglycans, inhibition of angiogenesis and blood coagulation homoeostasis (*Biochem. J.* 2005, 386, 15-27; *Arthritis Res. Ther.* 2005, 7, 160-169; *Curr. Med. Chem. Anti-Inflammatory Anti-Allergy Agents* 2005, 4, 251-264).

The mammalian MMP family has been reported to include at least 20 enzymes (*Chem. Rev.* 1999, 99, 2735-2776). Collagenase-3 (MMP-13) is among three collagenases that have been identified. Based on identification of domain structures for individual members of the MMP family, it has been determined that the catalytic domain of the MMPs contains two zinc atoms; one of these zinc atoms performs a catalytic function and is coordinated with three histidines contained within the conserved amino acid sequence of the catalytic domain. MMP-13 is over-expressed in rheumatoid arthritis, osteoarthritis, abdominal aortic aneurysm, breast carcinoma, squamous cell carcinomas of the head and neck, and vulvar squamous cell carcinoma. The principal substrates of MMP-13 are fibrillar collagens (types I, II, III) and gelatins, proteoglycans, cytokines and other components of ECM (extracellular matrix).

The activation of the MMPs involves the removal of a propeptide, which features an unpaired cysteine residue complexed with the catalytic zinc (II) ion. X-ray crystal structures of the complex between MMP-3 catalytic domain and TIMP-1 and MMP-14 catalytic domain and TIMP-2 also reveal ligation of the catalytic zinc (II) ion by the thiol of a cysteine residue. The difficulty in developing effective MMP inhibiting compounds comprises several factors, including choice of selective versus broad-spectrum MMP inhibitors and rendering such compounds bioavailable via an oral route of administration.

MMP-3 (stromelysin-1; transin-1) is another member of the MMP family (*FASEB J.* 1991, 5, 2145-2154). Human MMP-3 was initially isolated from cultured human synoviocytes. It is also expressed by chondrocytes and has been localized in OA cartilage and synovial tissues (*Am. J. Pathol.* 1989, 135, 1055-64).

MMP-3 is produced by basal keratinocytes in a variety of chronic ulcers. MMP-3 mRNA and Protein were detected in basal keratinocytes adjacent to but distal from the wound edge in what probably represents the sites of proliferating epidermis. MMP-3 may thus prevent the epidermis from healing (*J. Clin. Invest.* 1994, 94, 79-88).

MMP-3 serum protein levels are significantly elevated in patients with early and long-term rheumatoid arthritis (*Arthritis Rheum.* 2000, 43, 852-8) and in osteoarthritis patients (*Clin. Orthop. Relat. Res.* 2004, 428, 272-85) as well as in other inflammatory diseases like systemic lupus erythematosis and ankylosing spondylitis (*Rheumatology* 2006, 45, 414-20).

MMP-3 acts on components of the ECM as aggrecan, fibronectin, gelatin, laminin, elastin, fibrillin and others and on collagens of type III, IV, V, VII, IX, X (*Clin. Orthop. Relat. Res.* 2004, 428, 272-85). On collagens of type II and IX, MMP-3 exhibits telopeptidase activity (*Arthritis Res.* 2001, 3, 107-13; *Clin. Orthop. Relat. Res.* 2004, 427, S118-22). MMP-3 can activate other MMP family members such as MMP-1, MMP-7, MMP-8, MMP-9 and MMP-13 (*Ann. Rheum. Dis.* 2001, 60 Suppl 3:iii62-7).

MMP-3 is involved in the regulation of cytokines and chemokines by releasing TGFβ1 from the ECM, activating TNFα, inactivating IL-1β and releasing IGF (*Nat. Rev. Immunol.* 2004, 4, 617-29). A potential role for MMP-3 in the regulation of macrophage infiltration is based on the ability of the enzyme to convert active MCP species into antagonistic peptides (*Blood* 2002, 100, 1160-7).

MMP-8 (collagenase-2; neutrophil collagenase; EC 3.4.24.34) is another member of the MMP family (*Biochemistry* 1990, 29, 10628-34). Human MMP-8 was initially located in human neutrophils (*Biochemistry* 1990, 29, 10620-7). It is also expressed by macrophages, human mucosal keratinocytes, bronchial epithelial cells, ginigival fibroblasts, resident synovial and articular chondrodrocytes mainly in the course of inflammatory conditions (*Cytokine & Growth Factor Rev.* 2006, 17, 217-23).

The activity of MMP-8 is tightly regulated and mostly limited to the sites of inflammation. MMP-8 is expressed and stored as an inactive pro-enzyme in the granules of the neutrophils. Only after the activation of the neutrophils by proinflammatory mediators, MMP-8 is released and activated to exert its function.

MMP-8 plays a key role in the migration of immune cells to the sites of inflammation. MMP-8 degrades components of the extracellular matrix (ECM) such as collagen type I, II, III, VII, X, cartilage aggrecan, laminin-5, nidogen, fibronectin, proteoglycans and tenascin, thereby facilitating the cells migration through the ECM barrier. MMP-8 also influences the biological activity of its substrates. Through proteolytic processing of the chemokines IL-8, GCP-2, ENA-78, MMP-8 increases the chemokines ability to activate the infiltrating immune cells. While MMP-8 inactivates the serine protease inhibitor alpha-1 antitrypsin through its cleavage (*Eur. J. Biochem.* 2003, 270, 3739-49; *PloS One* 2007, 3, 1-10; *Cytokine & Growth Factor Rev.* 2006, 17, 217-23).

MMP-8 has been implicated in the pathogenesis of several chronic inflammatory diseases characterized by the excessive influx and activation of neutrophils, including cystic fibrosis (*Am. J. Resprir. Critic. Care Med.* 1994, 150, 818-22), rheumatoid arthritis (*Clin. Chim. Acta* 1996, 129-43), chronic periodontal disease (*Annals Med.* 2006, 38, 306-321) and chronic wounds (*J. Surg. Res.* 1999, 81, 189-195).

In osteoarthritis patients, MMP-8 protein expression is significantly elevated in inflamed human articular cartilage in the knee and ankle joints (*Lab Invest.* 1996, 74, 232-40; *J. Biol. Chem.* 1996, 271, 11023-6).

The levels of activated MMP-8 in BALF is an indicator of the disease severity and correlates with the airway obstruction in patients with asthma, COPD, pulmonary emphysema and bronchiectasis (*Lab Invest.* 2002, 82, 1535-45; *Am. J. Respir. Crit. Care Med.* 1999, 159, 1985-91; *Respir. Med.* 2005, 99, 703-10; *J. Pathol.* 2001, 194, 232-38).

SUMMARY OF THE INVENTION

The present invention relates to a new class of azabicyclic amide containing pharmaceutical agents which inhibits metalloproteases. In particular, the present invention provides a new class of metalloprotease inhibiting compounds that exhibit potent MMP-13 inhibiting activity and/or activity towards MMP-8, MMP-3 and MMP-2.

The present invention provides several new classes of amide containing azabicyclic metalloprotease compounds, which are represented by the following general formulas:

Formula (I)

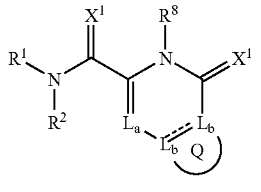

wherein all variables in the preceding Formula (I) are as defined hereinbelow.

The azabicyclic metalloprotease inhibiting compounds of the present invention may be used in the treatment of metalloprotease mediated diseases, such as rheumatoid arthritis, osteoarthritis, abdominal aortic aneurysm, cancer (e.g. but not limited to melanoma, gastric carcinoma or non-small cell lung carcinoma), inflammation, atherosclerosis, multiple sclerosis, chronic obstructive pulmonary disease, ocular diseases (e.g. but not limited to ocular inflammation, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, chronic wound healing, wound healing, hemorroid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayted type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, liver fibrosis, lupus, malaria, meningitis, multi-organ dysfunction, necrotizing enterocolitis, osteoporosis, chronic periodontitis, periodontitis, peritonitis associated with continuous ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, and wheeze.

In particular, the azabicyclic metalloprotease inhibiting compounds of the present invention may be used in the treatment of MMP-13, MMP-8, MMP-3 and MMP-2 mediated osteoarthritis and may be used for other MMP-13, MMP-8, MMP-3 and MMP-2 mediated symptoms, inflammatory, malignant and degenerative diseases characterized by excessive extracellular matrix degradation and/or remodelling, such as cancer, and chronic inflammatory diseases such as arthritis, rheumatoid arthritis, osteoarthritis, atherosclerosis, abdominal aortic aneurysm, inflammation, multiple sclerosis, and chronic obstructive pulmonary disease, and pain, such as inflammatory pain, bone pain and joint pain.

The present invention also provides azabicyclic metalloprotease inhibiting compounds that are useful as active ingredients in pharmaceutical compositions for treatment or prevention of metalloprotease—especially MMP-13, MMP-8, MMP-3 and MMP-2—mediated diseases. The present invention also contemplates use of such compounds in pharmaceutical compositions for oral or parenteral administration, comprising one or more of the azabicyclic metalloprotease inhibiting compounds disclosed herein.

The present invention further provides methods of inhibiting metalloproteases, by administering formulations, including, but not limited to, oral, rectal, topical, intravenous, parenteral (including, but not limited to, intramuscular, intravenous), ocular (ophthalmic), transdermal, inhalative (including, but not limited to, pulmonary, aerosol inhalation), nasal, sublingual, subcutaneous or intraarticular formulations, comprising the azabicyclic metalloprotease inhibiting compounds by standard methods known in medical practice, for the treatment of diseases or symptoms arising from or associated with metalloprotease, especially MMP-13, MMP-8, MMP-3 and MMP-2, including prophylactic and therapeutic treatment. Although the most suitable route in any given case will depend on the nature and severity of the conditions being treated and on the nature of the active ingredient. The compounds from this invention are conveniently presented in unit dosage form and prepared by any of the methods well-known in the art of pharmacy.

The azabicyclic metalloprotease inhibiting compounds of the present invention may be used in combination with a disease modifying antirheumatic drug, a nonsteroidal anti-inflammatory drug, a COX-2 selective inhibitor, a COX-1 inhibitor, an immunosuppressive, a steroid, a biological response modifier or other anti-inflammatory agents or therapeutics useful for the treatment of chemokines mediated diseases.

DETAILED DESCRIPTION OF THE INVENTION

One aspect of the invention relates to a compound having Formula (I):

Formula (I)

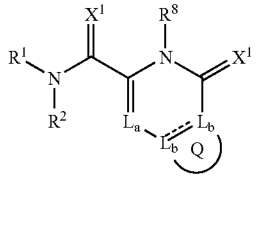

wherein:

$R^1$ is selected from cycloalkyl fused aryl, heterocycloalkyl fused aryl, cycloalkyl fused heteroaryl, heterocycloalkyl fused heteroaryl, cycloalkyl fused arylalkyl, heterocycloalkyl fused arylalkyl, cycloalkyl fused heteroarylalkyl, and heterocycloalkyl fused heteroarylalkyl, wherein $R^1$ is optionally substituted one or more times, or wherein $R^1$ is optionally substituted by one $R^{16}$ group and optionally substituted by one or more $R^9$ groups;

$R^2$ is selected from hydrogen and alkyl, wherein alkyl is optionally substituted one or more times or $R^1$ and $R^2$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;

$R^4$ in each occurrence is independently selected from $R^{10}$, hydrogen, alkyl, cycloalkyl, heterocycloalkyl, aryl, heteroaryl, halo, haloalkyl, $CF_3$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $(C_0-C_6)$-alkyl-C(O)—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$—$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—C(O)—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{10}$, O—$(C_0-C_6)$-alkyl-aryl and O—$(C_0-C_6)$-alkyl-heteroaryl, wherein each $R^4$ group is optionally substituted one or more times, or wherein each $R^4$ group is optionally substituted by one or more $R^{14}$ groups, or wherein optionally two $R^4$ groups, when taken together with the nitrogen or carbon to which they are attached complete a 3- to 8-membered saturated ring or multicyclic ring or unsaturated ring containing carbon atoms and optionally containing one or more heteroatom independently selected from O, $S(O)_x$, N, or $NR^{50}$ and which is optionally substituted one or more times, or optionally two $R^4$ groups taken together at one saturated carbon atom form =O, =S, $=NR^{10}R^{11}$ or $=NOR^{10}$;

$R^5$ is independently selected from hydrogen, alkyl, $C(O)NR^{10}R^{11}$, aryl, arylalkyl, $SO_2NR^{10}R^{11}$ and $C(O)OR^{10}$ wherein alkyl, aryl and arylalkyl are optionally substituted one or more times;

$R^8$ is independently selected from hydrogen, alkyl, cycloalkyl, heterocycloalkyl, aryl, heteroaryl, $R^{10}$ and $NR^{10}R^{11}$ wherein alkyl, cycloalkyl, heterocycloalkyl, aryl, and heteroaryl is optionally substituted one or more times;

$R^9$ in each occurrence is independently selected from $R^{10}$, hydrogen, alkyl, cycloalkyl, heterocycloalkyl, aryl, heteroaryl, halo, $CHF_2$, $CF_3$, $OR^{10}$, $SR^{10}$, $COOR^{10}$, $CH(CH_3)CO_2H$, $(C_0-C_6)$-alkyl-$COR^{10}$, $(C_0-C_6)$-alkyl-$OR^{10}$, $(C_0-C_6)$-alkyl-$NR^{10}R^{11}$, $(C_0-C_6)$-alkyl-$NO_2$, $(C_0-C_6)$-alkyl-CN, $(C_0-C_6)$-alkyl-$S(O)_yOR^{10}$, $(C_0-C_6)$-alkyl-$P(O)_2OH$, $(C_0-C_6)$-alkyl-$S(O)_yNR^{10}R^{11}$, $(C_0-C_6)$-alkyl-$NR^{10}CONR^{11}SO_2R^{30}$, $(C_0-C_6)$-alkyl-$S(O)_xR^{10}$, $(C_0-C_6)$-alkyl-$OC(O)R^{10}$, $(C_0-C_6)$-alkyl-$OC(O)NR^{10}R^{11}$, $(C_0-C_6)$-alkyl-$C(=NR^{10})NR^{10}R^{11}$, $(C_0-C_6)$-alkyl-$NR^{10}C(=NR^{11})NR^{10}R^{11}$, $(C_0-C_6)$-alkyl-$NR^{10}C(=N—CN)NR^{10}R^{11}$, $(C_0-C_6)$-alkyl-$C(=N—CN)NR^{10}R^{11}$, $(C_0-C_6)$-alkyl-$NR^{10}C(=N—NO_2)NR^{10}R^{11}$, $(C_0-C_6)$-alkyl-$C(=N—NO_2)NR^{10}R^{11}$, $(C_0-C_6)$-alkyl-$C(O)OR^{10}$, $(C_0-C_6)$-alkyl-$C(O)NR^{10}R^{11}$, $(C_0-C_6)$-alkyl-$C(O)NR^{10}SO_2R^{11}$, $C(O)NR^{10}$—$(C_0-C_6)$-alkyl-heteroaryl, $C(O)NR^{10}$—$(C_0-C_6)$-alkyl-aryl, $S(O)_2NR^{10}$—$(C_0-C_6)$-alkyl-aryl, $S(O)_2NR^{10}$—$(C_0-C_6)$-alkyl-heteroaryl, $S(O)_2NR^{10}$-alkyl, $S(O)_2$—$(C_0-C_6)$-alkyl-aryl, $S(O)_2$—$(C_0-C_6)$-alkyl-heteroaryl, $(C_0-C_6)$-alkyl-C(O)—$NR^{11}$—CN, O—$(C_0-C_6)$-alkyl-$C(O)NR^{10}R^{11}$, $S(O)_x$—$(C_0-C_6)$-alkyl-$C(O)OR^{10}$, $S(O)_x$ —$(C_0-C_6)$-alkyl-$C(O)NR^{10}R^{11}$, $(C_0-C_6)$-alkyl-$C(O)NR^{10}$—$(C_0-C_6)$-alkyl-$NR^{10}R^{11}$, $(C_0-C_6)$-alkyl-$NR^{10}$—$C(O)R^{10}$, $(C_0-C_6)$-alkyl-$NR^{10}$—$C(O)OR^{10}$, $(C_0-C_6)$-alkyl-$NR^{10}$—C(O)—$NR^{10}R^{11}$, $(C_0-C_6)$-alkyl-$NR^{10}$—$S(O)_yNR^{10}R^{11}$, $(C_0-C_6)$-alkyl-$NR^{10}$—$S(O)_yR^{11}$, O—$(C_0-C_6)$-alkyl-aryl and O—$(C_0-C_6)$-alkyl-heteroaryl, wherein each $R^9$ group is optionally substituted, or wherein each $R^9$ group is optionally substituted by one or more $R^{14}$ groups;

$R^{10}$ and $R^{11}$ in each occurrence are independently selected from hydrogen, alkyl, cycloalkyl, cycloalkylalkyl, heterocycloalkyl, bicycloalkyl, heterobicycloalkyl, spiroalkyl, spiroheteroalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, bicycloalkyl, heterobicycloalkyl, spiroalkyl, spiroheteroalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted one or more times, or $R^{10}$ and $R^{11}$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;

$R^{14}$ is independently selected from hydrogen, alkyl, arylalkyl, cycloalkylalkyl, heteroarylalkyl, heterocyclylalkyl and halo, wherein alkyl, arylalkyl, cycloalkylalkyl, heteroarylalkyl and heterocyclylalkyl are optionally substituted one or more times.

$R^{16}$ is selected from cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, (i) and (ii):

(i)

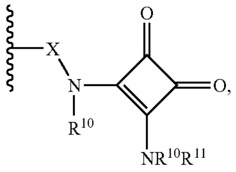

(ii)

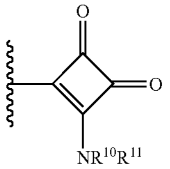

wherein cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, and heterocycloalkyl fused heteroarylalkyl are optionally substituted one or more times;

$R^{30}$ is selected from alkyl and $(C_0-C_6)$-alkyl-aryl, wherein alkyl and aryl are optionally substituted;

$R^{50}$ in each occurrence is independently selected from hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are optionally substituted one or more times;

$R^{80}$ and $R^{81}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{80}$ and $R^{81}$ when taken together with the nitrogen to which they are attached complete a 3- to 8-membered ring containing carbon atoms and optionally a heteroatom selected from O, $S(O)_x$, —NH, and —N(alkyl) and which is optionally substituted one or more times;

E is selected from a bond, $CR^{10}R^{11}$, O, $NR^5$, S, S═O, $S(═O)_2$, C(═O), $N(R^{10})(C═O)$, $(C═O)N(R^{10})$, $N(R^{10})S(═O)_2$, $S(═O)_2N(R^{10})$, C═N—$OR^{11}$, —$C(R^{10}R^{11})C(R^{10}R^{11})$—, —$CH_2$—$W^1$— and

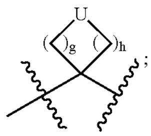;

$L_a$ is independently selected from $CR^9$ and N;

$L_b$ is independently selected from C and N with the proviso, that both $L_b$ are not N, and that the bond between $L_b$ and $L_b$ is optionally a double bond only if both $L_b$ are C;

Q is a 4- to 8-membered ring selected from cycloalkyl, heterocycloalkyl or a 5- or 6-membered ring selected from aryl and heteroaryl, wherein Q is optionally substituted one or more times, or wherein Q is optionally substituted one or more times with $R^4$;

U is selected from $C(R^5R^{10})$, $NR^5$, O, S, S═O and $S(═O)_2$;

$W^1$ is selected from O, $NR^5$, S, S═O, $S(═O)_2$, $N(R^{10})(C═O)$, $N(R^{10})S(═O)_2$ and $S(═O)_2N(R^{10})$;

X is selected from a bond and $(CR^{10}R^{11})_wE(CR^{10}R^{11})_w$;

$X^1$ is independently selected from O, S, $NR^{10}$, N—CN, $NCOR^{10}$, N—$NO_2$, or N—$SO_2R^{10}$;

g and h are independently selected from 0-2;

w is selected from 0-4;

x is selected from 0 to 2;

y is selected from 1 and 2;

the dotted line optionally represents a double bond; and

N-oxides, pharmaceutically acceptable salts, prodrugs, formulations, polymorphs, tautomers, racemic mixtures and stereoisomers thereof.

In one embodiment, in conjunction with any above or below embodiments, the compound has the structure:

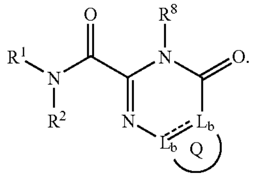

In another embodiment, in conjunction with any above or below embodiments, the compound is selected from:

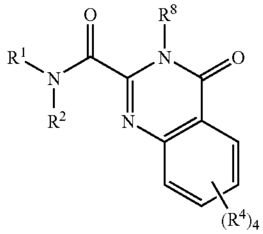

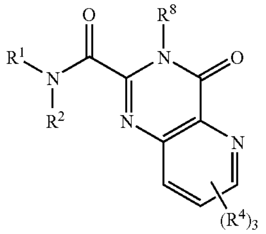

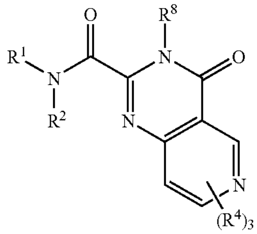

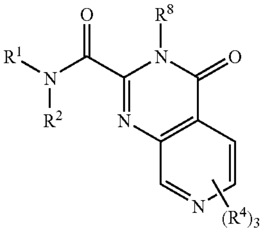

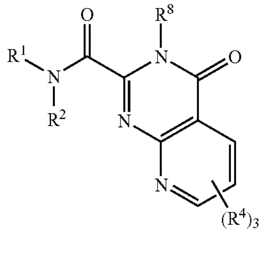

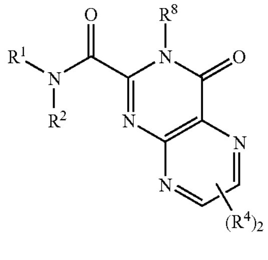

-continued
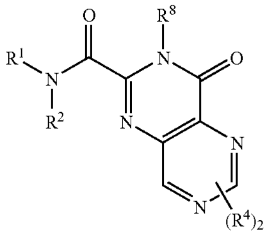
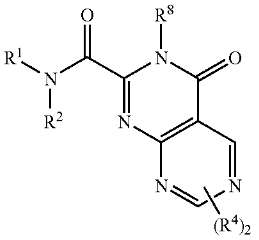
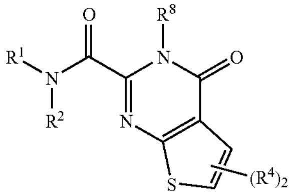
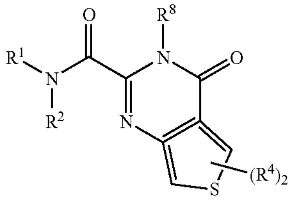
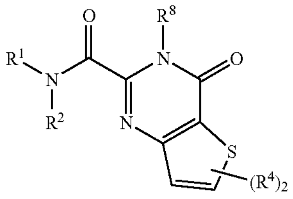
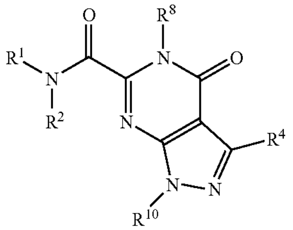
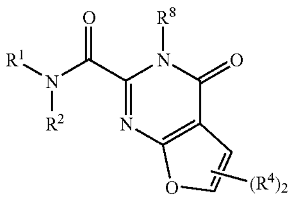
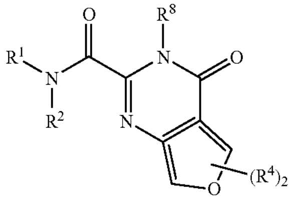
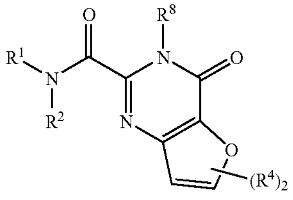
-continued
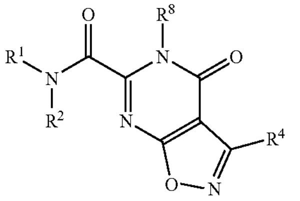
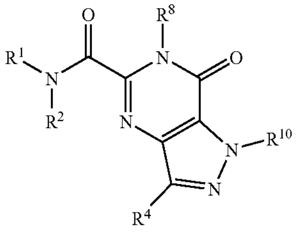
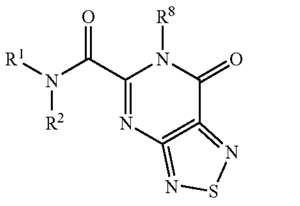
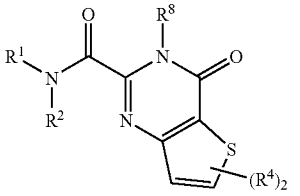
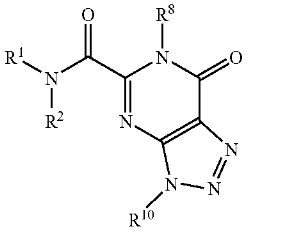
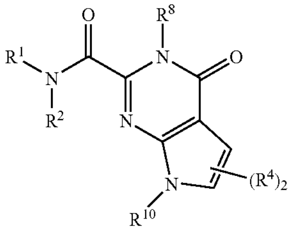
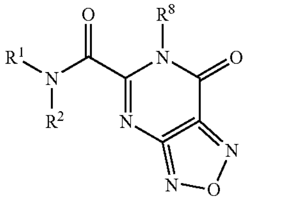
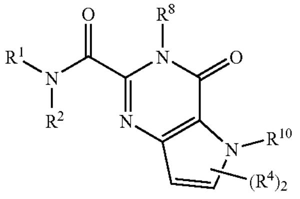

-continued
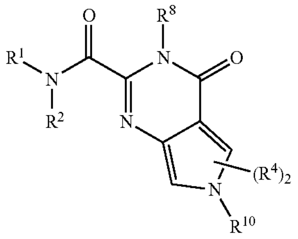
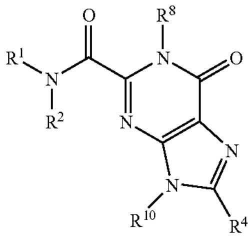
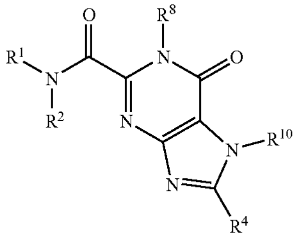
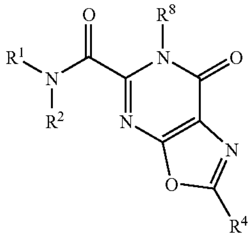
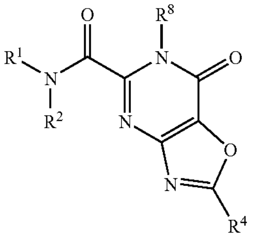
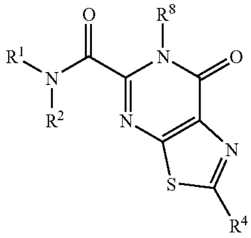
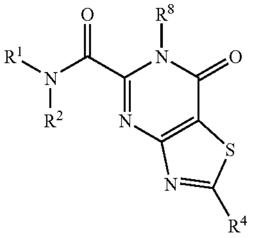
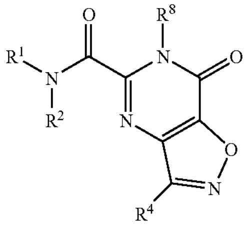
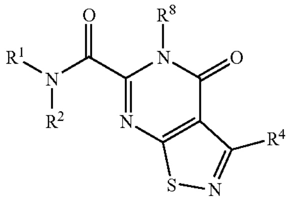
-continued
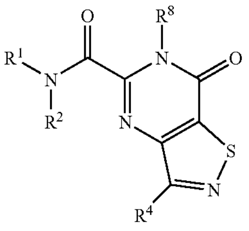
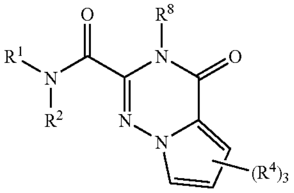
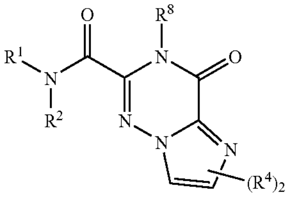
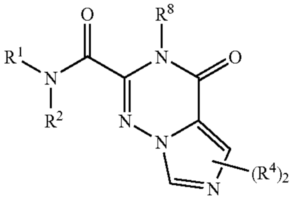
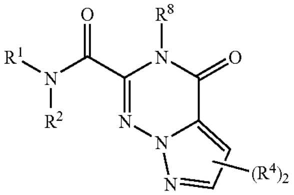
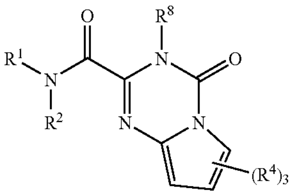
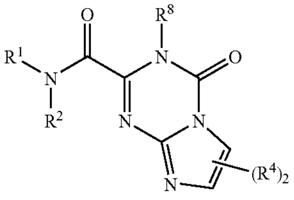
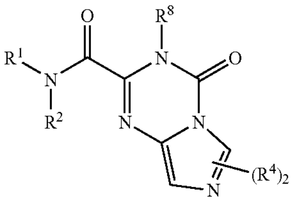

-continued
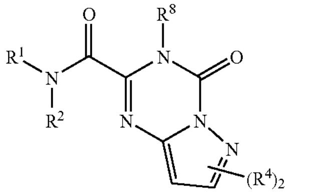
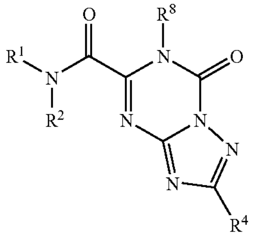
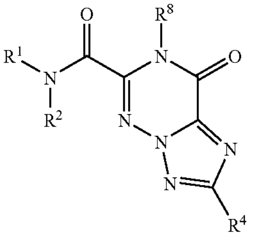
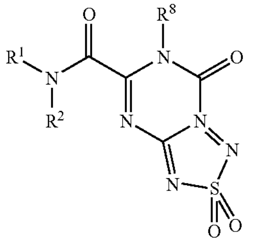
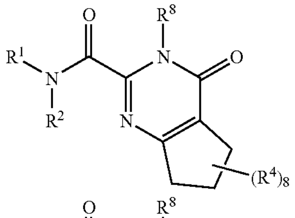
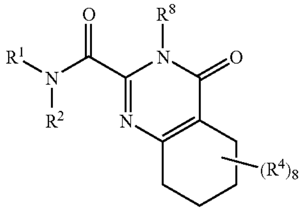
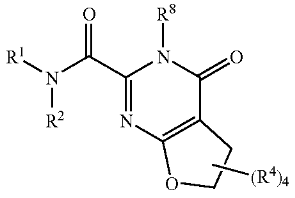
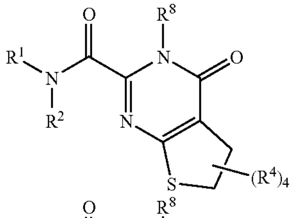
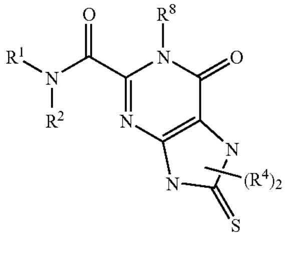
-continued
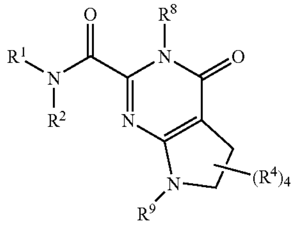
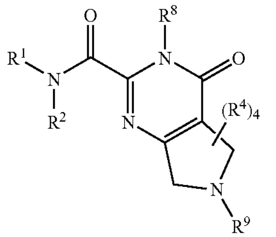
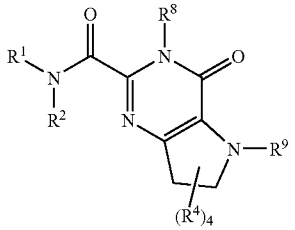
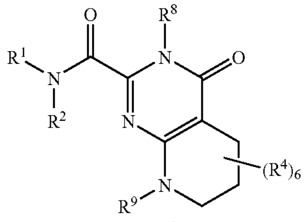
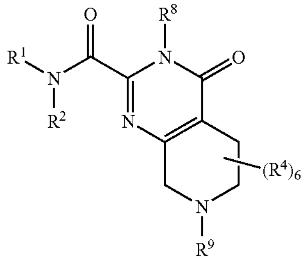
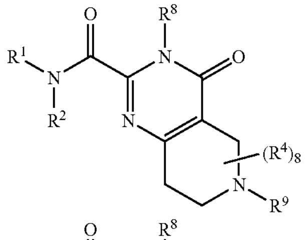
and
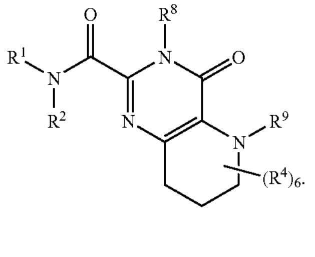

In another embodiment, in conjunction with any above or below embodiments, the compound is selected from:
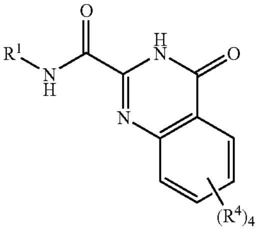
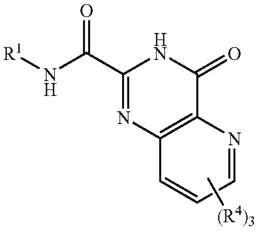
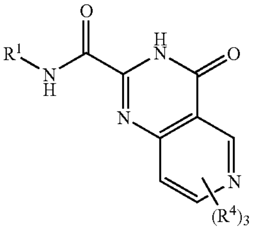
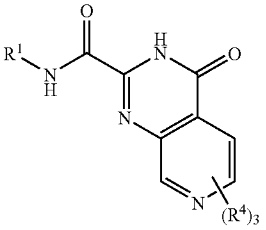
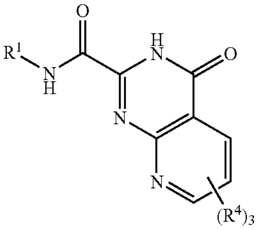
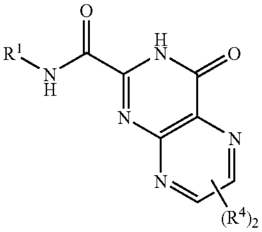
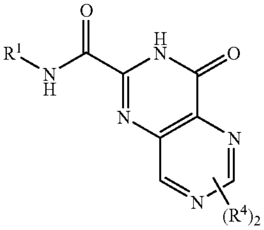
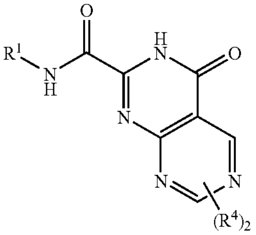
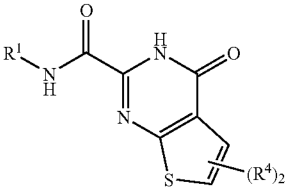
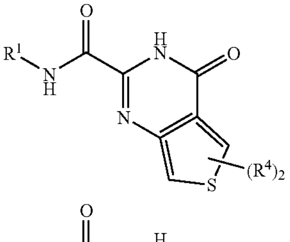
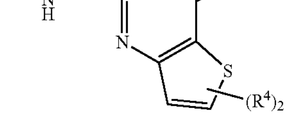
-continued
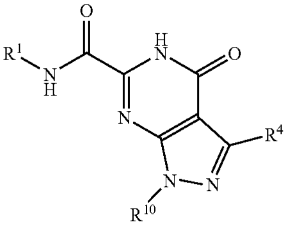
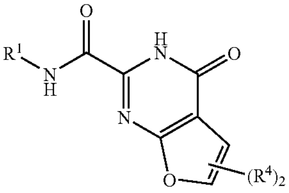
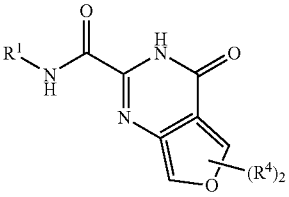
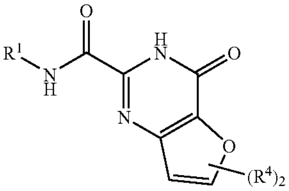
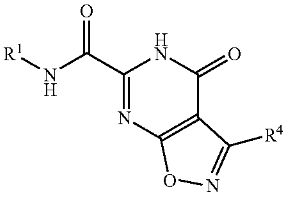
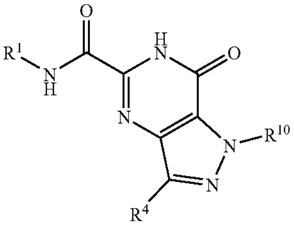
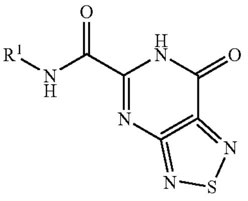
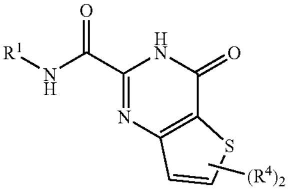

-continued
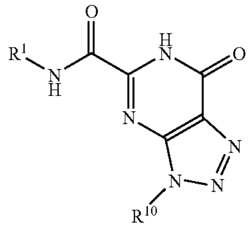
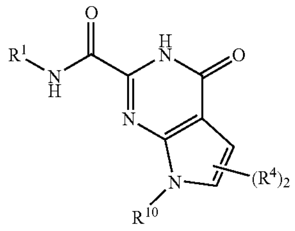
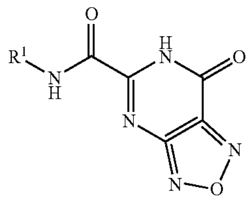
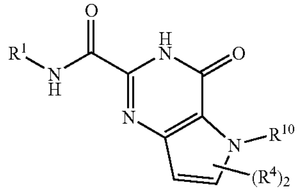
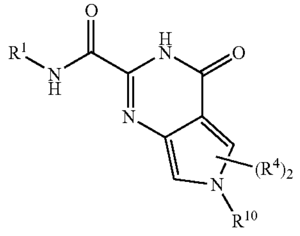
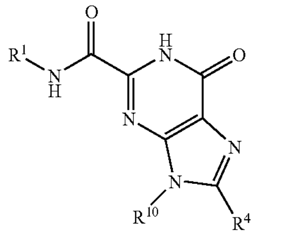
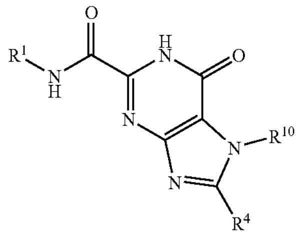
-continued
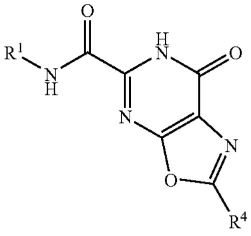
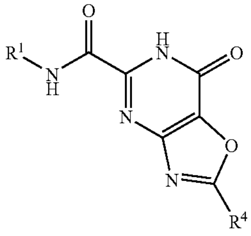
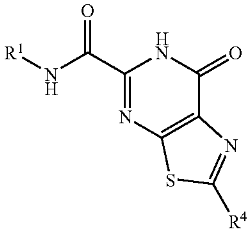
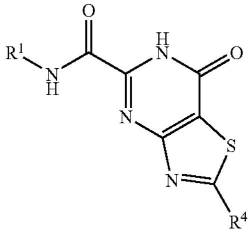
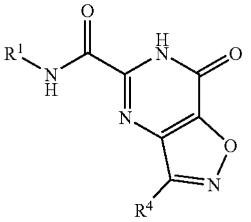
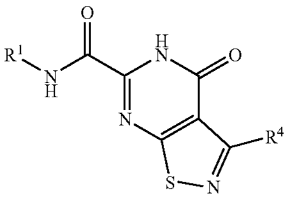
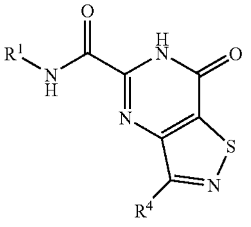
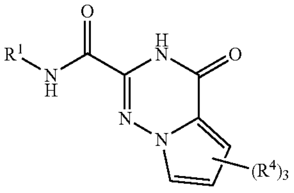
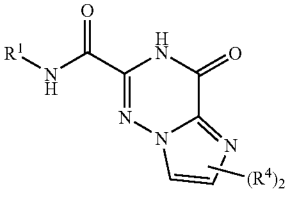
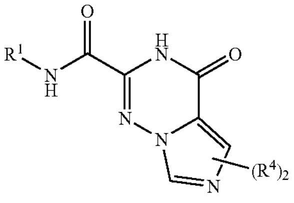

-continued
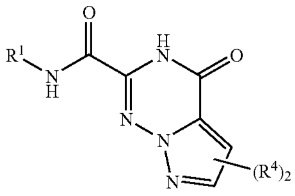
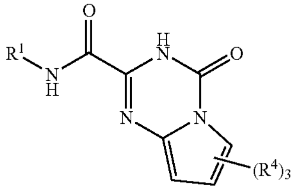
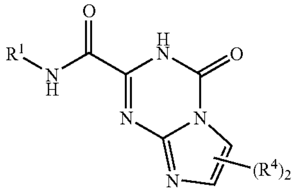
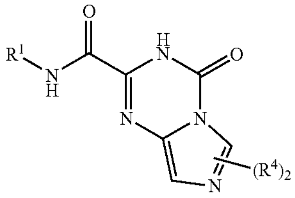
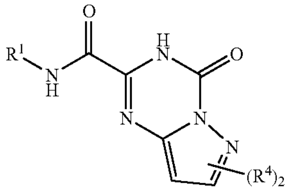
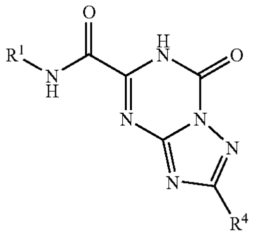
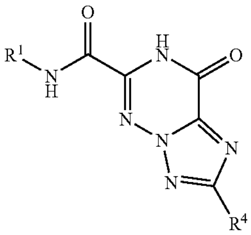
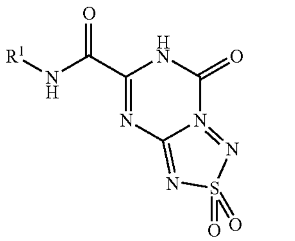
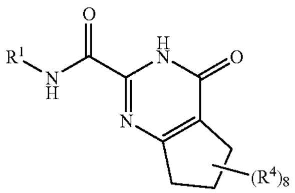
-continued
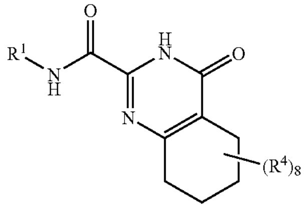
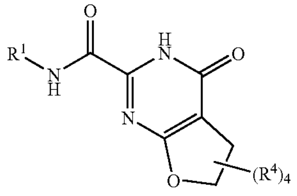
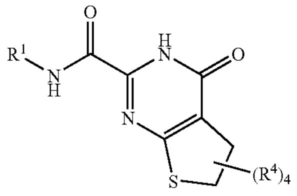
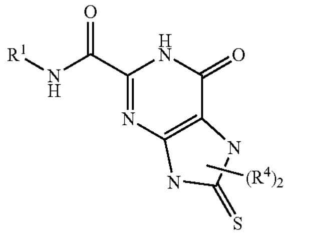
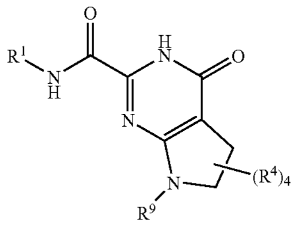
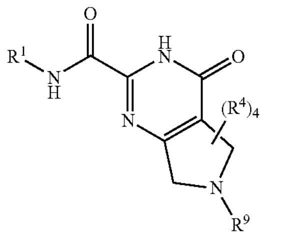
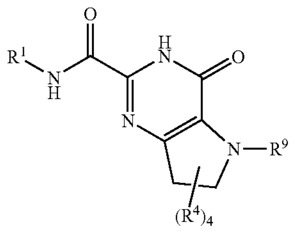

-continued
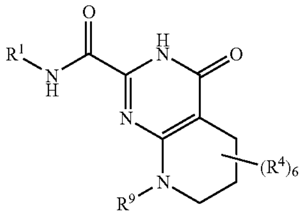
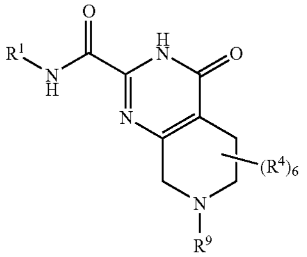
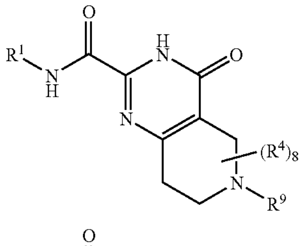
and
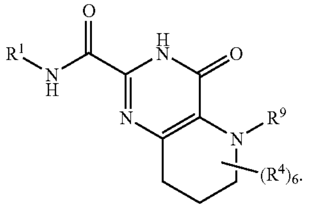
In another embodiment, in conjunction with any above or below embodiments, $R^1$ is selected from:
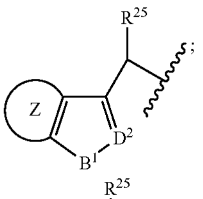
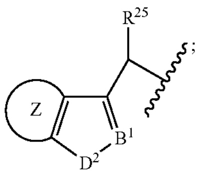
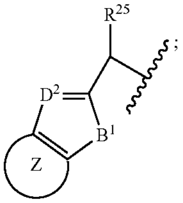
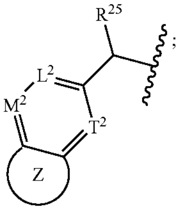
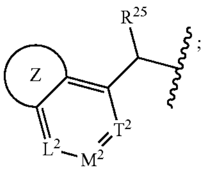
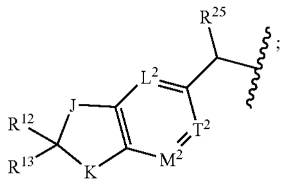
-continued
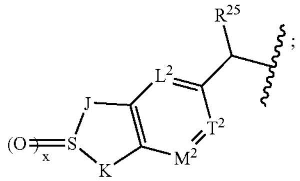
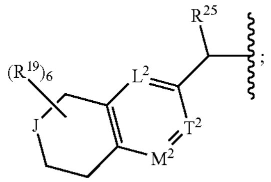
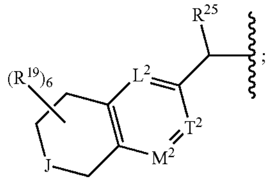
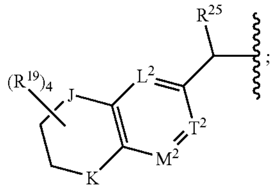
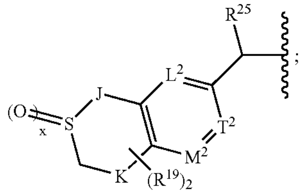
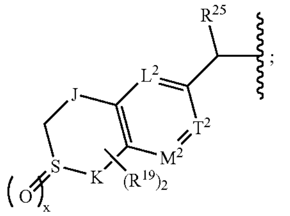
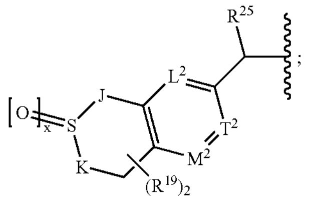
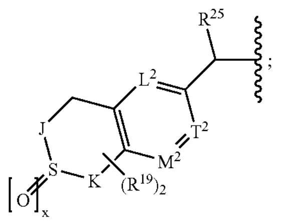

-continued

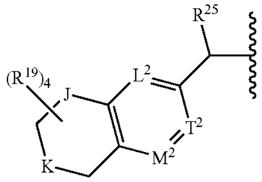

and

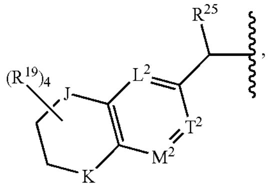

, wherein:

$R^{12}$ and $R^{13}$ are independently selected from hydrogen, alkyl and halo, wherein alkyl is optionally substituted one or more times, or optionally $R^{12}$ and $R^{13}$ together form =O, =S, $=NR^{10}$ or $=NOR^{10}$;

$R^{18}$ is independently selected from hydrogen, alkyl, haloalkyl, cycloalkyl, heterocycloalkyl, alkynyl, aryl, heteroaryl, OH, halo, CN, $C(O)NR^{10}R^{11}$, $CO_2R^{10}$, $OR^{10}$, $OCF_3$, $OCHF_2$, $NR^{10}CONR^{10}R^{11}$, $NR^{10}COR^{11}$, $NR^{10}SO_2R^{11}$, $NR^{10}SO_2NR^{10}R^{11}$, $SO_2NR^{10}R^{11}$ and $NR^{10}R^{11}$, wherein alkyl, haloalkyl, cycloalkyl, heterocycloalkyl, alkynyl, aryl, and heteroaryl are optionally substituted one or more times;

$R^{19}$ is independently selected from hydrogen, alkyl, haloalkyl, cycloalkyl, heterocycloalkyl, alkynyl, aryl, heteroaryl, OH, halo, CN, $C(O)NR^{10}R^{11}$, $CO_2R^{10}$, $OR^{10}$, $OCF_3$, $OCHF_2$, $NR^{10}CONR^{10}R^{11}$, $NR^{10}COR^{11}$, $NR^{10}SO_2R^{11}$, $NR^{10}SO_2NR^{10}R^{11}$, $SO_2NR^{10}R^{11}$ and $NR^{10}R^{11}$, wherein alkyl, haloalkyl, cycloalkyl, heterocycloalkyl, alkynyl, aryl, and heteroaryl are optionally substituted one or more times, or optionally two $R^{19}$ groups together at one carbon atom form =O, =S, $=NR^{10}$ or $=NOR^{10}$;

$R^{25}$ is selected from hydrogen, alkyl, cycloalkyl, $C(O)NR^{10}R^{11}$ and haloalkyl, wherein alkyl, cycloalkyl, and haloalkyl are optionally substituted one or more times;

J and K are independently selected from $CR^{10}R^{18}$, $NR^{10}$, O and $S(O)_x$;

$D^2$, $L^2$, $M^2$ and $T^2$ are independently selected from $CR^{18}$ and N; and Z is a 5- to 8-membered ring selected from cycloalkyl and heterocycloalkyl wherein cycloalkyl and heterocycloalkyl are optionally substituted one or more times.

In another embodiment, in conjunction with any above or below embodiments, $L_b$ is C.

In another embodiment, in conjunction with any above or below embodiments, $L_a$ is N.

In another embodiment, in conjunction with any above or below embodiments, $R^1$ is selected from:

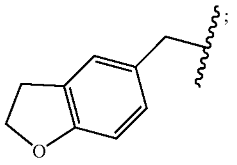

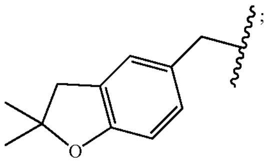

-continued

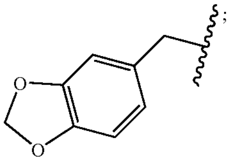

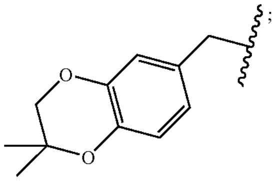

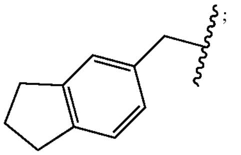

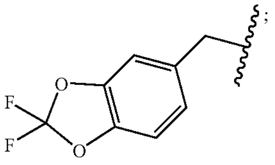

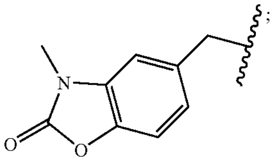

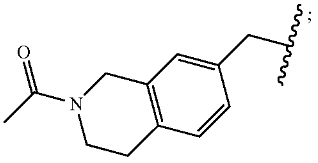

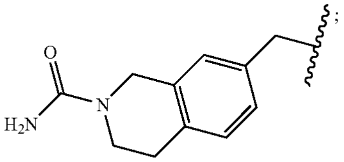

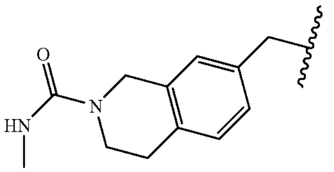

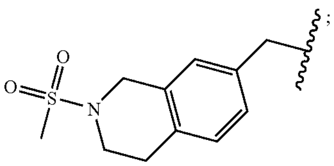

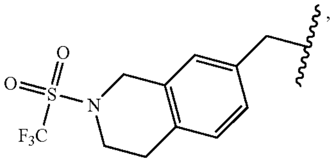

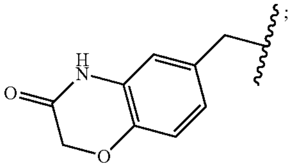

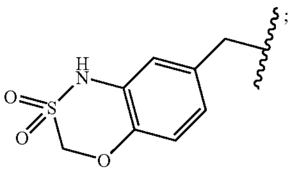

-continued
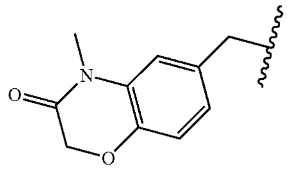
;
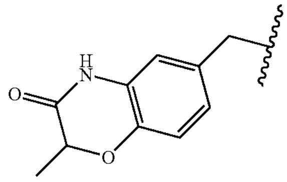
;
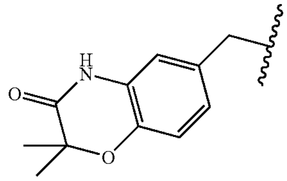
;
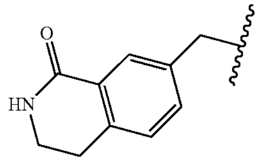
;
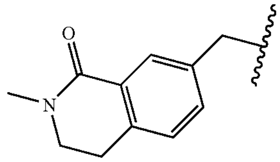
;
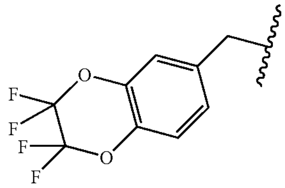
;
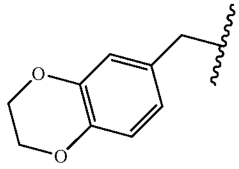
;
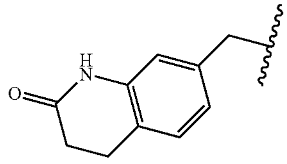
;
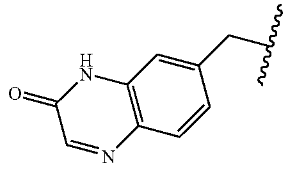
;
-continued
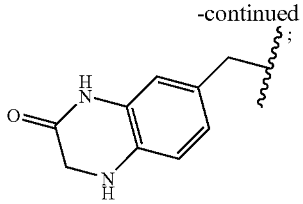
;
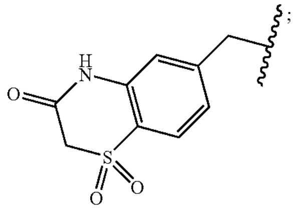
;
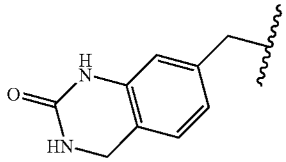
;
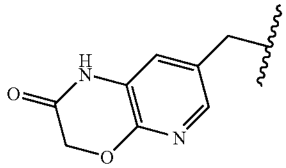
;
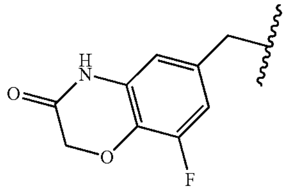
;
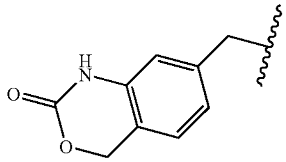
;
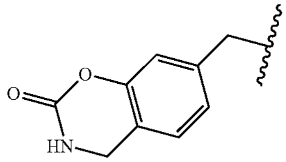
;
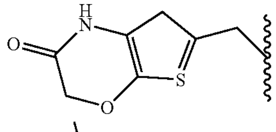
;
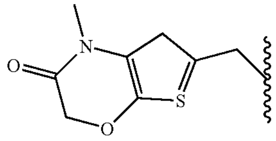
and
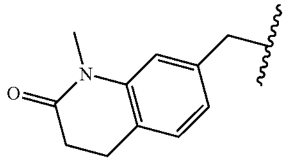
;

any of which are substituted by one or two substituents independently selected from $C_{1-2}$alkyl, $C_{1-2}$haloalkyl, halo, CN, OMe, $OCF_3$, $OCHF_2$.
In another embodiment, in conjunction with any above or below embodiments, $R^1$ is selected from:
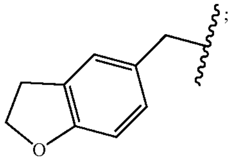
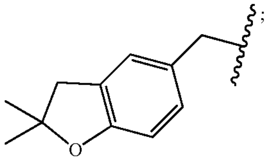
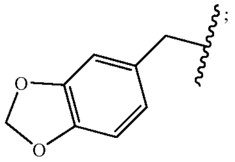
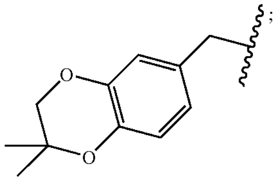
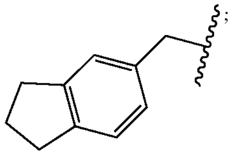
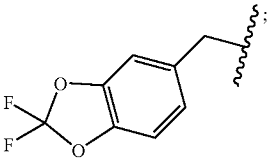
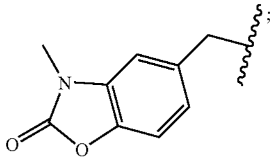
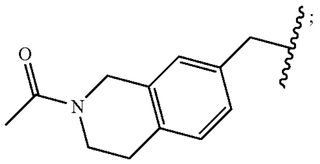
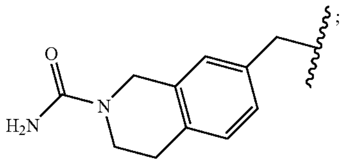
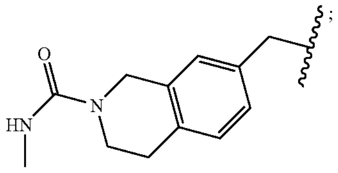
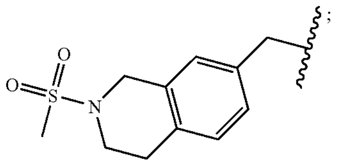
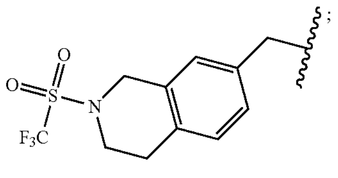
-continued
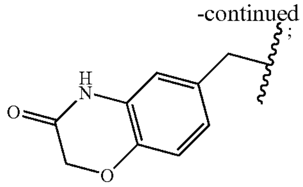
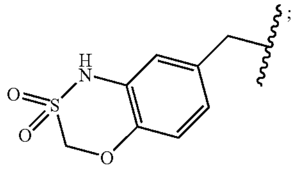
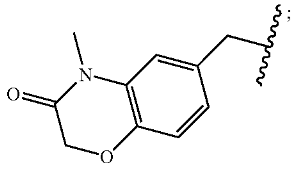
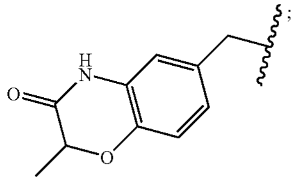
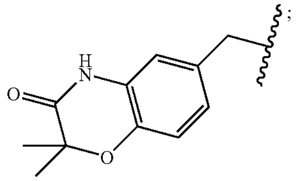
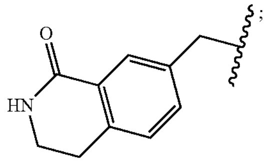
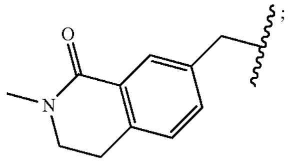
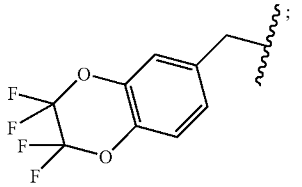
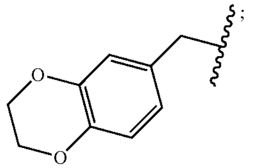
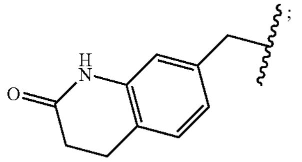

-continued
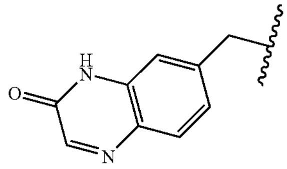
;
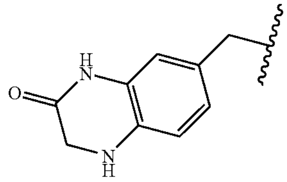
;
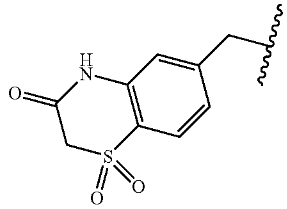
;
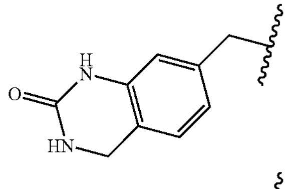
;
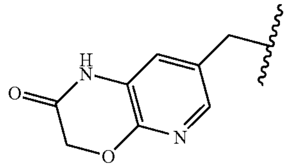
;
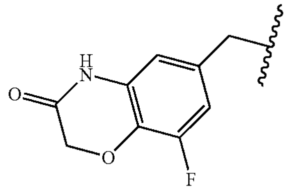
;
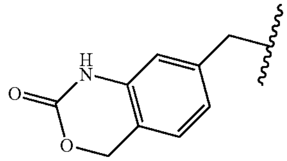
;
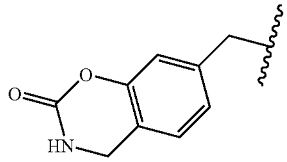
;
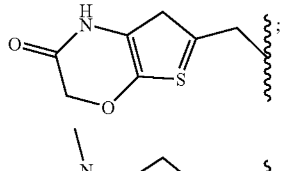
;
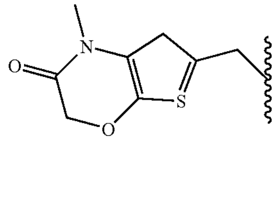
and
-continued
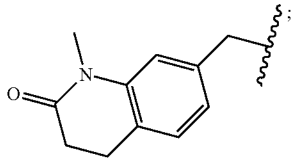
;
In another embodiment, in conjunction with any above or below embodiments, $R^1$ is selected from:
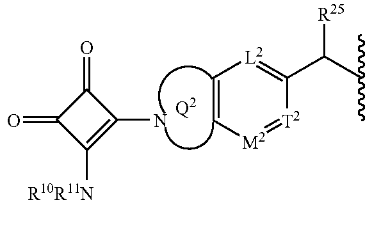
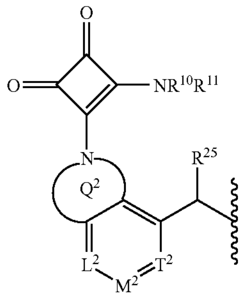
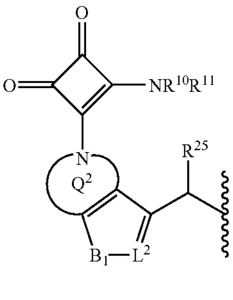
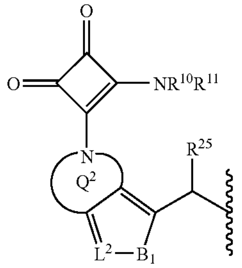
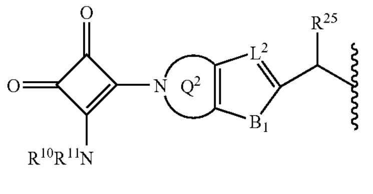
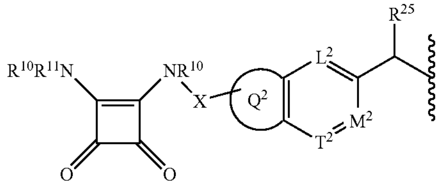
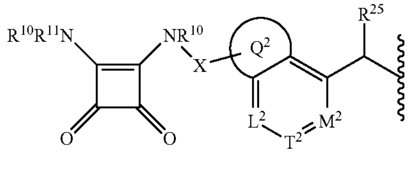

-continued

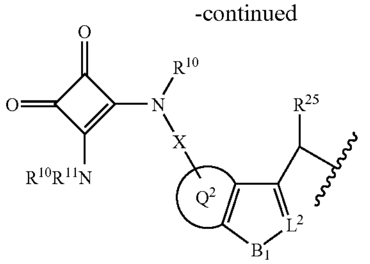

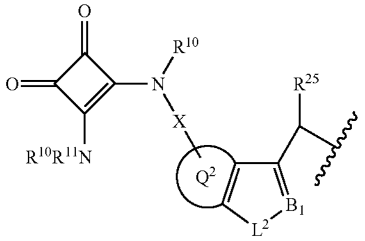

and

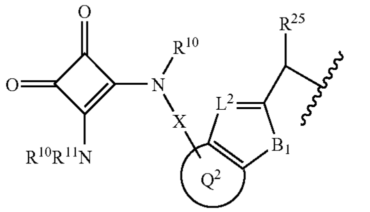

wherein:

$R^{18}$ is independently selected from hydrogen, alkyl, haloalkyl, cycloalkyl, heterocycloalkyl, alkynyl, aryl, heteroaryl, OH, halo, CN, $C(O)NR^{10}R^{11}$, $CO_2R^{10}$, $OR^{10}$, $OCF_3$, $OCHF_2$, $NR^{10}CONR^{10}R^{11}$, $NR^{10}COR^{11}$, $NR^{10}SO_2R^{11}$, $NR^{10}SO_2NR^{10}R^{11}$, $SO_2NR^{10}R^{11}$ and $NR^{10}R^{11}$, wherein alkyl, haloalkyl, cycloalkyl, heterocycloalkyl, alkynyl, aryl, and heteroaryl are optionally substituted one or more times;

$R^{19}$ is independently selected from hydrogen, alkyl, haloalkyl, cycloalkyl, heterocycloalkyl, alkynyl, aryl, heteroaryl, OH, halo, CN, $C(O)NR^{10}R^{11}$, $CO_2R^{10}$, $OR^{10}$, $OCF_3$, $OCHF_2$, $NR^{10}CONR^{10}R^{11}$, $NR^{10}COR^{11}$, $NR^{10}SO_2R^{11}$, $NR^{10}SO_2NR^{10}R^{11}$, $SO_2NR^{10}R^{11}$ and $NR^{10}R^{11}$, wherein alkyl, haloalkyl, cycloalkyl, heterocycloalkyl, alkynyl, aryl, and heteroaryl are optionally substituted one or more times, or optionally two $R^{19}$ groups together at one carbon atom form $=O$, $=S$, $=NR^{10}$ or $=NOR^{10}$;

$R^{25}$ is selected from hydrogen, alkyl, cycloalkyl, $CONR^{10}R^{11}$ and haloalkyl, wherein alkyl, cycloalkyl and haloalkyl are optionally substituted one or more times;

$L^2$, $M^2$, and $T^2$ are independently selected from $CR^{18}$ and N;

$D^3$, $G^3$, $L^3$, $M^3$, and $T^3$ are independently selected from N, $CR^{18}$, (i), or (ii), (i)

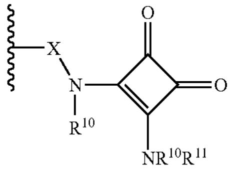

-continued (ii)

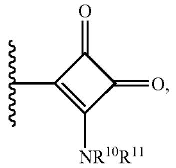

with the proviso that one of $L^3$, $M^3$, $T^3$, $D^3$, and $G^3$ is (i) or (ii)

$B_1$ is selected from the group consisting of $NR^{10}$, O and $S(O)_x$; and $Q^2$ is a 5- to 8-membered ring selected from cycloalkyl, heterocycloalkyl, aryl, and heteroaryl, which is optionally substituted one or more times with $R^{19}$.

In another embodiment, in conjunction with any above or below embodiments, $R^1$ is selected from:

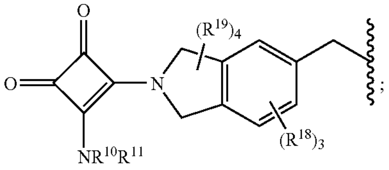

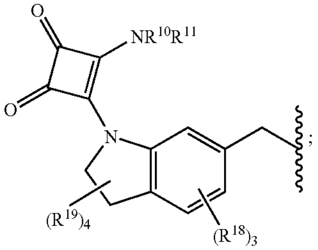

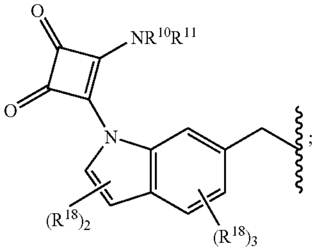

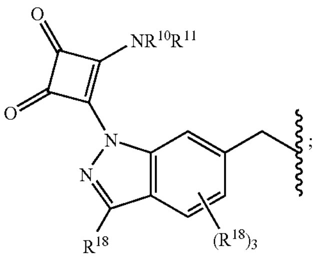

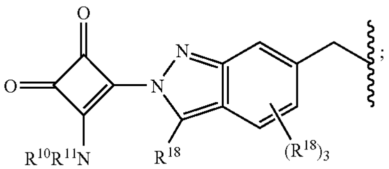

-continued
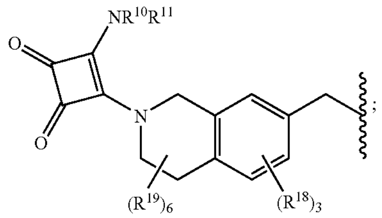
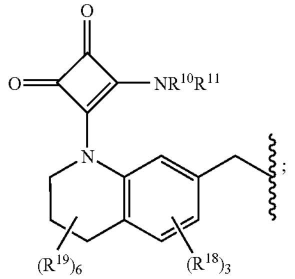
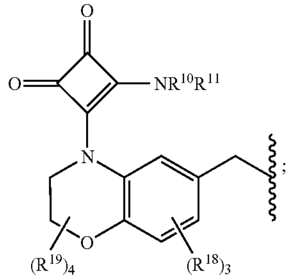
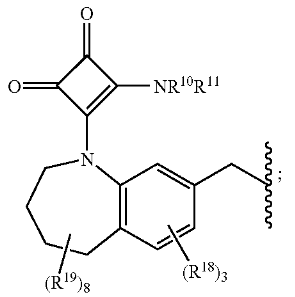
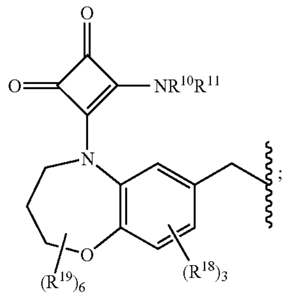
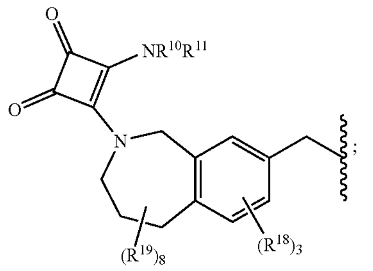
-continued
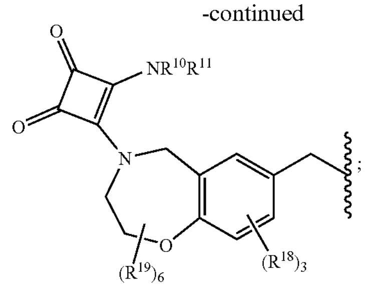
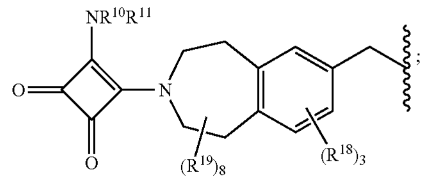
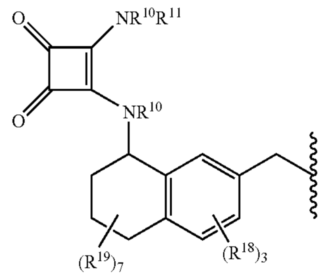
and
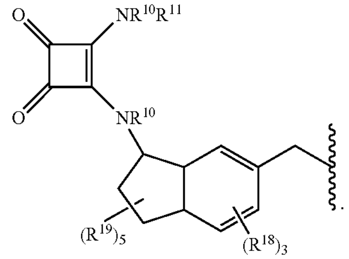
In another embodiment, in conjunction with any above or below embodiments, $R^1$ is selected from:
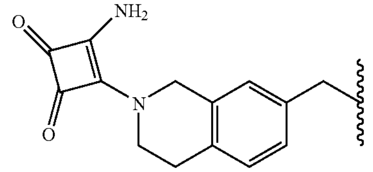
and
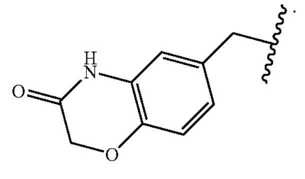

In another embodiment, in conjunction with any above or below embodiments, the compound is selected from:
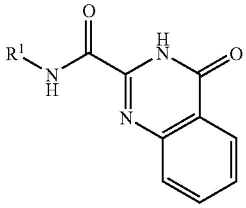
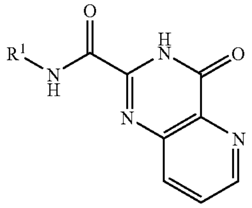
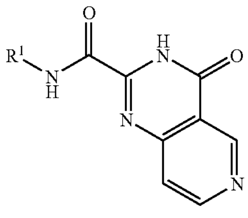
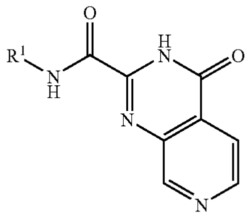
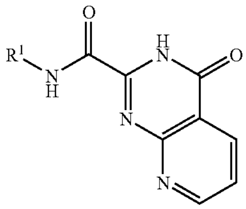
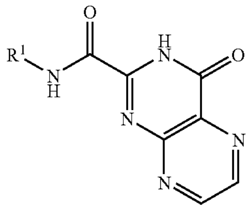
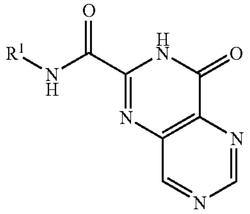
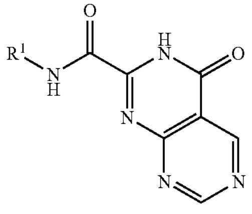
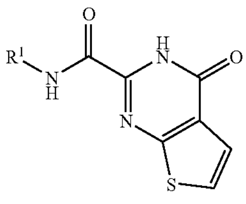
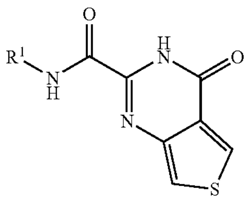
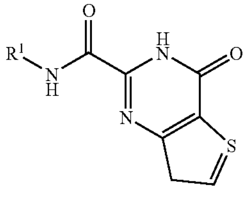
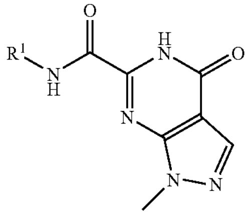
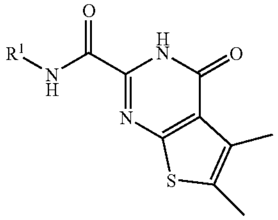
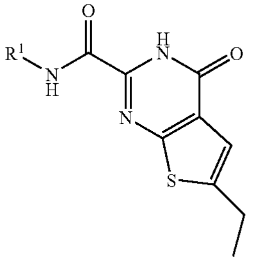
-continued
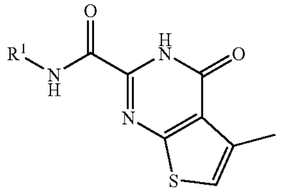
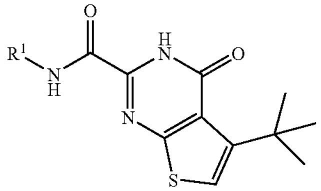
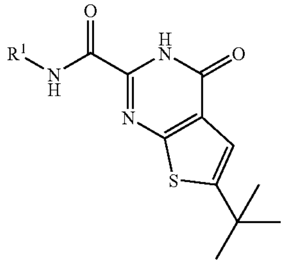
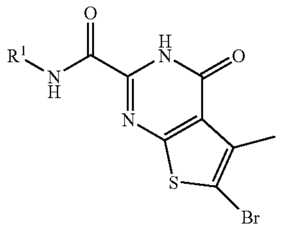
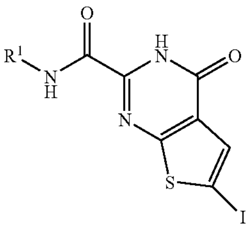
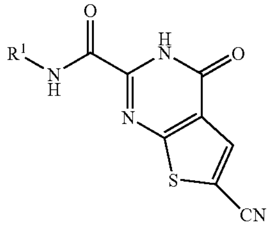
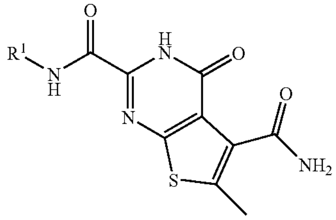
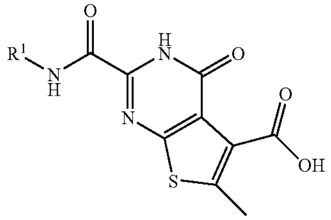

-continued
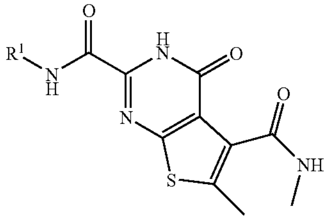
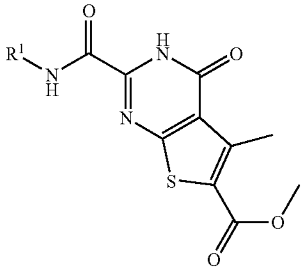
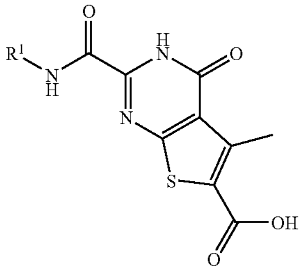
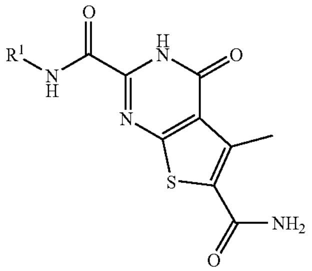
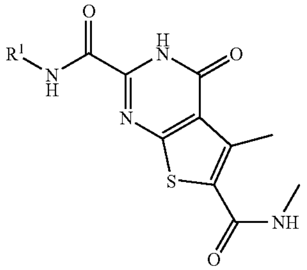
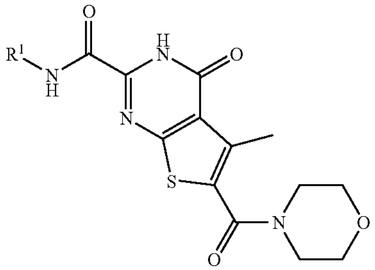
-continued
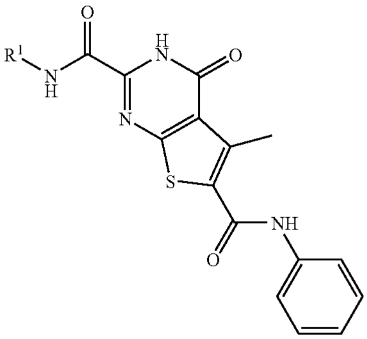
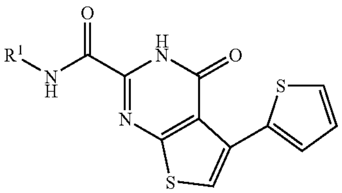
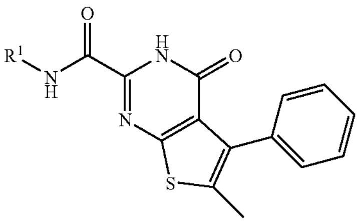
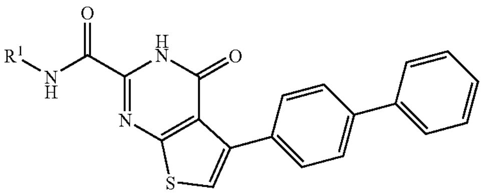
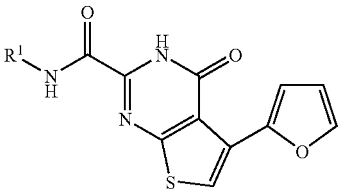
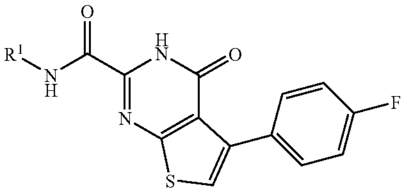
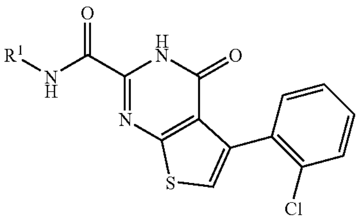

-continued
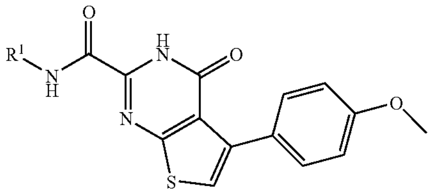
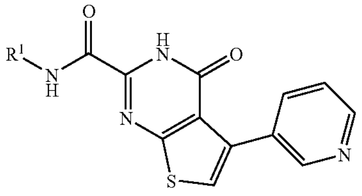
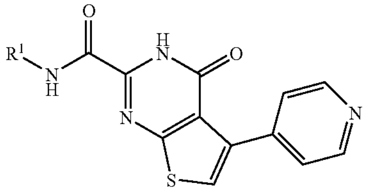
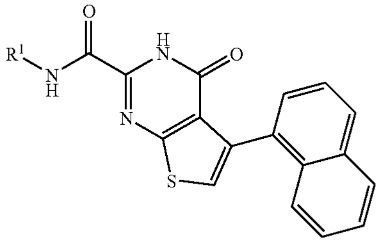
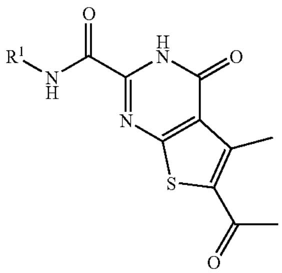
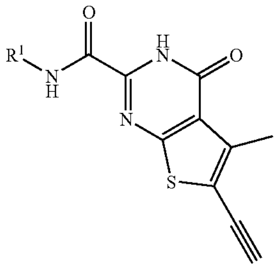
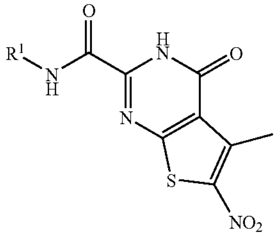
-continued
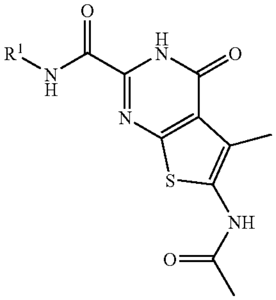
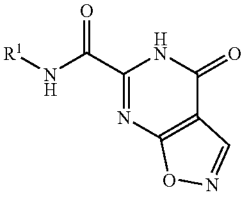
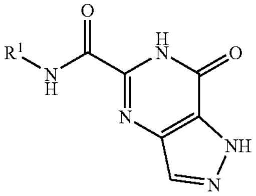
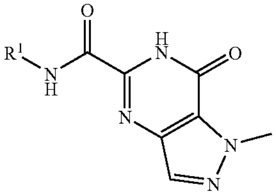
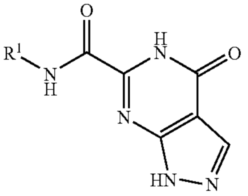
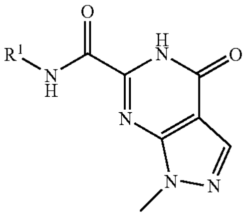
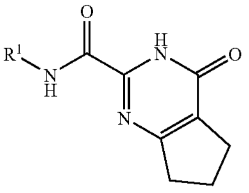
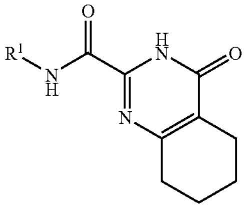
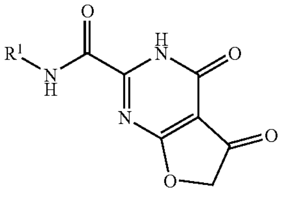
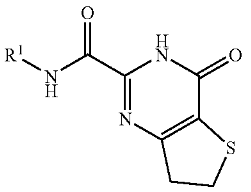
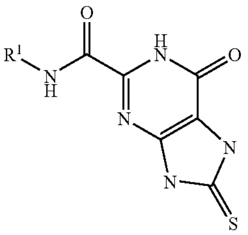
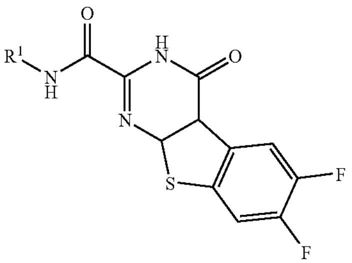

-continued
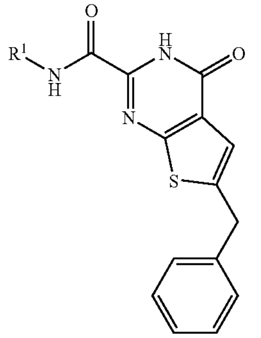
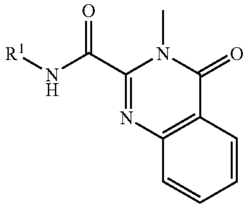
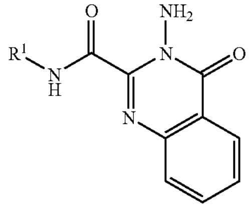
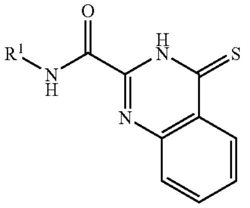
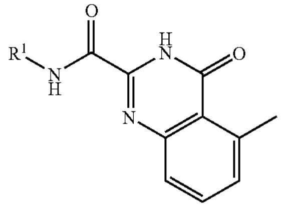
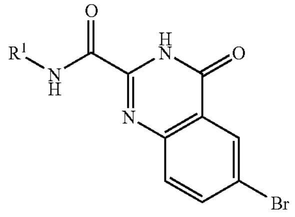
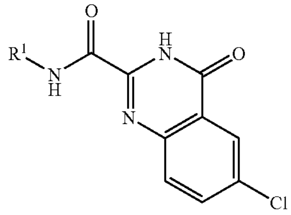
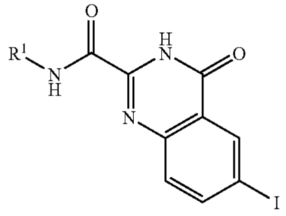
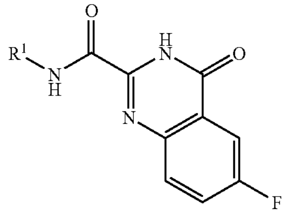
-continued
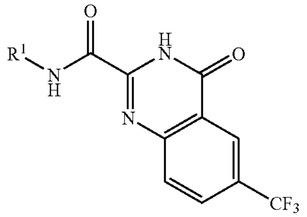
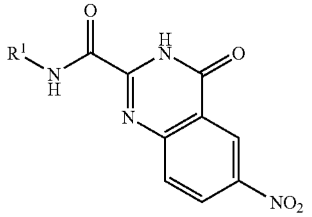
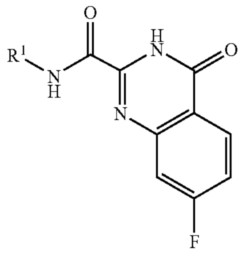
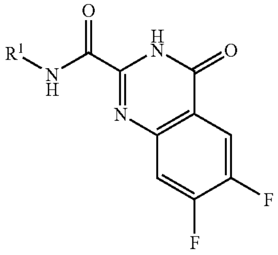
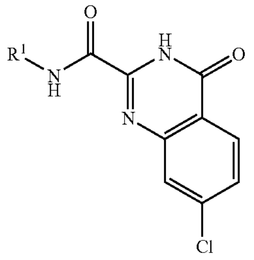
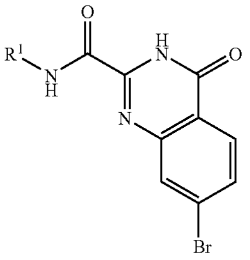
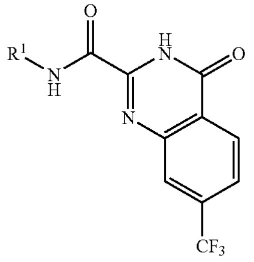
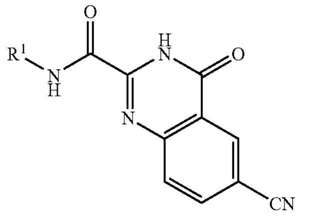
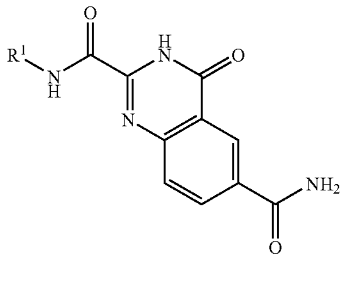

-continued
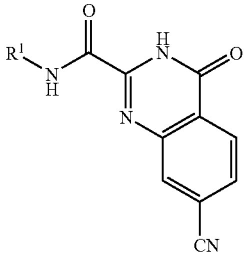
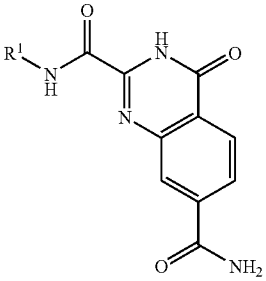
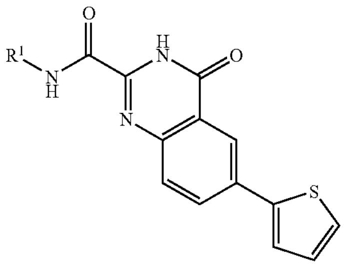
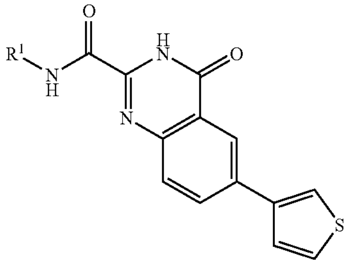
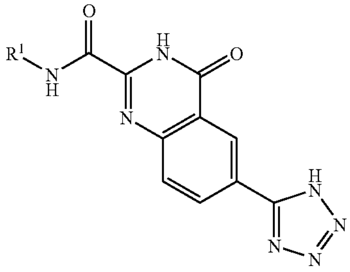
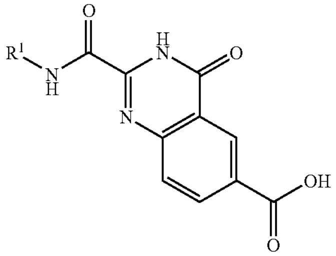
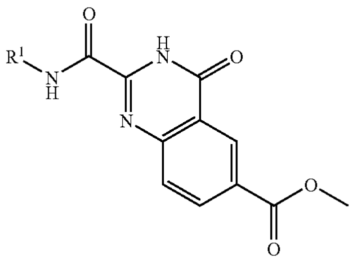
-continued
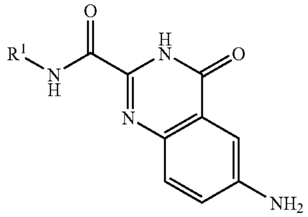
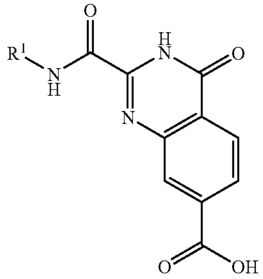
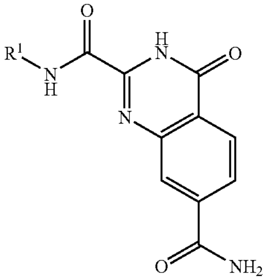
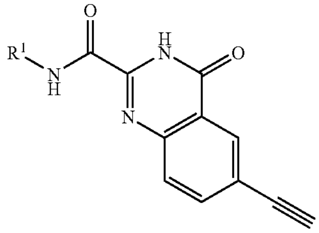
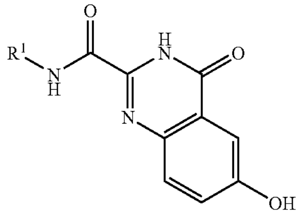
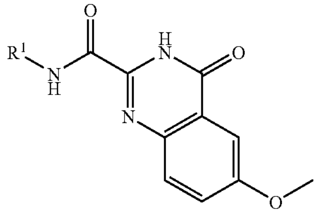
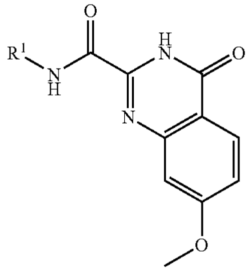
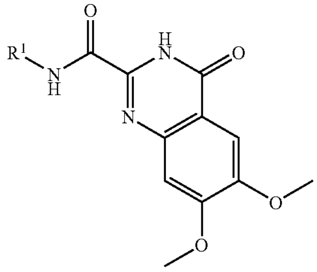

-continued
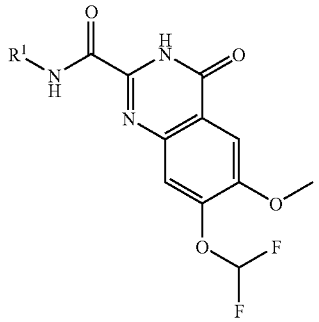
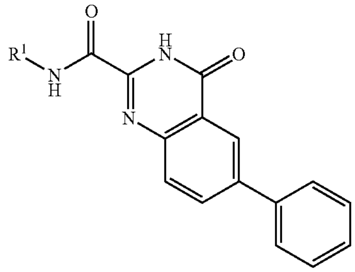
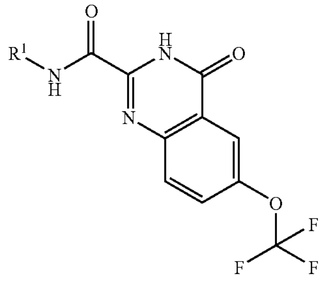
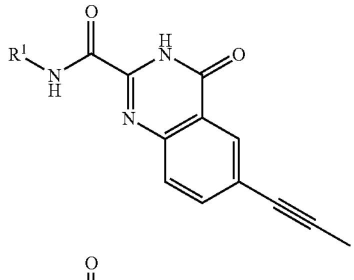
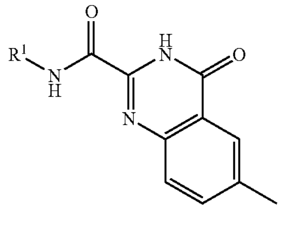
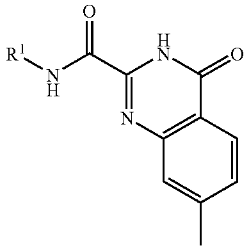
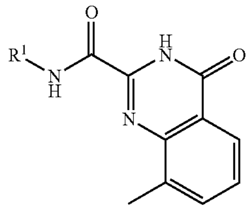
-continued
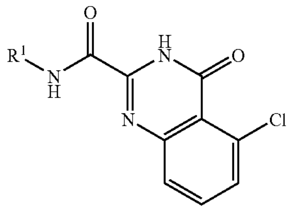
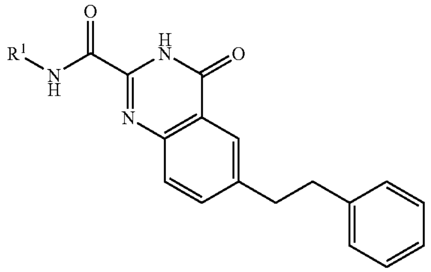
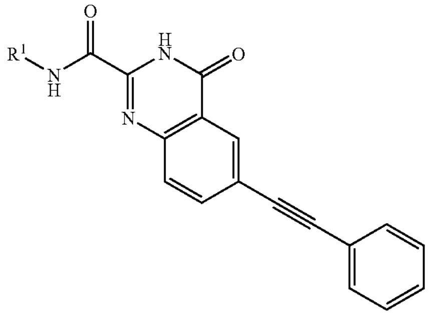
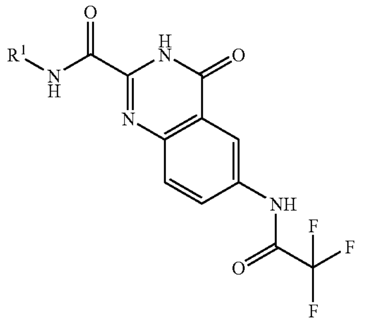
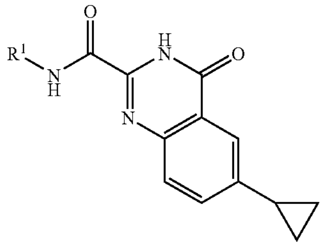
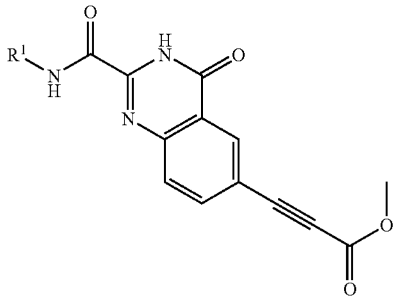

-continued
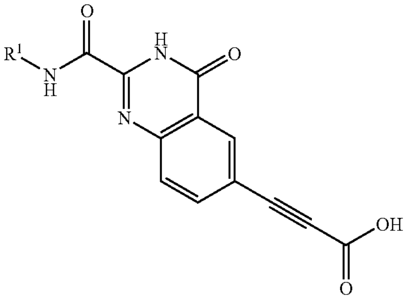
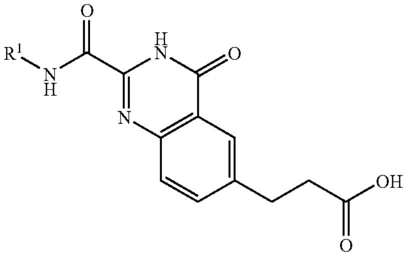
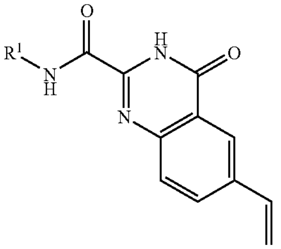
and
-continued
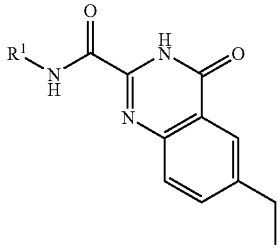
;
wherein $R^1$ is selected from:
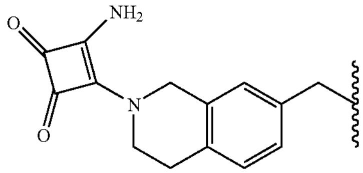
and
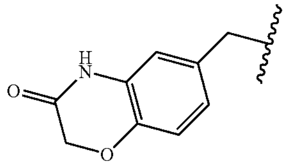
.
In another embodiment, in conjunction with any above or below embodiments, the compound is selected from
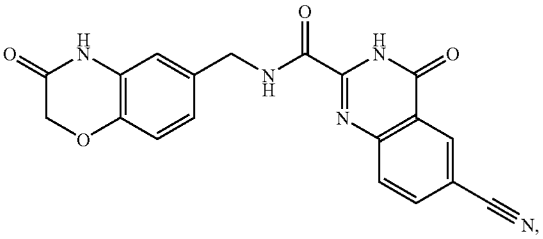
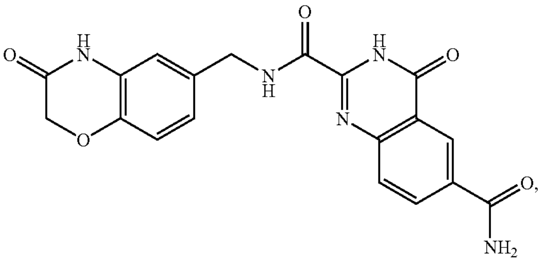
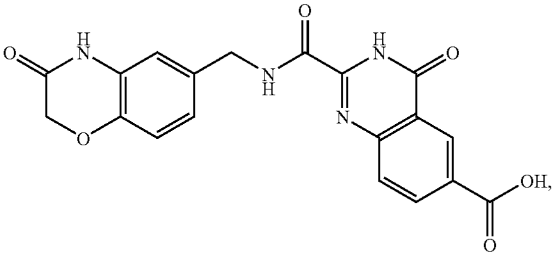

-continued
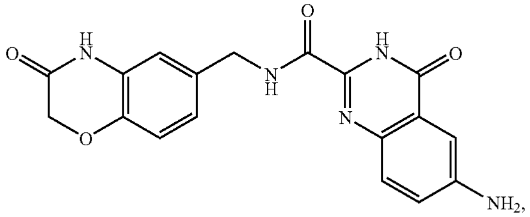
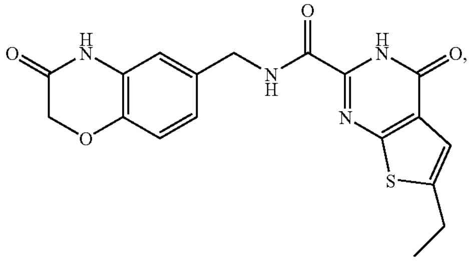
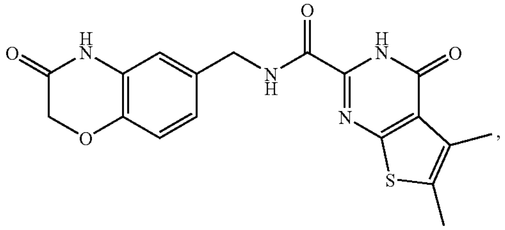
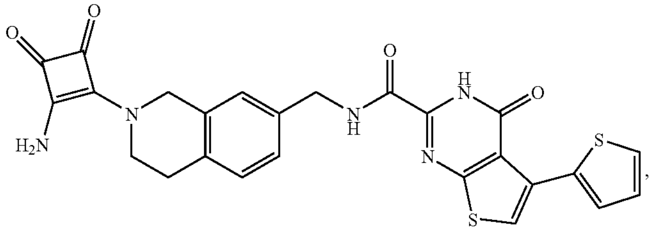
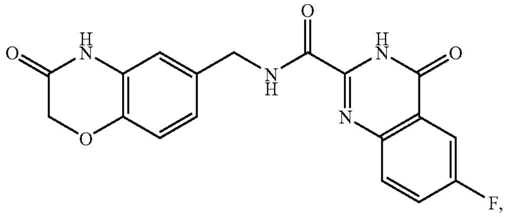
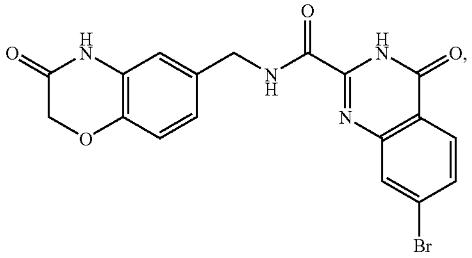
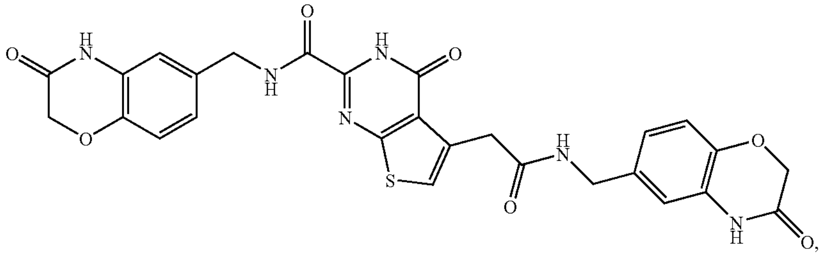

-continued
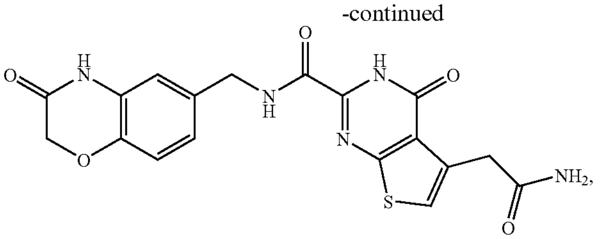
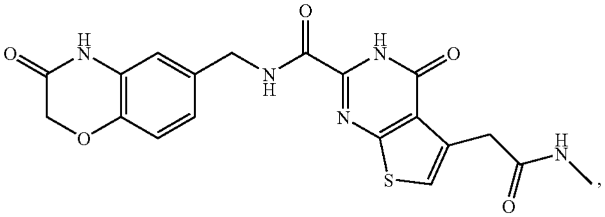
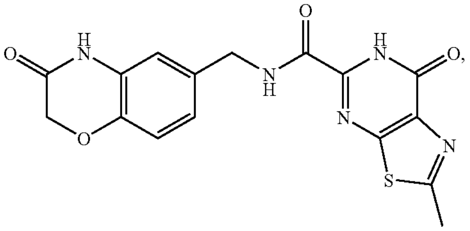
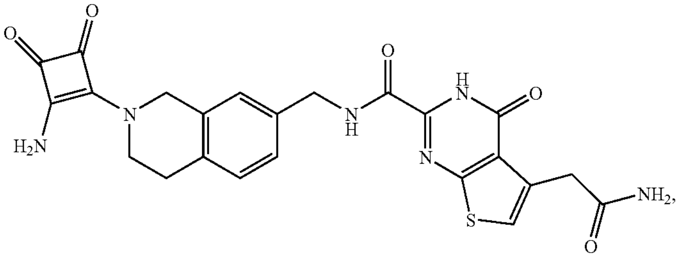
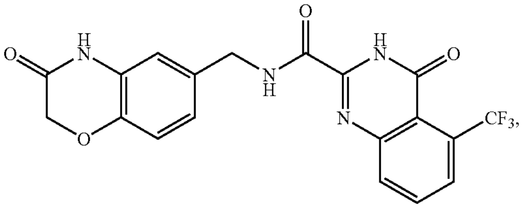
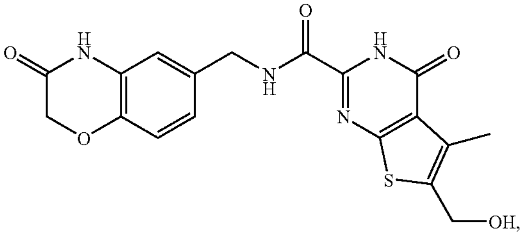
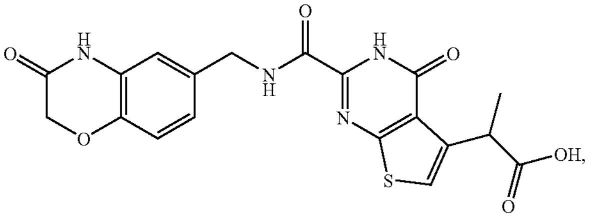

-continued
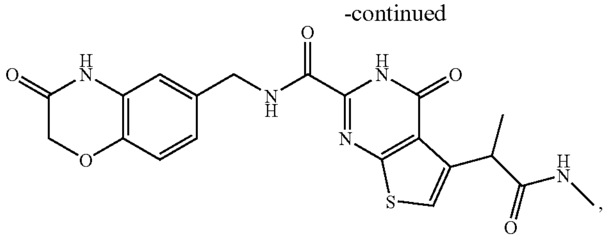
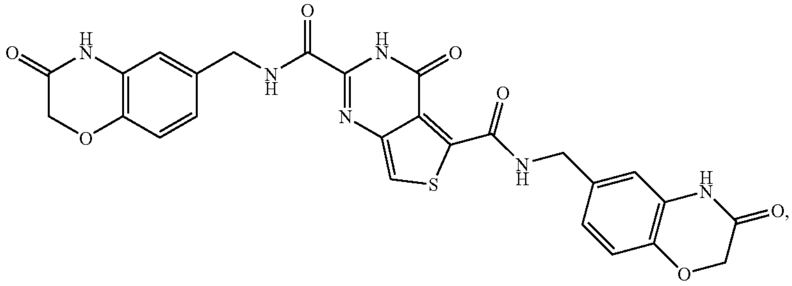
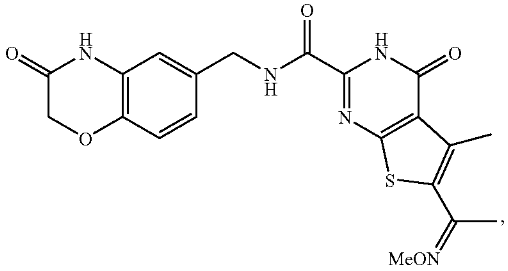
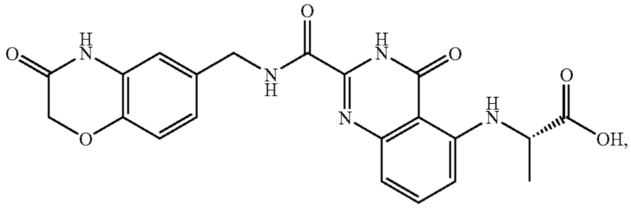
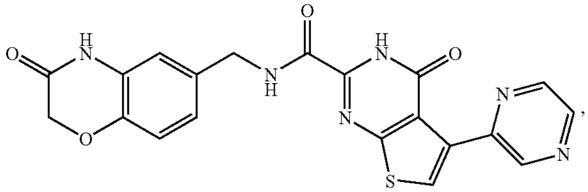
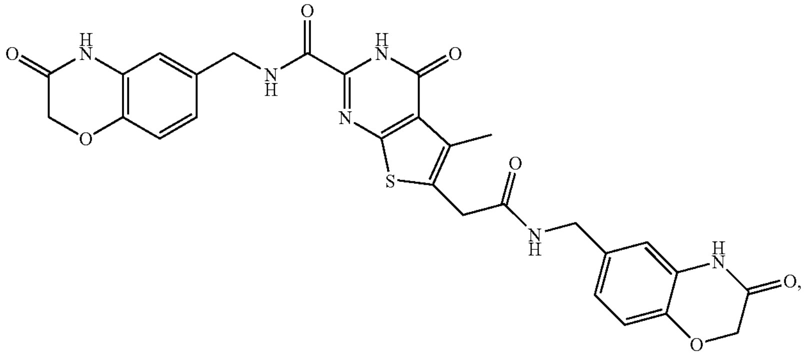

-continued
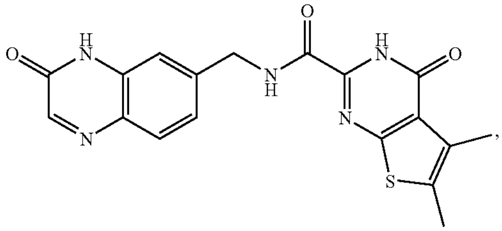
,
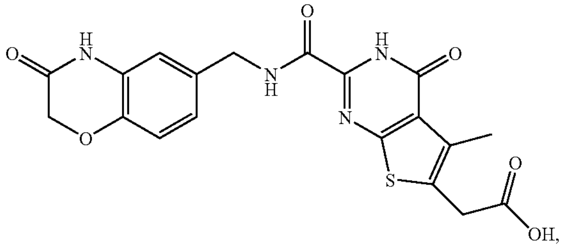
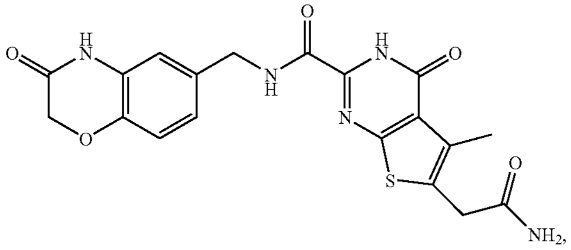
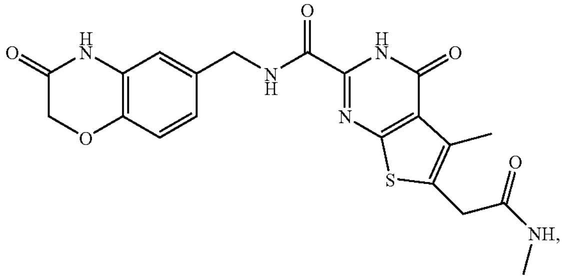
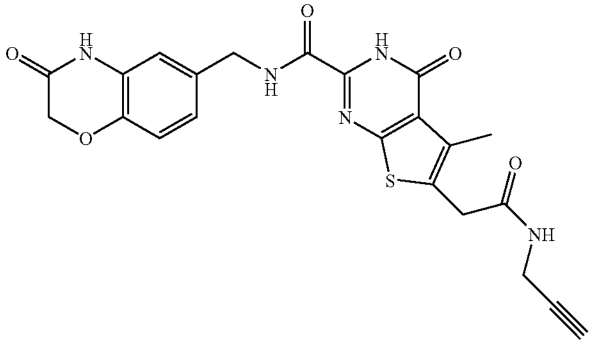
,
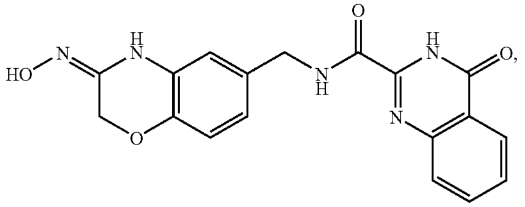

-continued
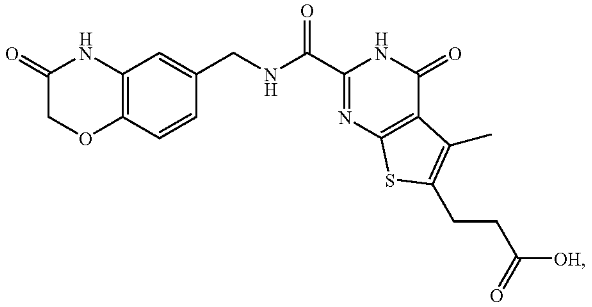
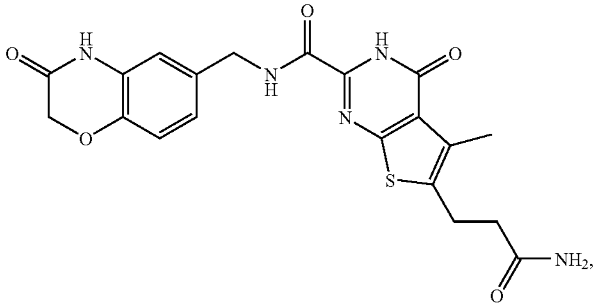
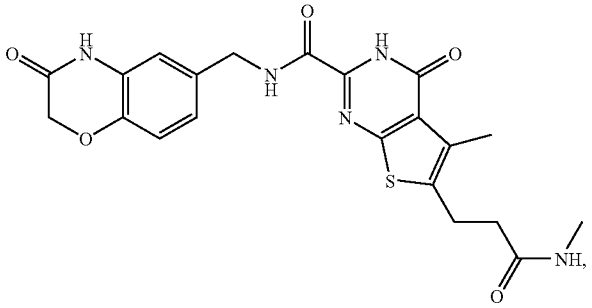
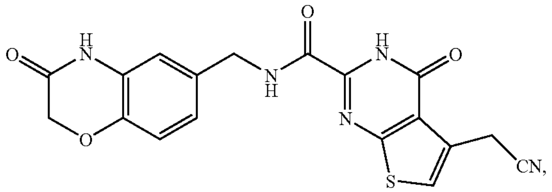
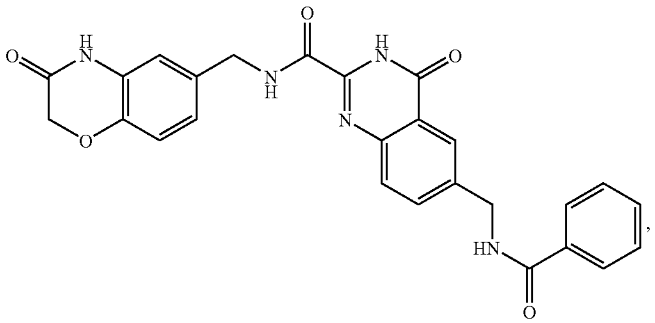

-continued
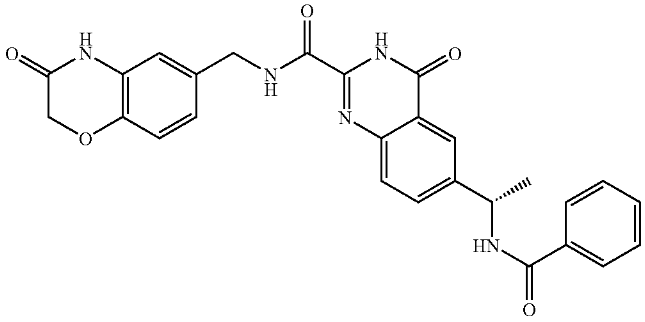
,
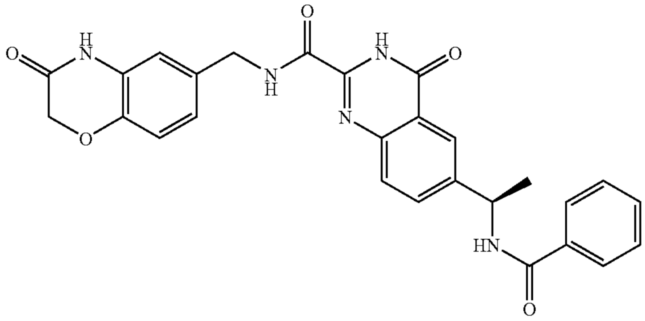
,
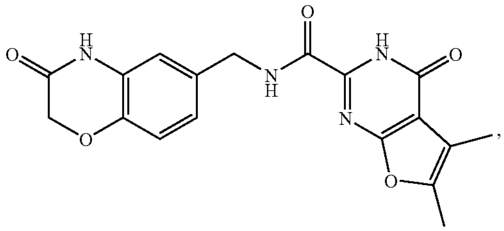
,
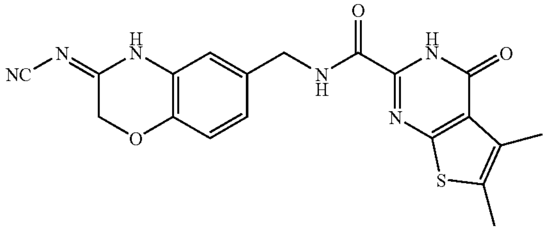
,
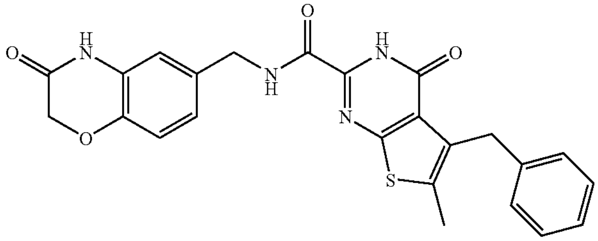
,
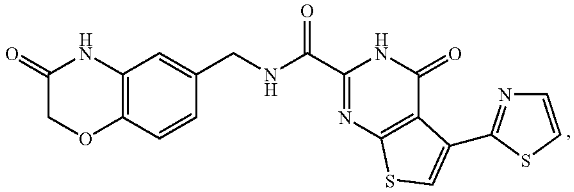
, -continued
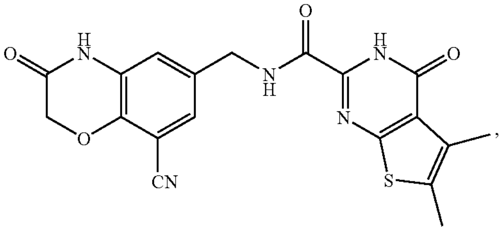
,
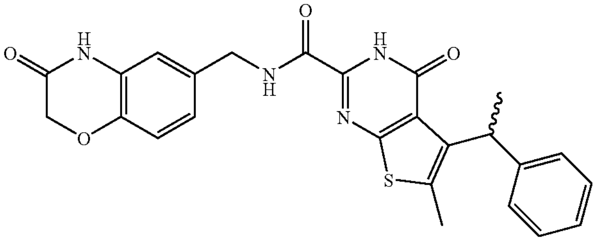
,
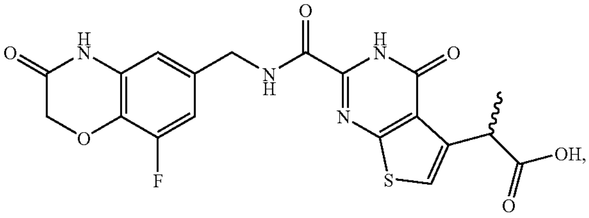
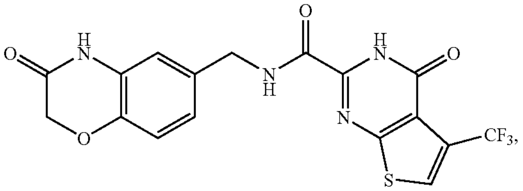
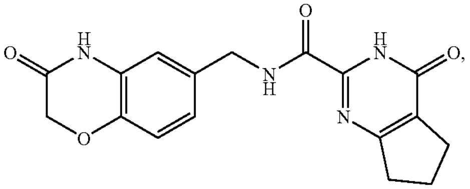
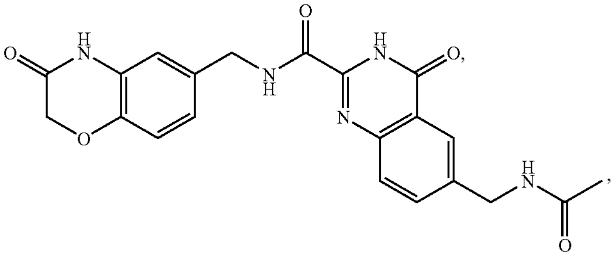
,
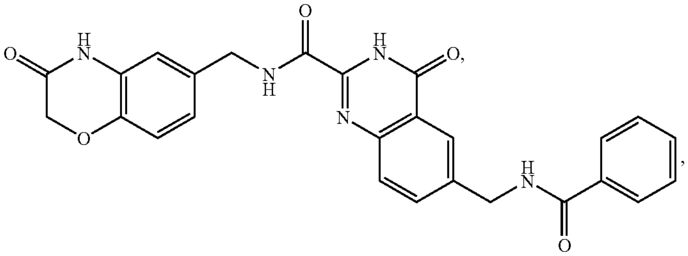
, -continued
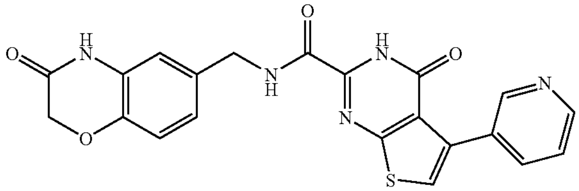
,
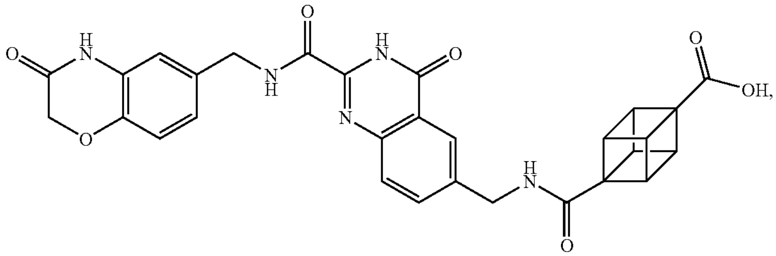
,
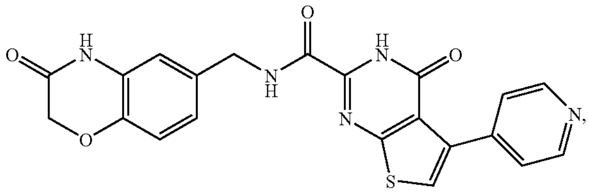
,
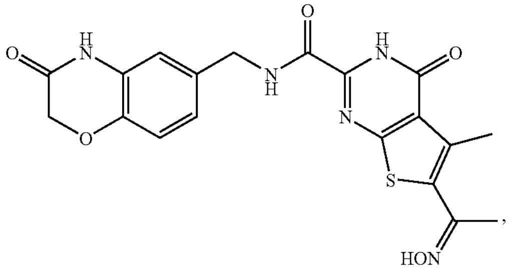
,
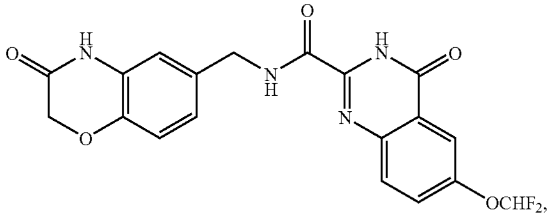
,
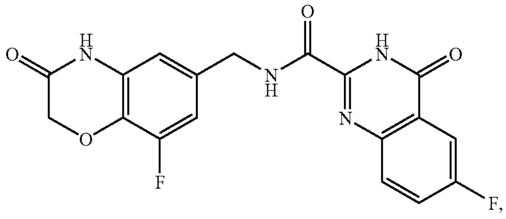
,
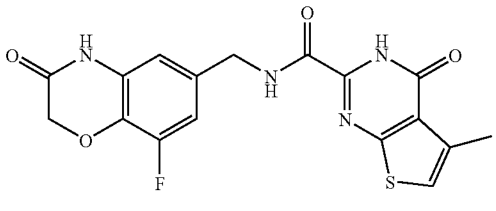
and -continued
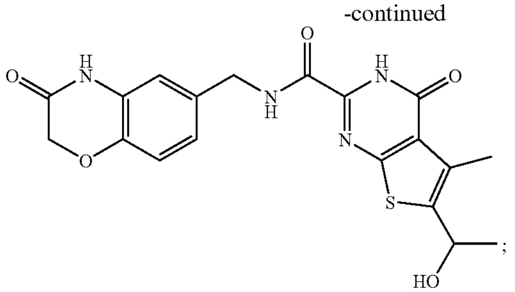
and N-oxides, pharmaceutically acceptable salts, prodrugs, formulations, polymorphs, tautomers, racemic mixtures and stereoisomers thereof.
In another embodiment, in conjunction with any above or below embodiments, $R^1$ is selected from:
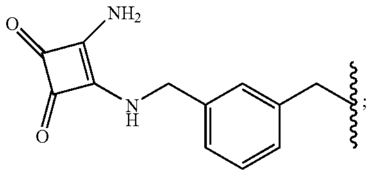
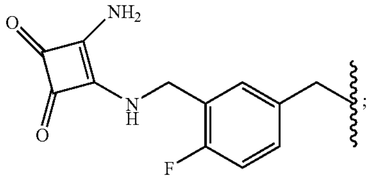
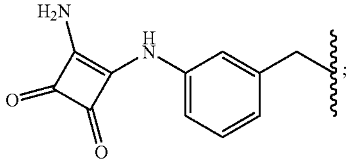
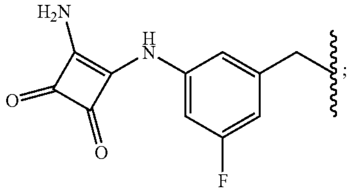
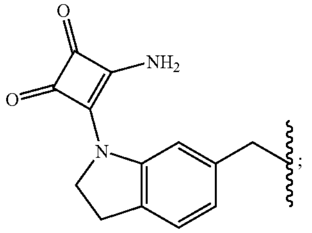
-continued
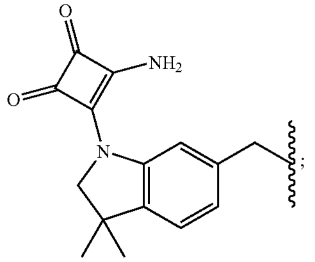
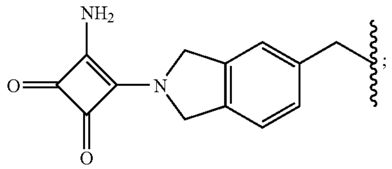
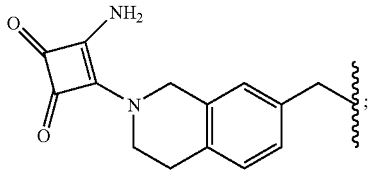
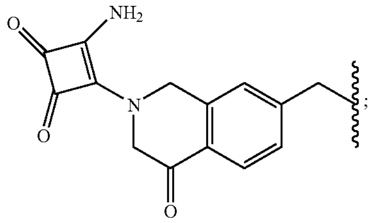
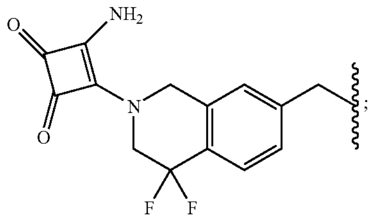
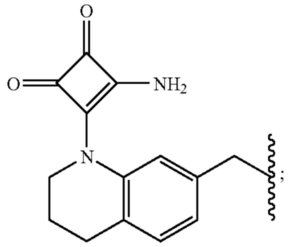

-continued

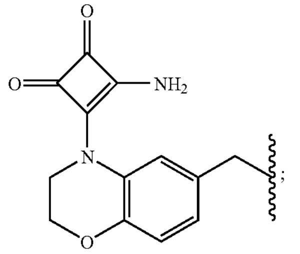

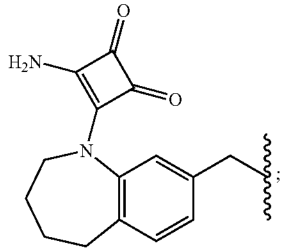

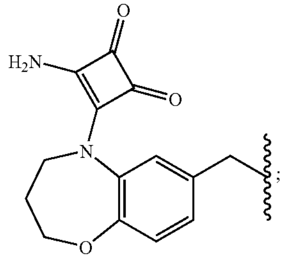

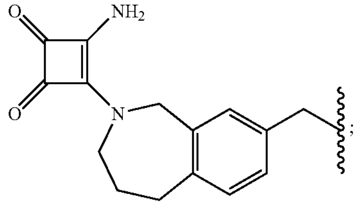

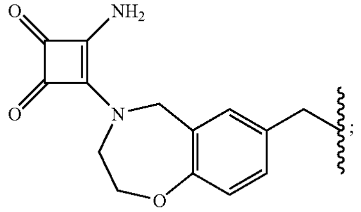

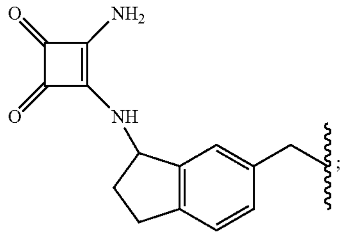

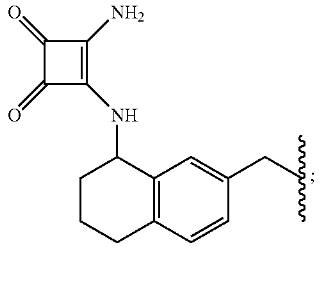

-continued

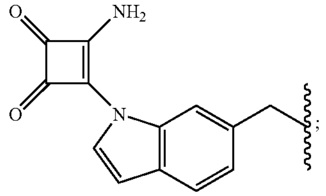

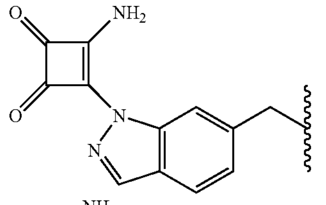

and

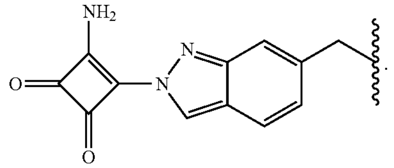

Another aspect of the invention relates to a pharmaceutical composition comprising an effective amount of the compound according to any of the above or below embodiments.

Another aspect of the invention relates to a method of treating a metalloprotease mediated disease, comprising administering to a subject in need of such treatment an effective amount of a compound according to any of the above or below embodiments.

In another embodiment, in conjunction with any above or below embodiments, the disease is selected from rheumatoid arthritis, osteoarthritis, inflammation, atherosclerosis and multiple sclerosis.

Another aspect of the invention relates to a pharmaceutical composition comprising:

A) an effective amount of a compound according to any of the above or below embodiments;

B) a pharmaceutically acceptable carrier; and

C) a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

Another aspect of the invention relates to a method of inhibiting a metalloprotease enzyme, comprising administering a compound according to any of the above or below embodiments.

In another embodiment, in conjunction with any above or below embodiments, the metalloproteinase is selected from MMP-2, MMP-3, MMP-8, and MMP-13.

In another embodiment, in conjunction with any above or below embodiments, the disease is selected from the group consisting of: rheumatoid arthritis, osteoarthritis, abdominal aortic aneurysm, cancer (e.g. but not limited to melanoma, gastric carcinoma or non-small cell lung carcinoma), inflammation, atherosclerosis, chronic obstructive pulmonary disease, ocular diseases (e.g. but not limited to ocular inflammation, retinopathy of prematurity, macular degeneration with the wet type preferred and corneal neovascularization), neurologic diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimers disease, arterial plaque formation, oncology, periodontal, viral infection, stroke, atherosclerosis, cardiovascular disease, reperfusion injury, trauma, chemical exposure or oxidative damage to tissues, wound healing, hemorroid, skin beautifying, pain, inflammatory pain, bone pain and joint pain, acne, acute alcoholic hepatitis, acute inflammation, acute pancreatitis, acute respiratory distress syndrome, adult respiratory disease, airflow obstruction, airway hyperresponsiveness, alcoholic liver disease, allograft rejections, angiogenesis, angiogenic ocular disease, arthritis, asthma, atopic dermatitis, bronchiectasis, bronchiolitis, bronchiolitis obliterans, burn therapy, cardiac and renal reperfusion injury, celiac disease, cerebral and cardiac ischemia, CNS tumors, CNS vasculitis, colds, contusions, cor pulmonae, cough, Crohn's disease, chronic bronchitis, chronic inflammation, chronic pancreatitis, chronic sinusitis, crystal induced arthritis, cystic fibrosis, delayted type hypersensitivity reaction, duodenal ulcers, dyspnea, early transplantation rejection, emphysema, encephalitis, endotoxic shock, esophagitis, gastric ulcers, gingivitis, glomerulonephritis, glossitis, gout, graft vs. host reaction, gram negative sepsis, granulocytic ehrlichiosis, hepatitis viruses, herpes, herpes viruses, HIV, hypercapnea, hyperinflation, hyperoxia-induced inflammation, hypoxia, hypersensitivity, hypoxemia, inflammatory bowel disease, interstitial pneumonitis, ischemia reperfusion injury, kaposi's sarcoma associated virus, lupus, malaria, meningitis, multi-organ dysfunction, necrotizing enterocolitis, osteoporosis, chronic periodontitis, periodontitis, peritonitis associated with continuous ambulatory peritoneal dialysis (CAPD), pre-term labor, polymyositis, post surgical trauma, pruritis, psoriasis, psoriatic arthritis, pulmatory fibrosis, pulmatory hypertension, renal reperfusion injury, respiratory viruses, restinosis, right ventricular hypertrophy, sarcoidosis, septic shock, small airway disease, sprains, strains, subarachnoid hemorrhage, surgical lung volume reduction, thrombosis, toxic shock syndrome, transplant reperfusion injury, traumatic brain injury, ulcerative colitis, vasculitis, ventilation-perfusion mismatching, and wheeze.

Another aspect of the invention relates to the use of a compound according to any of the above or below embodiments for the manufacture of a medicament for treating an metalloprotease mediated disease.

In another embodiment, in conjunction with any of the above or below embodiments, the metalloprotease mediated disease is selected from the group consisting of MMP-2, MMP-3, MMP-8 and MMP-13 mediated diseases.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butyryl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl) (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "cycloalkyl", as used herein alone or as part of another group, denotes optionally substituted, saturated cyclic hydrocarbon ring systems, containing one ring with 3 to 9 carbons. Exemplary unsubstituted such groups include, but are not limited to, cyclopropyl, cyclobutyl, cyclopentyl, cyclohexyl, cycloheptyl, cyclooctyl, cyclodecyl, and cyclododecyl. Exemplary substituents include, but are not limited to, one or more alkyl groups as described above, or one or more groups described above as alkyl substituents.

The term "bicycloalkyl", as used herein alone or as part of another group, denotes optionally substituted, saturated cyclic bridged hydrocarbon ring systems, desirably containing 2 or 3 rings and 3 to 9 carbons per ring. Exemplary unsubstituted such groups include, but are not limited to, adamantyl, bicyclo[2.2.2]octane, bicyclo[2.2.1]heptane and cubane. Exemplary substituents include, but are not limited to, one or more alkyl groups as described above, or one or more groups described above as alkyl substituents.

The term "spiroalkyl", as used herein alone or as part of another group, denotes optionally substituted, saturated hydrocarbon ring systems, wherein two rings of 3 to 9 carbons per ring are bridged via one carbon atom. Exemplary unsubstituted such groups include, but are not limited to, spiro[3.5]nonane, spiro[4.5]decane or spiro[2.5]octane. Exemplary substituents include, but are not limited to, one or more alkyl groups as described above, or one or more groups described above as alkyl substituents.

The term "spiroheteroalkyl", as used herein alone or as part of another group, denotes optionally substituted, saturated hydrocarbon ring systems, wherein two rings of 3 to 9 carbons per ring are bridged via one carbon atom and at least one carbon atom is replaced by a heteroatom independently selected from N, O and S. The nitrogen and sulfur heteroatoms may optionally be oxidized. Exemplary unsubstituted such groups include, but are not limited to, 1,3-diaza-spiro[4.5]decane-2,4-dione. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

Further examples of heterocycles include, but not are not limited to, "heterobicycloalkyl" groups such as 7-oxa-bicyclo[2.2.1]heptane, 7-aza-bicyclo[2.2.1]heptane, and 1-aza-bicyclo[2.2.2]octane.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The phrase "fused" means, that the group, mentioned before "fused" is connected via two adjacent atoms to the ring system mentioned after "fused" to form a bicyclic system. For example, "heterocycloalkyl fused aryl" includes, but is not limited to, 2,3-dihydro-benzo[1,4]dioxine, 4H-benzo[1,4]oxazin-3-one, 3H-Benzooxazol-2-one and 3,4-dihydro-2H-benzo[f][1,4]oxazepin-5-one.

The term "amino" denotes the radical $—NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. Illustrative examples include, but are not limited to, fluorene, 10,11-dihydro-5H-dibenzo[a,d]cycloheptene and 2,2a,7,7a-tetrahydro-1H-cyclobuta[a]indene.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Examples therefore may be, but are not limited to, sodium, potassium, choline, lysine, arginine or N-methyl-glucamine salts, and the like.

The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences,* 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The phrase "pharmaceutically acceptable carrier" denotes media generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Non-limiting examples of a pharmaceutically acceptable carrier are hyaluronic acid and salts thereof, and microspheres (including, but not limited to poly(D,L)-lactide-co-glycolic acid copolymer (PLGA), poly(L-lactic acid) (PLA), poly(caprolactone (PCL) and bovine serum albumin (BSA)). Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa., 1985, the contents of which are incorporated herein by reference.

Pharmaceutically acceptable carriers particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

The compositions of the invention may also be formulated as suspensions including a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Carriers suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

Cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. The amount of solubility enhancer employed will depend on the amount of the compound of the present invention in the composition.

The term "formulation" denotes a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing a compound of the present invention and a pharmaceutical carrier.

The term "N-oxide" denotes compounds that can be obtained in a known manner by reacting a compound of the present invention including a nitrogen atom (such as in a pyridyl group) with hydrogen peroxide or a peracid, such as 3-chloroperoxy-benzoic acid, in an inert solvent, such as dichloromethane, at a temperature between about −10-80° C., desirably about 0° C.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

The term "racemic mixture" denotes a mixture that is about 50% of one enantiomer and about 50% of the corresponding enantiomer relative to all chiral centers in the molecule. Thus, the invention encompasses all enantiomerically-pure, enantiomerically-enriched, and racemic mixtures of compounds of Formulas (I) and (II).

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S.

H., et al., Tetrahedron 33:2725 (1977); Eliel, E. L., Stereochemistry of Carbon Compounds (McGraw-Hill, N.Y., 1962); Wilen, S. H., Tables of Resolving Agents and Optical Resolutions p. 268 (E. L. Eliel, Ed., Univ. of Notre Dame Press, Notre Dame, Ind., 1972); Stereochemistry of Organic Compounds, Ernest L. Eliel, Samuel H. Wilen and Lewis N. Manda (1994 John Wiley & Sons, Inc.), and Stereoselective Synthesis A Practical Approach, Mihaly Nogradi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
$ONO_2$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;
OC(S)NH—($C_1$-$C_4$ alkyl);
OC(S)N($C_1$-$C_4$ alkyl)$_2$;
SH;
S—($C_1$-$C_4$ alkyl);
S(O)—($C_1$-$C_4$ alkyl);
S(O)$_2$—($C_1$-$C_4$ alkyl);
SC(O)—($C_1$-$C_4$ alkyl);
SC(O)O—($C_1$-$C_4$ alkyl);
$NH_2$;
N(H)—($C_1$-$C_4$ alkyl);
N($C_1$-$C_4$ alkyl)$_2$;
N(H)C(O)—($C_1$-$C_4$ alkyl);
N($CH_3$)C(O)—($C_1$-$C_4$ alkyl);
N(H)C(O)—$CF_3$;
N($CH_3$)C(O)—$CF_3$;
N(H)C(S)—($C_1$-$C_4$ alkyl);
N($CH_3$)C(S)—($C_1$-$C_4$ alkyl);
N(H)S(O)$_2$—($C_1$-$C_4$ alkyl);
N(H)C(O)$NH_2$;
N(H)C(O)NH—($C_1$-$C_4$ alkyl);
N($CH_3$)C(O)NH—($C_1$-$C_4$ alkyl);
N(H)C(O)N($C_1$-$C_4$ alkyl)$_2$;
N($CH_3$)C(O)N($C_1$-$C_4$ alkyl)$_2$;
N(H)S(O)$_2$$NH_2$);
N(H)S(O)$_2$NH—($C_1$-$C_4$ alkyl);
N($CH_3$)S(O)$_2$NH—($C_1$-$C_4$ alkyl);
N(H)S(O)$_2$N($C_1$-$C_4$ alkyl)$_2$;
N($CH_3$)S(O)$_2$N($C_1$-$C_4$ alkyl)$_2$;
N(H)C(O)O—($C_1$-$C_4$ alkyl);
N($CH_3$)C(O)O—($C_1$-$C_4$ alkyl);
N(H)S(O)$_2$O—($C_1$-$C_4$ alkyl);
N($CH_3$)S(O)$_2$O—($C_1$-$C_4$ alkyl);
N($CH_3$)C(S)NH—($C_1$-$C_4$ alkyl);
N($CH_3$)C(S)N($C_1$-$C_4$ alkyl)$_2$;
N($CH_3$)C(S)O—($C_1$-$C_4$ alkyl);
N(H)C(S)$NH_2$;
$NO_2$;
$CO_2H$;
$CO_2$—($C_1$-$C_4$ alkyl);
C(O)N(H)OH;
C(O)N($CH_3$)OH;
C(O)N($CH_3$)OH;
C(O)N($CH_3$)O—($C_1$-$C_4$ alkyl);
C(O)N(H)—($C_1$-$C_4$ alkyl);
C(O)N($C_1$-$C_4$ alkyl)$_2$;
C(S)N(H)—($C_1$-$C_4$ alkyl);
C(S)N($C_1$-$C_4$alkyl)$_2$;
C(NH)N(H)—($C_1$-$C_4$ alkyl);
C(NH)N($C_1$-$C_4$ alkyl)$_2$;
C($NCH_3$)N(H)—($C_1$-$C_4$ alkyl);
C($NCH_3$)N($C_1$-$C_4$ alkyl)$_2$;
C(O)—($C_1$-$C_4$ alkyl);
C(NH)—($C_1$-$C_4$ alkyl);
C($NCH_3$)—($C_1$-$C_4$ alkyl);
C(NOH)—($C_1$-$C_4$ alkyl);
C($NOCH_3$)—($C_1$-$C_4$ alkyl);
CN;
CHO;
$CH_2OH$;
$CH_2O$—($C_1$-$C_4$ alkyl);
$CH_2NH_2$;
$CH_2N$(H)—($C_1$-$C_4$ alkyl);
$CH_2N$($C_1$-$C_4$alkyl)$_2$;
aryl;
heteroaryl;
cycloalkyl; and
heterocyclyl.

In some cases, a ring substituent may be shown as being connected to the ring by a bond extending from the center of the ring. The number of such substituents present on a ring is indicated in subscript by a number. Moreover, the substituent may be present on any available ring atom, the available ring atom being any ring atom which bears a hydrogen which the ring substituent may replace. For illustrative purposes, if variable $R^X$ were defined as being:

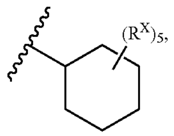

this would indicate a cyclohexyl ring bearing five $R^X$ substituents. The $R^X$ substituents may be bonded to any available ring atom. For example, among the configurations encompassed by this are configurations such as:

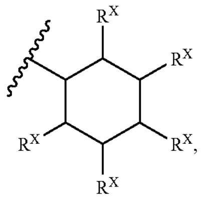

and

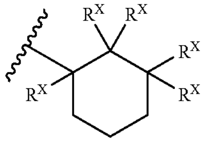

These configurations are illustrative and are not meant to limit the scope of the invention in any way.

Biological Activity

The inhibiting activity towards different metalloproteases of the heterocyclic metalloprotease inhibiting compounds of the present invention may be measured using any suitable assay known in the art. A standard in vitro assay for measuring the metalloprotease inhibiting activity is described in Examples 1700 to 1706. The heterocyclic metalloprotease inhibiting compounds show activity towards MMP-2, MMP-3, MMP-8, MMP-12, MMP-13, ADAMTS-4 and/or ADAMTS-5.

The heterocyclic metalloprotease inhibiting compounds of the invention have an MMP-13 inhibition activity ($IC_{50}$ MMP-13) ranging from below 0.2 nM to about 20 μM, and typically, from about 0.2 nM to about 1 μM. Heterocyclic metalloprotease inhibiting compounds of the invention desirably have an MMP inhibition activity ranging from about 0.2 nM to about 20 nM. Table 1 lists typical examples of heterocyclic metalloprotease inhibiting compounds of the invention that have an MMP-13 activity lower than 100 nM (Group A) and from 100 nM to 20 μM (Group B).

TABLE 1

Summary of MMP-13 Activity for Compounds

| Group | Ex. # |
|---|---|
| A | 1, 2/1, 2/3, 2/4, 2/5, 2/7, 2/9, 2/10, 2/11, 2/20, 2/21, 2/22, 2/23, 2/28, 2/39, 2/46, 2/51, 2/55, 2/57, 2/62, 2/69, 2/70, 2/74, 2/86, 2/93, 2/98, 2/101, 2/110, 2/111, 2/115, 2/138, 2/149, 2/157, 2/160, 2/179, 2/180, 2/185, 2/186, 2/193, 2/194, 2/198, 2/201, 2/221, 2/265, 2/271, 2/275, 2/281, 2/373, 2/379, 3, 4/3, 4/12, 4/13, 5, 8, 8/1, 9, 11, 14, 15, 16, 17, 19, 20a, 20c, 21, 23b, 24, 29/1, 35, 36, 36/2, 36/8, 36/12, 39/1, 39/22, 39/23, 39/24 |
| B | 2/6, 2/27, 2/43, 2/50, 2/65, 2/134, 2/136, 2/164, 2/205, 4/1, 4/2, 13/1, 20b, 25, 31/1, 38, 39/3, 39/6, 39/12, 39/13, 39/21 |

Some heterocyclic metalloprotease inhibiting compounds of the invention have an MMP-8 inhibition activity ($IC_{50}$ MMP-8) ranging from below 5 nM to about 20 μM, and typically, from about 10 nM to about 2 μM. Heterocyclic metalloprotease inhibiting compounds of the invention desirably have an MMP inhibition activity ranging below 100 nM. Table 2 lists typical examples of heterocyclic metalloprotease inhibiting compounds of the invention that have an MMP-8 activity lower than 250 nM (Group A) and from 250 nM to 20 μM (Group B).

TABLE 2

Summary of MMP-8 Activity for Compounds

| Group | Ex. # |
|---|---|
| A | 2/1, 2/9, 2/10, 2/11, 2/21, 2/23, 2/26, 2/39, 2/43, 2/46, 2/55, 2/69, 2/70, 2/74, 2/93, 2/149, 2/156, 2/157, 2/160, 2/183, 2/194, 2/199, 2/221, 2/275, 2/373, 4/3, 4/8, 4/13, 5, 8, 9, 14, 16, 17, 19, 20c, 21, 29/1, 35, 36/2, 36/6, 36/12, 36/13, 39/22 |
| B | 2/3, 2/5, 2/6, 2/7, 2/15, 2/17, 2/20, 2/22, 2/27, 2/28, 2/49, 2/51, 2/57, 2/62, 2/86, 2/98, 2/101, 2/105, 2/110, 2/115, 2/134, 2/185, 2/86, 2/265, 36, 39/24 |

Some heterocyclic metalloprotease inhibiting compounds of the invention have an MMP-3 inhibition activity ($IC_{50}$ MMP-3) ranging from below 10 nM to about 20 μM, and typically, from about 50 nM to about 2 μM. Heterocyclic metalloprotease inhibiting compounds of the invention desirably have an MMP inhibition activity ranging below 100 nM. Table 3 lists typical examples of heterocyclic metalloprotease inhibiting compounds of the invention that have an MMP-3 activity lower than 250 nM (Group A) and from 250 nM to 20 μM (Group B).

TABLE 3

Summary of MMP-3 Activity for Compounds

| Group | Ex. # |
|---|---|
| A | 2/1, 2/9, 2/10, 2/21, 2/23, 2/26, 2/49, 2/51, 2/71, 2/74, 2/86, 2/91, 2/98, 2/134, 2/185, 2/186, 2/265, 4/13, 9, 19, 35 |
| B | 2/11, 2/20, 2/39, 2/46, 2/55, 2/93, 2/105, 2/110, 2/160, 2/183, 2/221, 2/271, 2/373, 4/12, 14, 29/1, 36, 36/3, 39/13 |

The synthesis of metalloprotease inhibiting compounds of the invention and their biological activity assay are described in the following examples which are not intended to be limiting in any way.

Schemes

Provided below are schemes according to which compounds of the present invention may be prepared.

In some embodiments the compounds of Formula (I) and (II) are synthesized by the general methods shown in Scheme 1 to Scheme 3.

Scheme 1

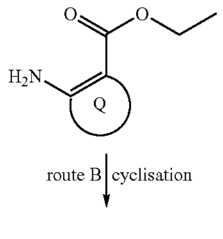

-continued

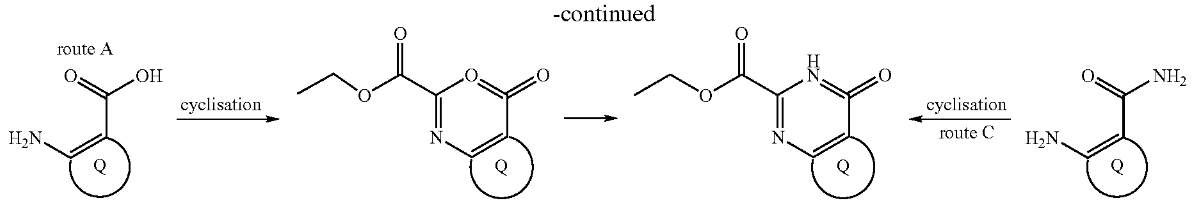

Route A

An carbonic acid and amino substituted compound (e.g. 4-amino-nicotinic acid) is condensed (e.g. EtOH/reflux) with chloro-oxo-acetic acid ethyl ester as previously described e.g. in WO2005/105760 in pyridine to give an oxazine ethyl ester (Scheme 1). This intermediate is then converted into the corresponding pyrimidine derivative using a suitable reagent (e.g. $NH_4OAc$, HOAc, EtOH/80° C.). For example, when ring Q is a pyridine ring. The compound can be obtained according this route A.

Route B

An ester and amino substituted compound (e.g. 2-amino-benzoic acid ethyl ester) is condensed (e.g. 4N HCl, dioxane/50° C.) with ethyl cyanoformate as previously described e.g. in WO2005/105760, to give a 1,3-pyrimidine-4-one ethyl ester (Scheme 1).

Route C

An carboxamide and amino substituted compound (e.g. 2-amino-benzamide) is condensed with an suitable reagent (e.g oxalic acid diethyl ester or acetic acid anhydride as described in DD272079A1 or chloro-oxo-acetic acid ethyl ester as described in *J. Med. Chem.* 1979, 22(5), 505-510) to give a 1,3-pyrimidine-4-one ethyl ester (Scheme 1).

Scheme 2

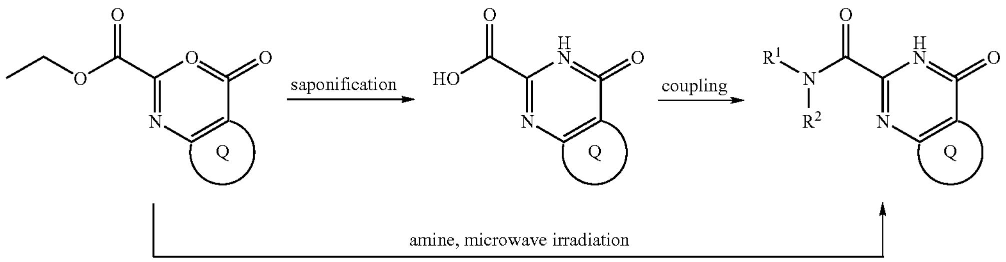

Saponification (e.g. aqueous LiOH) of the 1,3-pyrimidine-4-one derivative of Scheme 1 above gives the corresponding bicyclic carboxylic acid (Scheme 2). Activated acid coupling (e.g. EDCl/HOAt) with $R^1R^2NH$ (e.g. 6-aminomethyl-4H-benzo[1,4]oxazin-3-one) in a suitable solvent gives the desired amide. The saponification/coupling step can be combined by stirring the ester with the free amine at elevated temperature (e.g. 200° C., 15 min) under microwave irradiation.

Scheme 3

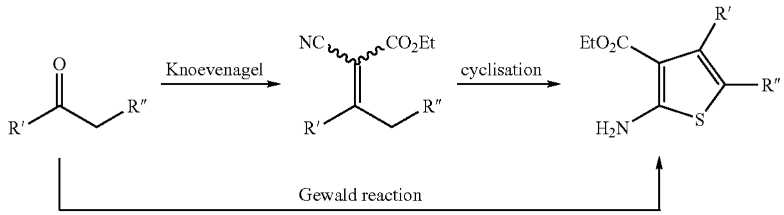

A substituted ketone (e.g. tetrahydrothiophen-3-one) is condensed (e.g. toluene/reflux with Dean-Stark apparatus) with ethyl cyanoacetate, acetic acid and ammonium acetate to afford the desired ethyl ester-cyano substituted double bond. (Scheme 3). This intermediate is then converted into the corresponding thiophene derivative using suitable reagents (e.g. sulphur, $Et_2NH$, EtOH/50° C.) as previously described e.g. in *J. prakt. Chem.* 1973, 315, 39-43 or *Monatsh. Chem.* 2001, 132, 279-293.

The Knoevenagel/cyclisation step can be combined by stirring the ketone with ethyl cyanoacetate, sulphur and a base (e.g. $Et_3N$) in a suitable solvent (e.g EtOH/50° C.), following the Gewald type reaction as described e.g. in *J. prakt. Chem.* 1973, 315, 39-43 or *Bioorg. Med. Chem.* 2002, 10, 3113-3122.

In compounds, where the one $L_b$ in formula (I) is a nitrogen atom, the following procedure can be applied (Scheme 4).

Scheme 4

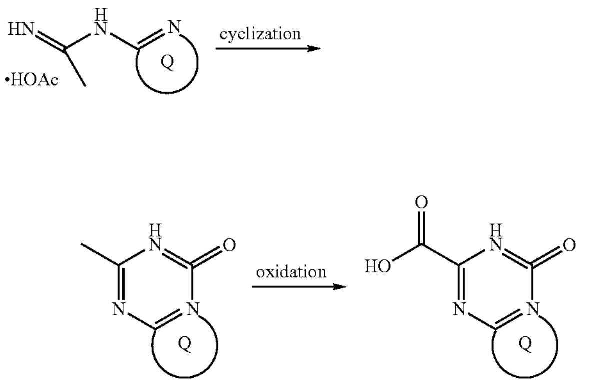

For example, N-(pyrazol-3-yl)acetamide acetate can be cyclizised with carbonic acid diethyl ester to 2-methylpyrazolo[1,5a]-s-triazine-4-one (*J. Heterocycl. Chem.* 1985, 22, 601-634) and further oxidized to the corresponding acid (e.g. by $SeO_2$ and then oxone).

In ring Q of the product in Scheme 1 to Scheme 4, further functional group manipulation can be applied (e.g. J. March, Advanced Organic Chemistry, Wiley&Sons), e.g. palladium catalyzed halogen-cyanide exchange or nucleophilic substitution.

EXAMPLES AND METHODS

All reagents and solvents were obtained from commercial sources and used without further purification. Proton spectra ($^1H$-NMR) were recorded on a 400 MHz and a 250 MHz NMR spectrometer in deuterated solvents. Purification by column chromatography was performed using silica gel, grade 60, 0.06-0.2 mm (chromatography) or silica gel, grade 60, 0.04-0.063 mm (flash chromatography) and suitable organic solvents as indicated in specific examples. Preparative thin layer chromatography was carried out on silica gel plates with UV detection.

Preparative Examples are directed to intermediate compounds useful in preparing the compounds of the present invention.

Preparative Example 1

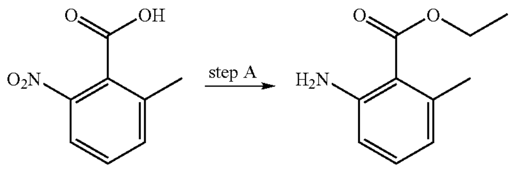

Step A

2-Methyl-6-nitro-benzoic acid (4.72 g) was dissolved in dry $CH_2Cl_2$ and DMF (3 drops) and thionyl chloride (3 mL) was added. The mixture was stirred for 4 h at 40° C., evaporated, coevaporated with toluene and dissolved in ethanol. The mixture was stirred at 70° C. overnight and then evaporated. The solid was dissolved in 6 N HCl and $SnCl_2.2H_2O$ (15 g) was added. The mixture was stirred for 2 h at room temperature, evaporated to give the title compound (4.86 g; quant.) which was used without further purification.

Preparative Example 2

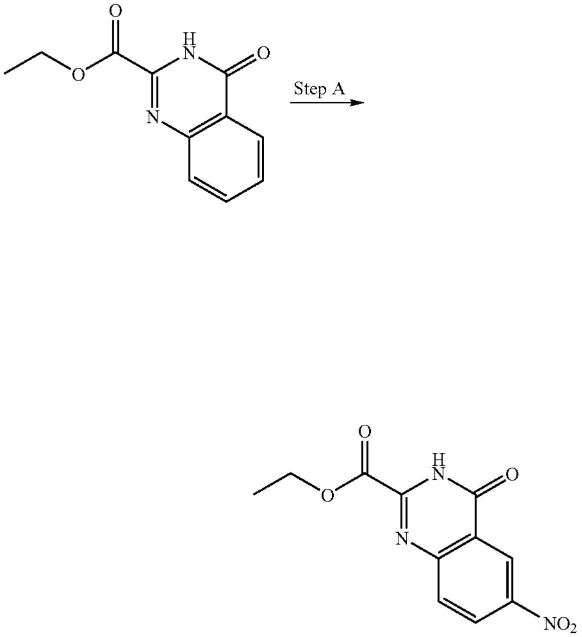

Step A

4-Oxo-3,4-dihydro-quinazoline-2-carboxylic acid ethyl ester (710 mg) was dissolved in conc. $H_2SO_4$ and cooled to 5° C., then conc. $HNO_3$ (4 mL) was added. After 15 min the mixture was quenched by adding ice. The precipitate was filtered, washed with water and dried to give the title compound (809 mg; 94%). $[MH]^+$=264.

Preparative Example 2/1 to 2/3

Following similar procedures as described in the Preparative Example 2 except using the ethyl esters indicated in Table I.1 below, the following compounds were prepared.

TABLE I.1

| Ex. # | Amine | product | yield |
|---|---|---|---|
| 2/1 | 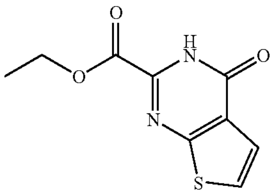 | 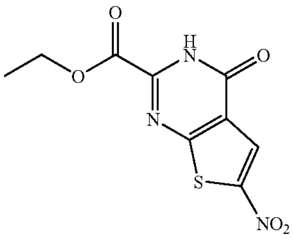 | 77% [MH]$^+$ = 270 |
| 2/2 | 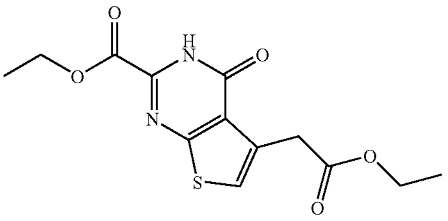 | 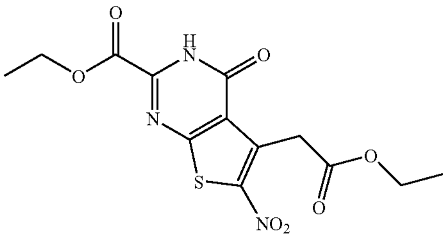 | 70% [MH]$^+$ = 356 |
| 2/3 | 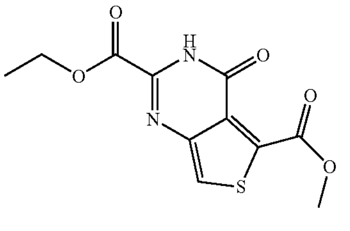 | 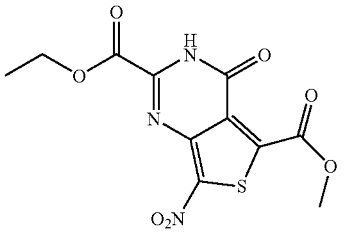 | 81% [MH]$^+$ = 328 |

Preparative Example 3

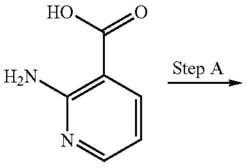

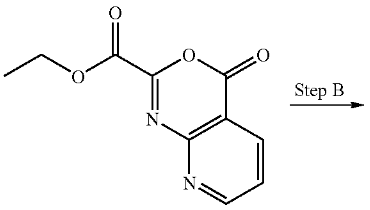

-continued

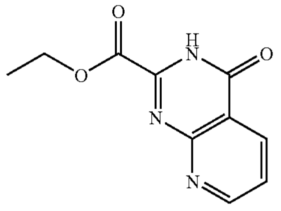

Step A

2-Aminonicotinic acid (2.5 g) was suspended in dry pyridine (40 mL) and ethyloxalyl chloride (4 mL) was added under ice cooling. The ice bath was removed and the mixture was stirred for 1 h at room temperature, then heated to 50° C. for 2 h, cooled and evaporated. After adding water to the residue, the solid was filtered to give the title compound (3.17 g; 80%) as a colorless solid. [MH]$^+$=221.

Step B

The intermediate from step A above (3.17 g), $NH_4OAc$ (1.11 g) and AcOH (330 μL) was dissolved in EtOH and heated to reflux for 1 h. After cooling, the precipitate was triturated with 0.1N hydrochloric acid, filtered and washed with few water and dried to give the title compound (314 mg; 10%) as a colorless solid. $[MH]^+$=220.

Preparative Example 3a

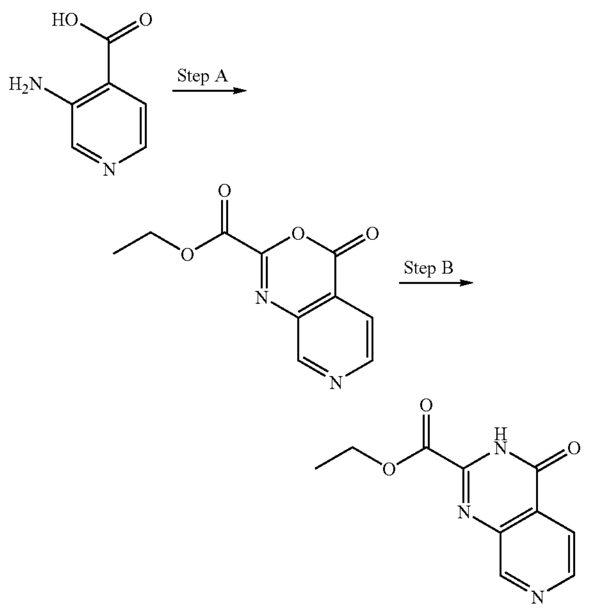

Step A

3-Amino-isonicotinic acid (500 mg) was suspended in dry pyridine (8 mL) and ethyloxalyl chloride (2 mL) was added under ice cooling. The ice bath was removed and the mixture was stirred for 1 h at room temperature, then heated to 50° C. for 2 h, cooled and evaporated. After adding water to the residue, the solid was filtered and dissolved in acetic anhydride (10 mL) and heated to reflux to give the title compound which was used for the next step without further purification. $[MH]^+$=221.

Step B

The intermediate from step A above, $NH_4OAc$ (400 mg) and AcOH (150 μL) was dissolved in EtOH (10 mL) and heated to reflux for 1 h. After cooling, the precipitate was titurated with 0.1N hydrochloric acid, filtered and washed with few water and dried to give the title compound. $[MH]^+$=220.

Preparative Example 4

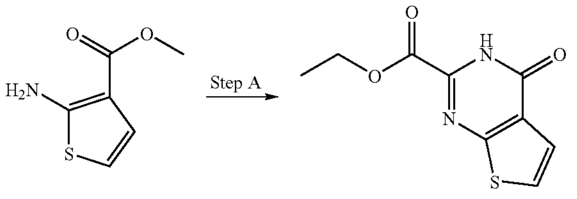

Step A

2-Amino-thiophene-3-carboxylic acid methyl ester (1.1 g) was dissolved in a 4M solution of HCl in 1,4-dioxane (20 mL) and cyanoacetic acid ethyl ester (0.85 mL) was added. The mixture was stirred at 40° C. for 3 hours, concentrated and purified by extraction with ethyl acetate from an aqueous solution to afford the title compound (420 mg, 26%). $[MH]^+$=225.

Preparative Examples 5/1 to 5/114

Following similar procedures as described in the Preparative Examples 4 except using the amines indicated in Table I.2 below, the following compounds were prepared.

TABLE I.2

| Ex. # | Amine | product | yield |
|---|---|---|---|
| 5/1 | 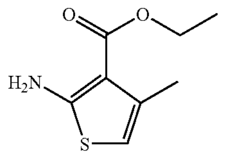 | 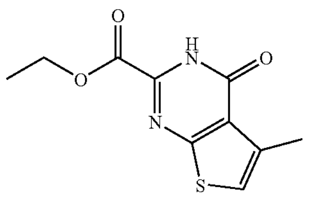 | 77% $[MH]^+$ = 239 |
| 5/2 | 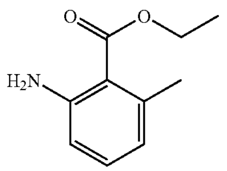 | 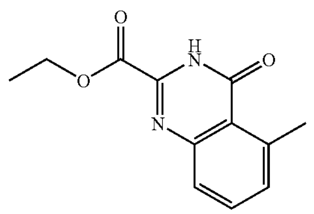 | 49% $[MH]^+$ = 233 |

TABLE I.2-continued
| Ex. # | Amine | product | yield |
|---|---|---|---|
| 5/3 | 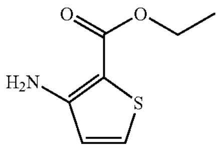 | 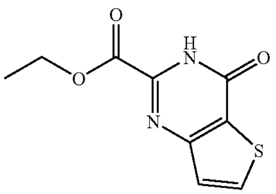 | n.d.<br>$[MH]^+ = 213$ |
| 5/4 | 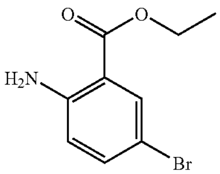 | 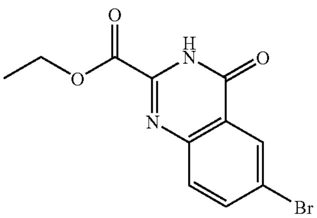 | 54%<br>$[MH]^+ = 297/299$ |
| 5/5 | 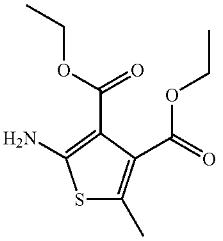 | 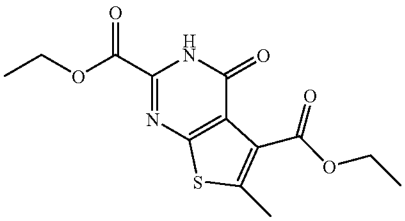 | >99%<br>$[MH]^+ = 311$ |
| 5/6 | 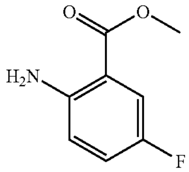 | 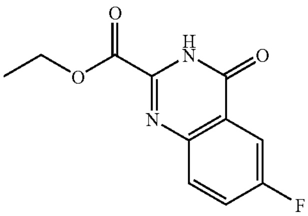 | 95%<br>$[MH]^+ = 237$ |
| 5/8 | 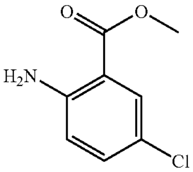 | 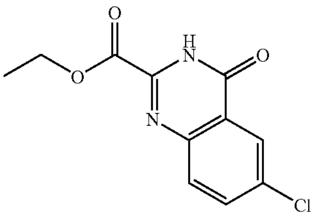 | >99%<br>$[MH]^+ = 253$ |
| 5/9 | 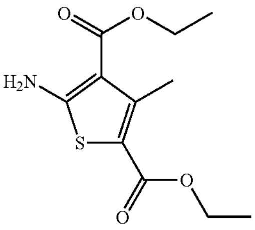 | 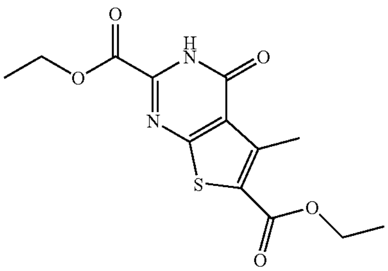 | 71%<br>$[MH]^+ = 311$ |

TABLE I.2-continued
| Ex. # | Amine | product | yield |
| --- | --- | --- | --- |
| 5/11 | 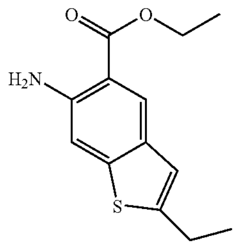 | 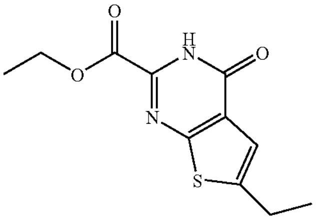 | 99%<br>$[MH]^+ = 253$ |
| 5/13 | 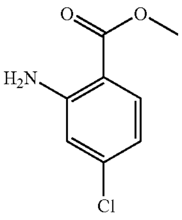 | 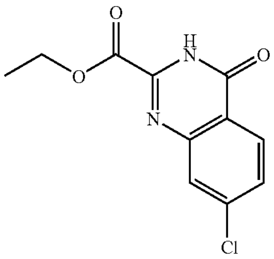 | 56%<br>$[MH]^+ = 253$ |
| 5/14 | 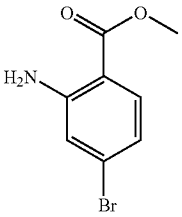 | 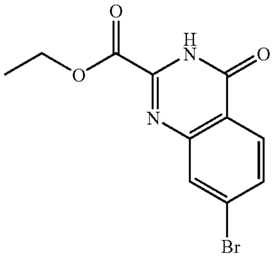 | 56%<br>$[MH]^+ = 297/299$ |
| 5/15 | 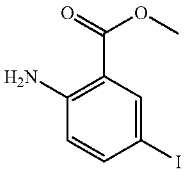 | 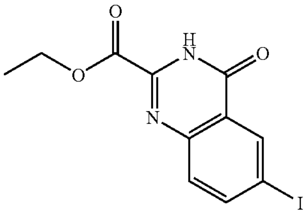 | 99%<br>$[MH]^+ = 345$ |
| 5/16 | 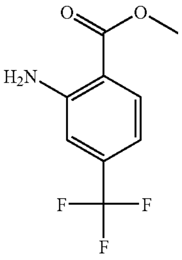 | 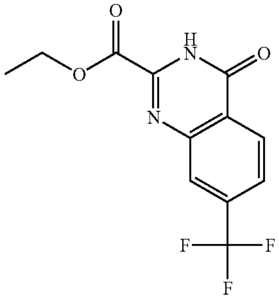 | 90%<br>$[MH]^+ = 287$ |
| 5/17 | 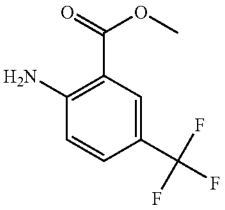 | 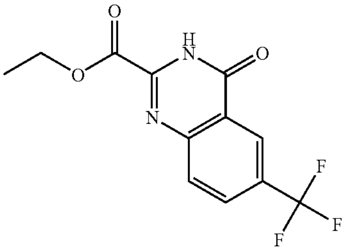 | 92%<br>$[MH]^+ = 287$ |

TABLE I.2-continued
| Ex. # | Amine | product | yield |
|---|---|---|---|
| 5/18 | 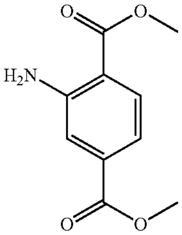 | 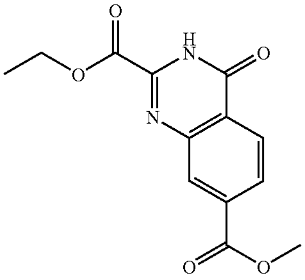 | 88%<br>$[MH]^+ = 277$ |
| 5/19 | 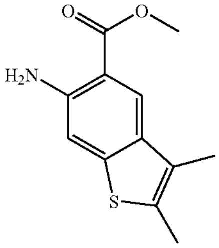 | 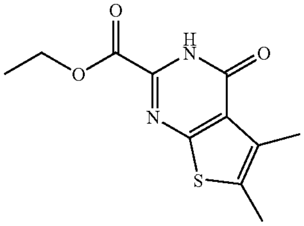 | 99%<br>$[MH]^+ = 253$ |
| 5/20 | 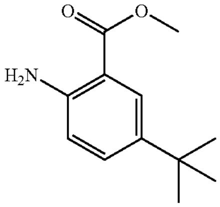 | 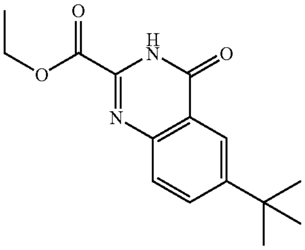 | 83%<br>$[MH]^+ = 275$ |
| 5/21 | 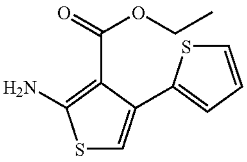 | 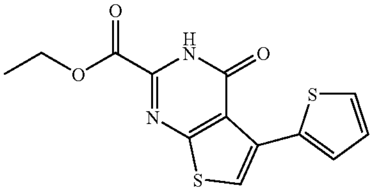 | 75%<br>$[MH]^+ = 307$ |
| 5/22 | 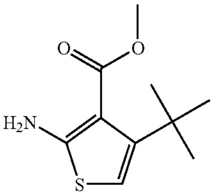 | 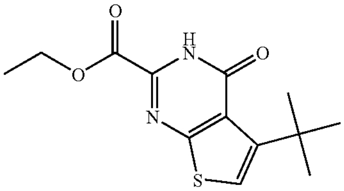 | 99%<br>$[MH]^+ = 281$ |
| 5/23 | 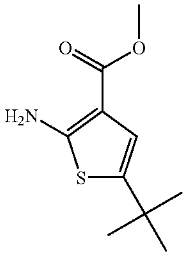 | 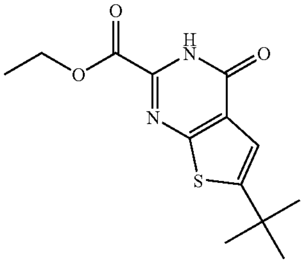 | n.d.<br>$[MH]^+ = 281$ |

TABLE I.2-continued
| Ex. # | Amine | product | yield |
| --- | --- | --- | --- |
| 5/24 | 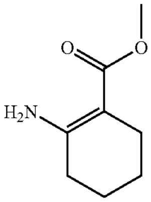 | 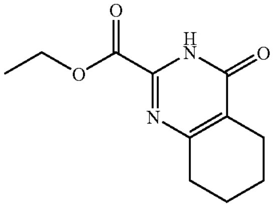 | 96%<br>$[MH]^+ = 223$ |
| 5/25 | 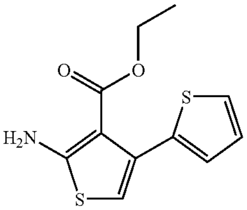 | 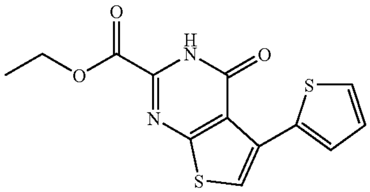 | 75%<br>$[MH]^+ = 307$ |
| 5/26 | 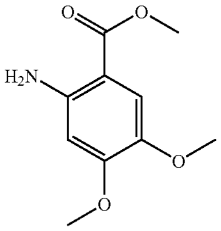 | 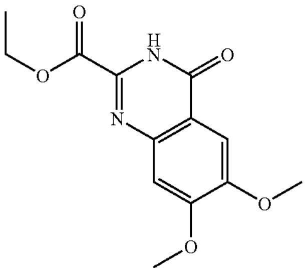 | 83%<br>$[MH]^+ = 279$ |
| 5/27 | 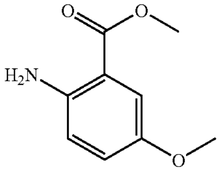 | 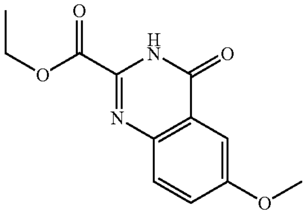 | 40%<br>$[MH]^+ = 249$ |
| 5/28 | 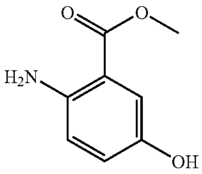 | 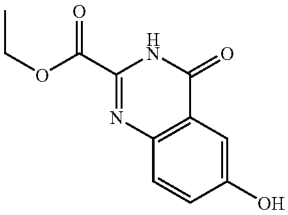 | 33%<br>$[MH]^+ = 235$ |
| 5/29 | 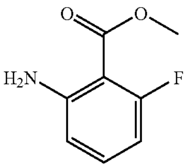 | 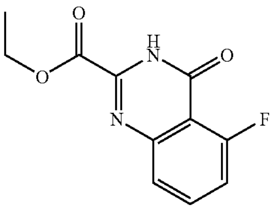 | 85%<br>$[MH]^+ = 237$ |

TABLE I.2-continued
| Ex. # | Amine | product | yield |
|---|---|---|---|
| 5/30 | 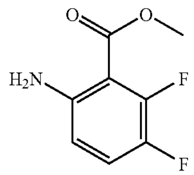 | 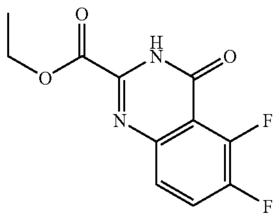 | 60%<br>$[MH]^+ = 279$ |
| 5/31 | 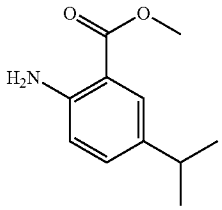 | 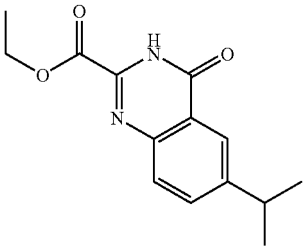 | 75%<br>$[MH]^+ = 261$ |
| 5/32 | 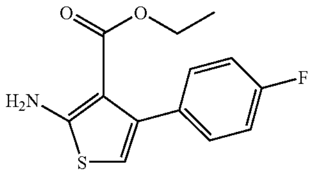 | 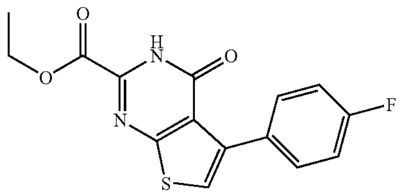 | 72%<br>$[MH]^+ = 319$ |
| 5/33 | 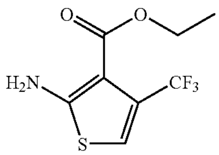 | 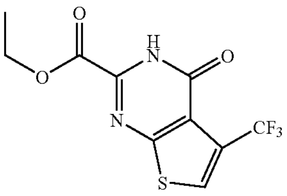 | 89%<br>$[MH]^+ = 293$ |
| 5/34 | 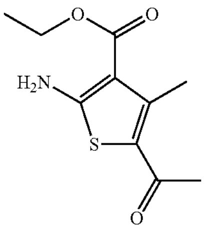 | 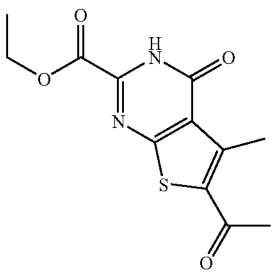 | 77%<br>$[MH]^+ = 281$ |
| 5/37 | 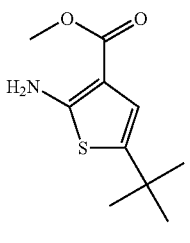 | 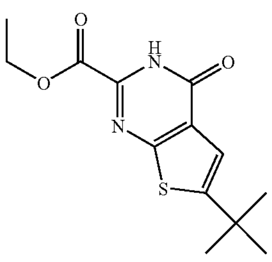 | n.d.<br>$[MH]^+ = 281$ |

TABLE I.2-continued
| Ex. # | Amine | product | yield |
| --- | --- | --- | --- |
| 5/38 | 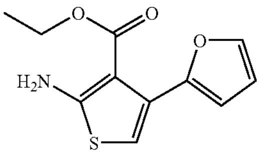 | 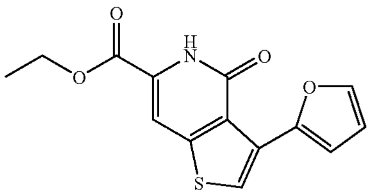 | 95%<br>[MH]$^+$ = 291 |
| 5/39 | 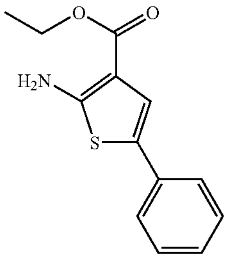 | 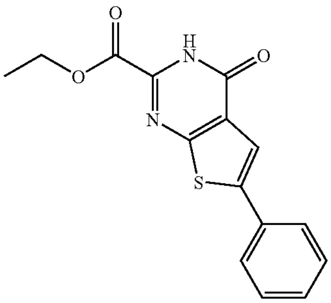 | 26%<br>[MH]$^+$ = 301 |
| 5/40 | 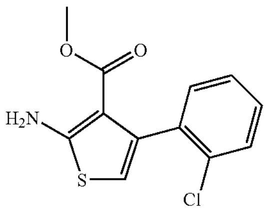 | 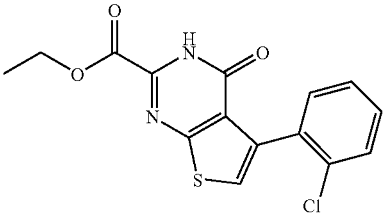 | 98%<br>[MH]$^+$ = 335 |
| 5/42 | 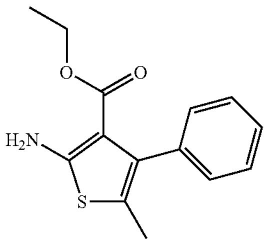 | 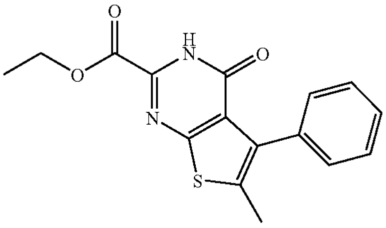 | 85%<br>[MH]$^+$ = 315 |
| 5/44 | 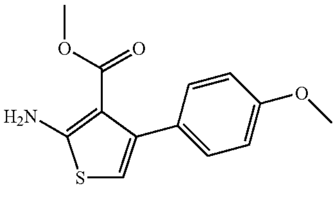 | 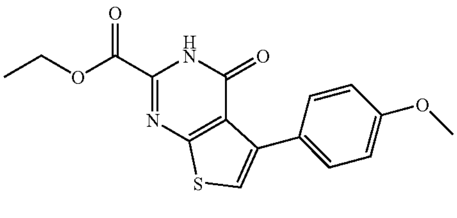 | 99%<br>[MH]$^+$ = 331 |
| 5/44 | 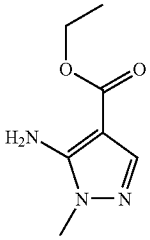 | 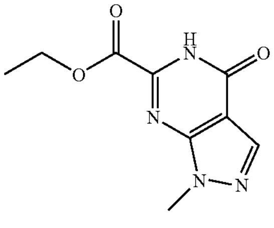 | 35%<br>[MH]$^+$ = 223 |

TABLE I.2-continued
| Ex. # | Amine | product | yield |
|---|---|---|---|
| 5/46 | 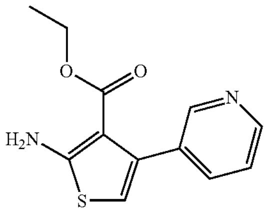 | 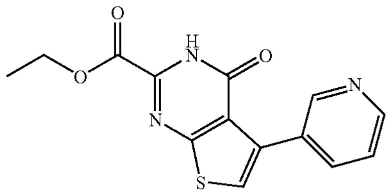 | 16%<br>$[MH]^+ = 302$ |
| 5/50 | 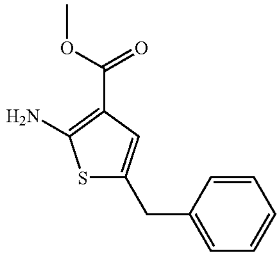 | 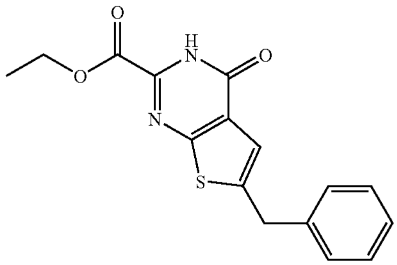 | 87%<br>$[MH]^+ = 315$ |
| 5/52 | 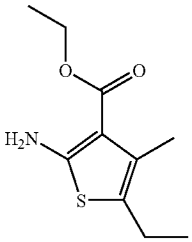 | 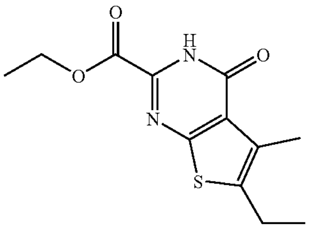 | 100%<br>$[MH]^+ = 267$ |
| 5/54 | 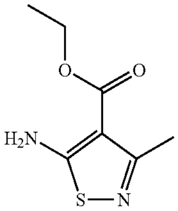 | 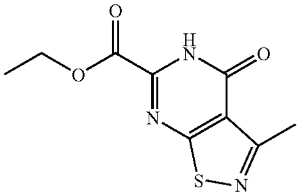 | 86%<br>$[MH]^+ = 240$ |
| 5/55 | 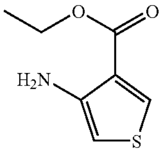 | 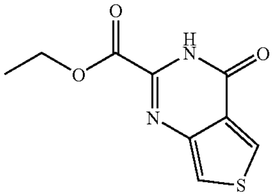 | 31%<br>$[MH]^+ = 225$ |
| 5/56 | 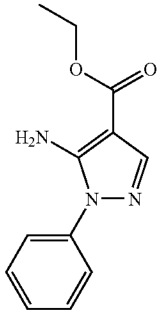 | 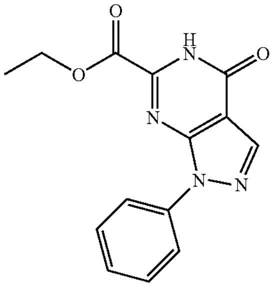 | 34%<br>$[MH]^+ = 285$ |

TABLE I.2-continued
| Ex. # | Amine | product | yield |
| --- | --- | --- | --- |
| 5/57 | 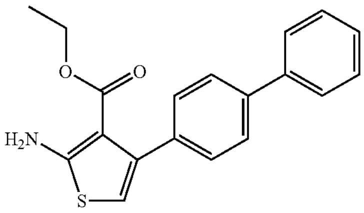 | 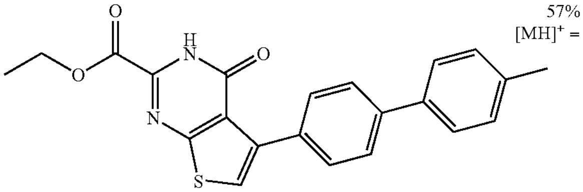 | 57% [MH]$^+$ = 377 |
| 5/58 | 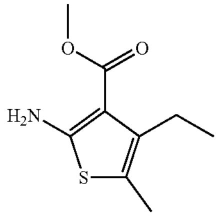 | 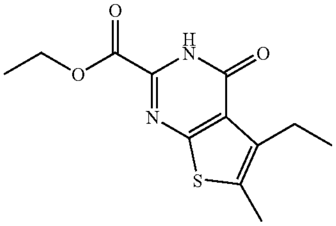 | 84% [MH]$^+$ = 267 |
| 5/61 | 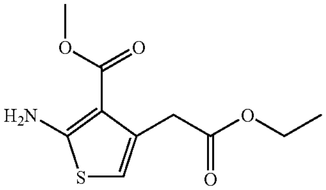 | 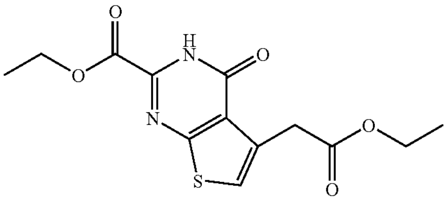 | 100% [MH]$^+$ = 311 |
| 5/62 | 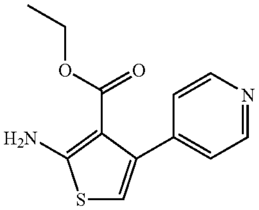 | 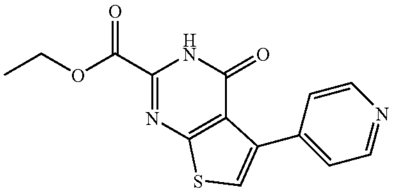 | 100% [MH]$^+$ = 302 |
| 5/65 | 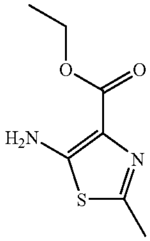 | 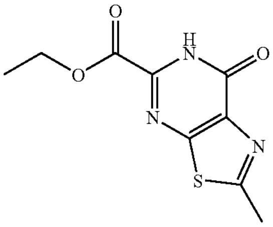 | 84% [MH]$^+$ = 240 |
| 5/66 | 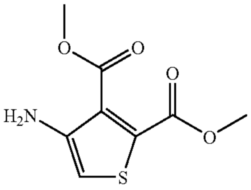 | 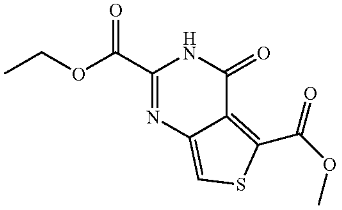 | 75% [MH]$^+$ = 283 |
| 5/67 | 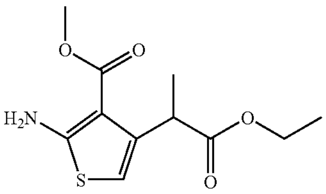 | 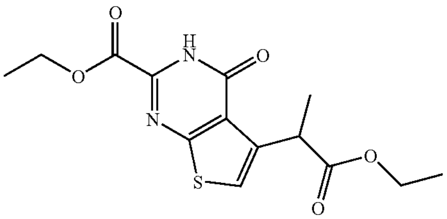 | 87% [MH]$^+$ = 325 |

TABLE I.2-continued
| Ex. # | Amine | product | yield |
|---|---|---|---|
| 5/68 | 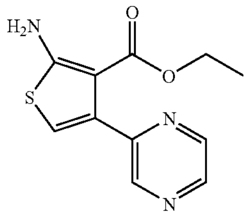 | 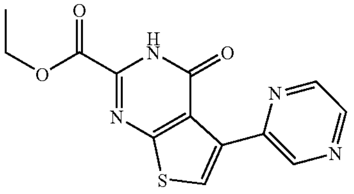 | 59% [MH]$^+$ = 303 |
| 5/70 | 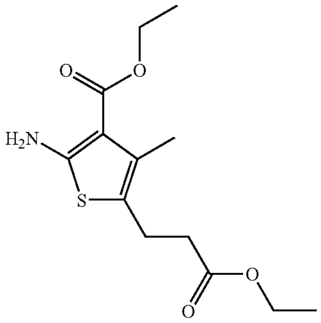 | 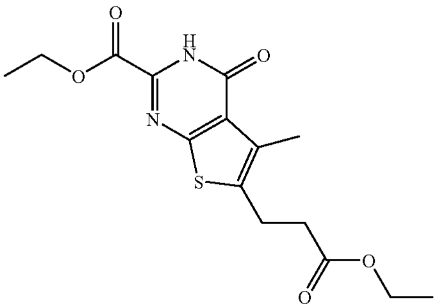 | 20% [MH]$^+$ = 339 |
| 5/75 | 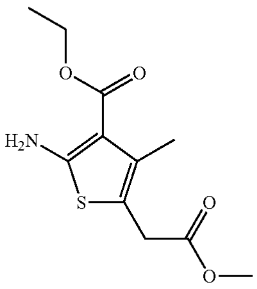 | 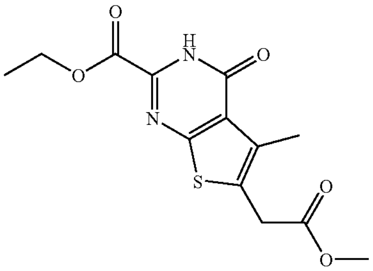 | 90% [MH]$^+$ = 311 |
| 5/77 | 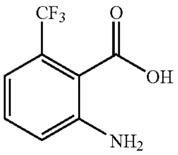 | 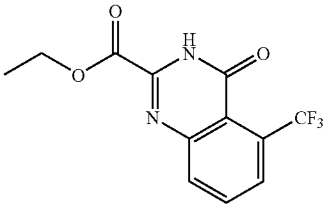 | 50% [MH]$^+$ = 287 |
| 5/78 | 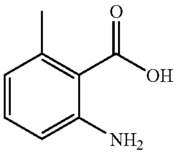 | 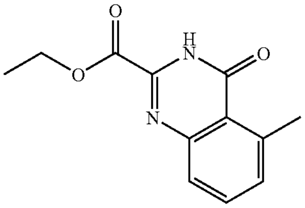 | 60% [MH]$^+$ = 233 |
| 5/79 | 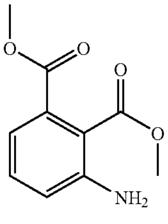 | 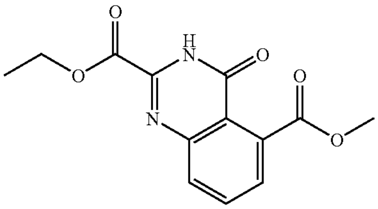 | 20% [MH]$^+$ = 277 |

TABLE I.2-continued
| Ex. # | Amine | product | yield |
| --- | --- | --- | --- |
| 5/80 | 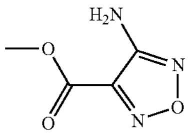 | 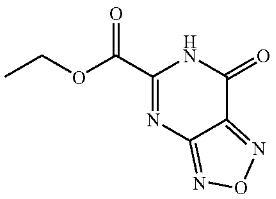 | 68% $[MH]^+ = 210$ |
| 5/81 | 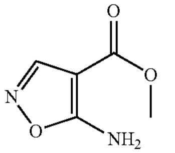 | 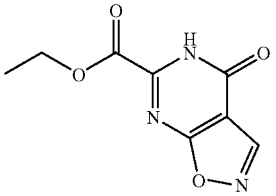 | 30% $[MH]^+ = 210$ |
| 5/82 | 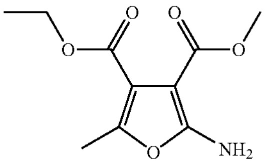 | 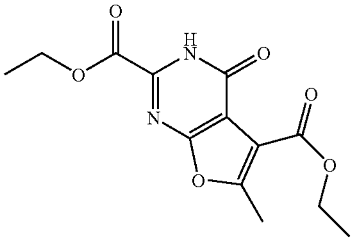 | 23% $[MH]^+ = 295$ |
| 5/83 | 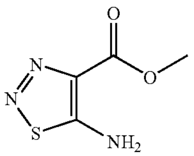 | 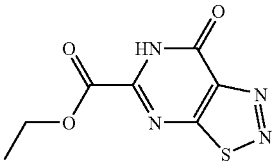 | 50% $[MH]^+ = 227$ |
| 5/85 | 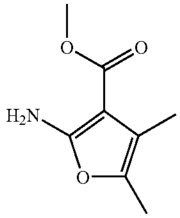 | 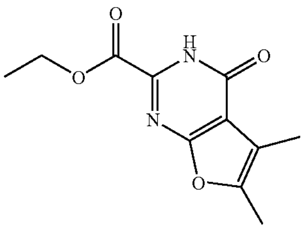 | 30% $[MH]^+ = 237$ |
| 5/86 | 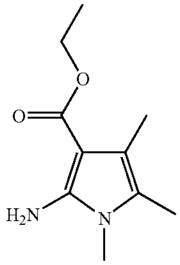 | 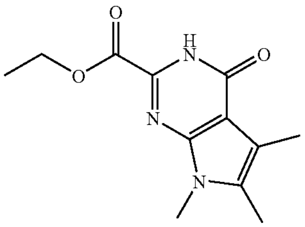 | 87% $[MH]^+ = 250$ |
| 5/90 | 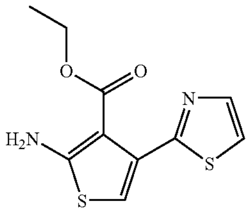 | 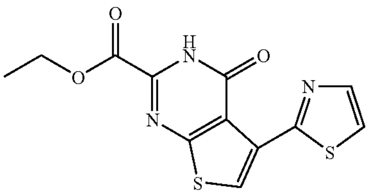 | n.d. $[MH]^+ = 308$ |

TABLE I.2-continued
| Ex. # | Amine | product | yield |
|---|---|---|---|
| 5/92 | 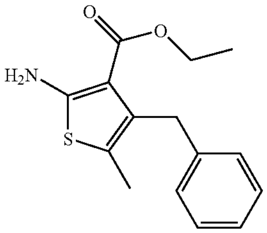 | 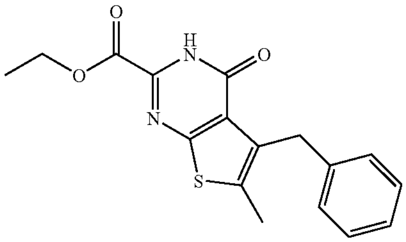 | n.d.<br>$[MH]^+$ 329 |
| 5/93 | 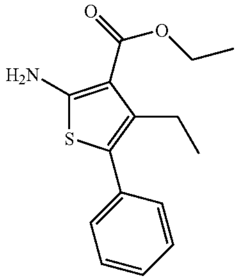 | 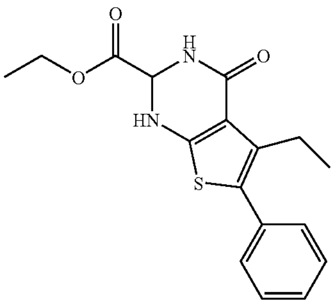 | n.d.<br>$[MH]^+$ = 329 |
| 5/94 | 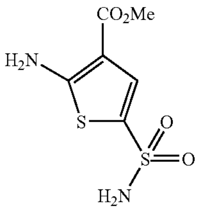 | 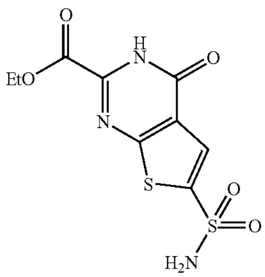 | n.d.<br>$[MH]^+$ = 304 |
| 5/97 | 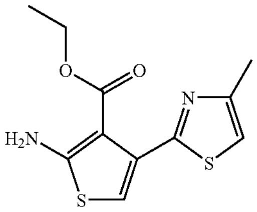 | 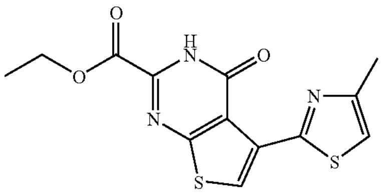 | 21%<br>$[MH]^+$ = 322 |
| 5/98 | 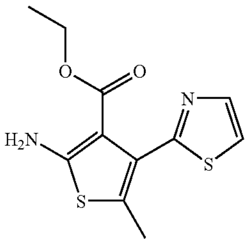 | 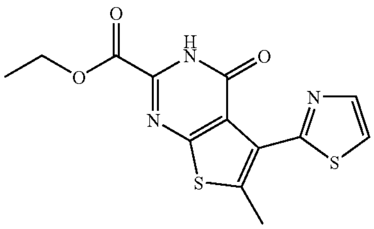 | 68%<br>$[MH]^+$ = 322 |

TABLE I.2-continued
| Ex. # | Amine | product | yield |
|---|---|---|---|
| 5/100 | 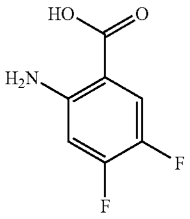 | 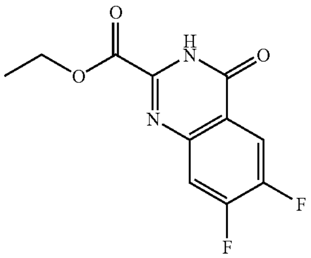 | n.d. [MH]$^+$ = 255 |
| 5/101 | 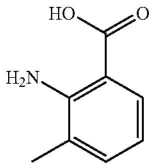 | 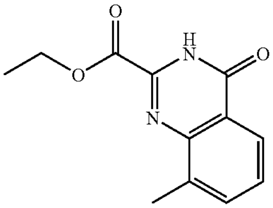 | n.d. [MH]$^+$ = n.d. |
| 5/102 | 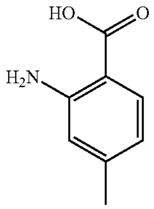 | 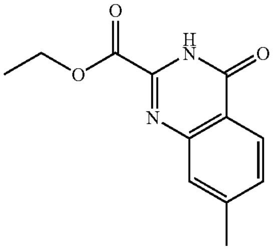 | n.d. [MH]$^+$ = n.d. |
| 5/103 | 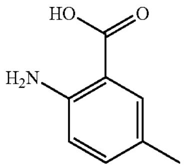 | 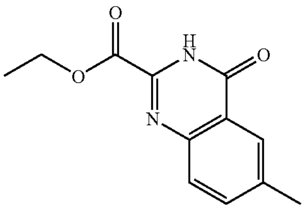 | n.d. [MH]$^+$ = n.d. |
| 5/104 | 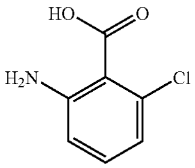 | 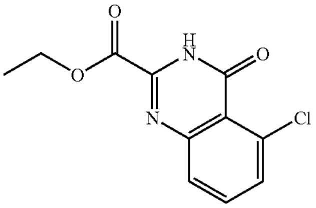 | n.d. [MH]$^+$ = n.d. |
| 5/105 | 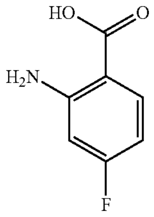 | 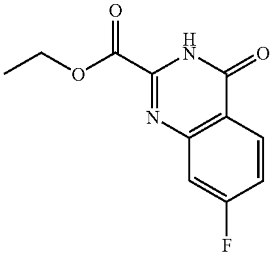 | n.d. [MH]$^+$ = n.d. |

TABLE I.2-continued
| Ex. # | Amine | product | yield |
|---|---|---|---|
| 5/107 | 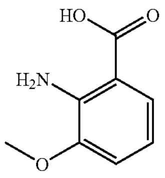 | 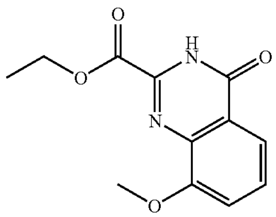 | n.d.<br>$[MH]^+$ = n.d. |
| 5/108 | 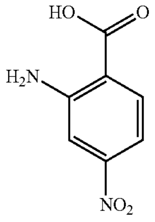 | 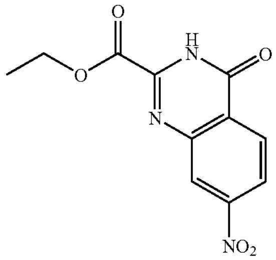 | n.d.<br>$[MH]^+$ = n.d. |
| 5/109 | 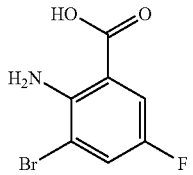 | 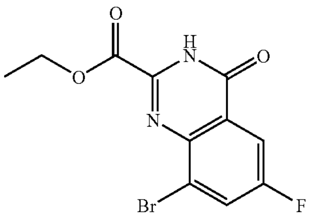 | n.d.<br>$[MH]^+$ = n.d. |
| 5/110 | 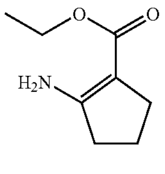 | 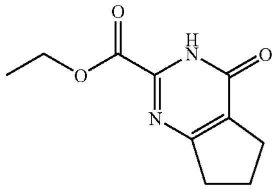 | n.d.<br>$[MH]^+$ = 209 |
| 5/111 | 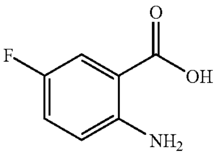 | 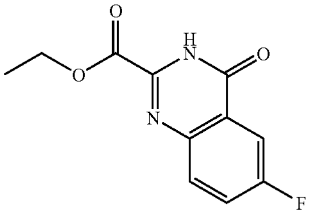 | 50%<br>$[MH]^+$ = 237 |
| 5/112 | 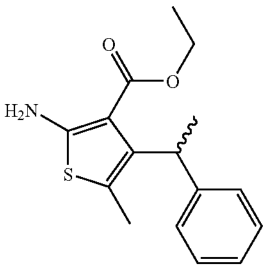 | 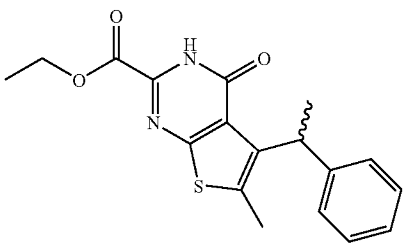 | 40%<br>$[MH]^+$ = 343 |

TABLE I.2-continued

| Ex. # | Amine | product | yield |
|---|---|---|---|
| 5/113 | 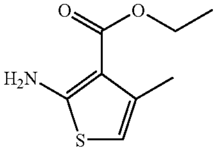 | 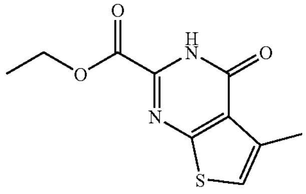 | 66% $[MH]^+ = 239$ |
| 5/114 | 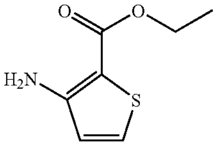 | 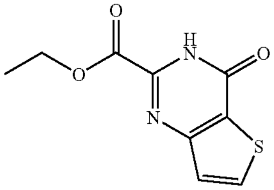 | 72% $[MH]^+ = 225$ |

Preparative Example 6

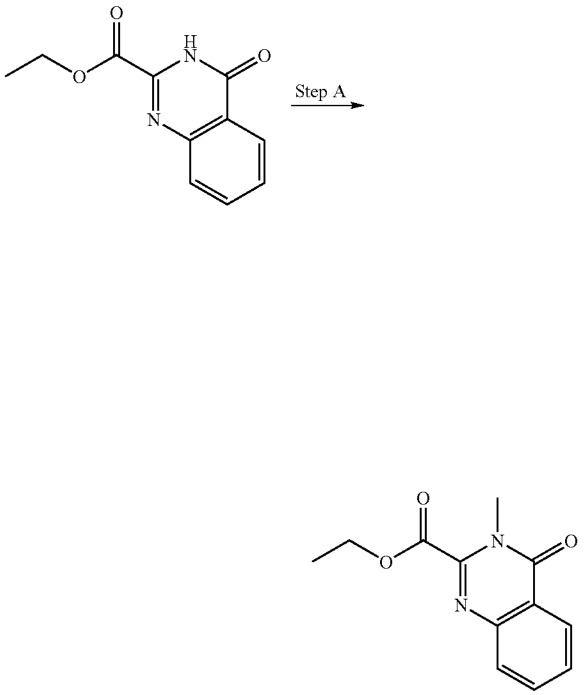

Step A

To an ice cooled solution of commercially available 4-Oxo-3,4-dihydro-quinazoline-2-carboxylic acid ethyl ester (400 mg) in dry DMF (10 mL) were successively added a 1M solution of NaHDMS in THF (2.2 mL) and methyl iodide (1.3 g). The cooling bath was removed and the resulting mixture was stirred at room temperature overnight. Concentration and purification by chromatography (silica, cyclohexane/EtOAc) afforded the title compound as a colorless solid (370 mg, 87%). $[MH]^+=233$.

Preparative Example 7

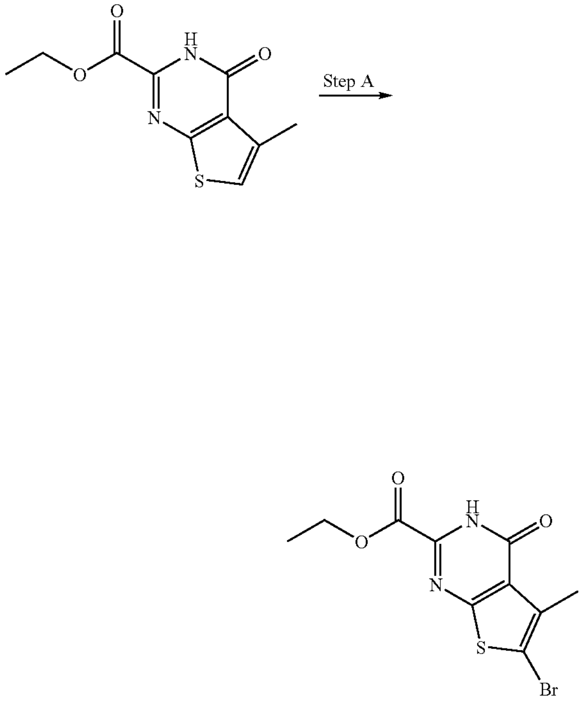

Step A

To a solution of the preparative example 5/1 above (3.69 g) in acetic acid (80 mL) was added bromine (4 mL) at room temperature. After 1.5 h the reaction was evaporated, water was added, residue was filtered and washed with water and dried to give the title compound (4.86 g; 99%). $[MH]^+=317/319$.

Preparative Example 7/1

Following similar procedures as described in the Preparative Example 7 except using the educt derivative indicated in Table I.3 below, the following compounds were prepared.

TABLE I.3

| Ex. # | Educt | product | yield |
|---|---|---|---|
| 7/1 | 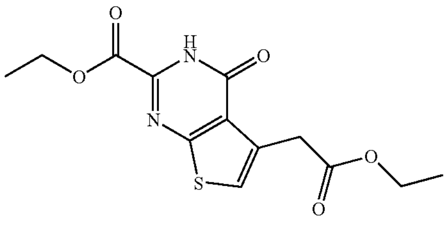 | 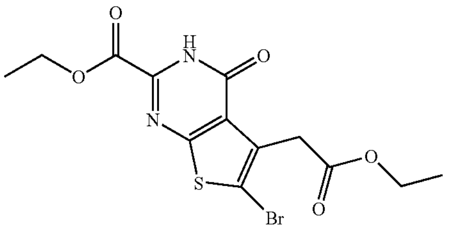 | 58%<br>$[MH]^+ = 389/391$ |

Preparative Example 8

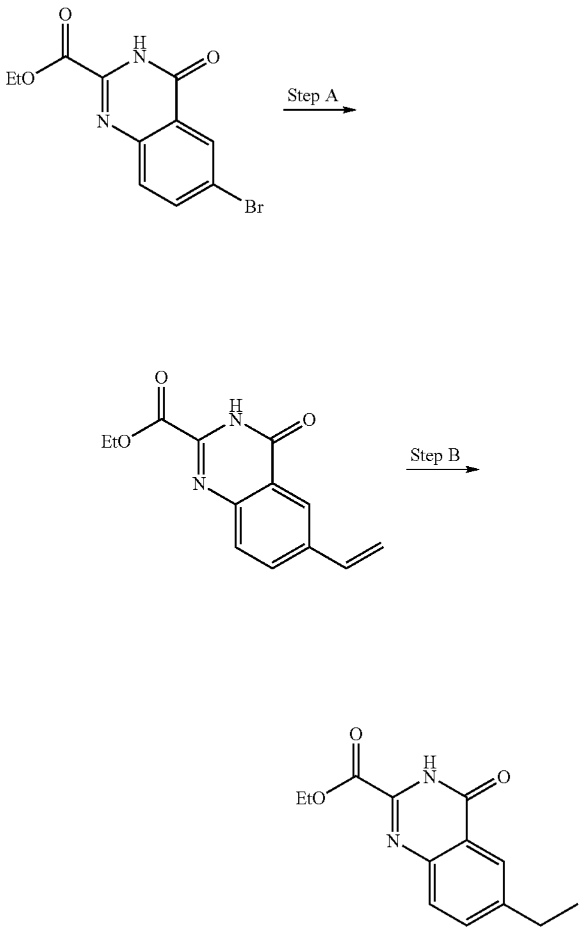

Step A

A solution of the preparative example 5/4 above (120 mg) and tributylvinyltin (160 mg), palladium tetrakis(triphenylphosphine) (55 mg) in THF (2 mL) was heated in microwave at 160° C. for 30 min. The solution was concentrated and purified by chromatography (silica, hexane/EtOAc) to afford the title compound (100 mg, 29%). $[MH]^+$=245.

Step B

A solution of the intermediate from Step A above (30 mg) and palladium on charcoal in methanol (2 mL) was hydrogenated for 1 h. The solution was filtered through a bed of celite and concentrated to afford the title compound (28 mg, 98%). $[MH]^+$=247.

Preparative Example 9

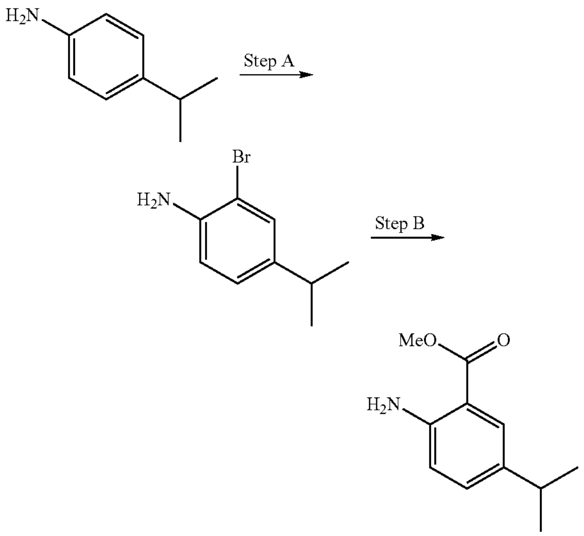

Step A

A solution of the commercially available 4-Isopropyl-phenylamine (1.35 g) and N-Bromosuccinimide (2.0 g) in benzene (20 mL) was stirred at room temperature. After 12 h, the precipitated solid was filtered off, and the filtrate was concentrated and purified by chromatography (silica, hexane/EtOAc) to afford the title compound (1.8 g, 89%). $[MH]^+$=214.

Step B

A solution of the intermediate from Step A above (800 mg), xantphos (36 mg), $Pd_2(dba)_3$ (20 mg), triethylamine (1.4 mL) in methanol (10 mL) was heated in autoclave under carbon monoxide at 50 psi at 100° C. for 6 h. The solution was concentrated and purified by chromatography (silica, hexane/EtOAc) to afford the title compound (360 mg, 49%). $[MH]^+$=194.

Preparative Example 10/1 and 10/3

Following similar procedures as described in the Preparative Example 9 except using the aniline derivative indicated in Table I.4 below, the following compounds were prepared.

TABLE I.4

| Ex. # | Aniline | product | yield |
|---|---|---|---|
| 10/1 | 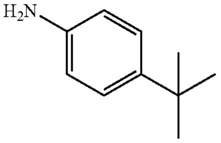 | 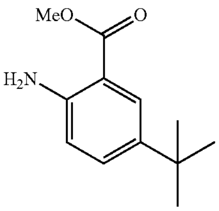 | 80%<br>$[MH]^+ = 208$ |
| 10/3 | 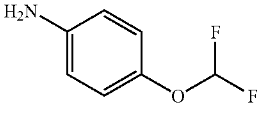 | 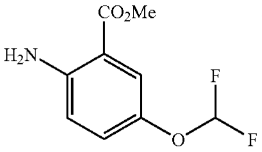 | 24%<br>$[MH]^+ = 285$ |

Preparative Example 11

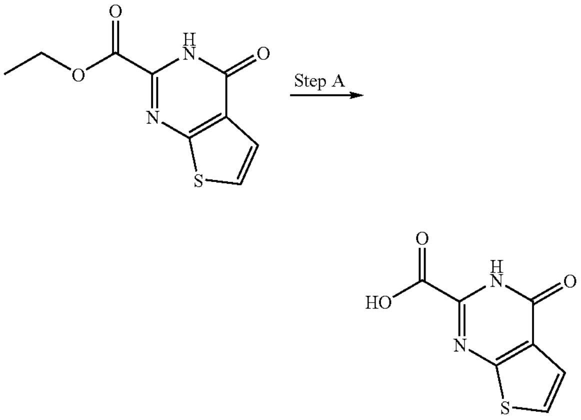

Step A

To a solution of the Preparative Example 4 above (420 mg) in THF (20 mL) was added 1M aqueous LiOH (5 mL). The resulting mixture was stirred at room temperature overnight, concentrated and neutralized with 1M aqueous HCl. The residue was filtered off and used without further purification (55 mg, 15%). $[MH]^+=197$.

Preparative Examples 12/1-12/110

Following a similar procedure as described in the Preparative Example 11 except using the ester indicated in Table I.5 below, the following compounds were prepared.

TABLE I.5

| Ex. # | Ester | product | Yield |
|---|---|---|---|
| 12/1 | 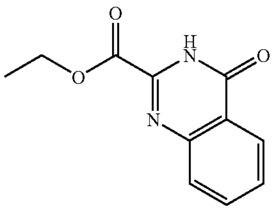 | 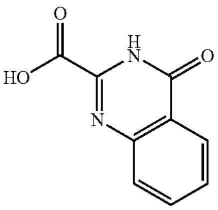 | 85%<br>$[MH]^+ = 191$ |
| 12/2 | 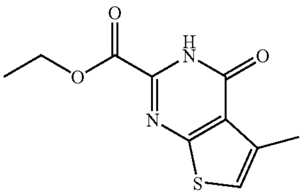 | 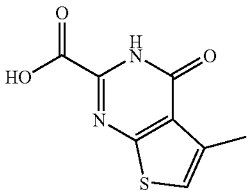 | 88%<br>$[MH]^+ = 211$ |

TABLE I.5-continued
| Ex. # | Ester | product | Yield |
|---|---|---|---|
| 12/3 | 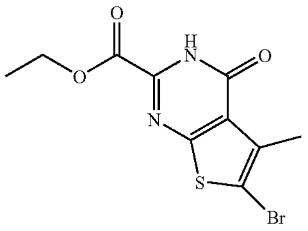 | 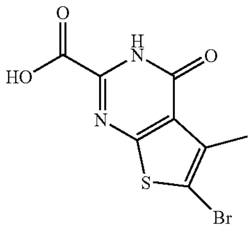 | n.d. [MH]$^+$ = 289/291 |
| 12/4 | 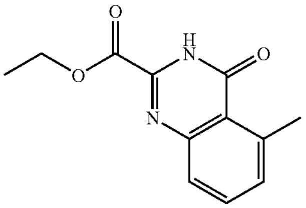 | 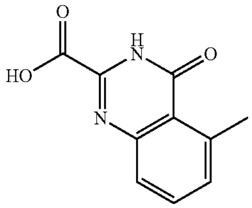 | 93% [MH]$^+$ = 205 |
| 12/5 | 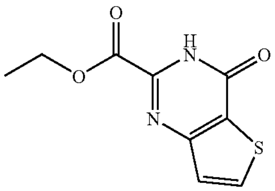 | 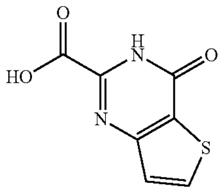 | n.d. [MH]$^+$ = 197 |
| 12/6 | 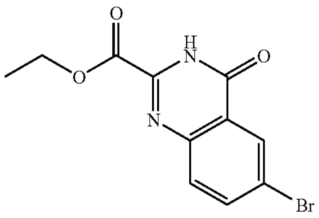 | 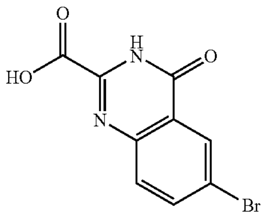 | 99% [MH]$^+$ = 269/271 |
| 12/7 | 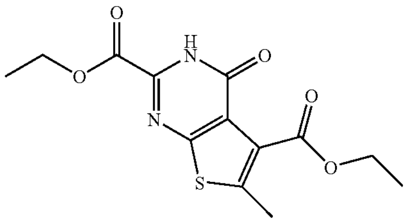 | 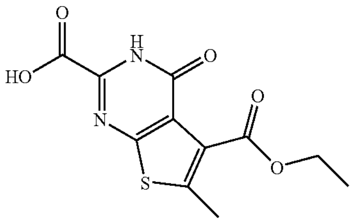 | 71% [MH]$^+$ = 283 |
| 12/8 | 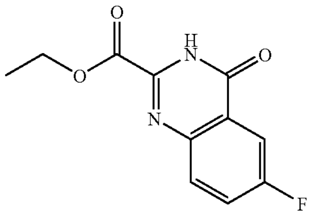 | 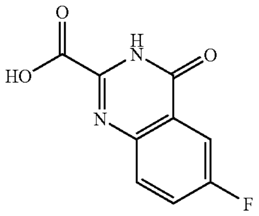 | 91% [MH]$^+$ = 209 |
| 12/10 | 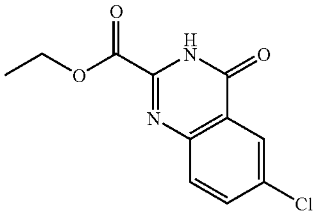 | 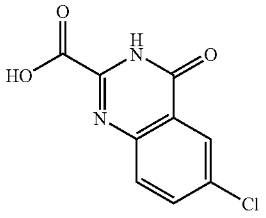 | >99% [MH]$^+$ = 225 |

TABLE I.5-continued
| Ex. # | Ester | product | Yield |
|---|---|---|---|
| 12/11 | 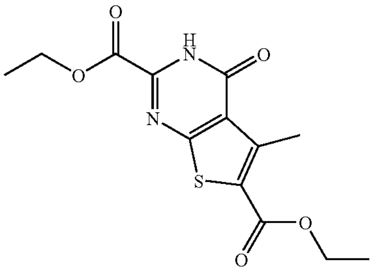 | 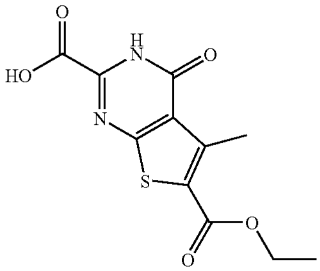 | >99% [MH]$^+$ = 283 |
| 12/14 | 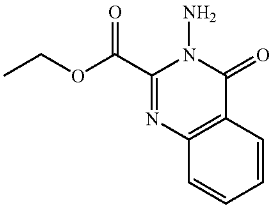 | 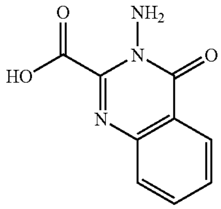 | 47% [MH]$^+$ = 206 |
| 12/15 | 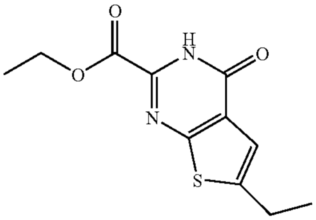 | 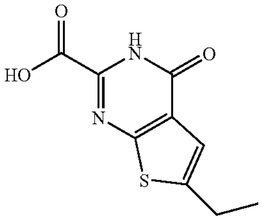 | 28% [MH]$^+$ = 225 |
| 12/17 | 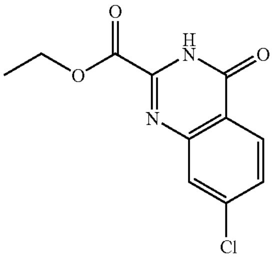 | 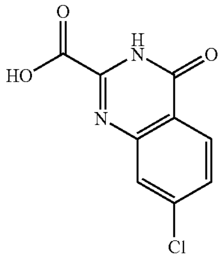 | 94% [MH]$^+$ = 225 |
| 12/18 | 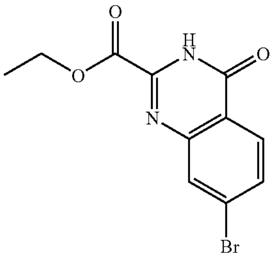 | 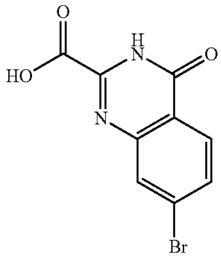 | 93% [MH]$^+$ = 269 271 |
| 12/19 | 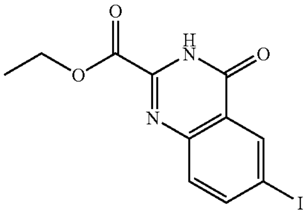 | 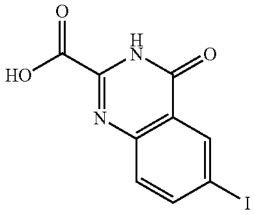 | 85% [MH]$^+$ = 317 |

TABLE I.5-continued
| Ex. # | Ester | product | Yield |
|---|---|---|---|
| 12/20 | 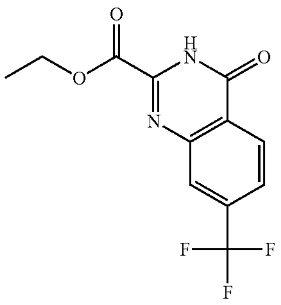 | 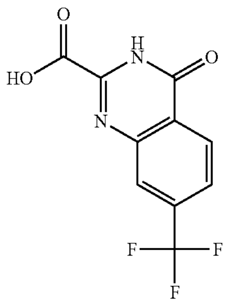 | 94%<br>$[MH]^+ = 259$ |
| 12/21 | 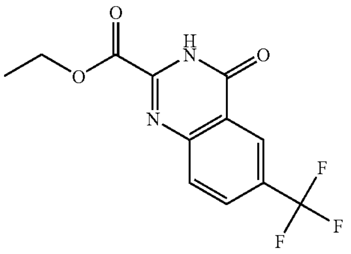 | 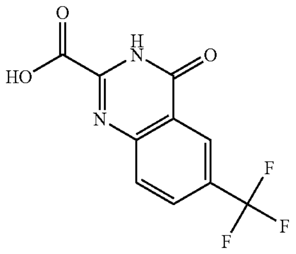 | 78%<br>$[MH]^+ = 259$ |
| 12/22 | 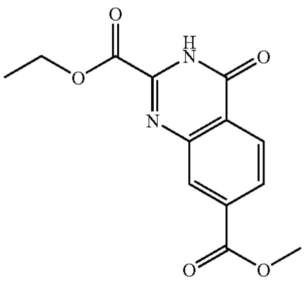 | 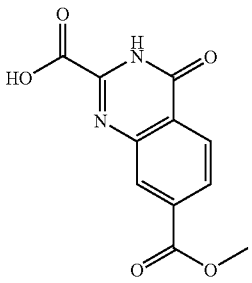 | 55%<br>$[MH]^+ = 249$ |
| 12/23 | 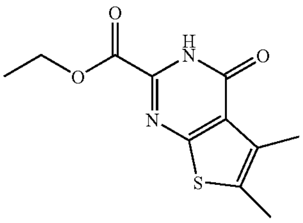 | 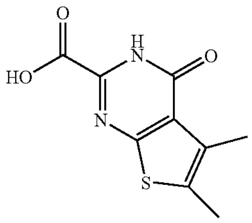 | 47%<br>$[MH]^+ = 225$ |
| 12/24 | 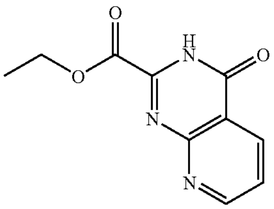 | 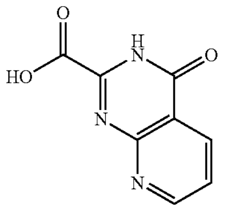 | 62%<br>$[MH]^+ = 192$ |
| 12/25 | 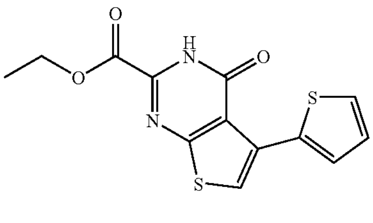 | 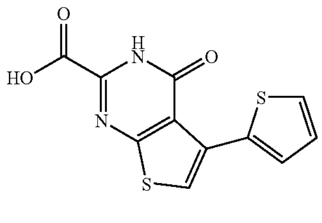 | 98%<br>$[MH]^+ = 279$ |

TABLE I.5-continued
| Ex. # | Ester | product | Yield |
|---|---|---|---|
| 12/26 | 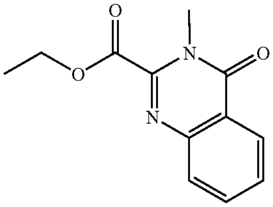 | 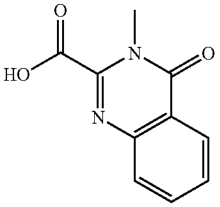 | n.d.<br>$[MH]^+ = 205$ |
| 12/27 | 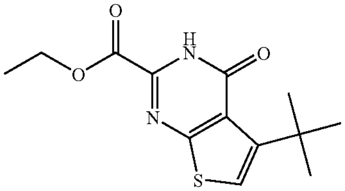 | 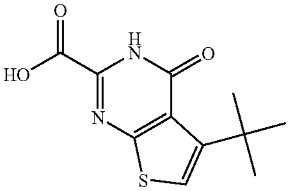 | 51%<br>$[MH]^+ = 253$ |
| 12/28 | 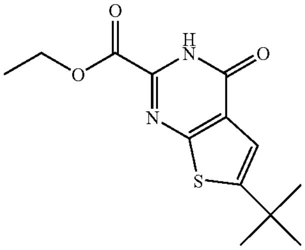 | 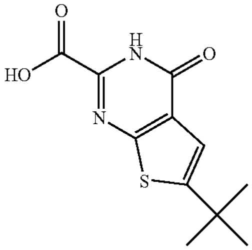 | 85%<br>$[MH]^+ = 253$ |
| 12/29 | 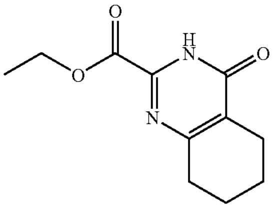 | 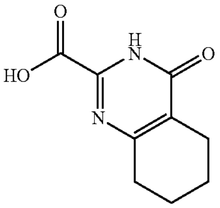 | 48%<br>$[MH]^+ = 195$ |
| 12/30 | 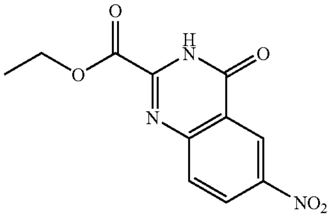 | 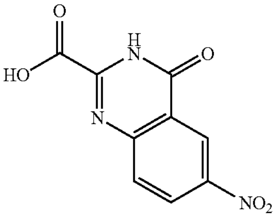 | 36%<br>$[MH]^+ = 236$ |
| 12/31 | 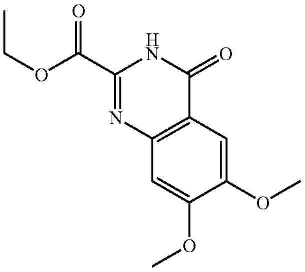 | 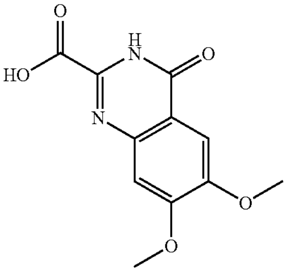 | 71%<br>$[MH]^+ = 251$ |

TABLE I.5-continued
| Ex. # | Ester | product | Yield |
|---|---|---|---|
| 12/32 | 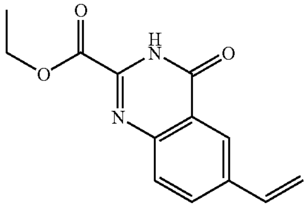 | 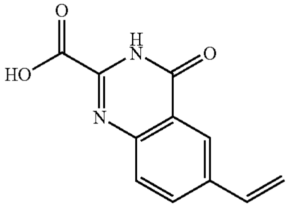 | 91%<br>$[MH]^+ = 217$ |
| 12/33 | 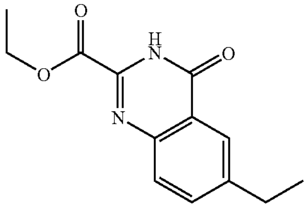 | 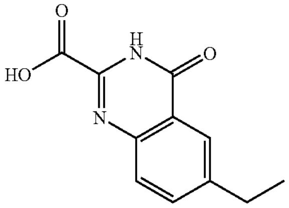 | 90%<br>$[MH]^+ = 219$ |
| 12/34 | 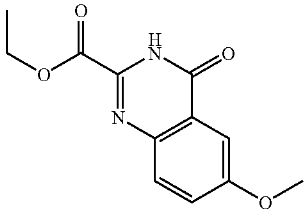 | 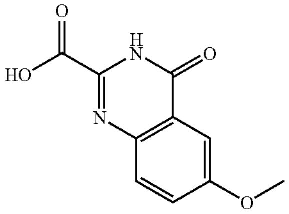 | 86%<br>$[MH]^+ = 221$ |
| 12/35 | 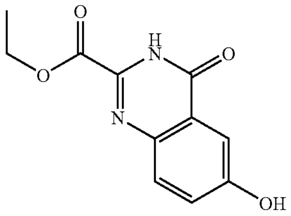 | 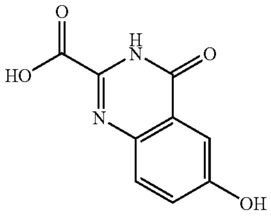 | 96%<br>$[MH]^+ = 207$ |
| 12/36 | 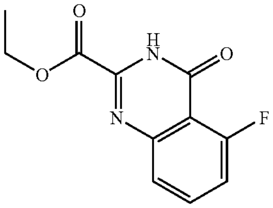 | 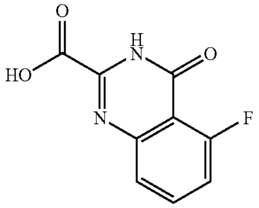 | 92%<br>$[MH]^+ = 209$ |
| 12/37 | 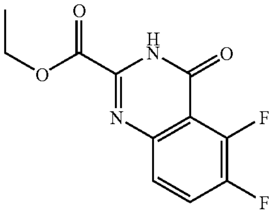 | 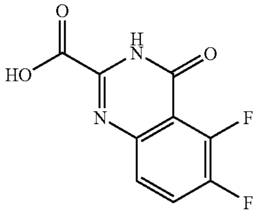 | 88%<br>$[MH]^+ = 227$ |
| 12/38 | 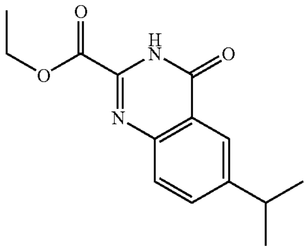 | 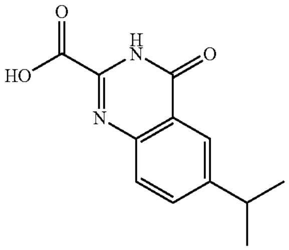 | 86%<br>$[MH]^+ = 233$ |

TABLE I.5-continued
| Ex. # | Ester | product | Yield |
|---|---|---|---|
| 12/39 | 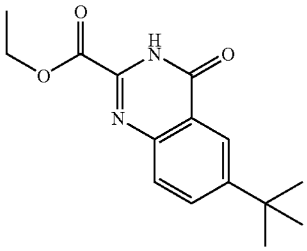 | 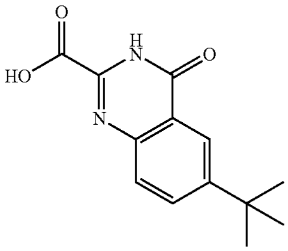 | 85%<br>$[MH]^+ = 247$ |
| 12/40 | 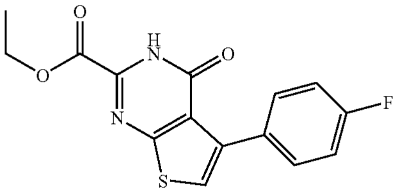 | 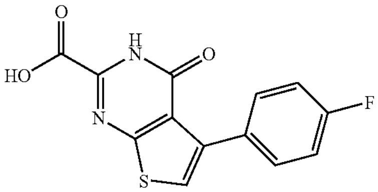 | 97%<br>$[MH]^+ = 291$ |
| 12/41 | 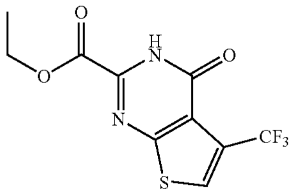 | 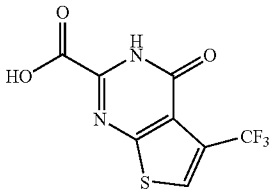 | 85%<br>$[MH]^+ = 265$ |
| 12/42 | 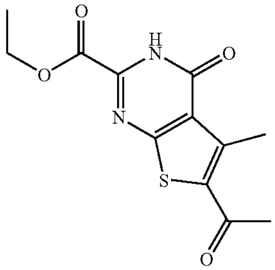 | 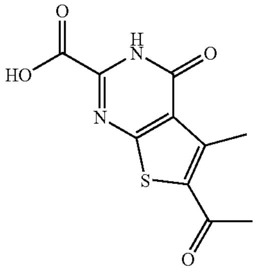 | >99%<br>$[MH]^+ = 253$ |
| 12/45 | 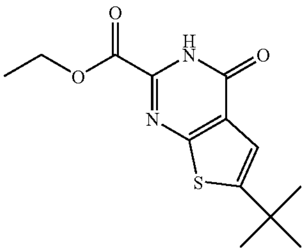 | 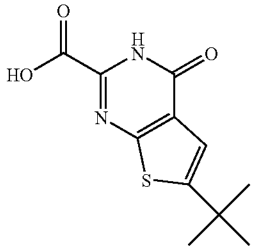 | 85%<br>(2 steps)<br>$[MH]^+ = 253$ |
| 12/46 | 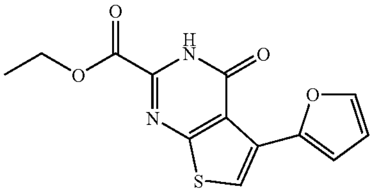 | 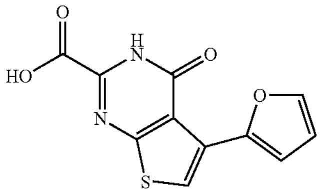 | 75%<br>$[MH]^+ = 263$ |

TABLE I.5-continued
| Ex. # | Ester | product | Yield |
| --- | --- | --- | --- |
| 12/47 | 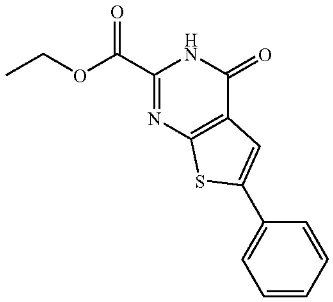 | 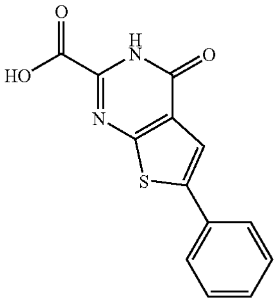 | Quant.<br>$[MH]^+ = 273$ |
| 12/48 | 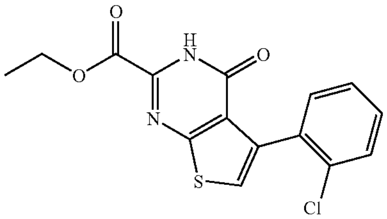 | 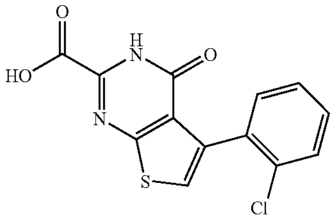 | 38%<br>$[MH]^+ = 307$ |
| 12/50 | 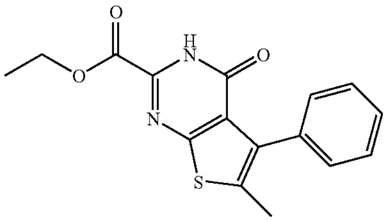 | 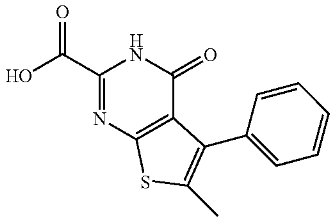 | 62%<br>$[MH]^+ = 287$ |
| 12/52 | 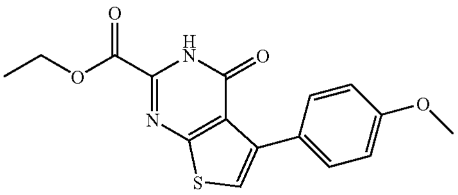 | 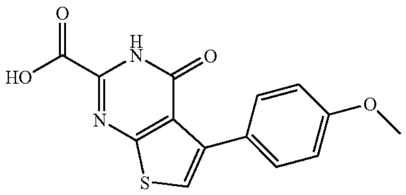 | 73%<br>$[MH]^+ = 303$ |
| 12/53 | 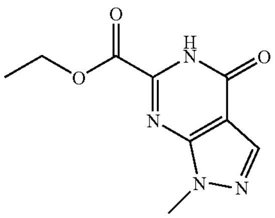 | 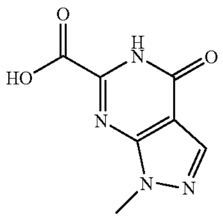 | 53%<br>$[MH]^+ = 195$ |
| 12/55 | 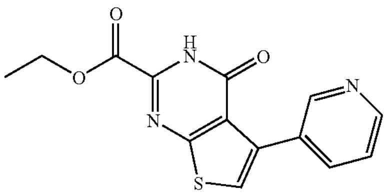 | 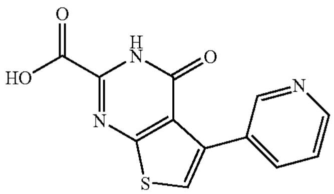 | 27%<br>$[MH]^+ = 274$ |

TABLE I.5-continued
| Ex. # | Ester | product | Yield |
|---|---|---|---|
| 12/59 | 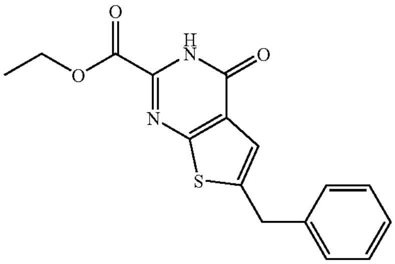 | 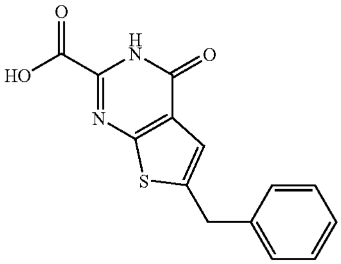 | 91%<br>$[MH]^+ = 288$ |
| 12/61 | 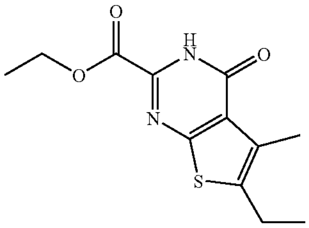 | 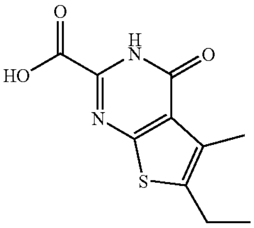 | 69%<br>$[MH]^+ = 239$ |
| 12/63 | 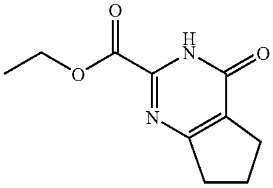 | 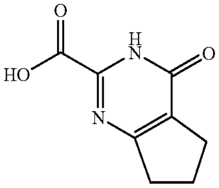 | n.d.<br>$[MH]^+ = 181$ |
| 12/64 | 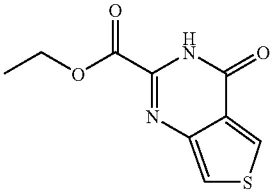 | 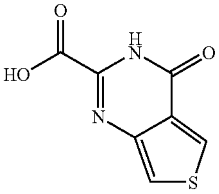 | n.d.<br>$[MH]^+ = 197$ |
| 12/65 | 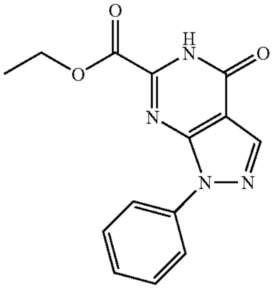 | 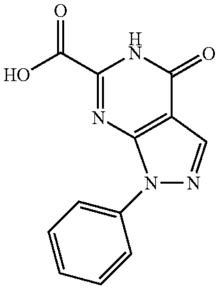 | 60%<br>$[MH]^+ = 257$ |
| 12/66 | 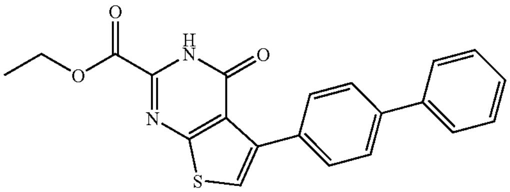 | 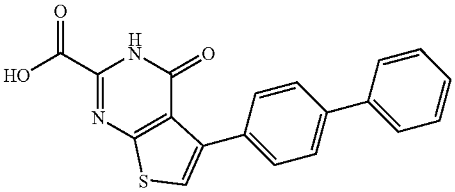 | 95%<br>$[MH]^+ = 349$ |

TABLE I.5-continued
| Ex. # | Ester | product | Yield |
|---|---|---|---|
| 12/67 | 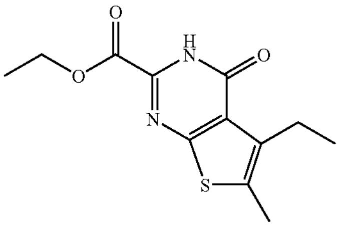 | 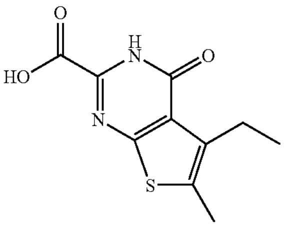 | 91%<br>$[MH]^+ = 239$ |
| 12/70 | 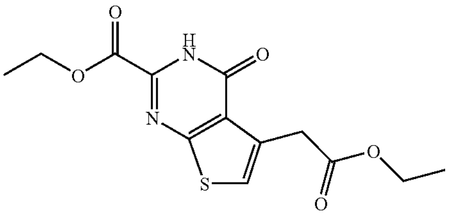 | 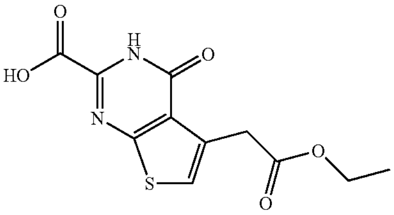 | n.d.<br>$[MH]^+ = 283$ |
| 12/71 | 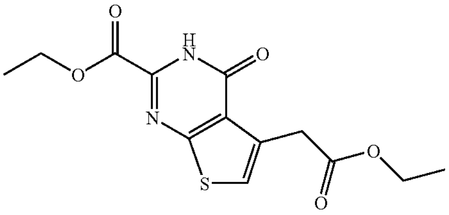 | 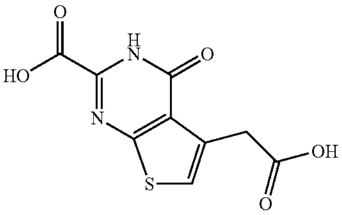 | n.d.<br>$[MH]^+ = 255$ |
| 12/72 | 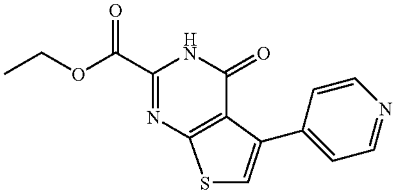 | 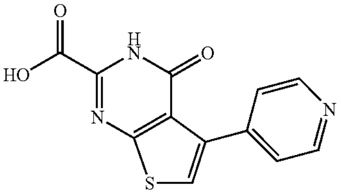 | 97%<br>$[MH]^+ = 274$ |
| 12/74 | 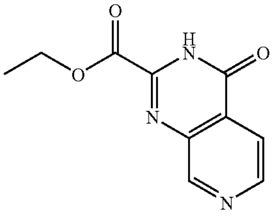 | 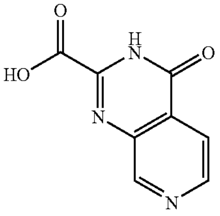 | 18%<br>over 3 steps<br>$[MH]^+ = 192$ |
| 12/75 | 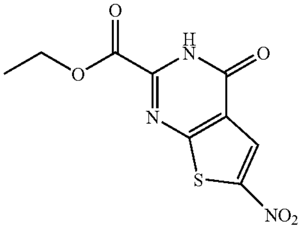 | 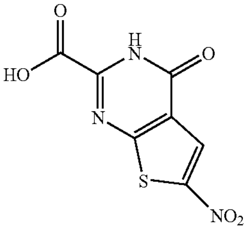 | 63%<br>$[MH]^+ = 242$ |

TABLE I.5-continued
| Ex. # | Ester | product | Yield |
| --- | --- | --- | --- |
| 12/76 | 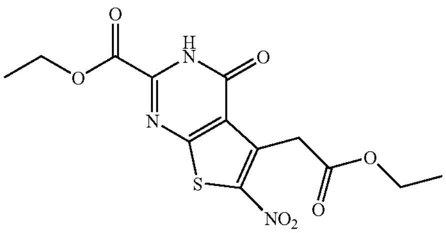 | 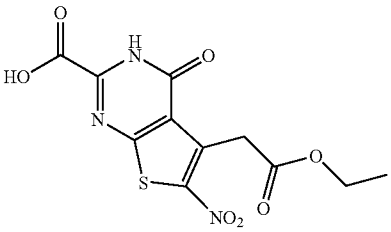 | 96%<br>$[MH]^+ = 328$ |
| 12/78 | 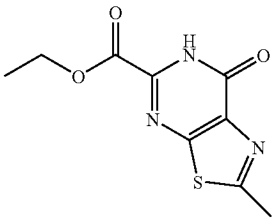 | 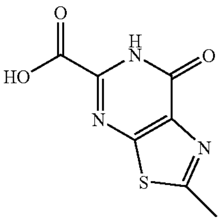 | Quant.<br>$[MH]^+ = 212$ |
| 12/79 | 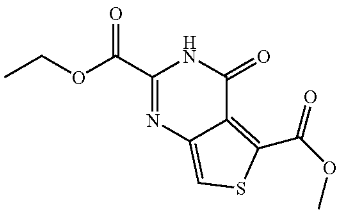 | 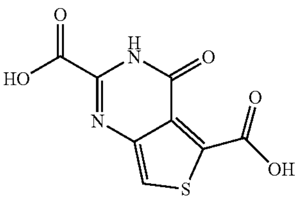 | n.d.<br>$[MH]^+ = 241$ |
| 12/80 | 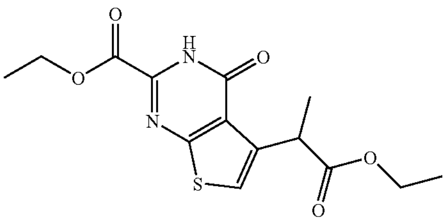 | 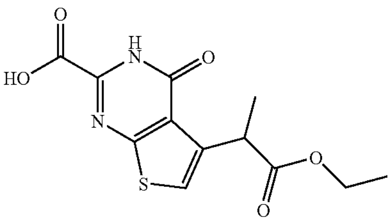 | 45%<br>$[MH]^+ = 297$ |
| 12/81 | 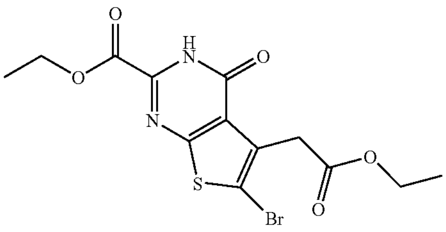 | 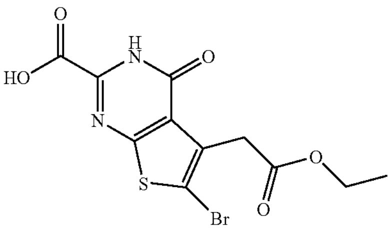 | 74%<br>$[MH]^+ =$<br>361/363 |
| 12/82 | 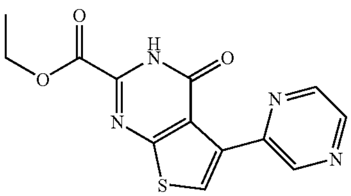 | 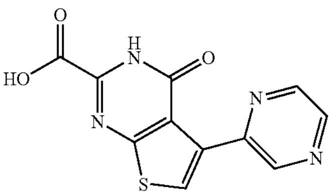 | 90%<br>$[MH]^+ = 275$ |

TABLE I.5-continued
| Ex. # | Ester | product | Yield |
|---|---|---|---|
| 12/83 | 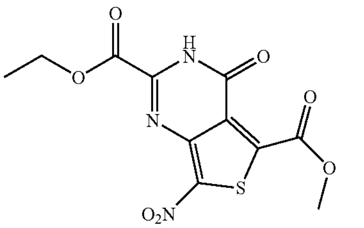 | 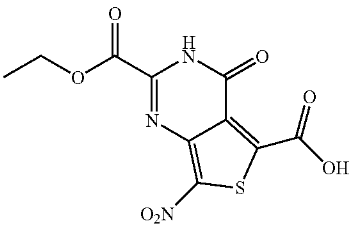 | 74%<br>$[MH]^+ = 314$ |
| 12/88 | 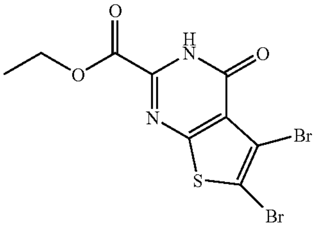<br>Synthesis:<br>WO2005/105760 | 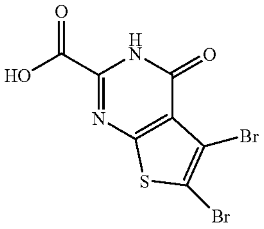 | n.d.<br>$[MH]^+ =$<br>353/355/357 |
| 12/90 | 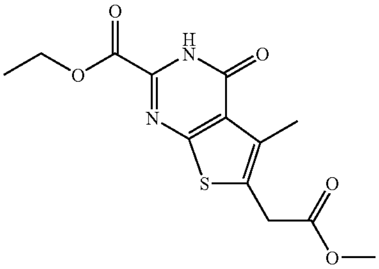 | 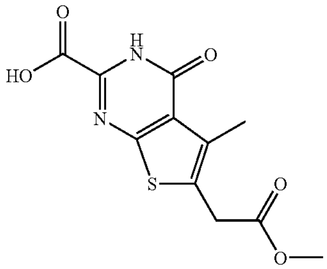 | 95%<br>$[MH]^+ = 283$ |
| 12/95 | 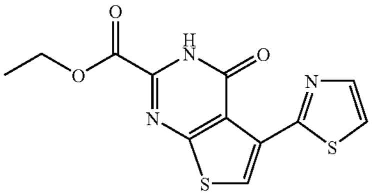 | 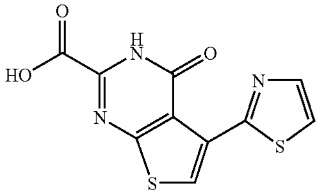 | n.d.<br>$[MH]^+ = 280$ |
| 12/98 | 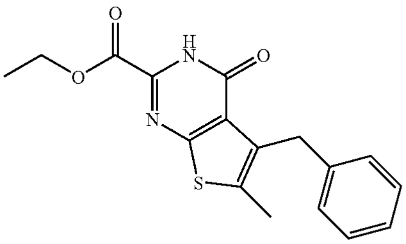 | 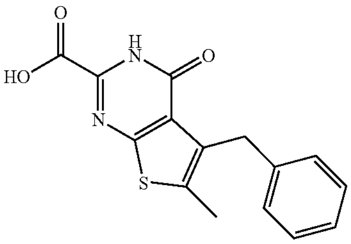 | n.d.<br>$[MH]^+ = 301$ |
| 12/99 | 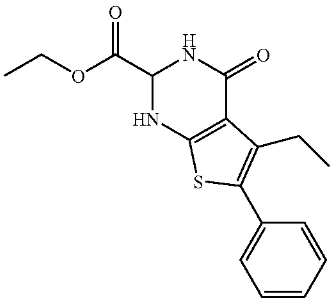 | 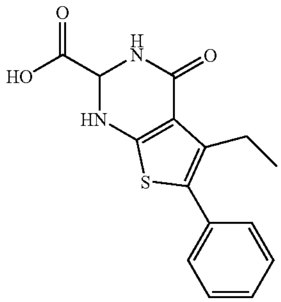 | n.d.<br>$[MH]^+ = 301$ |

TABLE I.5-continued
| Ex. # | Ester | product | Yield |
|---|---|---|---|
| 12/100 | 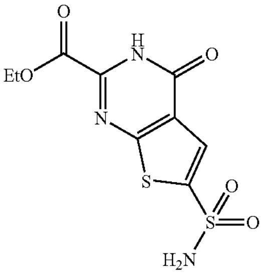 | 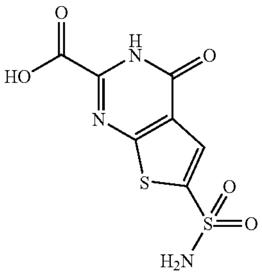 | 41% [MH]+ = 276 |
| 12/101 | 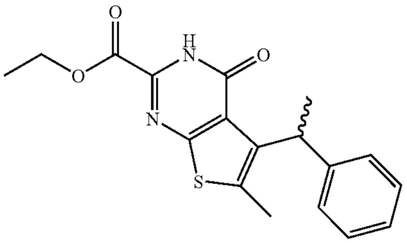 | 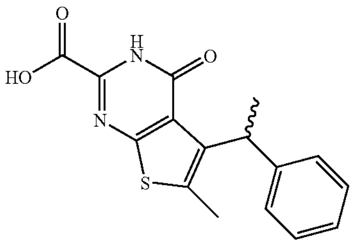 | 84% [MH]+ = 315 |
| 12/102 | 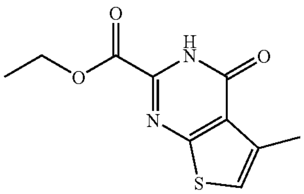 | 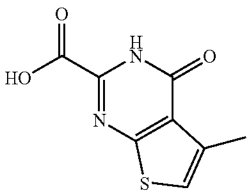 | 92% [MH]+ = 211 |
| 12/103 | 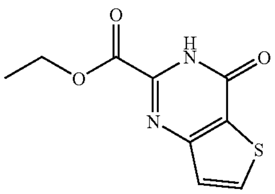 | 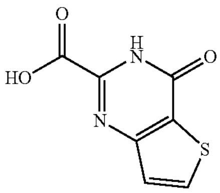 | 83% [MH]+ = 197 |
| 12/106 | 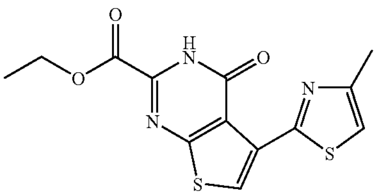 | 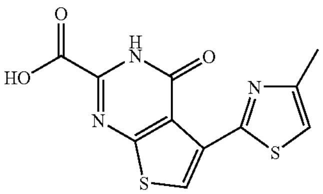 | 30% [MH]+ = 294 |
| 12/107 | 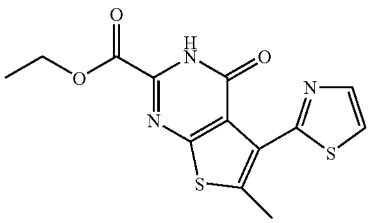 | 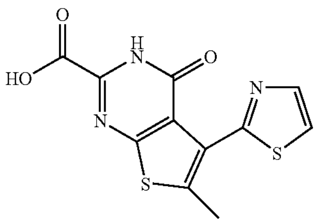 | 46% [MH]+ = 294 |

TABLE I.5-continued

| Ex. # | Ester | product | Yield |
|---|---|---|---|
| 12/109 | 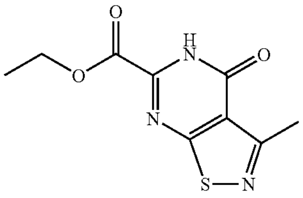 | 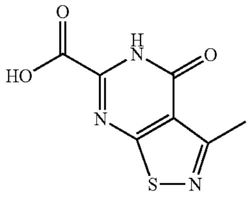 | 33% [MH]$^+$ = 212 |
| 12/110 | 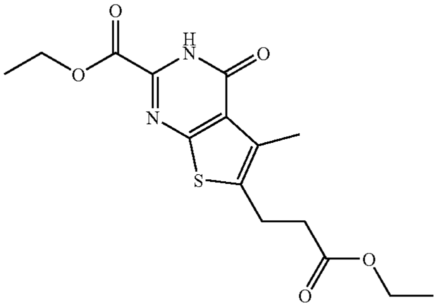 | 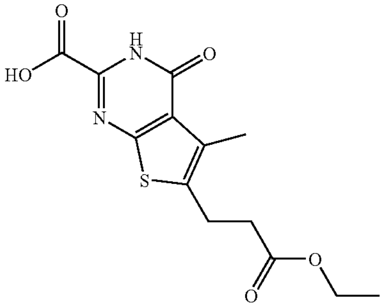 | 67% [MH]$^+$ = 311 |

Preparative Example 13

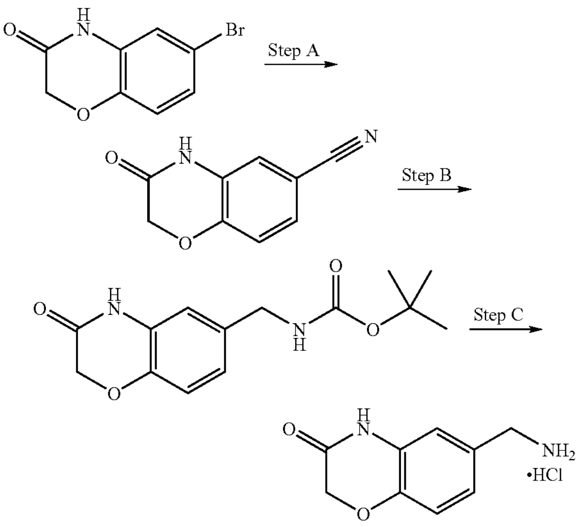

Step A

A degassed suspension of commercially available 6-Bromo-4H-benzo[1,4]oxazin-3-one (8.39 g), $Zn(CN)_2$ (3.46 g) and $Pd(PPh_3)_4$ (2.13 g) in DMF (70 mL) was stirred in a oil bath (80° C.) overnight. The mixture was cooled to room temperature and then poured into water (500 mL). The precipitate was collected by suction, air dried, washed with pentane, dissolved in $CH_2Cl_2$/MeOH (1:1), filtered through an silica pad and concentrated to yield a yellow solid (5.68 g, 89%). [MH]$^+$=175.

Step B

To an ice cooled solution of the title compound from Step A above (5.6 g), di-tert-butyl dicarbonate (14.06 g) and $NiCl_2.6H_2O$ (1.53 g) in MeOH, $NaBH_4$ (8.51 g) was added in portions. The mixture was vigorously stirred for 1 h at 0° C. and 1 h at room temperature. After the addition of diethylenetriamine (3.5 mL) the mixture was concentrated, diluted with EtOAc, washed subsequently with 1N HCl, saturated aqueous $NaHCO_3$ and saturated aqueous NaCl, dried ($MgSO_4$), concentrated to afford the title compound as an off-white solid (7.91 g, 88%). [M+Na]$^+$=397.

Step C

The title compound from Step B above (7.91 g) was dissolved in a 4M solution of HCl in 1,4-dioxane (120 mL), stirred for 14 h, concentrated, suspended in $Et_2O$, filtered and dried to afford the title compound as an off-white solid (5.81 g, 96%). [M—$NH_3Cl$]$^+$=162.

Preparative Example 14

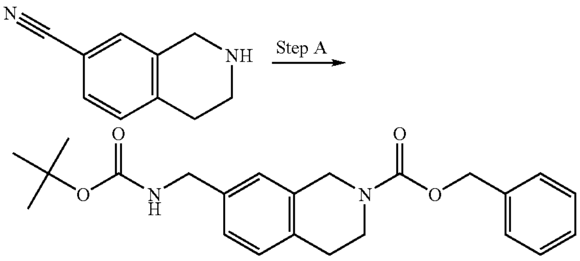

Step A

A solution of commercially available 7-cyano-1,2,3,4-tetrahydroisoquinoline (2.75 g), $K_2CO_3$ (3.60 g) and benzylchloroformate (2.7 mL) in THF/$H_2O$ was stirred overnight and then concentrated. The residue was diluted with EtOAc, washed with 10% aqueous citric acid, saturated aqueous $NaHCO_3$ and brine, dried ($MgSO_4$) and concentrated. The residue was dissolved in MeOH (100 mL) and di-tert-butyl dicarbonate (7.60 g) and $NiCl_2.6H_2O$ (400 mg) was added.

The solution was cooled to 0° C. and $NaBH_4$ (2.60 g) was added in portions. The mixture was allowed to reach room temperature and then vigorously stirred overnight. After the addition of diethylenetriamine (2 mL) the mixture was concentrated, diluted with EtOAc, washed subsequently with 10% aqueous citric acid, saturated aqueous $NaHCO_3$ and saturated aqueous NaCl, dried ($MgSO_4$), concentrated and purified by chromatography (silica, $CH_2Cl_2$/MeOH) to afford the title compound as a colorless oil (1.81 g, 26%). $[MH]^+$=397.

Preparative Example 15

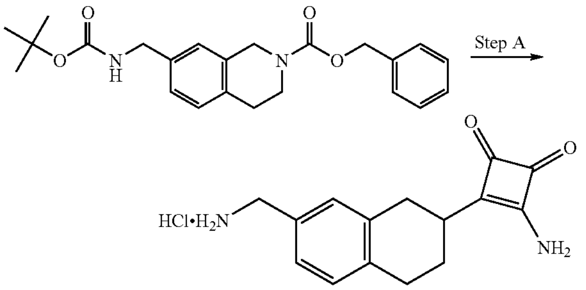

Step A

A mixture of the title compound from the Preparative Example 14 (1.81 g) and Pd/C (10 wt %, 200 mg) in EtOH (50 mL) was hydrogenated at atmospheric pressure overnight, filtered and concentrated to a volume of ~20 mL. 3,4-Diethoxy-3-cyclobutene-1,2-dione (0.68 mL) and $NEt_3$ (0.5 mL) were added and the mixture was heated to reflux for 4 h. Concentration and purification by chromatography (silica, cyclohexane/EtOAc) afforded a slowly crystallizing colorless oil. This oil was dissolved in EtOH (20 mL) and a 28% solution of $NH_3$ in $H_2O$ (100 mL) was added. The mixture was stirred for 3 h, concentrated, slurried in $H_2O$, filtered and dried under reduced pressure. The remaining residue was dissolved in a 4M solution of HCl in 1,4-dioxane (20 mL), stirred for 14 h, concentrated, suspended in $Et_2O$, filtered and dried to afford the title compound as an off-white solid (1.08 g, 92%). $[M—Cl]^+$=258.

Preparative Example 16

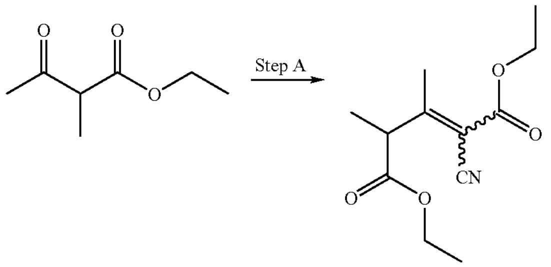

Step A

The title compound from step A above (1 g), ethyl cyanoacetate (1.44 g), acetic acid (70 μL) and ammonium acetate (30 mg) in toluene were heated to reflux in presence of a Dean-Stark overnight. After concentration of the mixture, the product was used without further purification. $[MH]^+$=240.

Preparative Examples 17/4 to 17/23

Following similar procedures as described in the Preparative Examples 16 except using the ketones indicated in Table I.6 below, the following compounds were prepared.

TABLE I.6

| Ex. # | Ketone | product | yield |
| --- | --- | --- | --- |
| 17/4 | 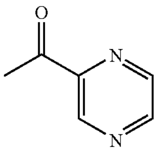 | 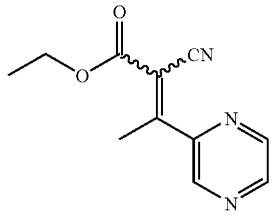 | n.d.<br>$[MH]^+$ = n.d. |
| 17/6 | 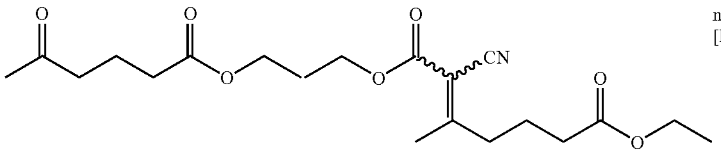 | | n.d.<br>$[MH]^+$ = n.d. |
| 17/11 | 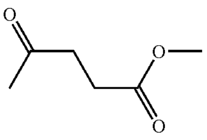 | 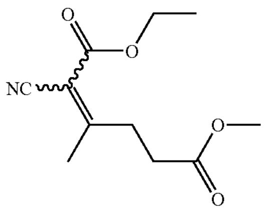 | n.d.<br>$[MH]^+$ = 216 |

TABLE I.6-continued
| Ex. # | Ketone | product | yield |
| --- | --- | --- | --- |
| 17/16 | 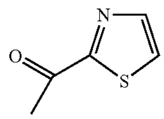 | 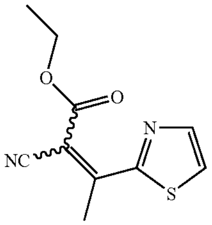 | n.d.<br>$[MH]^+$ = 223 |
| 17/18 | 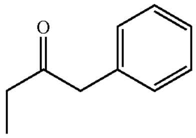 | 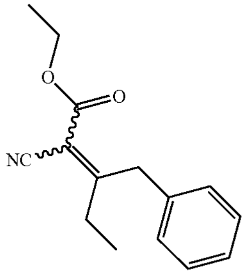 | n.d.<br>$[MH]^+$ = n.d. |
| 17/19 | 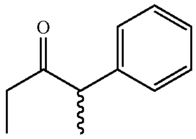 | 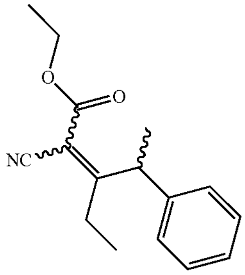 | n.d.<br>$[MH]^+$ = n.d. |
| 17/22 | 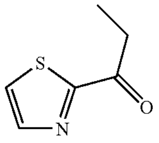 | 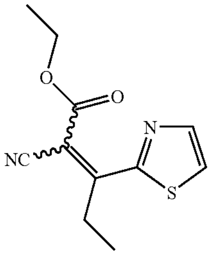 | n.d.<br>$[MH]^+$ = 237 |
| 17/23 | 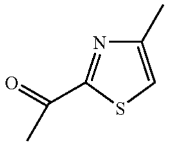 | 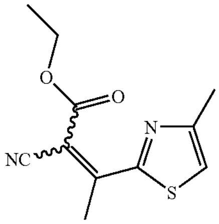 | n.d.<br>$[MH]^+$ = 237 |

Preparative Example 18

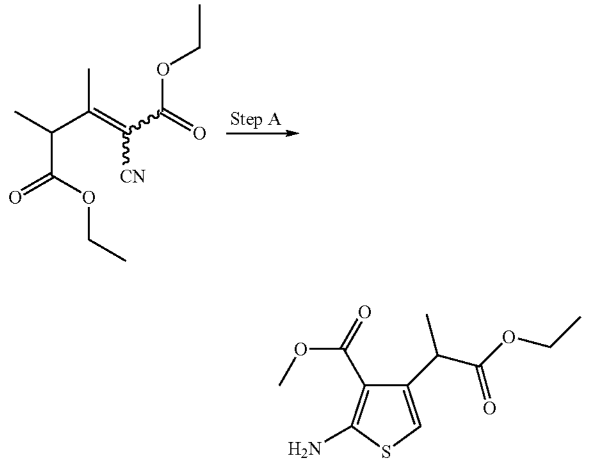

Step A

A mixture of the title compound from the Preparative Example 16 (0.5 g) and sulfur (86 mg) in MeOH (5 mL) were heated at 50° C. Diethylamine (135 μL) was added slowly and the mixture was stirred at 50° C. for 2 h. After concentration of the mixture, a purification by chromatography (silica cyclohexane/EtOAc 9/1) afforded a orange solid (44% for 2 steps). $[MH]^+$=258.

Preparative Examples 18/4 to 18/24

Following similar procedures as described in the Preparative Examples 18 except using the adduct indicated in Table I.7 below, the following compounds were prepared.

TABLE I.7

| Ex. # | Adduct | product | yield |
|---|---|---|---|
| 18/4 | 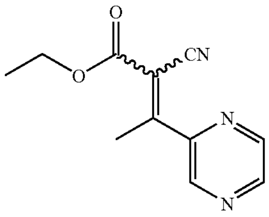 | 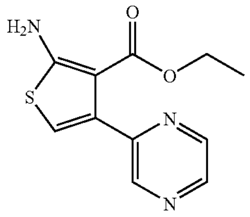 | 39% (2 steps) $[MH]^+$ = 250 |
| 18/6 | 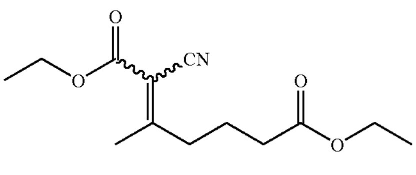 | 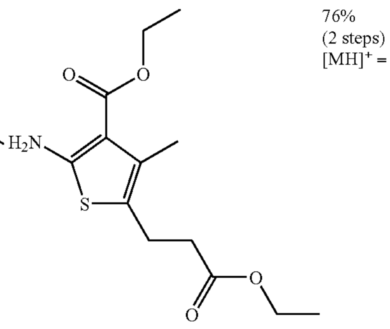 | 76% (2 steps) $[MH]^+$ = 286 |
| 18/11 | 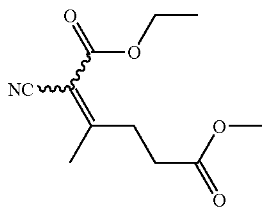 | 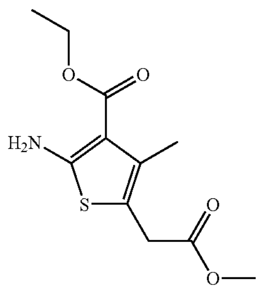 | 49% (2 steps) $[MH]^+$ = 258 |

TABLE I.7-continued
| Ex. # | Adduct | product | yield |
|---|---|---|---|
| 18/16 | 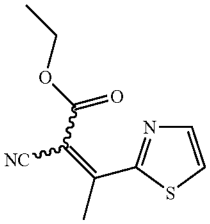 | 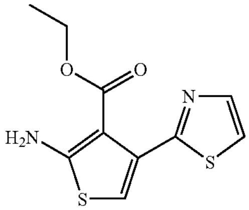 | n.d.<br>$[MH]^+$ = 255 |
| 18/18 | 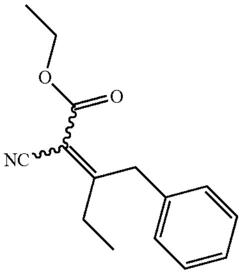 | 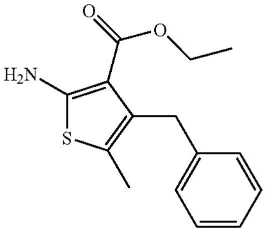 | n.d.<br>$[MH]^+$ = n.d. |
| 18/19 | 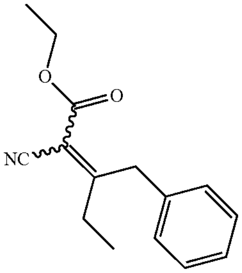 | 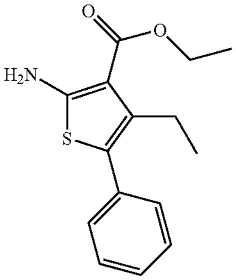 | n.d.<br>$[MH]^+$ = n.d. |
| 18/20 | 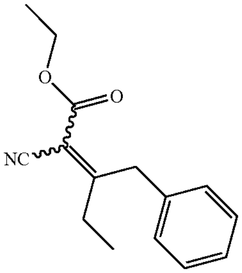 | 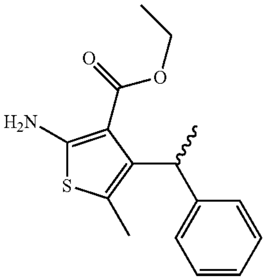 | n.d.<br>$[MH]^+$ = 290 |
| 18/23 | 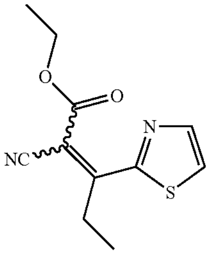 | 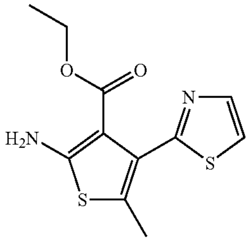 | 16%<br>(2 steps).<br>$[MH]^+$ = 269 |

TABLE I.7-continued

| Ex. # | Adduct | product | yield |
| --- | --- | --- | --- |
| 18/24 | 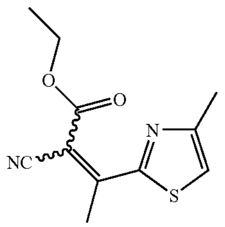 | 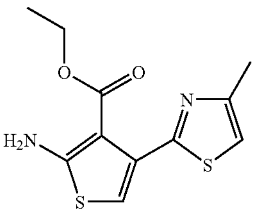 | 25% (2 steps). $[MH]^+ = 269$ |

Preparative Example 92

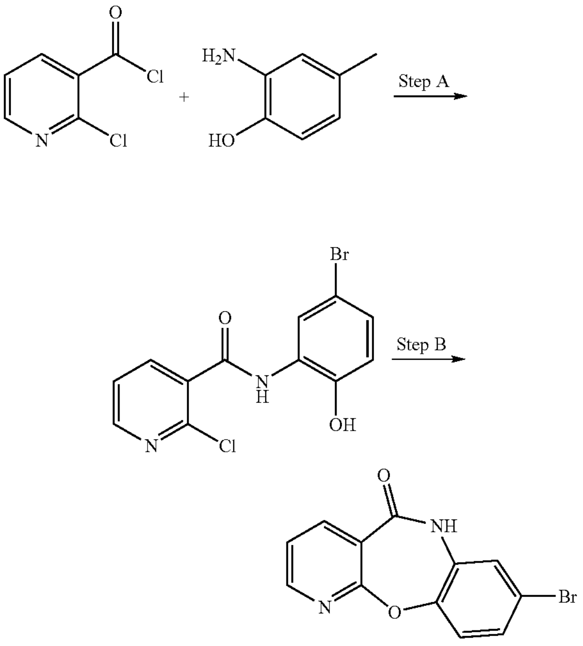

Step A

To a solution of commercially available 2-amino-4-bromophenol (1.00 g) in THF (10 mL) a solution of 2-chloropyridine-3-carbonyl chloride (0.91 g) in THF (5 mL) was added at room temperature and the mixture was refluxed for 1 h. The mixture was cooled to room temperature and within 2 d needles precipitated out which were filtered of to give 0.43 g of the title compound. To the filtrate water was added (100 ml) and the formed precipitate was filtered off and evaporated to dryness to afford additional 0.91 g of the title compound. (total yield 1.34 g, 77%). $[MH]^+$=327/329.

Step B

To a solution of the title compound from step A above (0.91 g) in DMF (30 ml) sodium methoxide (209 mg) was added in one portion and the mixture was refluxed for 3 h, cooled to room temperature overnight and refluxed again for 8 h. The mixture was concentrated to dryness and dissolved in EtOAc. The organic layer was washed with saturated $NaHCO_3$ and the formed precipitate was filtered off and dried to afford the title compound (0.42 g). The organic layer was dried ($MgSO_4$) and concentrated to afford additional 0.23 g of the title compound. (total yield 0.65 g, 81%). $[MH]^+$=291/293.

Preparative Example 93

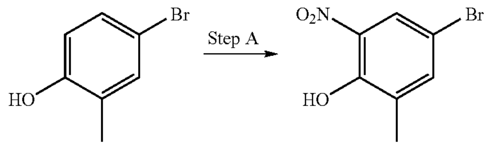

Step A

A solution of 4-bromo-2-methylphenol was stirred in 30% aqueous $HNO_3$ at about 5° C. for 30 min, filtered and used immediately without further purification.

Preparative Example 94

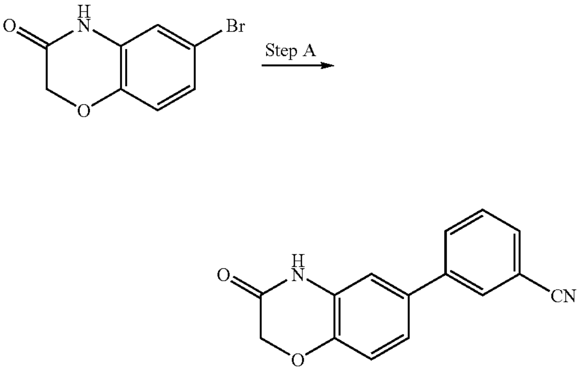

Step A

A solution of 6-bromo-4H-benzo[1,4]oxazin-3-one (1.5 g), 3-cyanophenylboronic acid (1.17 g), $Pd(OAc)_2$ (81 mg), dppf (221 mg) in degassed dry DMF (~60 mL) and $NEt_3$ (~1 mL) was stirred overnight under Argon at 100° C., evaporated and diluted with ethyl acetate, washed with 1N HCl and brine, dried and absorbed on silica. Flash chromatography (cyclohexane/ethyl acetate 8:2 to 6:4) afforded the title compound (163 mg, 9%) as a colorless solid. $[MNa]^+$=251.

Preparative Example 95

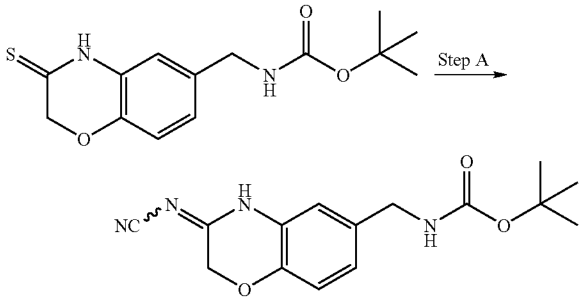

Step A

A suspension of the title compound from Preparative Example 98 (48 mg), cyanamide (80 mg), $NEt_3$ (20 μL) in dry MeOH (10 mL) was stirred at 60° C. overnight, evaporated, absorbed on silica and purified by flash chromatography (cyclohexane/ethyl acetate 6:4) to give the title compound (41 mg) as a colorless solid. $[MNa]^+$=325.

Preparative Example 96

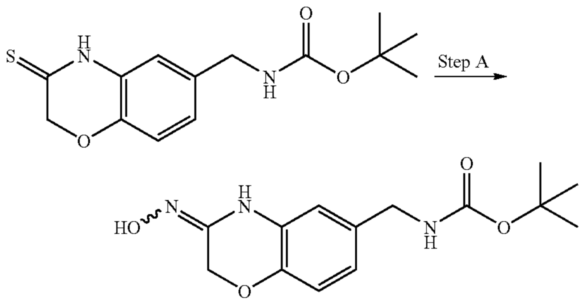

Step A

A suspension of the title compound from Preparative Example 98 (81 mg), $HONH_2$.HCl (60 mg), $NEt_3$ (100 μL) in dry MeOH (10 mL) was stirred at room temperature overnight, evaporated, diluted with EtOAc and washed with water and brine, dried and evaporated to give the title compound (90 mg, quant.) as a colourless solid. $[MNa]^+$=316.

Preparative Example 97

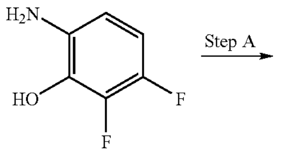

-continued

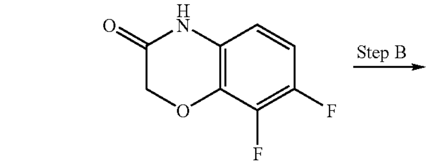

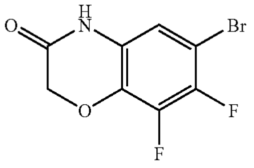

and

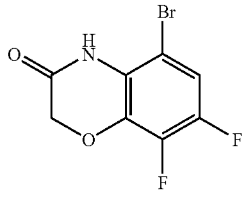

Step A

A suspension of 6-amino-2,3-difluorophenol (1.0 g), $K_2CO_3$ (3 g), bromoacetyl chloride (750 μL) and a catalytic amount of TBAI in dry acetonitrile was stirred at reflux overnight, evaporated and diluted with ethyl acetate, washed with 1N HCl, brine and a saturated solution of $NaHCO_3$, dried and evaporated to give the title compound (1.1 g, 86%) as a brown solid $[MH]^+$=186.

Step B

The title compound of Step A above (1.1 g) was dissolved in acetic acid and bromine (1 mL) was added. The solution was stirred at room temperature overnight, then additional bromine (1 mL) was added and the temperature was elevated to 40° C. for 3 h. The solution was evaporated and diluted with ethyl acetate, washed with a aqueous solution of sodium sulfite, brine and a saturated solution of sodium hydrogen carbonate, dried, absorbed on silica and purified by flash chromatography (cyclohexane/ethyl acetate 8:2 to 7:3) to give the 5-bromo-isomer (787 mg, 50%) and 6-bromo-isomer (567 mg, 36%) as off-white solids. $[MH]^+$=264/266.

Preparative Example 98

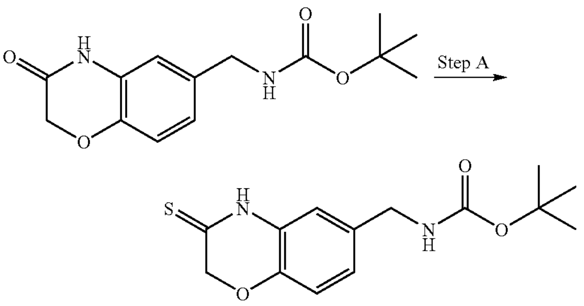

Step A

A suspension of the title compound from Preparative Example 13, Step B (380 mg) and Lawesson's reagent (660 mg) in dry THF was stirred at room temperature for 4 h, evaporated and diluted with ethyl acetate, washed with water and purified by flash chromatography (cyclohexane/ethyl acetate 85:15 to 8:2) to afford the title compound (312 mg, 78%) as a colourless solid. $[MNa]^+$=317.

Preparative Example 99

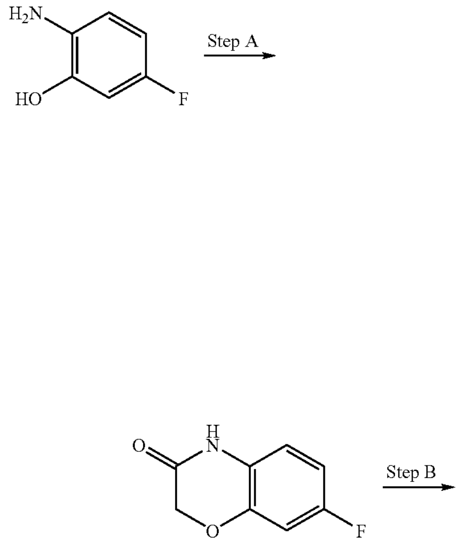

-continued

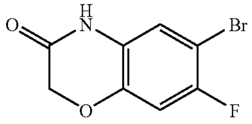

Step A

A suspension of 2-amino-5-fluorophenol (1.0 g), catalytic amounts of TBAI and $K_2CO_3$ (3.2 g) in dry $CH_3CN$ (40 mL) was added slowly bromoacetyl chloride (790 μL) at room temperature and then heated to reflux for 4 h, evaporated and diluted with 1N hydrochloric acid, filtered and dried to afford the title compound (1.21 g, 92%) as a brown solid. $[MH]^+$=168.

Step B

To a suspension of the title compound from Step A above (1.21 g) in formic acid (20 mL) and added bromine (850 μL) and stirred for 4 h, evaporated and redissolved in ethyl acetate, washed with water and absorbed on silica. Purification by flash chromatography (cyclohexane/ethyl acetate 8:2 to 7:3) to afford the title compound (382 mg, 21%) as an off-white solid. $[MH]^+$=246/248.

Preparative Example 99/1 and 99/2

Following similar procedures as described in the Preparative Examples 99, except using the educt indicated in Table I.7 below, the following compounds were prepared.

TABLE I.7

| Ex. # | Bromide | product | yield |
|---|---|---|---|
| 99/1 | 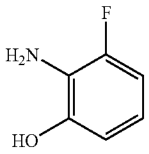 | 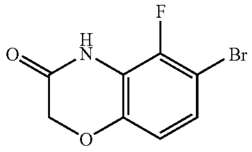 | n.d.<br>$[MH]^+$ = 246/248 |
| 99/2 | 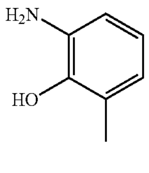 | 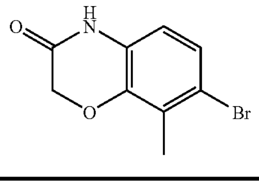 | 40%<br>$[MH]^+$ = 242/244 |

Preparative Example 100

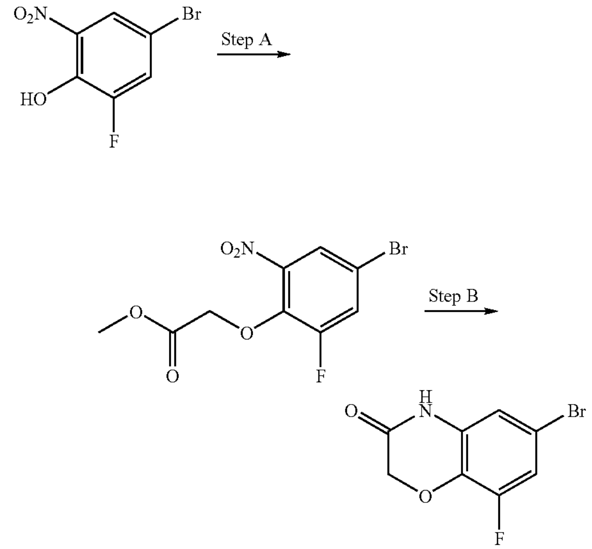

Step A

A suspension of 4-bromo-2-fluoro-6-nitrophenol (6.91 g), methylbromoacetate (3.3 mL), catalytic amounts of TBAI and $K_2CO_3$ (7.4 g) in dry DMF (100 mL) was stirred at 0° C. and allowed to reach room temperature for 2 d, evaporated and redissolved in ethyl acetate, washed with water, 1N hydrochloric acid, saturated aqueous $NaHCO_3$ and brine, dried and evaporated to give crude intermediate, which was absorbed on silica and purified by flash chromatography (cyclohexane/ethyl acetate 9:1 to 8:2) to afford the title compound (8.2 g, 91%) as a colourless solid. $[MH]^+$=308/310.

Step B

A suspension of the title compound from Step A above (1.35 g) and tin (1.3 g; 10-40 mesh) in methanol (2 mL) and concentrated hydrochloric acid (10 mL) was heated to reflux for 2 h, cooled, evaporated and suspended in water, filtered and dried to afford the title compound (985 mg, 91%) as colourless solid. $[MH]^+$=246/48.

Preparative Example 100/1

Following similar procedures as described in the Preparative Examples 100, except using the educt indicated in Table I.8 below, the following compounds were prepared.

TABLE I.8

| Ex. # | Bromide | product | yield |
| --- | --- | --- | --- |
| 100/1 | 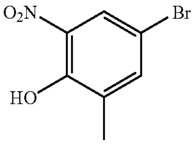 | 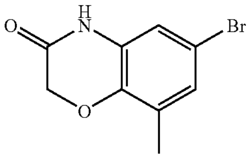 | n.d.<br>$[MH]^+$ = 242/244 |

Preparative Example 101/4 to 101/4

Following similar procedures as described in the Preparative Examples 13, Step A, except using the bromide indicated in Table I.9 below, the following compounds were prepared.

TABLE I.9

| Ex. # | Bromide | product | yield |
| --- | --- | --- | --- |
| 101/1 | 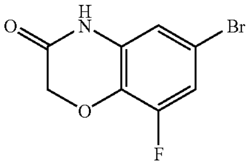 | 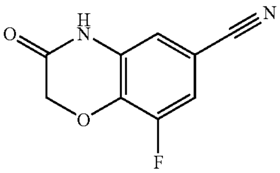 | 93%<br>$[MH]^+$ = 193 |
| 101/2 | 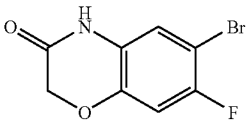 | 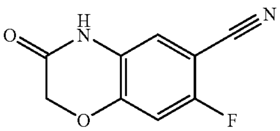 | n.d.<br>$[MH]^+$ = 193 |
| 101/3 | 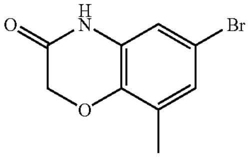 | 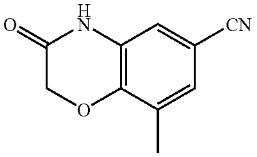 | n.d.<br>$[MH]^+$ = 189 |

TABLE I.9-continued

| Ex. # | Bromide | product | yield |
| --- | --- | --- | --- |
| 101/4 | 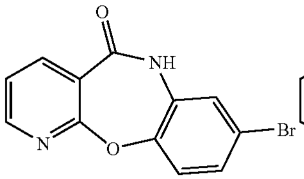 | 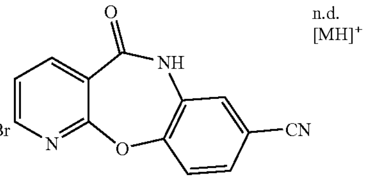 | n.d.<br>$[MH]^+ = 238$ |

Preparative Example 102/1 to 102/9

Following similar procedures as described in the Preparative Examples 13, Step B, except using the cyanide indicated in Table I.10 below, the following compounds were prepared.

TABLE I.10

| Ex. # | Cyanide | product | yield |
| --- | --- | --- | --- |
| 102/1 | 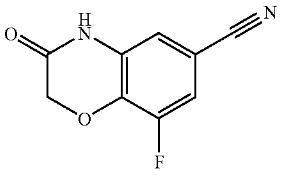 | 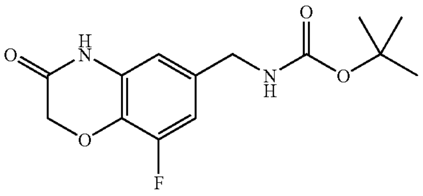 | 56%<br>$[MNa]^+ = 319$ |
| 102/2 | 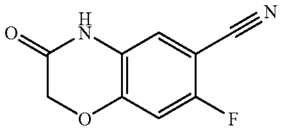 | 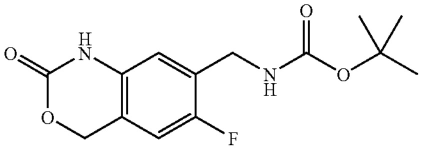 | 28%<br>(two steps)<br>$[MNa]^+ = 319$ |
| 102/3 | 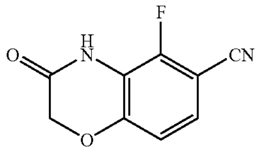 | 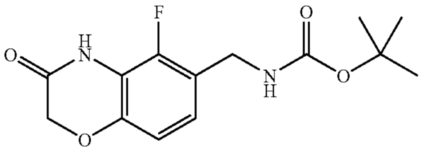 | 32%<br>(3 steps)<br>$[MNa]^+ = 319$ |
| 102/4 | 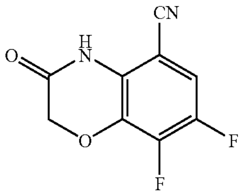 | 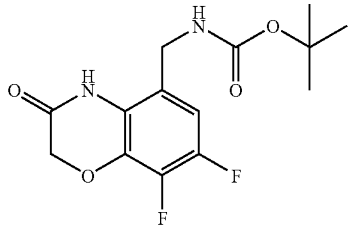 | 64%<br>$[MNa]^+ = 337$ |
| 102/5 | 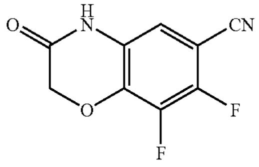 | 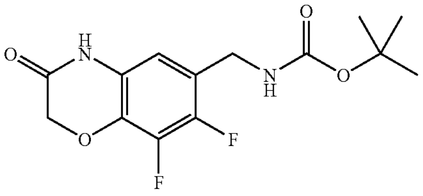 | 47%<br>(two steps)<br>$[MNa]^+ = 337$ |

TABLE I.10-continued

| Ex. # | Cyanide | product | yield |
|---|---|---|---|
| 102/6 | 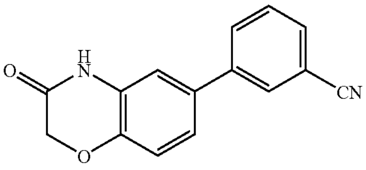 | 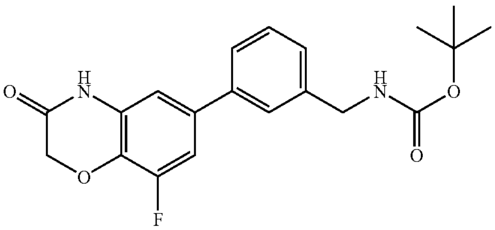 | 83%<br>$[MNa]^+ = 377$ |
| 102/7 | 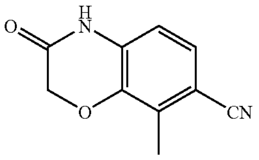 | 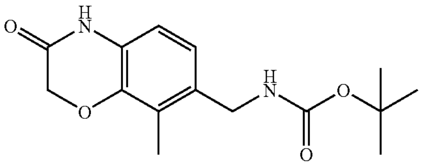 | 61%<br>$[MNa]^+ = 315$ |
| 102/8 | 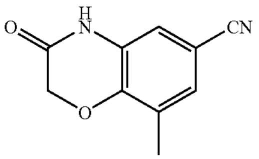 | 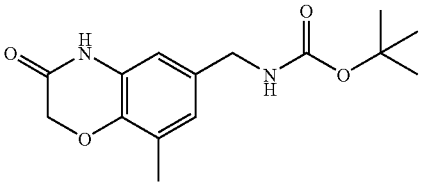 | 41%<br>(two steps)<br>$[MNa]^+ = 315$ |
| 102/9 | 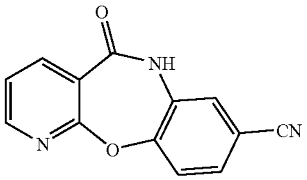 | 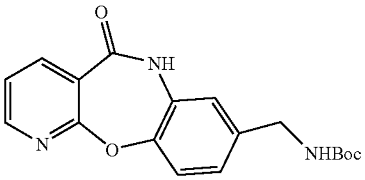 | 36%<br>$[MH]^+ = 225$ |

Preparative Example 103/1 to 103/12

Following similar procedures as described in the Preparative Examples 13, Step C, except using the educt indicated in Table I.11 below, the following compounds were prepared.

TABLE I.11

| Ex. # | Educt | product | yield |
|---|---|---|---|
| 103/1 | 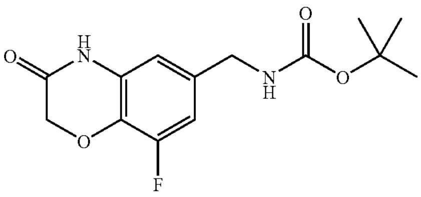 | 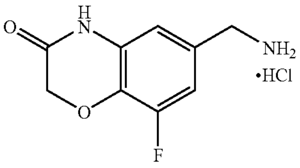 | quant.<br>$[M - NH_3Cl]^+ = 180$ |
| 103/2 | 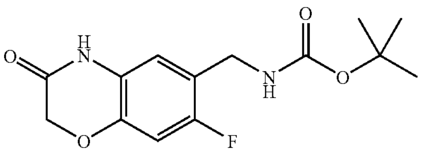 | 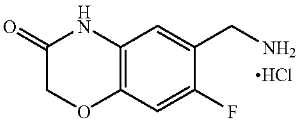 | quant.<br>$[M - NH_3Cl]^+ = 180$ |

TABLE I.11-continued
| Ex. # | Educt | product | yield |
|---|---|---|---|
| 103/3 | 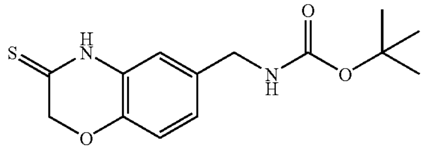 | 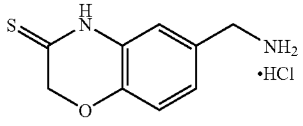 | quant.<br>$[M - Cl]^+ = 194$ |
| 103/4 | 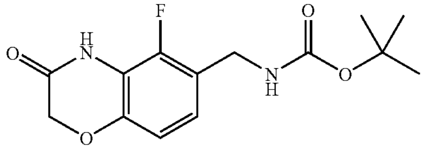 | 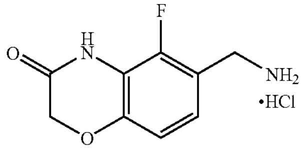 | quant.<br>$[M - NH_3Cl]^+ = 180$ |
| 103/5 | 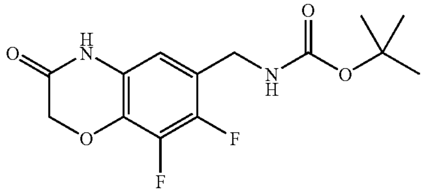 | 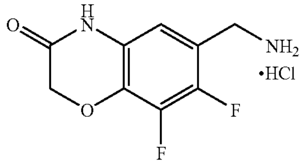 | quant.<br>$[M - Cl]^+ = 215$ |
| 103/6 | 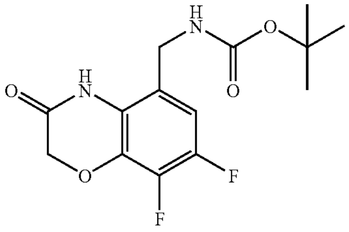 | 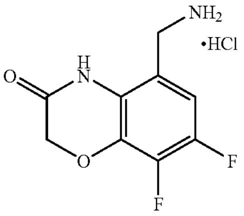 | quant.<br>$[M - Cl]^+ = 215$ |
| 103/7 | 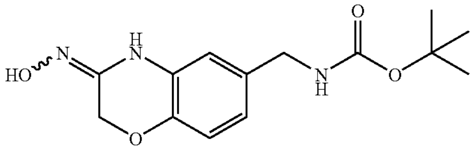 | 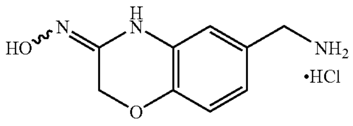 | quant.<br>$[M - Cl]^+ = 194$ |
| 103/8 | 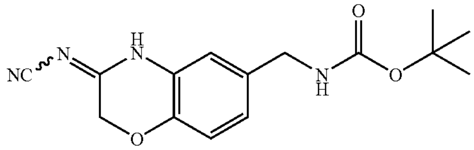 | 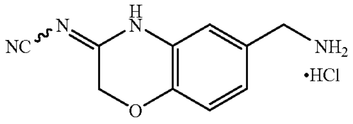 | quant.<br>$[M - Cl]^+ = 200$ |
| 103/9 | 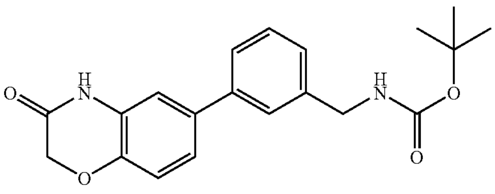 | 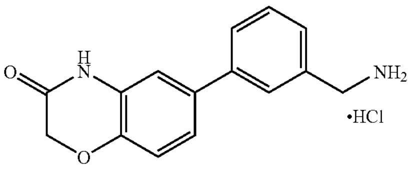 | quant.<br>$[M - Cl]^+ = 255$ |
| 103/10 | 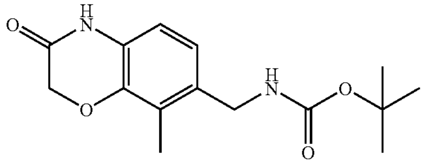 | 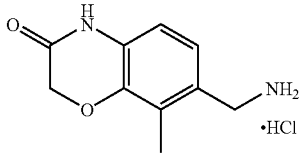 | quant.<br>$[M - Cl]^+ = 193$ |

TABLE I.11-continued

| Ex. # | Educt | product | yield |
|---|---|---|---|
| 103/11 | 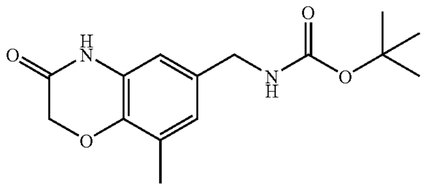 | 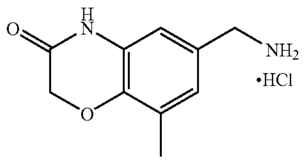 | n.d.<br>$[M-NH_3Cl]^+ = 193$ |
| 103/12 | 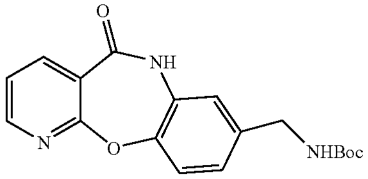 | 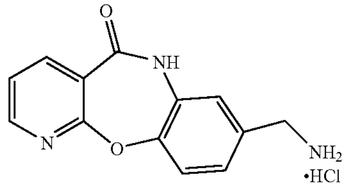 | quant.<br>$[M-NH_3Cl]^+ = 225$ |

Preparative Example 104

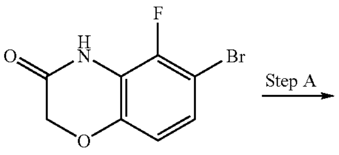

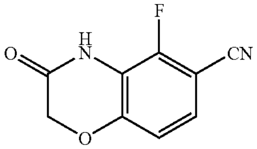

Step A

A suspension of the title compound from Preparative Example 99/1 (~1.3 g) and CuCN (820 mg) in degassed NMP was stirred in a closed vial under microwave irradiation at 180° C. for 10 h, evaporated and redissolved in ethyl acetate, washed with water, 1N hydrochloric acid, saturated aqueous $NaHCO_3$ and brine, dried and evaporated to give crude intermediate, which was used without further purification. $[MH]^+= 193$.

Preparative Example 104/1 to 104/3

Following similar procedures as described in the Preparative Examples 104, except using the bromide indicated in Table I.12 below, the following compounds were prepared.

TABLE I.12

| Ex. # | Bromide | product | yield |
|---|---|---|---|
| 104/1 | 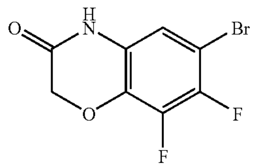 | 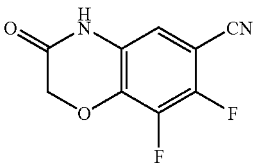 | n.d.<br>$[MH]^+ = 211$ |
| 104/2 | 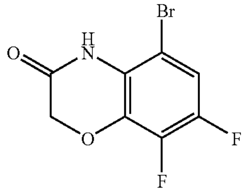 | 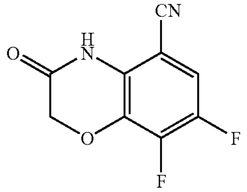 | 55%<br>$[MH]^+ = 211$ |
| 104/3 | 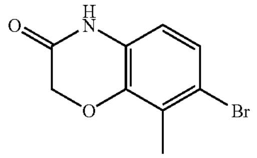 | 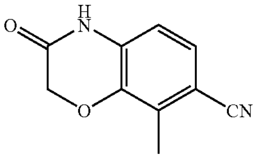 | 91%<br>$[MH]^+ = 189$ |

Preparative Example 105

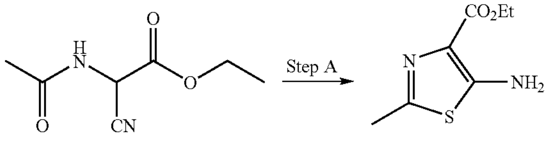

Step A

Ethyl acetamidocyanoacetate (1 g) and Lawesson's reagent (1.2 g) were placed in benzene and refluxed for 24 h in presence of a Dean-Stark apparatus. After evaporation, a purification by flash chromatography (dichloromethane/methanol 98/2) afforded the title product (0.6 g, 30%) as a yellow oil. $[MH]^+$=187.

Preparative Example 110

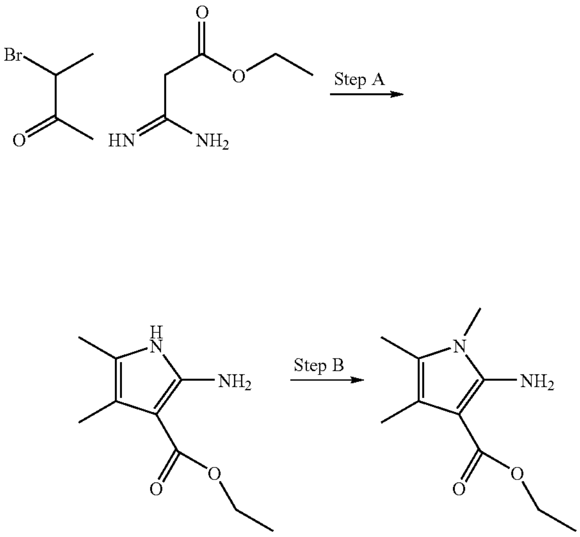

Step A

To a solution of Carbamimidoyl-acetic acid ethyl ester (0.5 g) in ethyl acetate (6 mL) was added triethylamine (0.5 mL) and mixture was stirred at 5° C. Than 3-Bromo-butan-2-one (0.4 mL) was added under a nitrogen atmosphere and the mixture was refluxed for 1 h. The reaction mixture was then filtered through a medium porosity fitted glass funnel containing a thin layer of silica gel. The filtrate was washed with 100 mL of ethyl acetate and the combined washes were then evaporated under reduced pressure to give (0.25 g, 35%) of 2-Amino-4,5-dimethyl-1H-pyrrole-3-carboxylic acid ethyl ester $[MH]^+$=183.

Step B

To a round bottom flask containing a stir bar was added NaH (65 mg; 60% in oil) and the mixture was placed under a nitrogen atmosphere. To the solid was then added of pyrole product (0.25 g) dissolved in 4 ml of anhydrous dimethylformamide and the mixture was stirred at 0° C. for 30 minutes and then 30 minutes at room temperature. To the mixture was then added methyl iodide (0.23 mL) at 0° C. and the mixture was stirred for 30 minutes. To the mixture was then added 50 ml of 10% aqueous ammonium acetate solution and mixture acidified to pH ~7 using acetic acid. The aqueous layer was then extracted with 100 mL of diethyl ether. The organic layer was separated, dried over MgSO4, filtered and the volatile components removed under reduced pressure to give the desired product (150 mg, 55%). $[MH]^+$=197.

Preparative Example 111

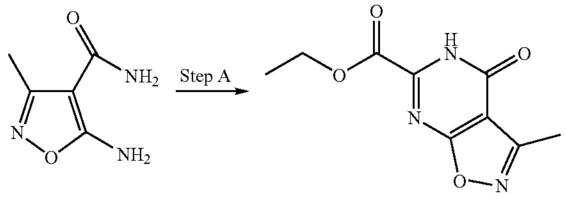

Step A

A mixture of 5-amino-3-methylisoxazole-4-carboxamide (283 mg), diethyl oxalate (1168 mg) and NaOEt (3 mL, 21% wt in EtOH) in EtOH (17 mL) was heated to reflux. The reaction mixture was concentrated under reduced pressure and the residue was dissolved in water (~20 ml). The resulting solution was acidified with AcOH and the separated solid was collected. The solid was dried to afford desired compound (307 mg, 69%). $[MH]^+$=224.

Preparative Example 111/1

Following similar procedures as described in the Preparative Examples 111, except using the bromide indicated in Table I.14 below, the following compounds were prepared.

TABLE I.14

| Ex. # | Amine | product | yield |
|---|---|---|---|
| 111/1 | 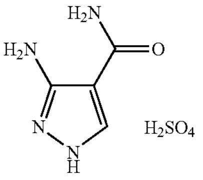 | 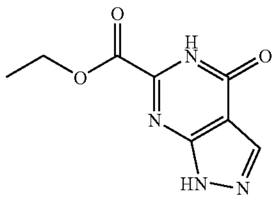 | 80% $[MH]^+$ = 209 |

Example 1

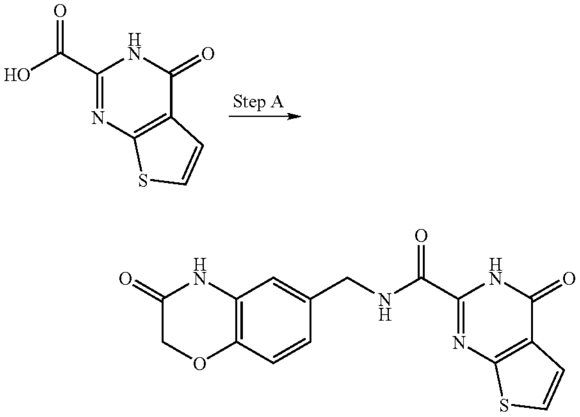

Step A

To a solution of the title compound from Preparative Example 11 above (55 mg), EDCI (108 mg) and HOAt (46 mg) in DMF (10 mL) were added N-methylmorpholine (100 μL) and the title compound from the Preparative Example 13 (72 mg). The mixture was stirred overnight and then concentrated. The remaining residue was suspended in 10% aqueous citric acid and the residue was filtered to afford the title compound as an off white solid (65 mg, 65%). $[MH]^+ = 357$.

Examples 2/1-2/548

Following similar procedures as described in the Examples 1, except using the amines and acids indicated in Table II.1 below, the following compounds were prepared.

TABLE II.1

| Ex. # | amine, acid |
|---|---|
| 2/1 | 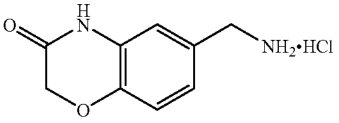 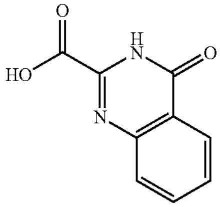 |
| 2/2 | 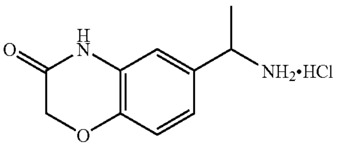 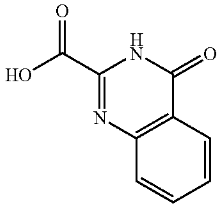 |
| 2/3 | 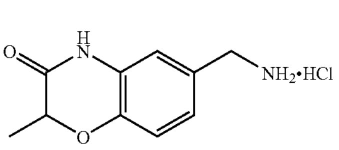 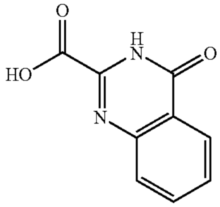 |
| 2/4 | 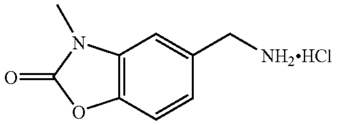 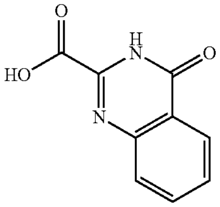 |

TABLE II.1-continued
2/5
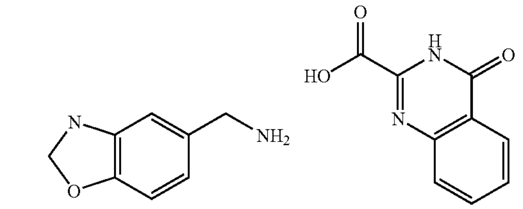
2/6
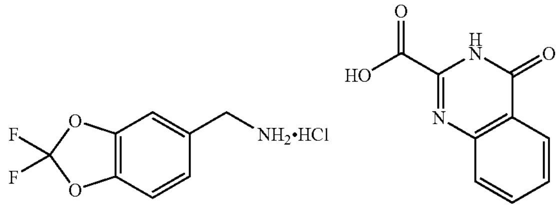
2/7
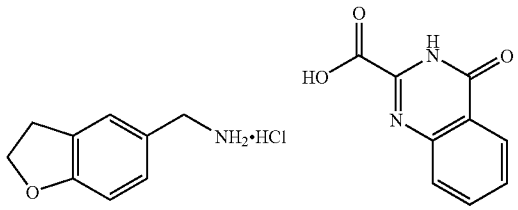
2/8
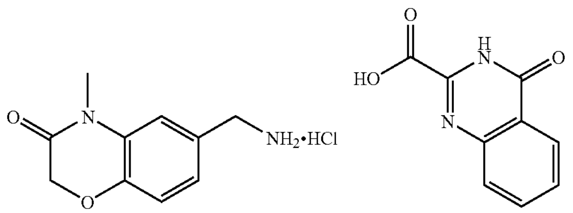
2/9
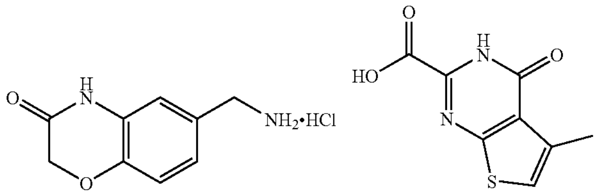
2/10
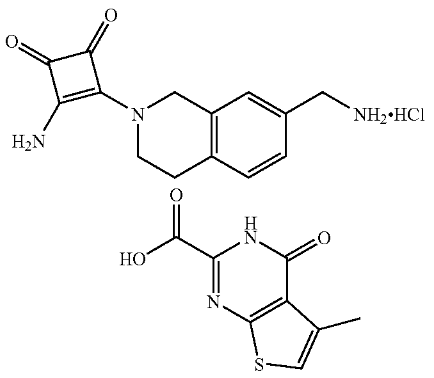

TABLE II.1-continued
| | |
|---|---|
| 2/11 | 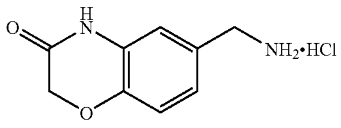 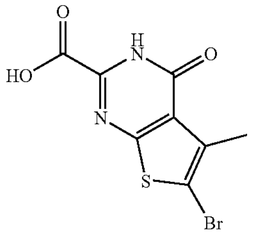 |
| 2/12 | 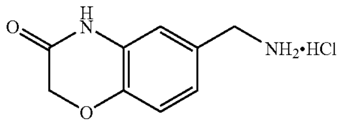 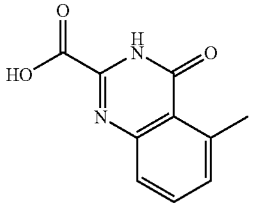 |
| 2/13 | 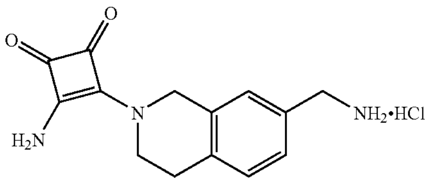 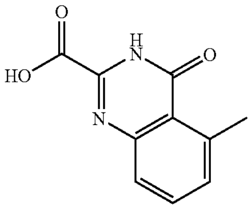 |
| 2/14 | 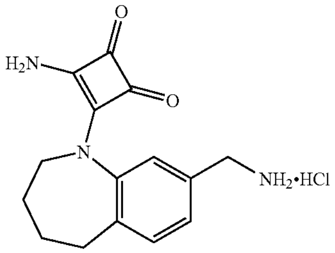 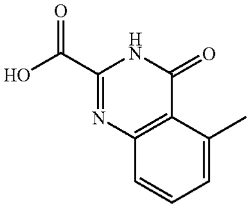 |
| 2/15 | 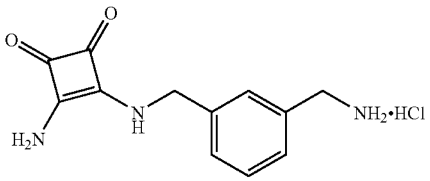 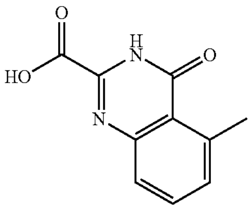 |

TABLE II.1-continued
2/16
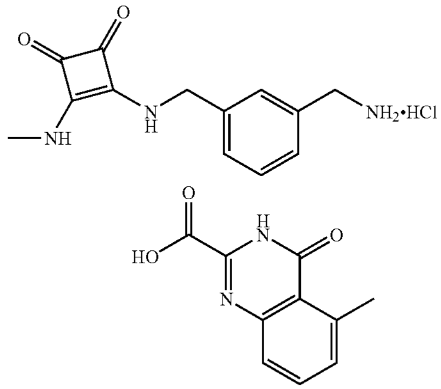
2/17
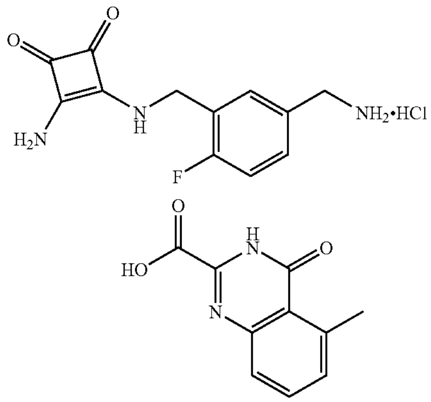
2/18
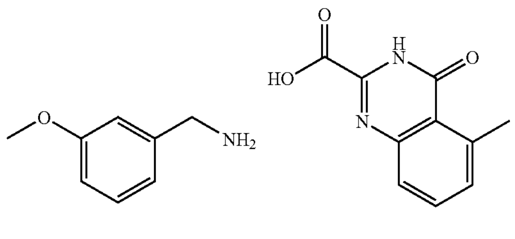
2/19
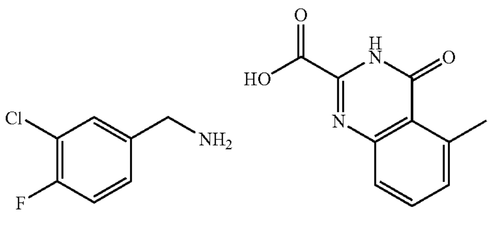
2/20
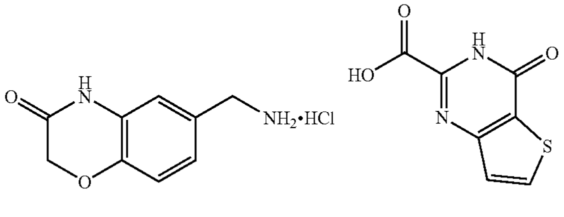

TABLE II.1-continued
2/21
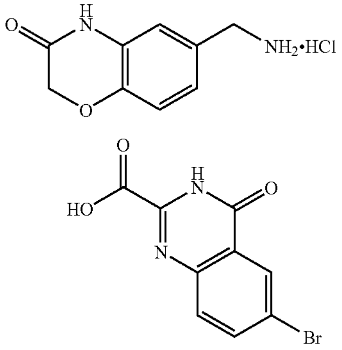
2/22
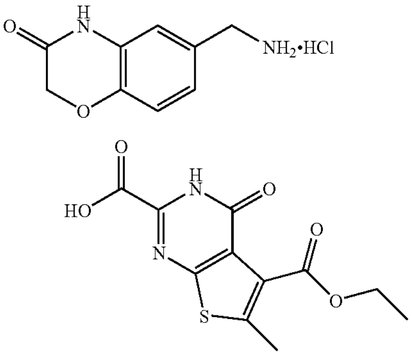
2/23
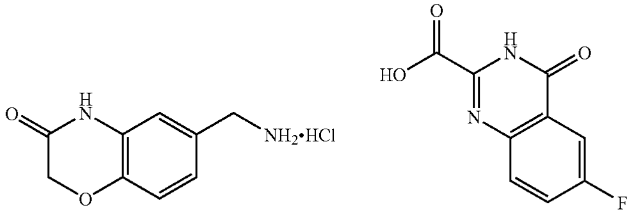
2/26
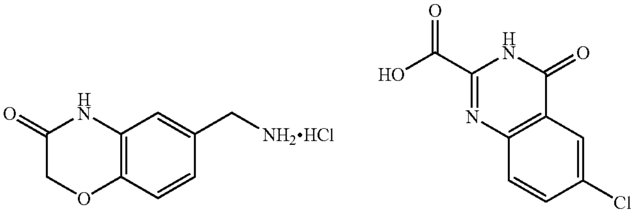
2/27
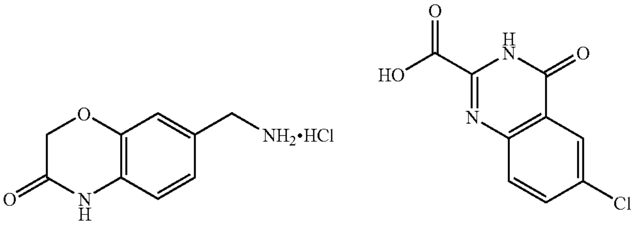

TABLE II.1-continued
| | | |
|---|---|---|
| 2/28 | 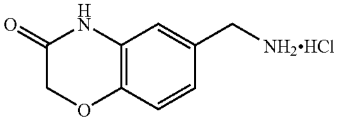 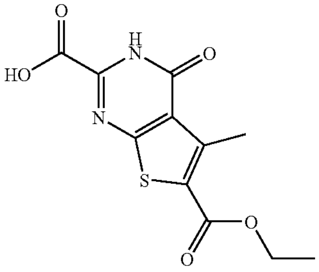 | |
| 2/31 | 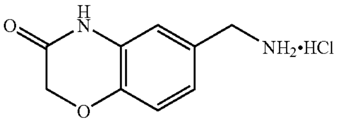 | 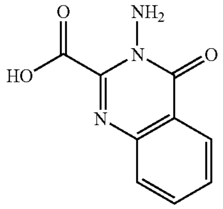 |
| 2/32 | 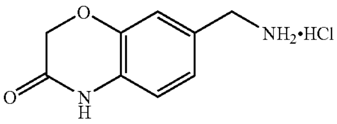 | 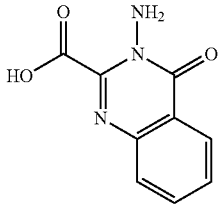 |
| 2/35 | 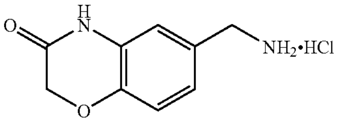 | 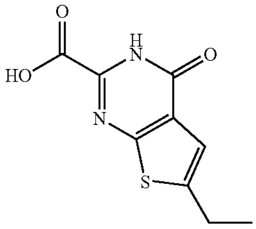 |
| 2/37 | 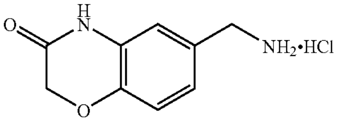 | 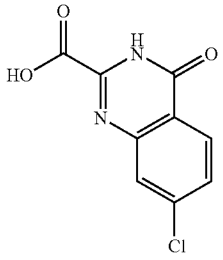 |
| 2/38 | 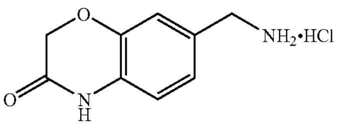 | 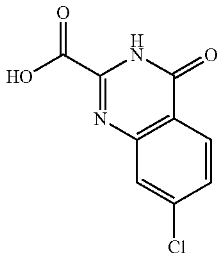 |

TABLE II.1-continued
2/39
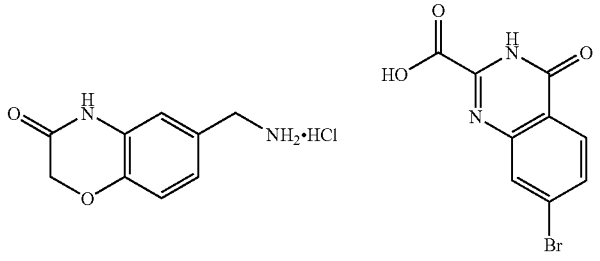
2/40
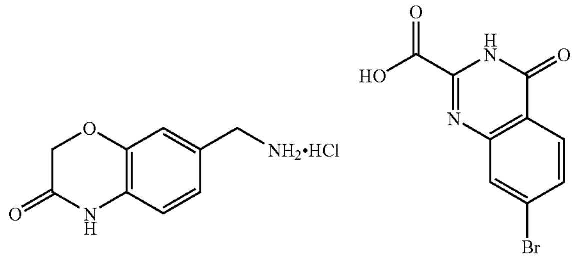
2/41
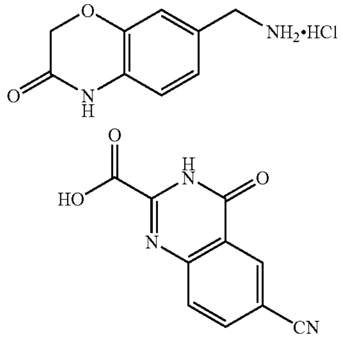
2/42
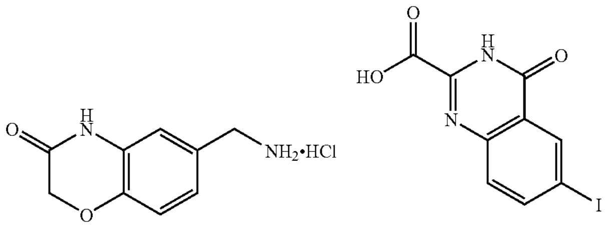
2/43
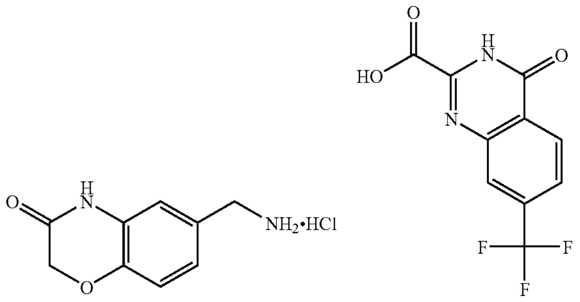

TABLE II.1-continued
| | |
|---|---|
| 2/44 | 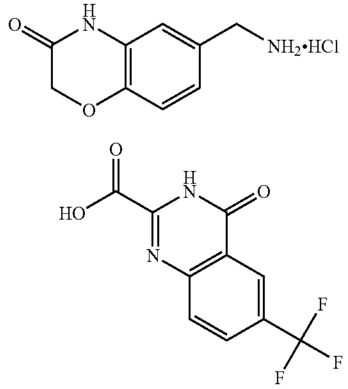 |
| 2/45 | 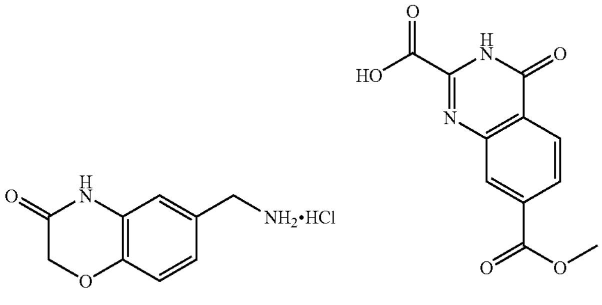 |
| 2/46 | 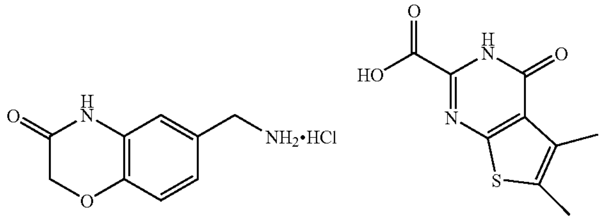 |
| 2/47 | 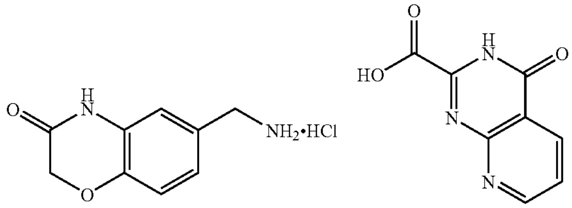 |
| 2/48 | 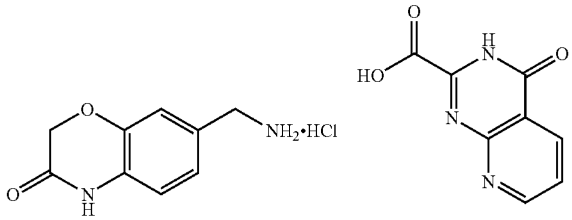 |

TABLE II.1-continued
| | |
|---|---|
| 2/49 | 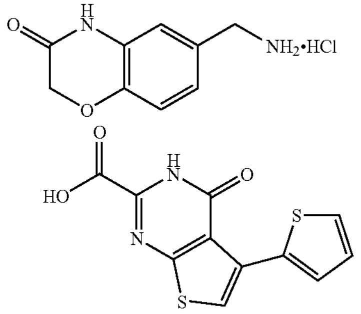 |
| 2/50 | 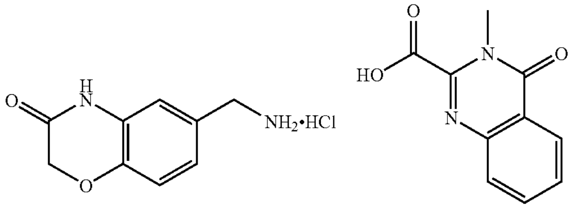 |
| 2/51 | 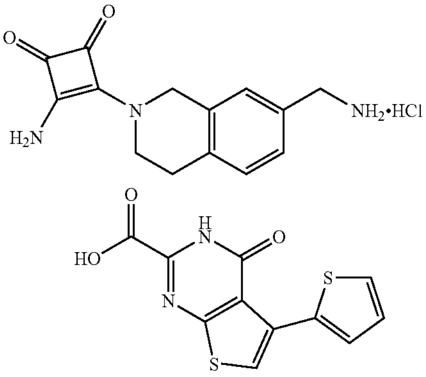 |
| 2/53 | 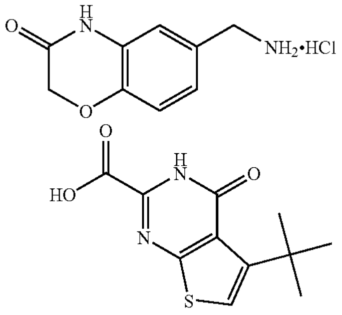 |
| 2/54 | 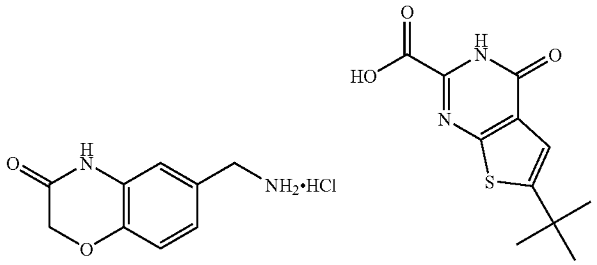 |

TABLE II.1-continued
2/55
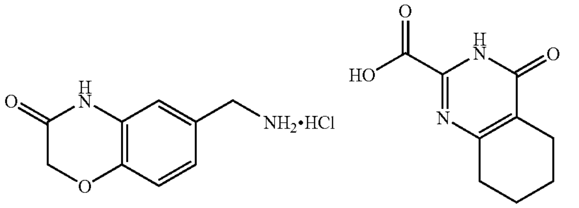
2/56
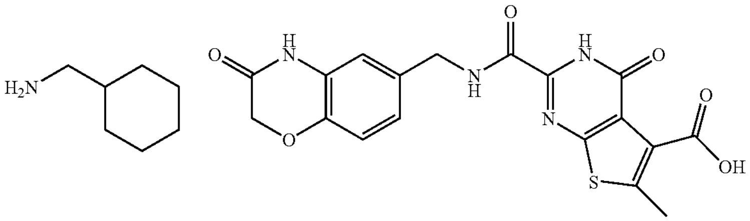
2/57
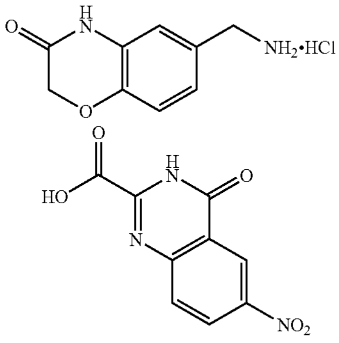
2/58
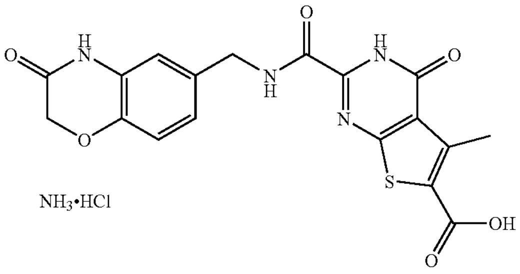
2/59
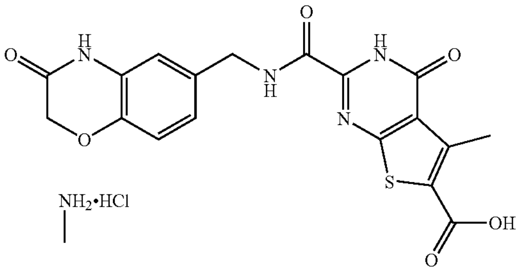

TABLE II.1-continued
2/60
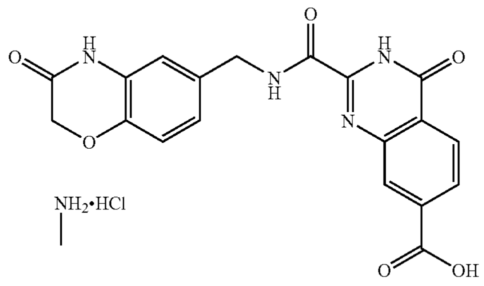
2/61
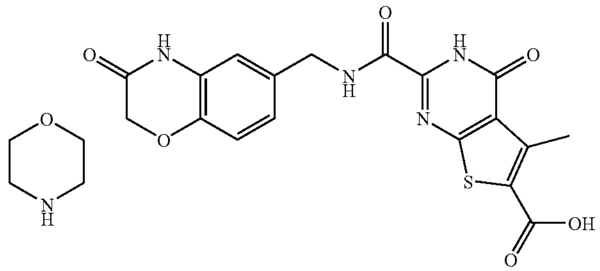
2/62
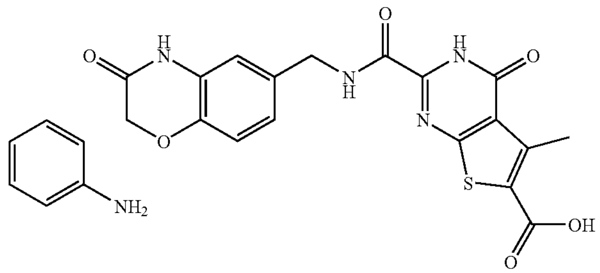
2/63
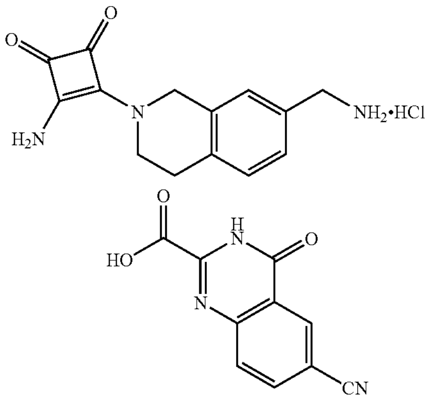

TABLE II.1-continued
2/64
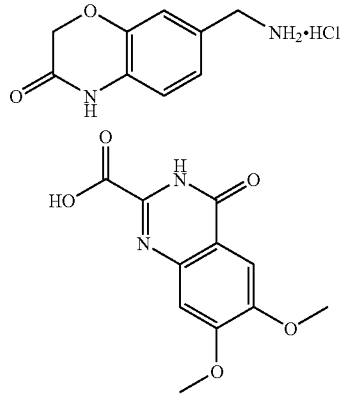
2/65
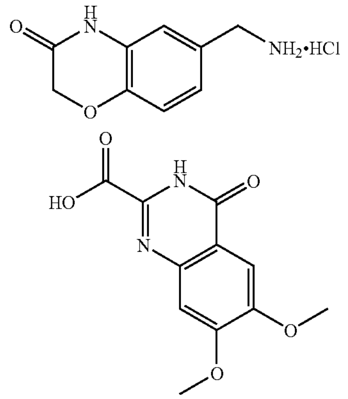
2/66
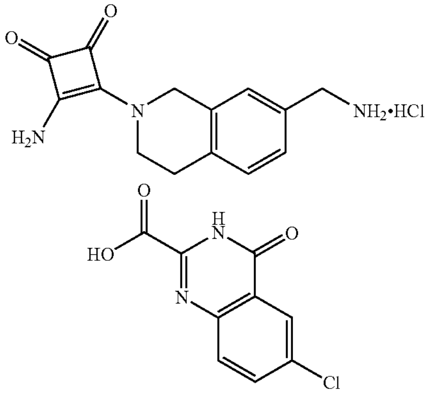
2/68
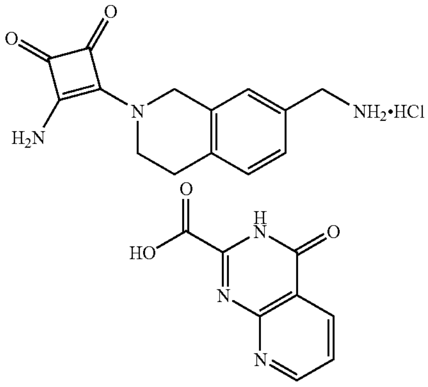

TABLE II.1-continued
2/69
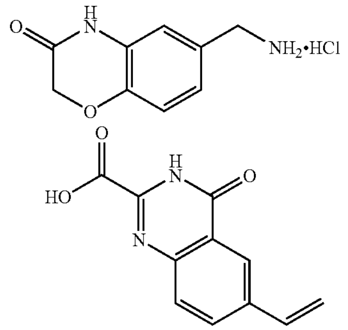
2/70
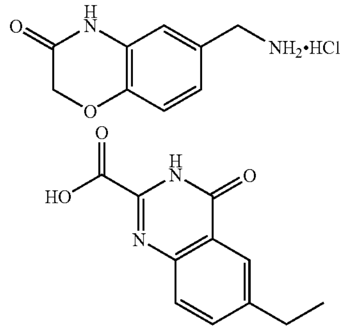
2/71
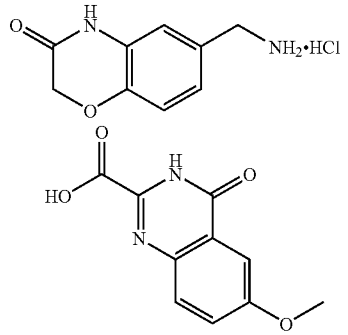
2/72
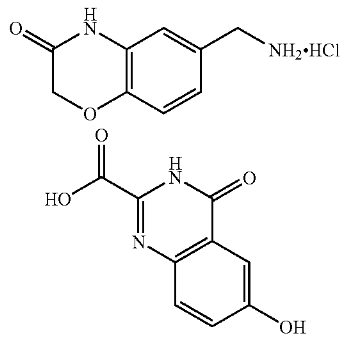
2/73
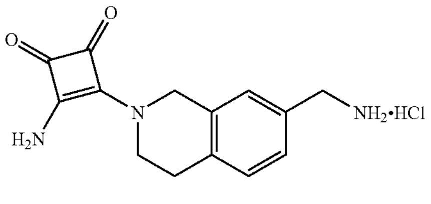

TABLE II.1-continued
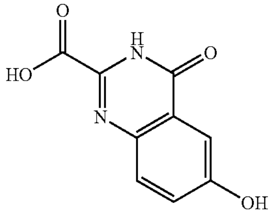
2/74 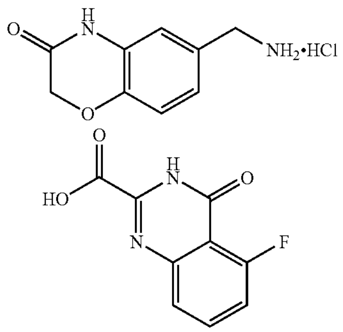
2/75 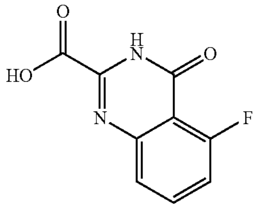
2/76 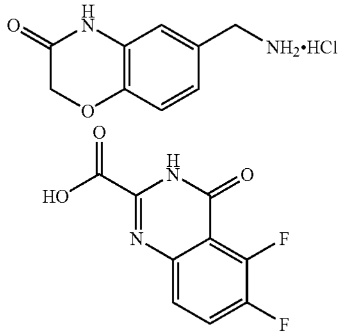
2/77 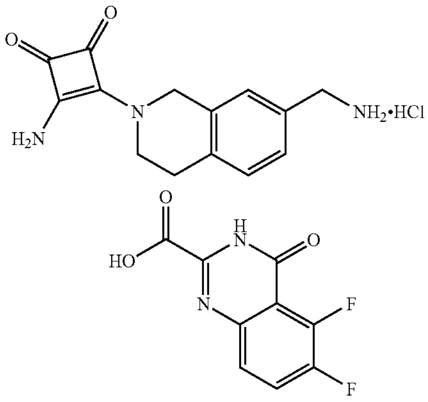

TABLE II.1-continued
| | |
|---|---|
| 2/78 | 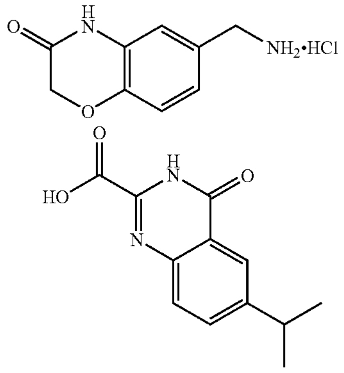 |
| 2/79 | 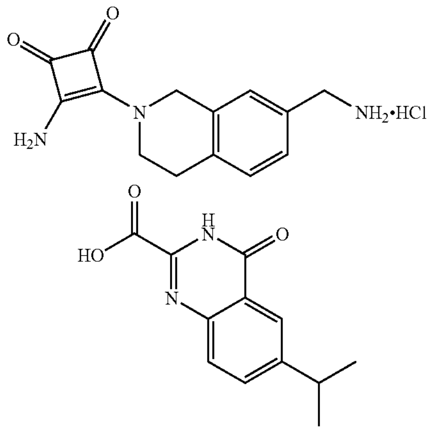 |
| 2/80 | 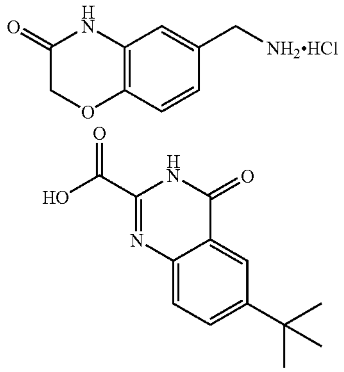 |
| 2/81 | 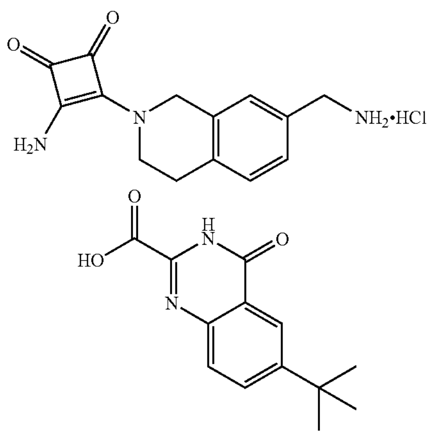 |

TABLE II.1-continued
| | |
|---|---|
| 2/82 | 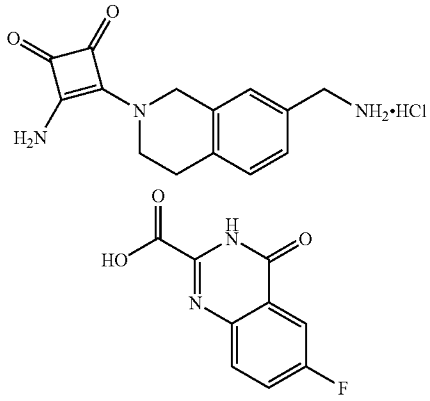 |
| 2/83 | 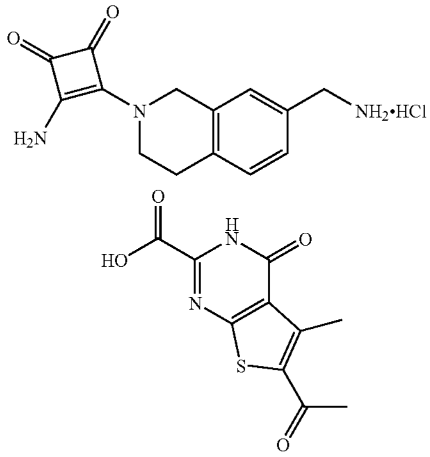 |
| 2/84 | 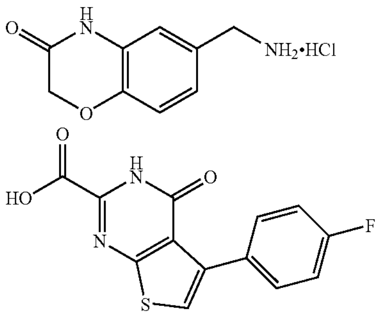 |
| 2/85 | 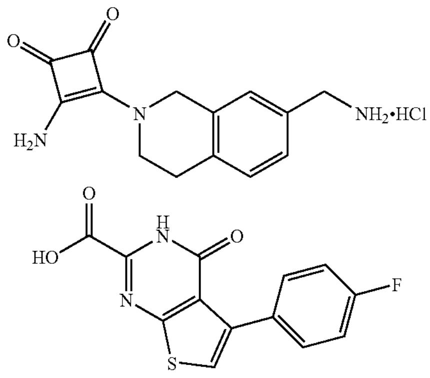 |

TABLE II.1-continued
2/86
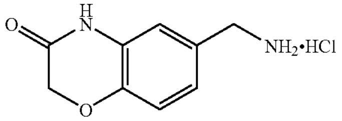
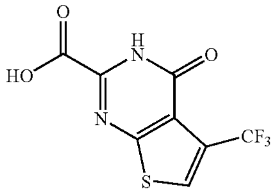
2/87
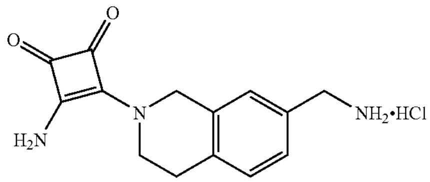
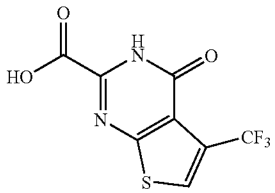
2/88
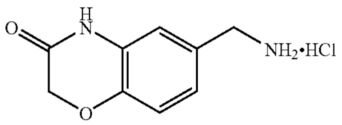
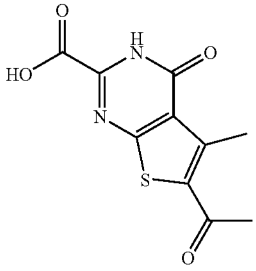
2/91
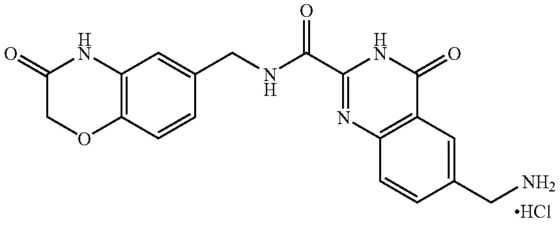
excess
AcOH TABLE II.1-continued
2/92
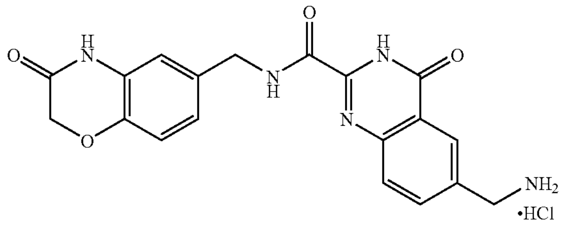
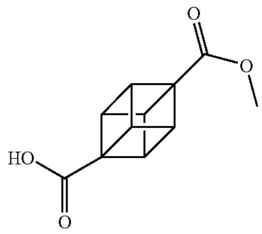
2/93
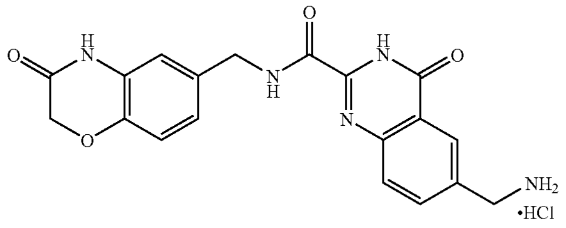
benzoic acid
2/96
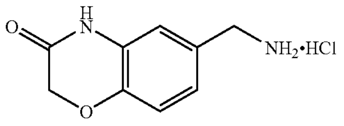
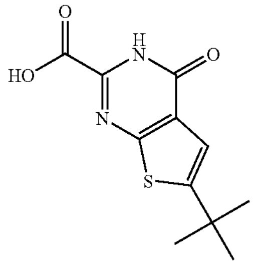
2/97
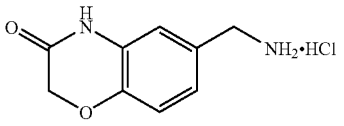
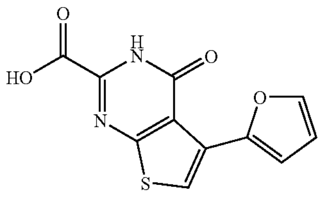
2/98
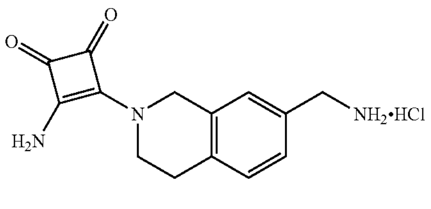

TABLE II.1-continued
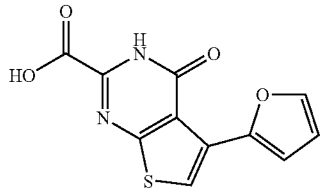
2/99
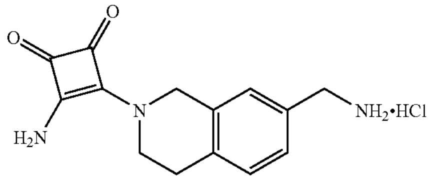
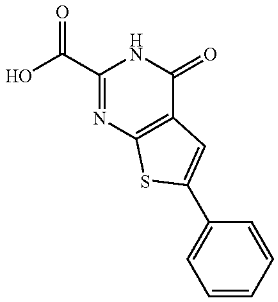
2/100
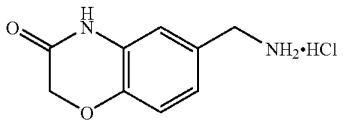
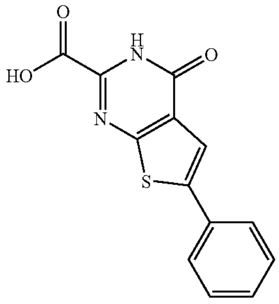
2/101
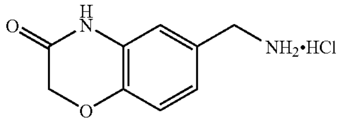
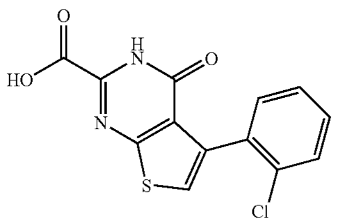

TABLE II.1-continued
| | |
|---|---|
| 2/102 | 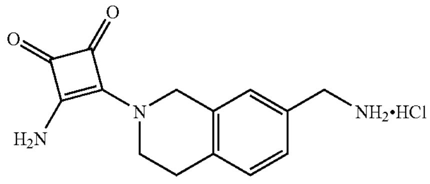 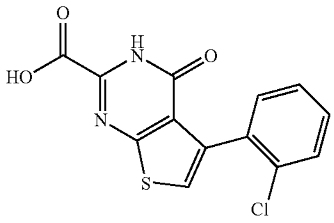 |
| 2/105 | 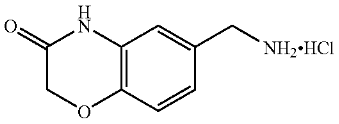 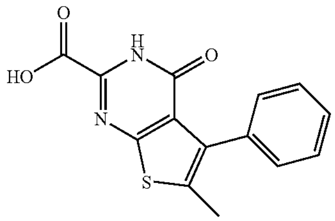 |
| 2/106 | 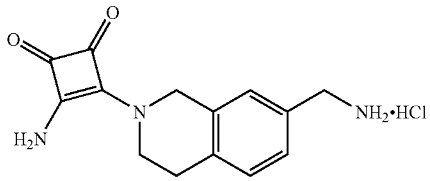 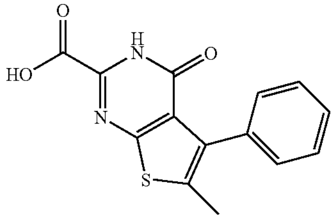 |
| 2/109 | 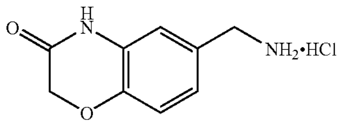 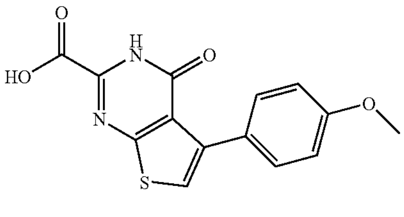 |

TABLE II.1-continued
2/110
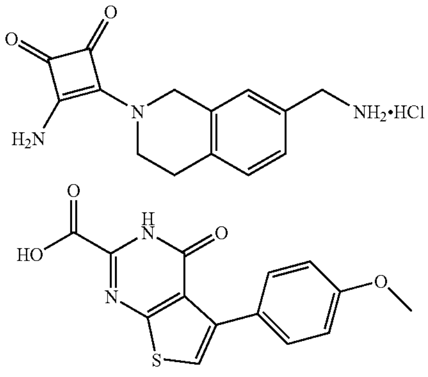
2/111
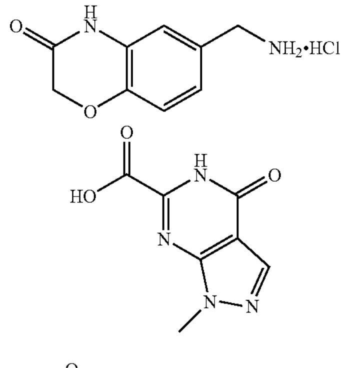
2/112
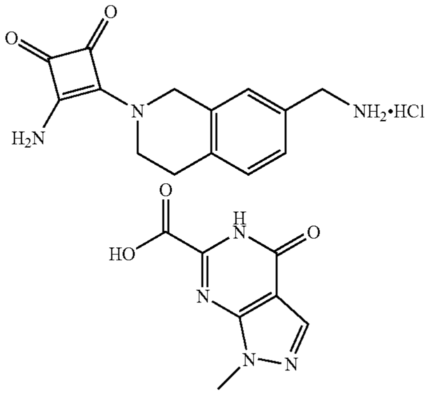
2/115
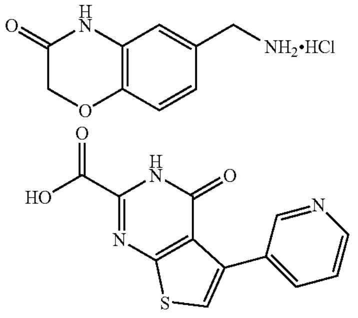
2/116
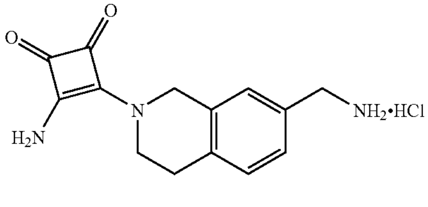

TABLE II.1-continued
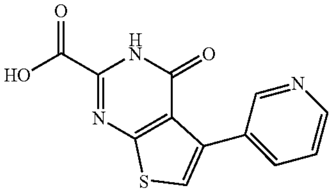
2/123
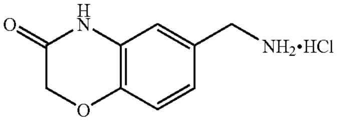
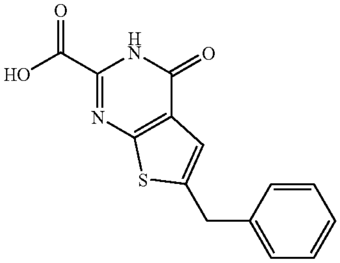
2/124
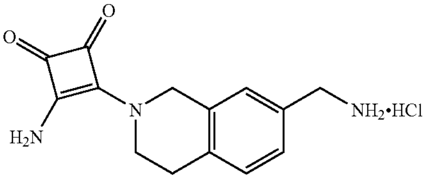
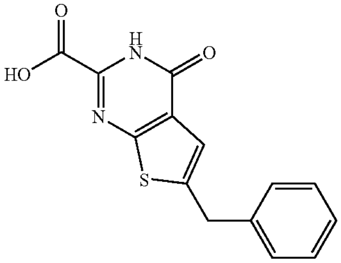
2/127
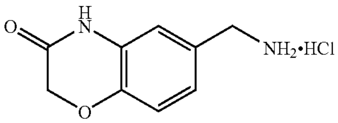
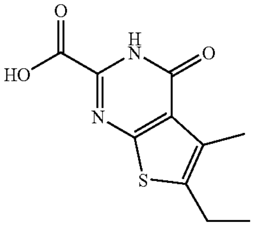
2/128
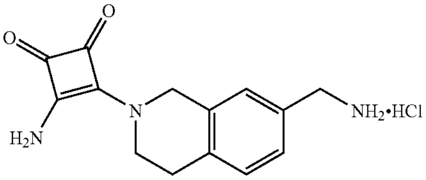

TABLE II.1-continued
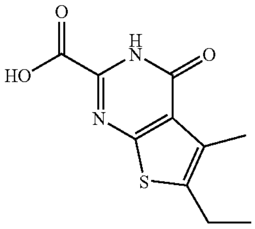
2/133
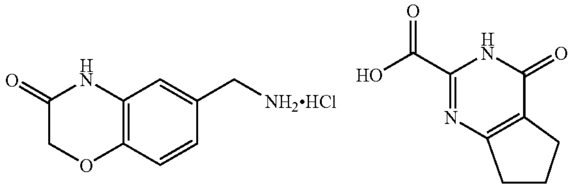
2/134
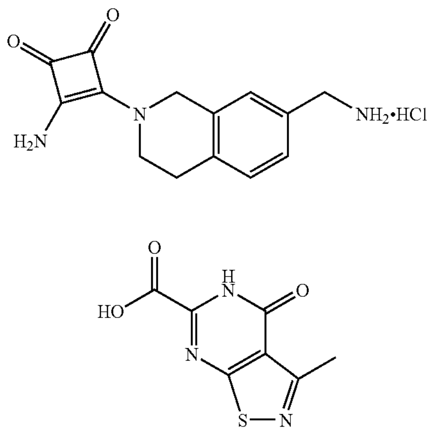
2/135
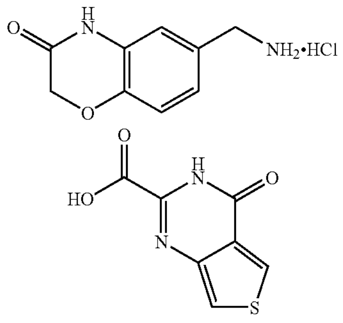
2/136
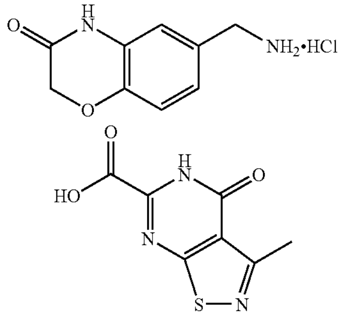

TABLE II.1-continued
2/137
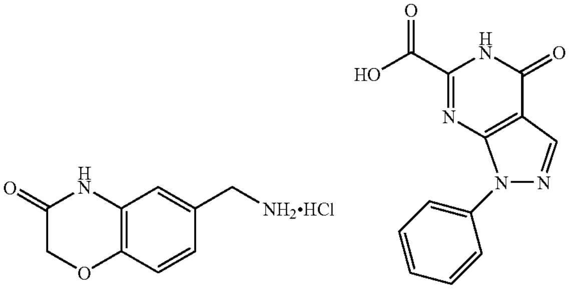
2/138
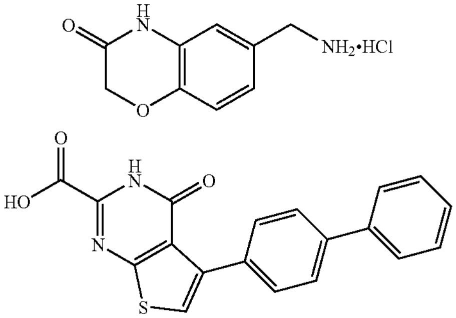
2/139
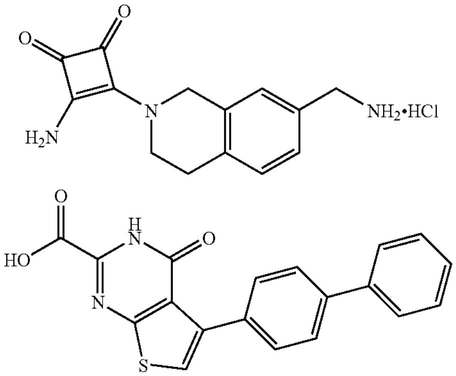
2/140
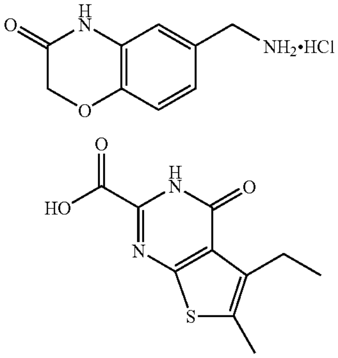
2/141
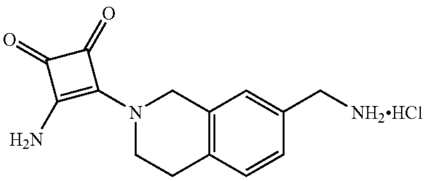

TABLE II.1-continued
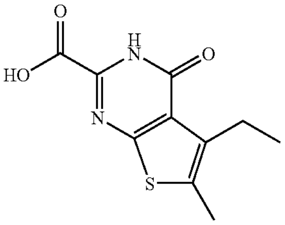
2/142
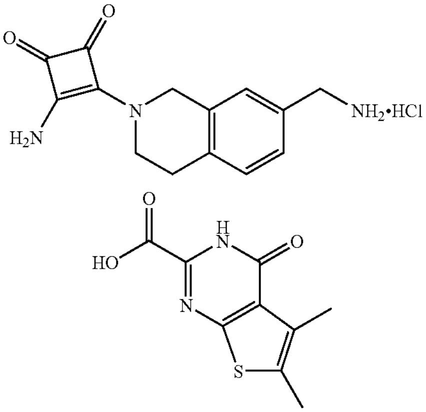
2/147
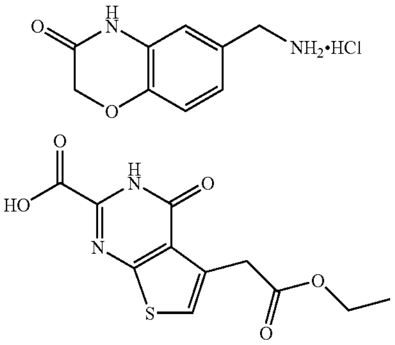
2/148
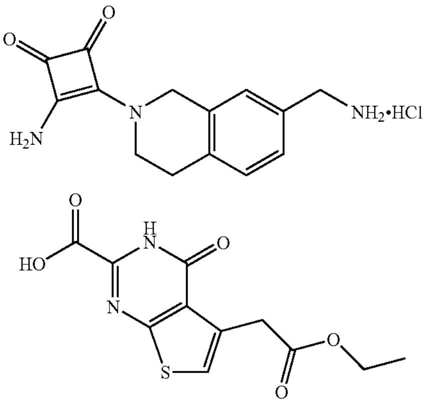
2/149
2
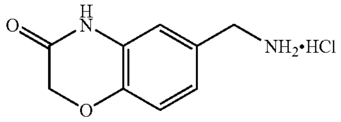

TABLE II.1-continued
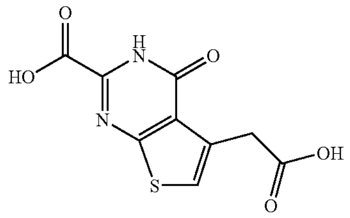
2/150
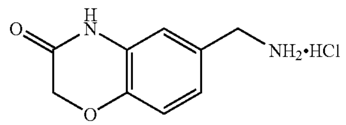
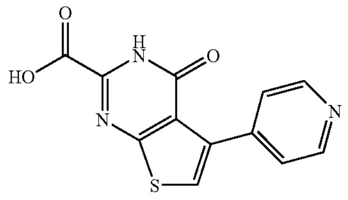
2/151
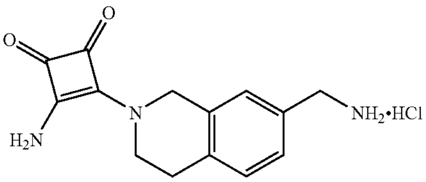
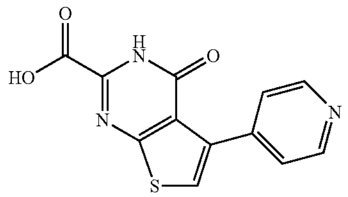
2/154
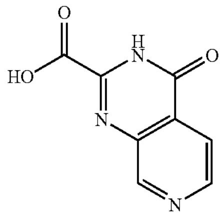
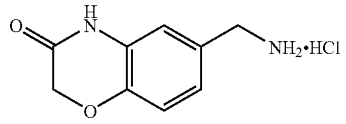

TABLE II.1-continued
2/155
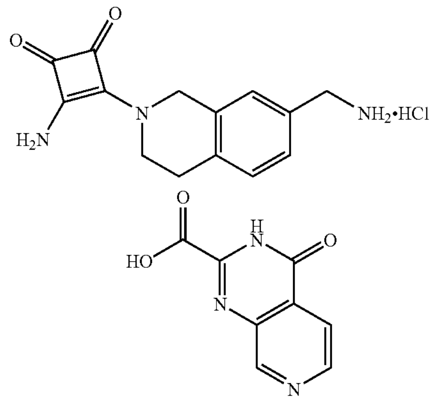
2/156
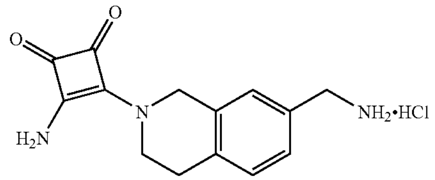
$MeNH_3Cl$
2/157
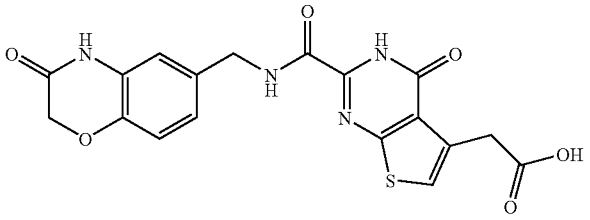
2/158
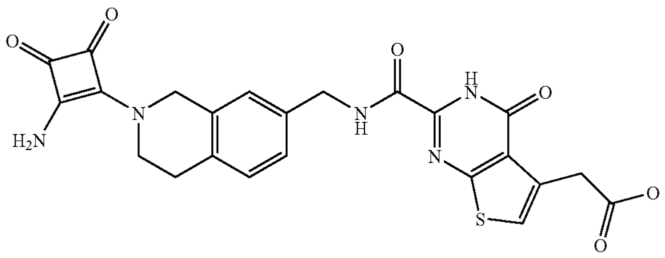
$NH_4Cl$
2/159
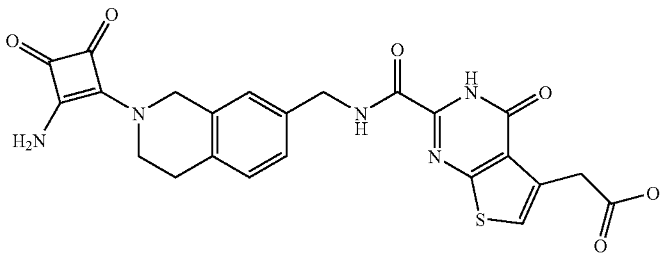
$Me_2NH \bullet HCl$ TABLE II.1-continued
2/160
$Me_2NH•HCl$
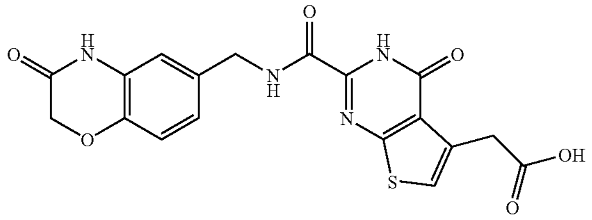
2/161
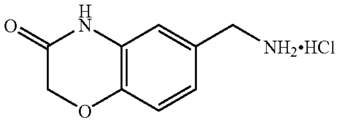
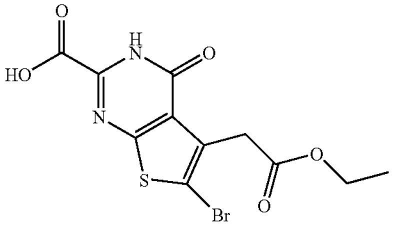
2/162
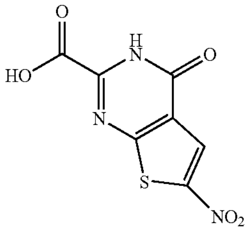
2/163
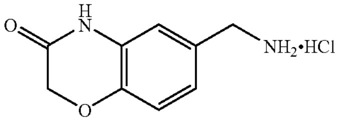
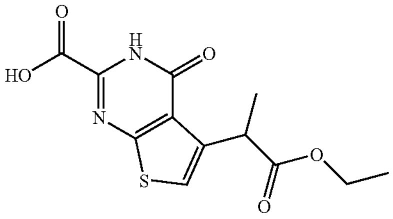
2/164
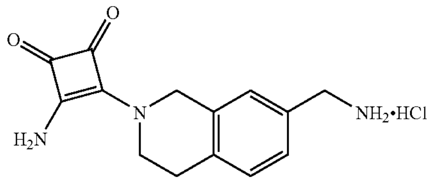
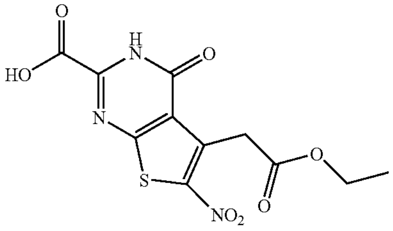

TABLE II.1-continued
2/165
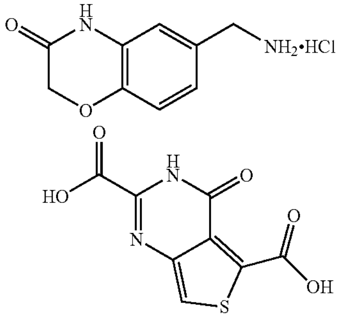
2/179
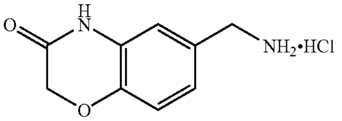
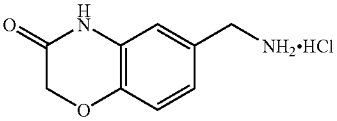
2/180
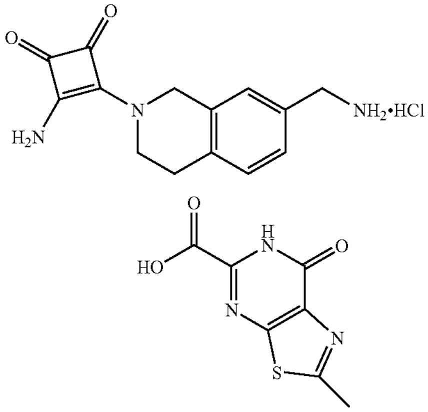
2/181
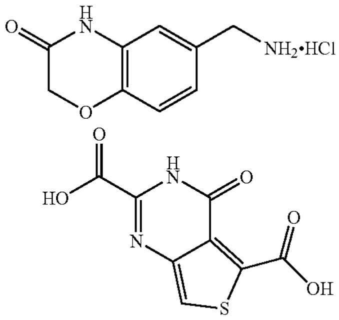
2/182
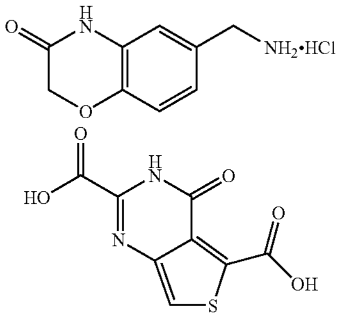

TABLE II.1-continued
2/183
MeNH$_2$•HCl
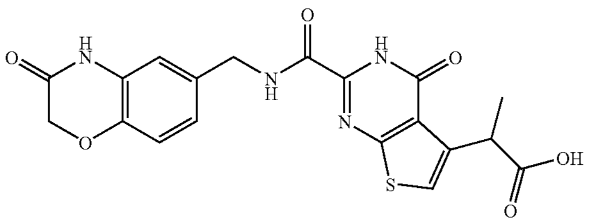
2/184
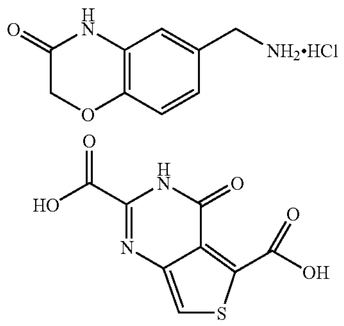
2/185
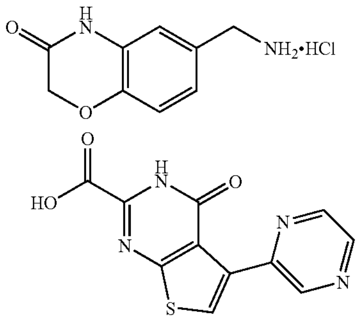
2/186
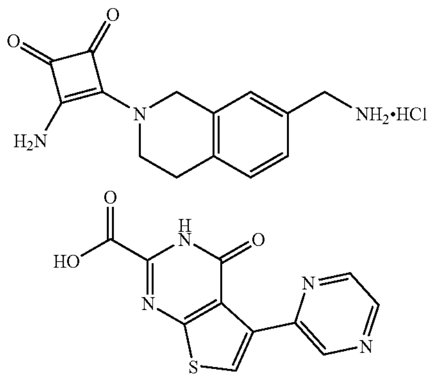
2/189
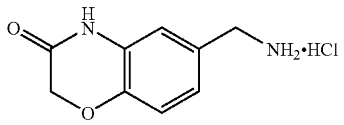

TABLE II.1-continued
| | |
|---|---|
| | 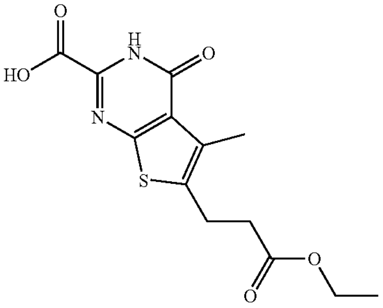 |
| 2/190 | NH4Cl<br>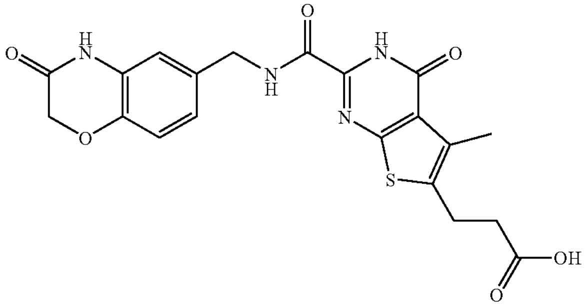 |
| 2/191 | $MeNH_2$•HCl<br>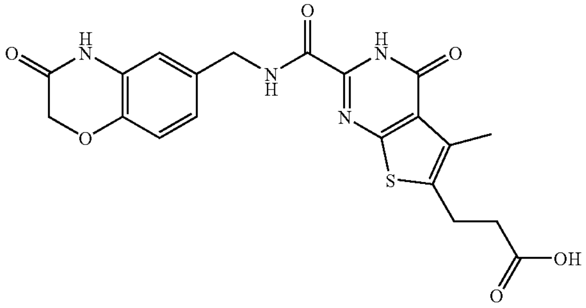 |
| 2/192 | 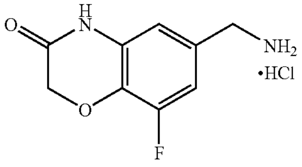<br>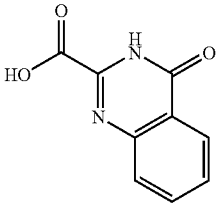 |
| 2/193 | 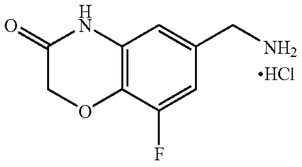 |

TABLE II.1-continued
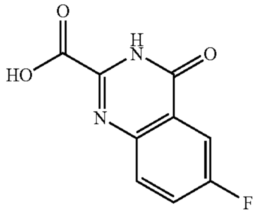
2/194
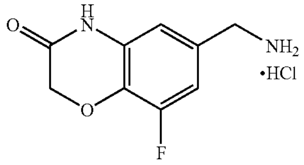
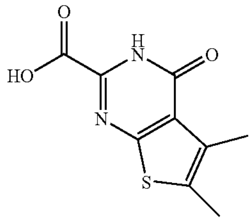
2/195
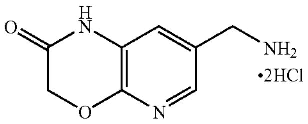
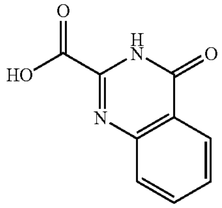
2/196
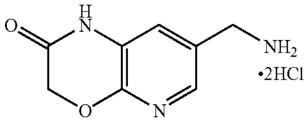
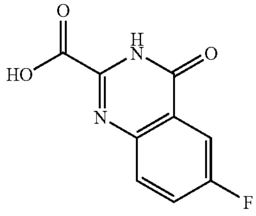
2/197
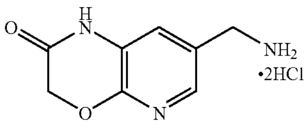

TABLE II.1-continued
| | |
|---|---|
| | 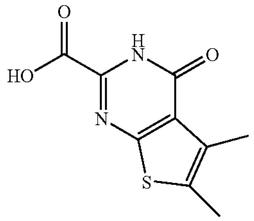 |
| 2/198 | 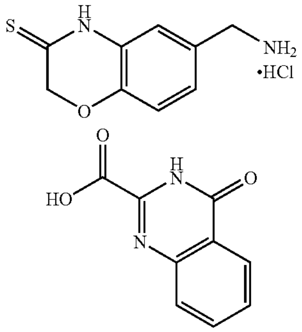 |
| 2/199 | 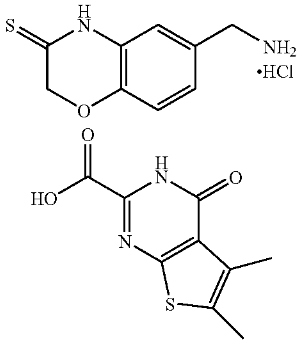 |
| 2/200 | 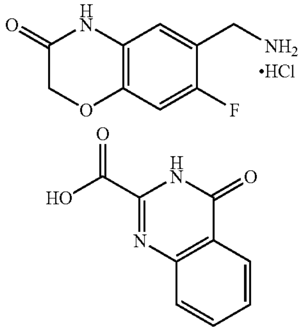 |
| 2/201 | 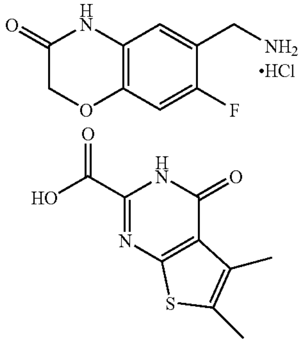 |

TABLE II.1-continued
2/202
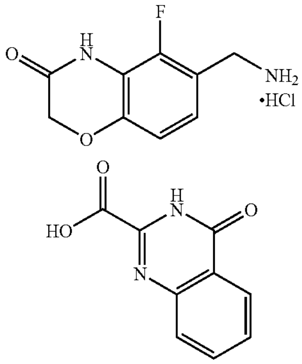
2/203
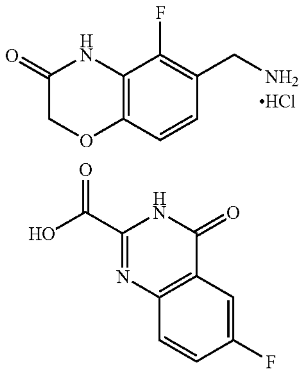
2/204
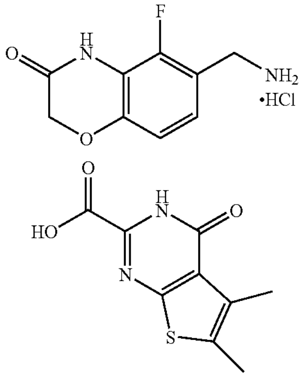
2/205
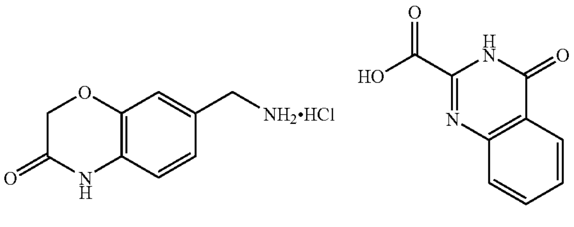
2/206
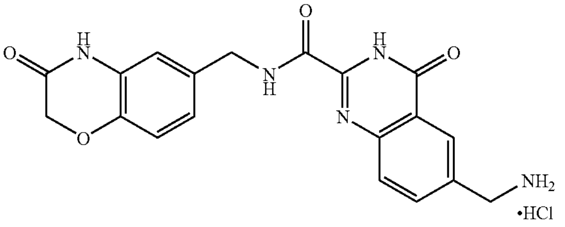

TABLE II.1-continued
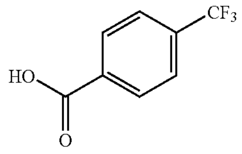
2/207
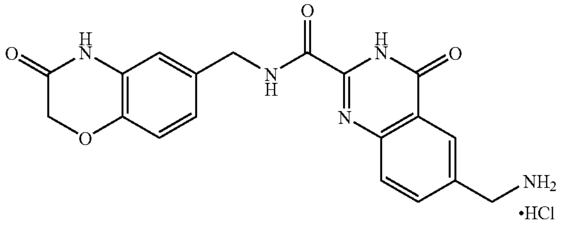
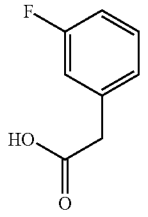
2/213
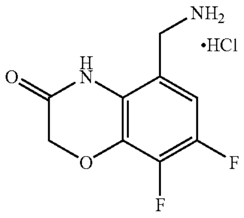
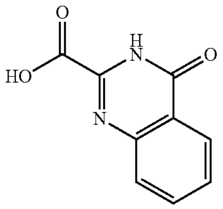
2/214
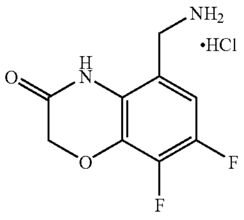
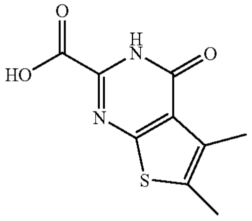
2/215
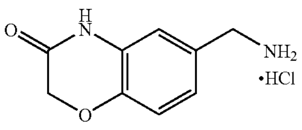
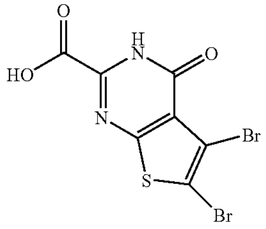

TABLE II.1-continued
2/216
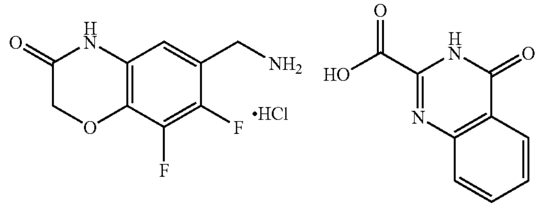
2/217
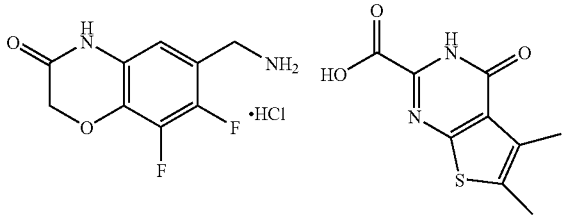
2/220
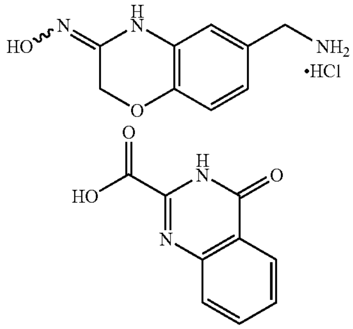
2/221
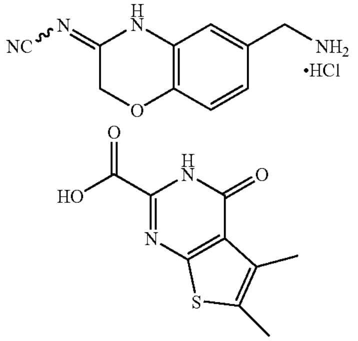
2/222
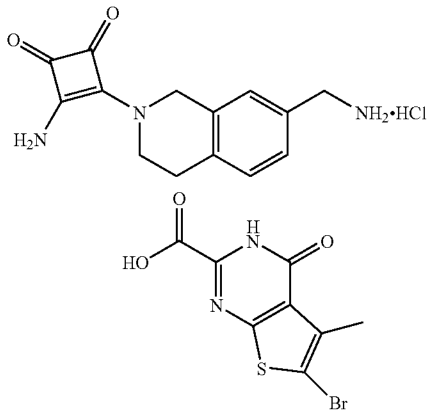

TABLE II.1-continued
2/226
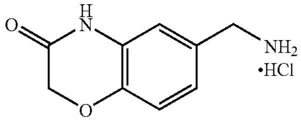
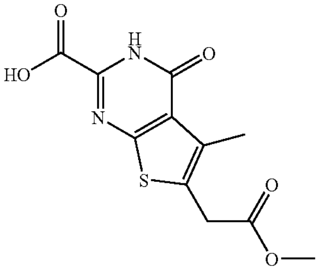
2/227
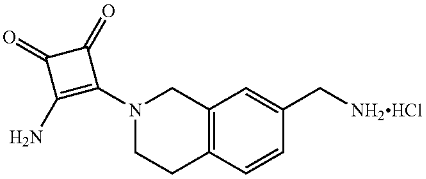
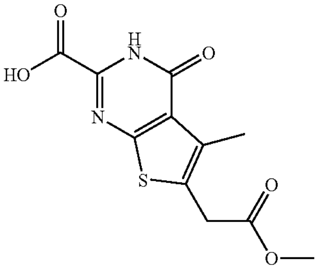
2/228
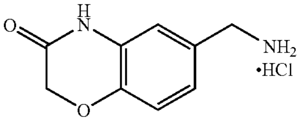
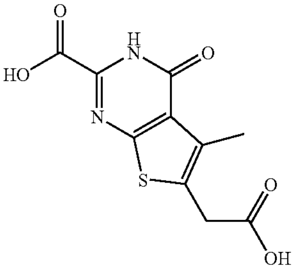
2/229
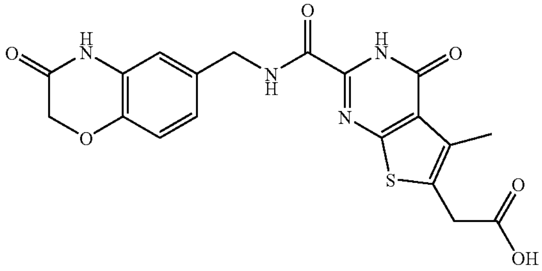
$NH_3$ (0.5M in dioxanne)

TABLE II.1-continued
2/233
MeNH$_2$•HCl
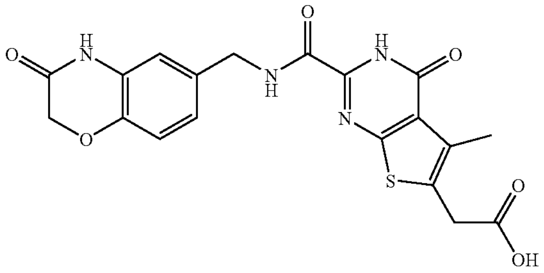
2/234
$(CH_3)_2$NH•HCl
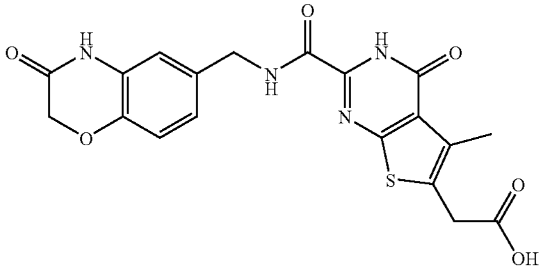
2/235
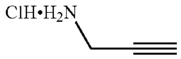
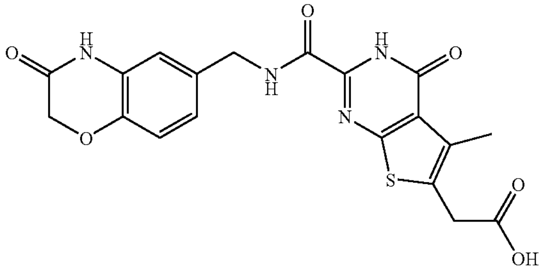
2/241
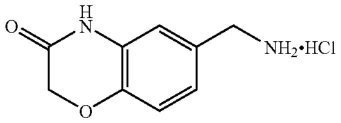
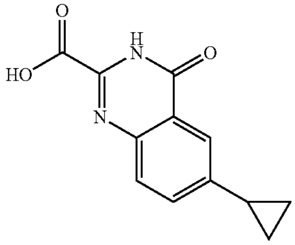
2/242
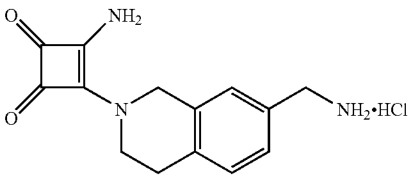

TABLE II.1-continued
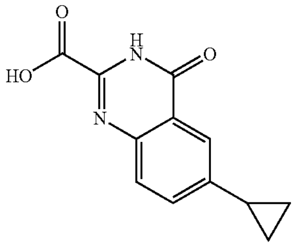
2/243
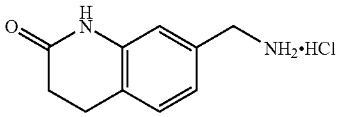
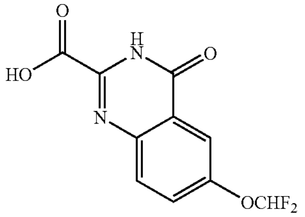
2/244
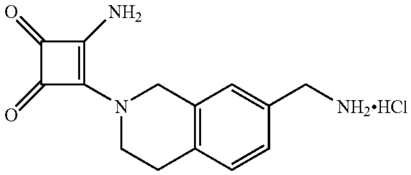
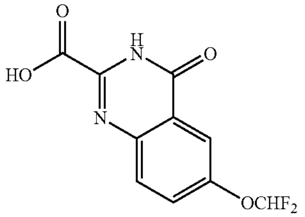
2/247
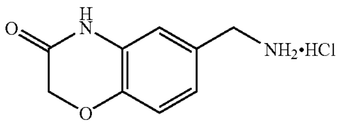
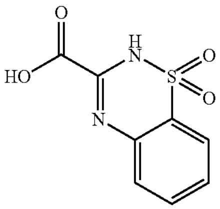
2/248
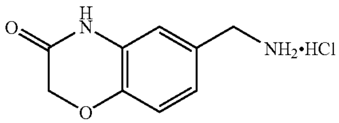

TABLE II.1-continued
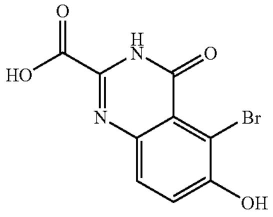
2/265
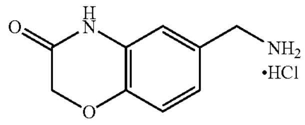
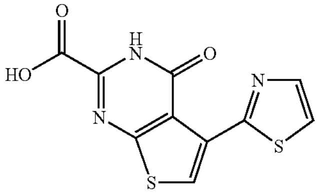
2/271
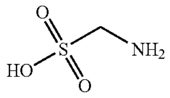
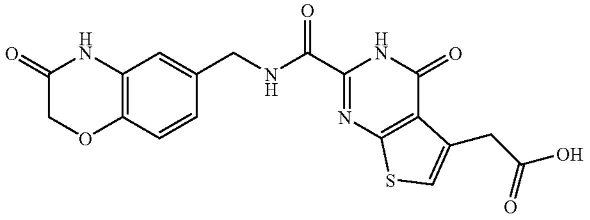
2/273
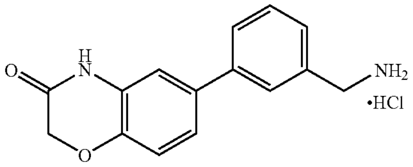
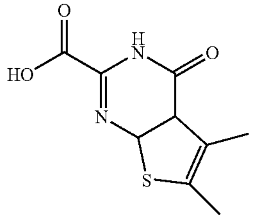
2/275
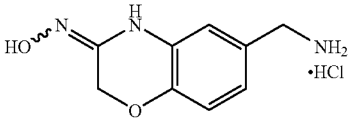
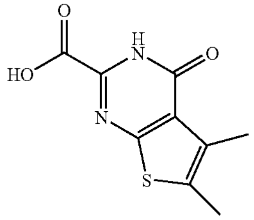

TABLE II.1-continued
| | |
|---|---|
| 2/276 | 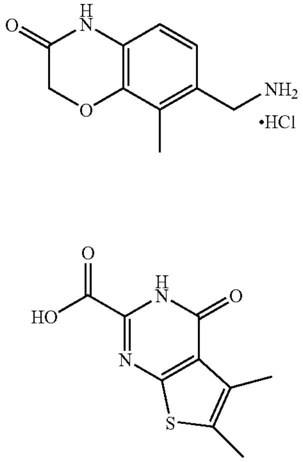 |
| 2/277 | 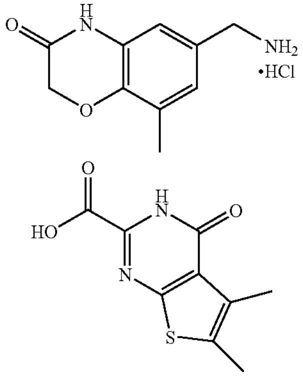 |
| 2/278 | 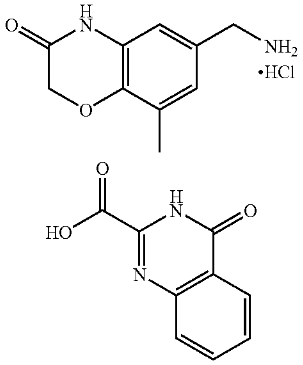 |
| 2/279 | 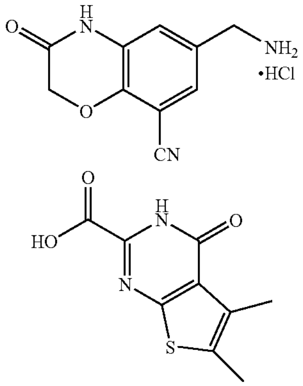 |

TABLE II.1-continued
| | |
|---|---|
| 2/280 | 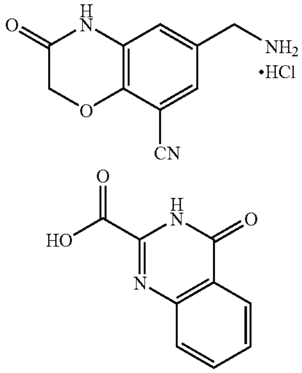 |
| 2/281 | 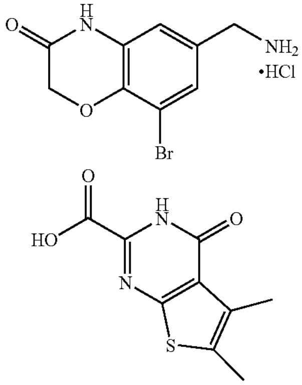 |
| 2/282 | 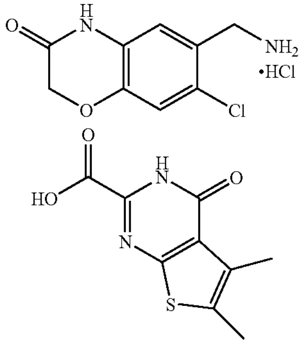 |
| 2/283 | 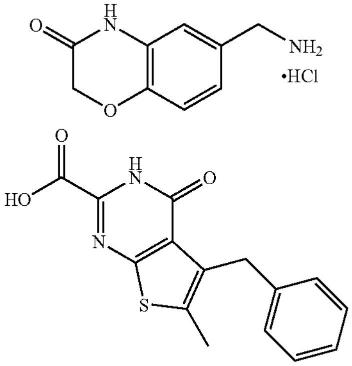 |
| 2/284 | 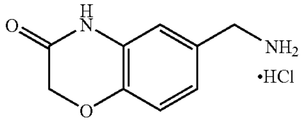 |

TABLE II.1-continued
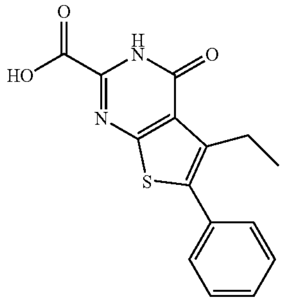
2/285
$NH_3$
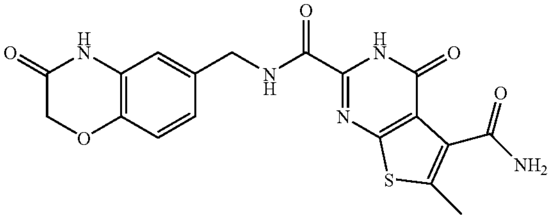
2/286
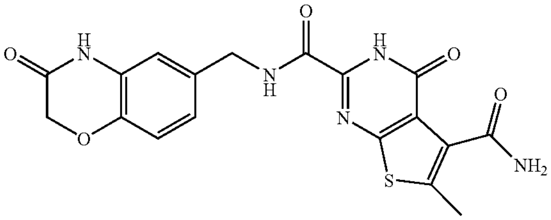
2/287
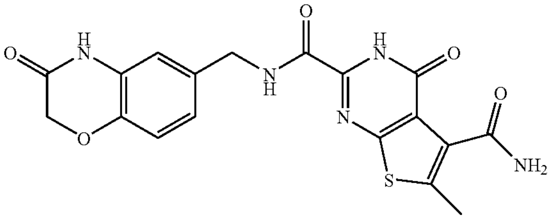
2/288
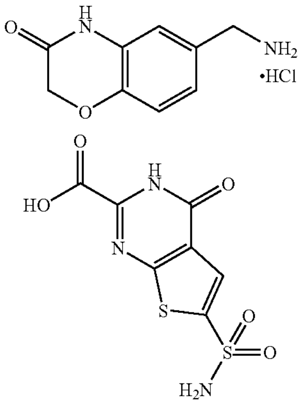
2/373
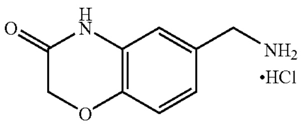

TABLE II.1-continued
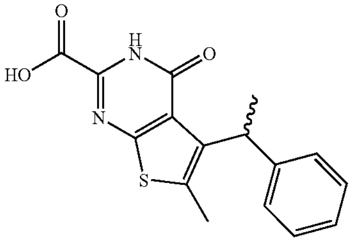
2/374
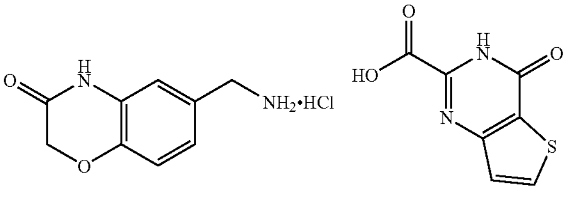
2/375
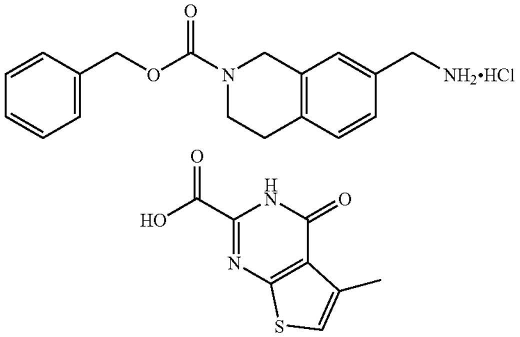
2/378
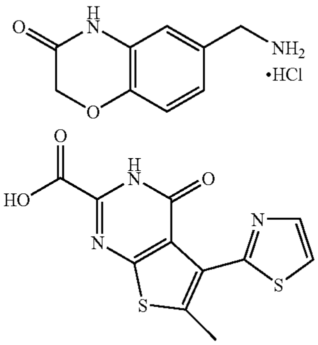
2/379
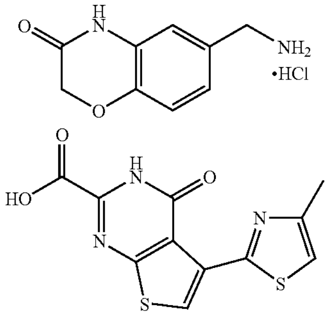

TABLE II.1-continued
| | | |
|---|---|---|
| 2/380 | 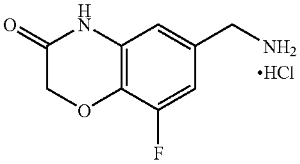 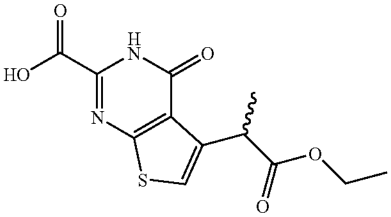 | |
| 2/381 | 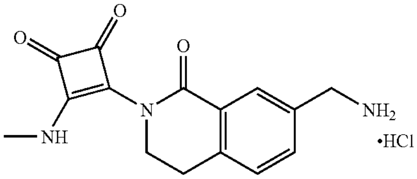 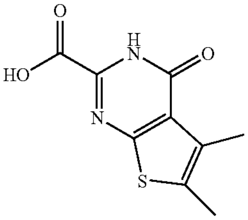 | |
| 2/548 | 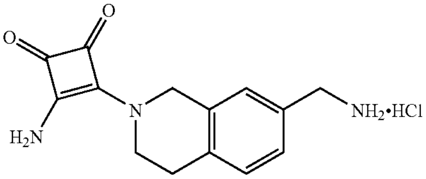 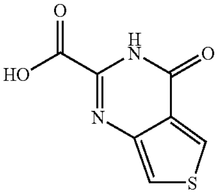 | |
| Ex. # | product | yield |
| 2/1 | 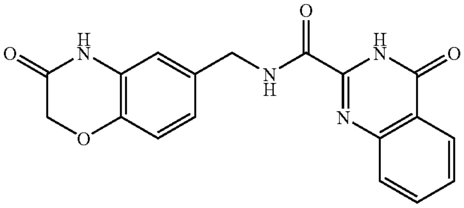 | 77%<br>$[MH]^+ = 351$ |

TABLE II.1-continued
| | | |
|---|---|---|
| 2/2 | 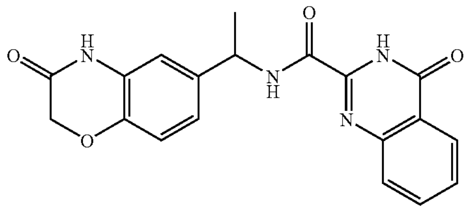 | 57%<br>$[MH]^+ = 365$ |
| 2/3 | 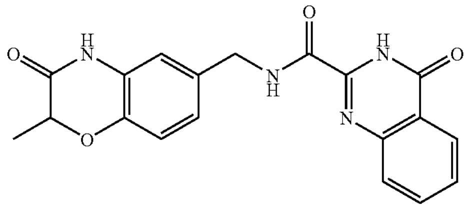 | 80%<br>$[MH]^+ = 365$ |
| 2/4 | 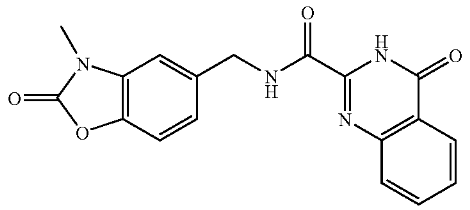 | 76%<br>$[MH]^+ = 351$ |
| 2/5 | 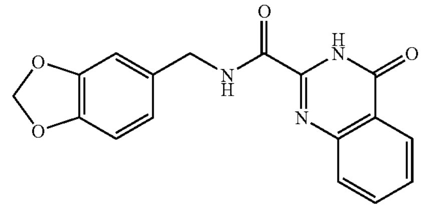 | 25%<br>$[MH]^+ = 324$ |
| 2/6 | 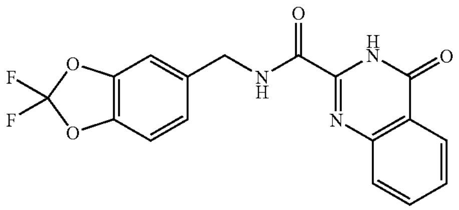 | 87%<br>$[MH]^+ = 360$ |
| 2/7 | 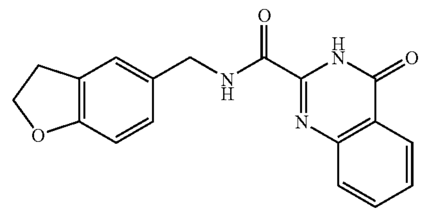 | 71%<br>$[MH]^+ = 322$ |
| 2/8 | 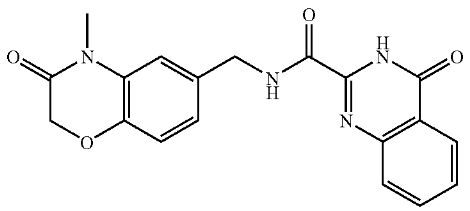 | 74%<br>$[MH]^+ = 365$ |

TABLE II.1-continued
| | | |
|---|---|---|
| 2/9 | 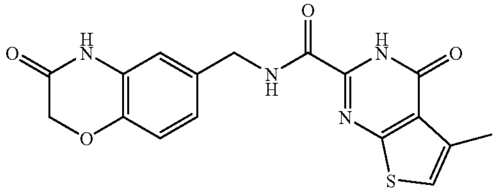 | 98% [MH]$^+$ = 371 |
| 2/10 | 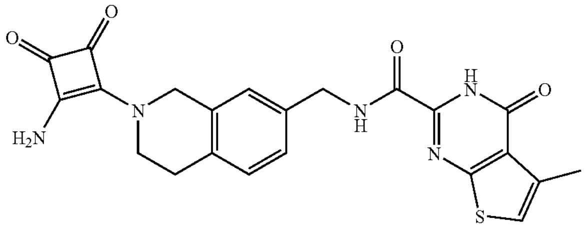 | 90% [MH]$^+$ = 450 |
| 2/11 | 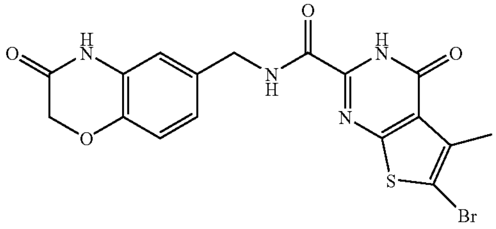 | 67% [MH]$^+$ = 449/451 |
| 2/12 | 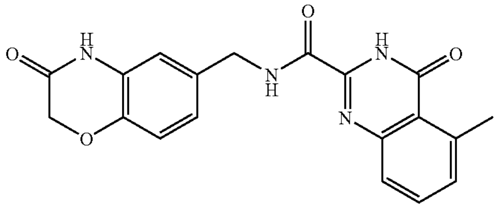 | 72% [MH]$^+$ = 365 |
| 2/13 | 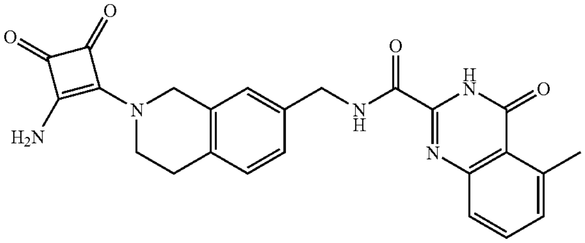 | 82% [MH]$^+$ = 444 |
| 2/14 | 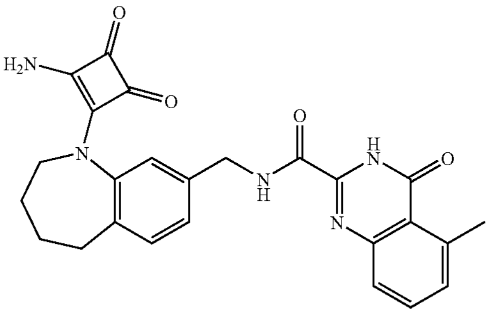 | 83% [MH]$^+$ = 458 |

TABLE II.1-continued
| | | |
|---|---|---|
| 2/15 | 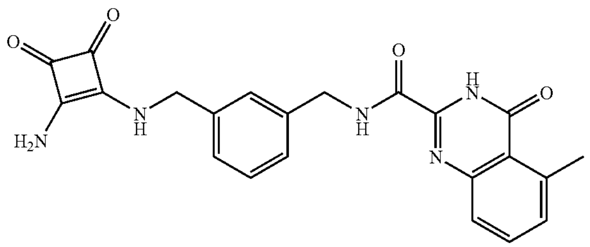 | 83%<br>$[MH]^+ = 418$ |
| 2/16 | 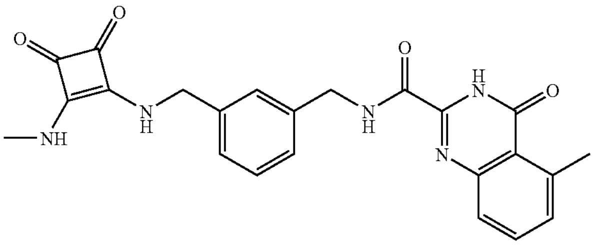 | 73%<br>$[MH]^+ = 432$ |
| 2/17 | 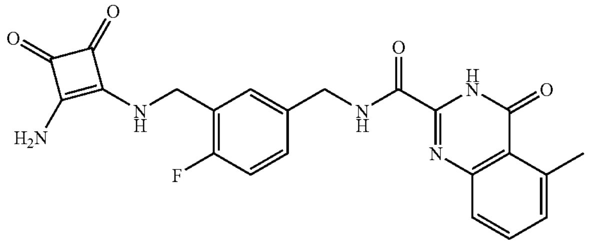 | 79%<br>$[MH]^+ = 426$ |
| 2/18 | 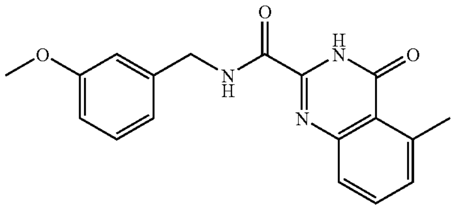 | 65%<br>$[MH]^+ = 324$ |
| 2/19 | 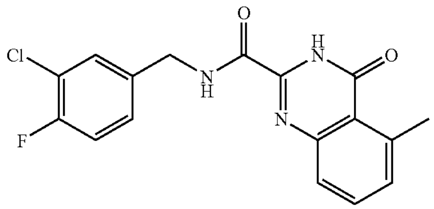 | 73%<br>$[MH]^+ = 346$ |
| 2/20 | 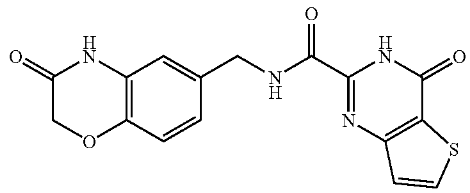 | n.d.<br>$[MH]^+ = 357$ |
| 2/21 | 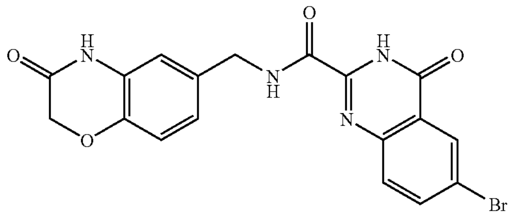 | 77%<br>$[MH]^+ = 429/431$ |

TABLE II.1-continued
| | | |
|---|---|---|
| 2/22 | 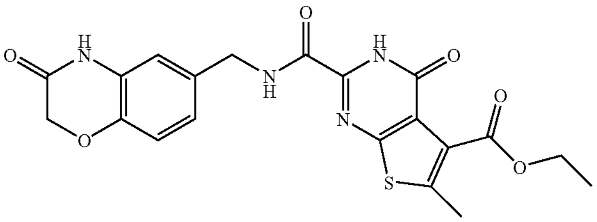 | 78%<br>$[MH]^+ = 443$ |
| 2/23 | 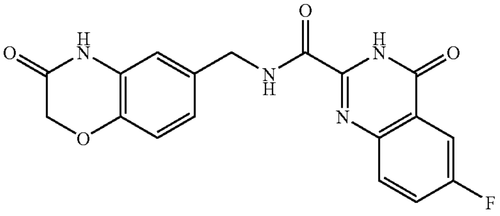 | 62%<br>$[MH]^+ = 369$ |
| 2/26 | 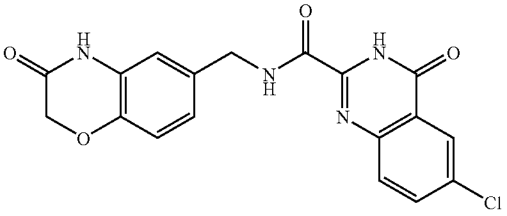 | 63%<br>$[MH]^+ = 385$ |
| 2/27 | 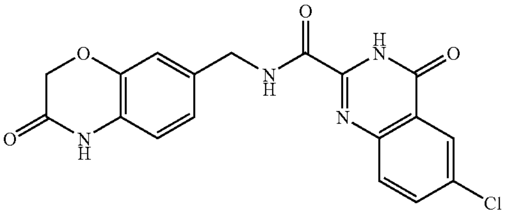 | 93%<br>$[MH]^+ = 385$ |
| 2/28 | 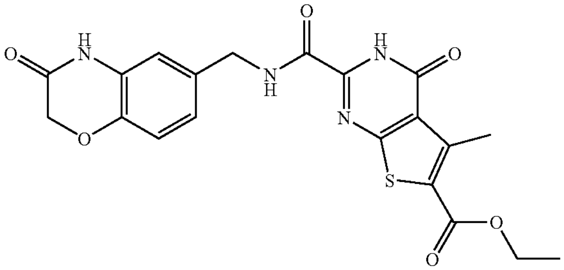 | 88%<br>$[MH]^+ = 443$ |
| 2/31 | 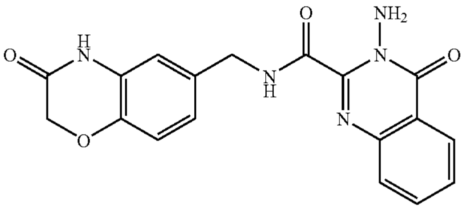 | 10%<br>$[MH]^+ = 366$ |

TABLE II.1-continued
| | | |
|---|---|---|
| 2/32 | 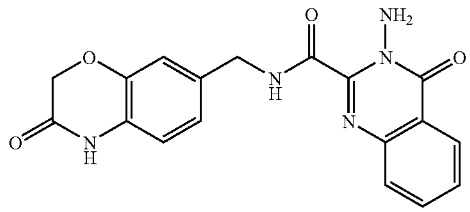 | 13%<br>$[MH]^+ = 366$ |
| 2/35 | 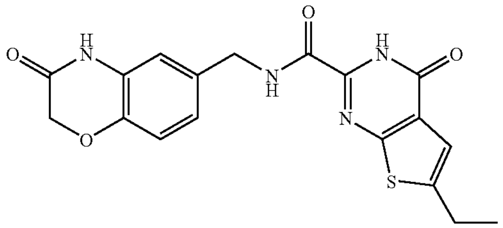 | 67%<br>$[MH]^+ = 385$ |
| 2/37 | 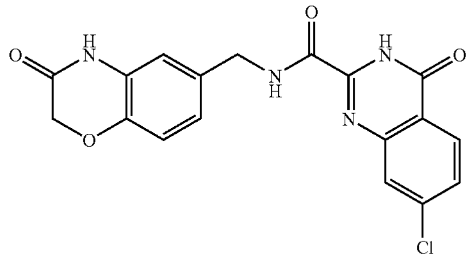 | 55%<br>$[MH]^+ = 385$ |
| 2/38 | 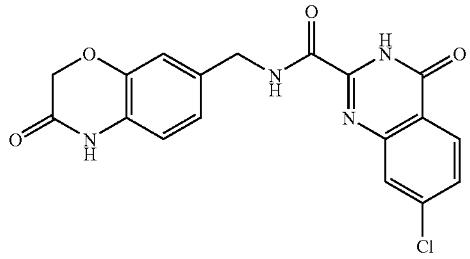 | 87%<br>$[MH]^+ = 385$ |
| 2/39 | 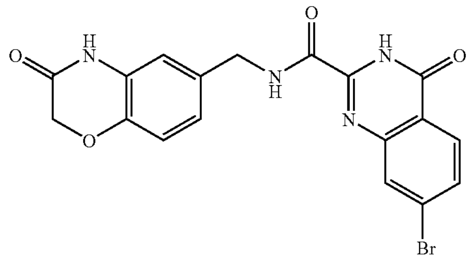 | 73%<br>$[MH]^+ = 419/431$ |
| 2/40 | 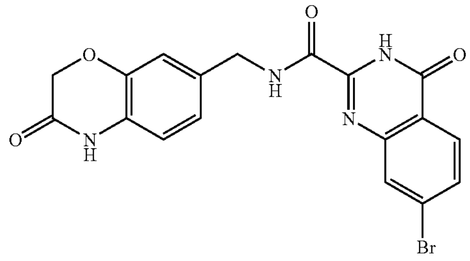 | 80%<br>$[MH]^+ = 429/431$ |

TABLE II.1-continued
2/41
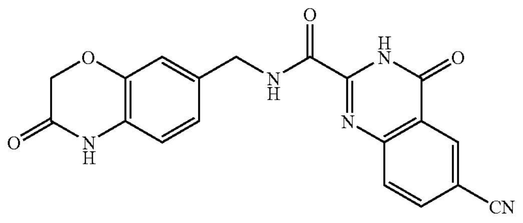
79%
$[MH]^+ = 376$
2/42
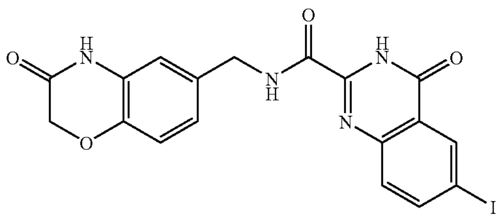
71%
$[MH]^+ = 477$
2/43
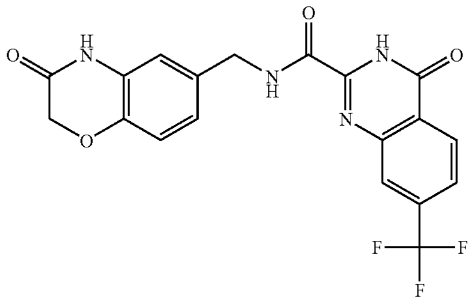
12%
$[MH]^+ = 419$
2/44
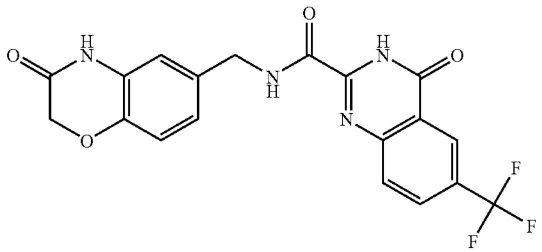
12%
$[MH]^+ = 419$
2/45
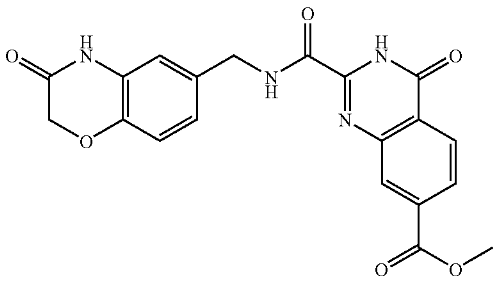
54%
$[MH]^+ = 409$
2/46
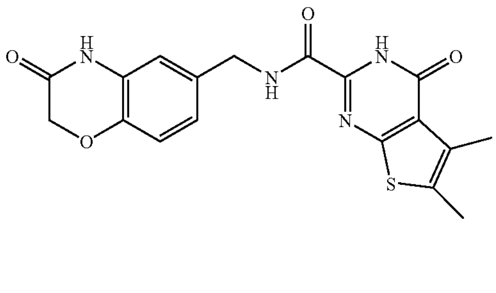
63%
$[MH]^+ = 385$ TABLE II.1-continued
| | | |
|---|---|---|
| 2/47 | 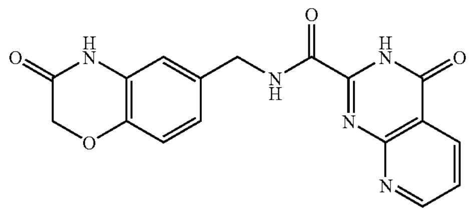 | 86%<br>$[MH]^+ = 352$ |
| 2/48 | 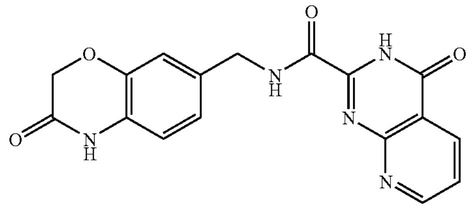 | 79%<br>$[MH]^+ = 352$ |
| 2/49 | 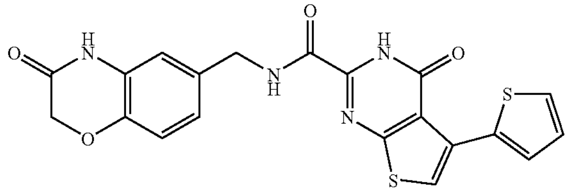 | 11%<br>$[MH]^+ = 439$ |
| 2/50 | 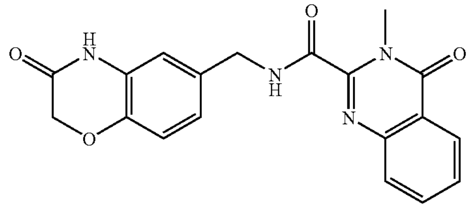 | 33%<br>$[MH]^+ = 365$ |
| 2/51 | 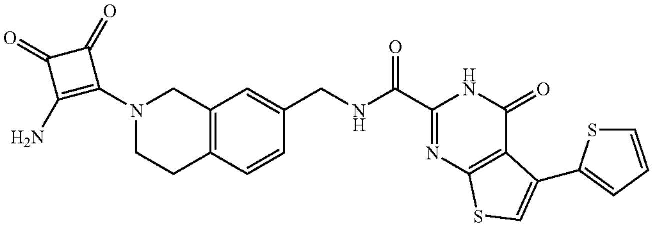 | 15%<br>$[MH]^+ = 518$ |
| 2/53 | 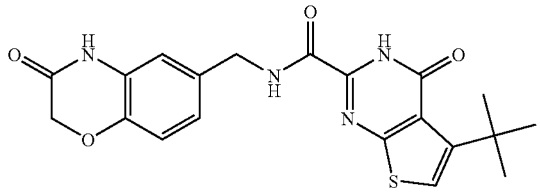 | 85%<br>$[MH]^+ = 413$ |
| 2/54 | 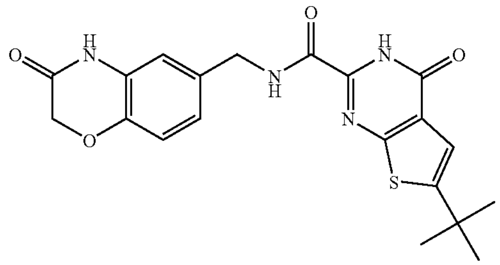 | 64%<br>$[MH]^+ = 413$ |

TABLE II.1-continued
| | | |
|---|---|---|
| 2/55 | 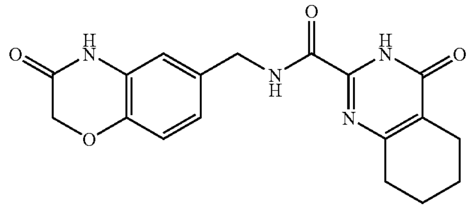 | 15%<br>$[MH]^+ = 355$ |
| 2/56 | 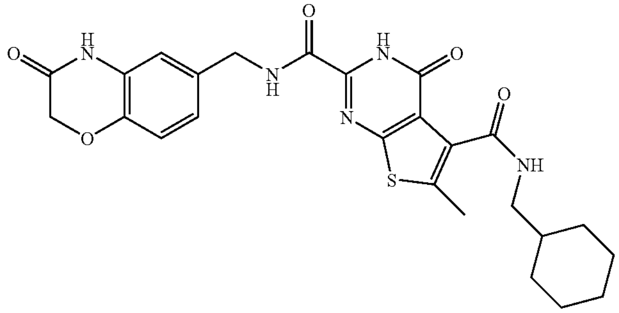 | 85%<br>$[MH]^+ = 510$ |
| 2/57 | 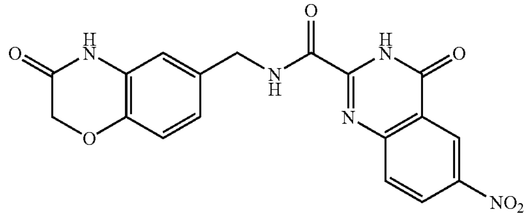 | 26%<br>$[MH]^+ = 396$ |
| 2/58 | 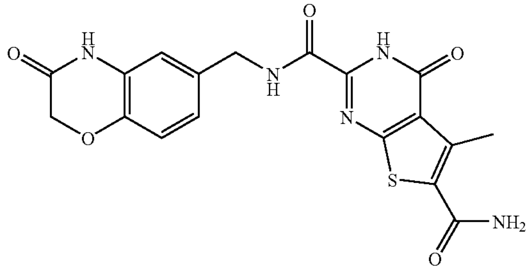 | 48%<br>$[MH]^+ = 414$ |
| 2/59 | 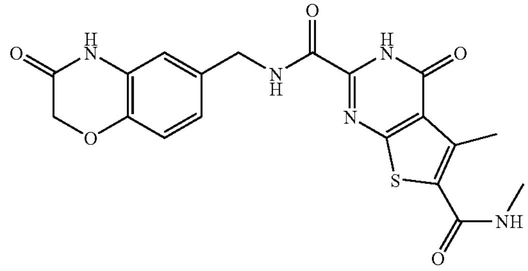 | 4%<br>$[MH]^+ = 428$ |
| 2/60 | 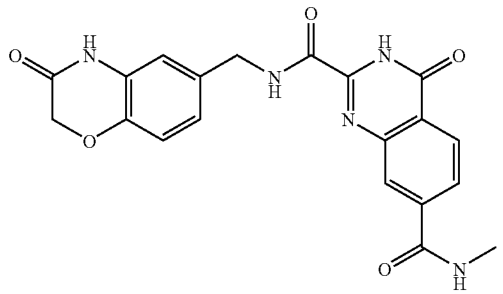 | 39%<br>$[MH]^+ = 408$ |

TABLE II.1-continued
| | | |
|---|---|---|
| 2/61 | 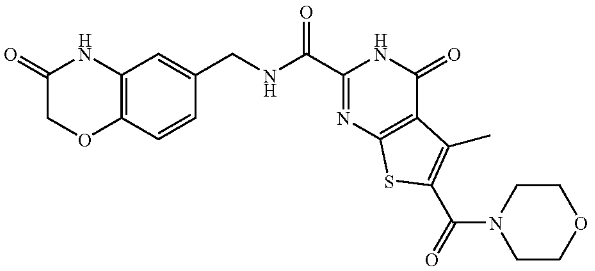 | 24%<br>$[MH]^+ = 484$ |
| 2/62 | 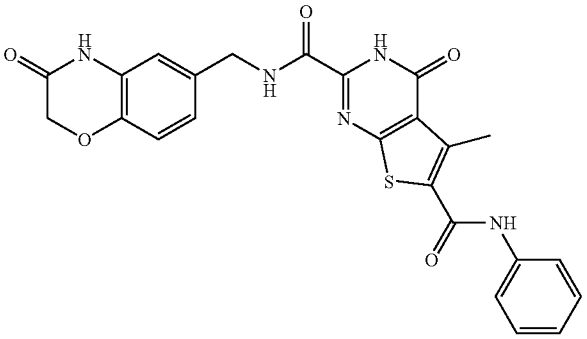 | 21%<br>$[MH]^+ = 490$ |
| 2/63 | 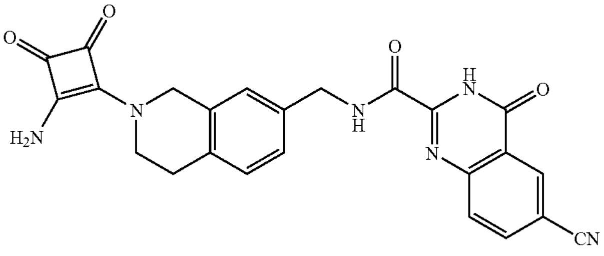 | 55%<br>$[MH]^+ = 455$ |
| 2/64 | 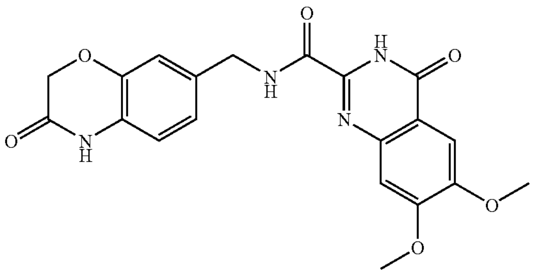 | 79%<br>$[MH]^+ = 411$ |
| 2/65 | 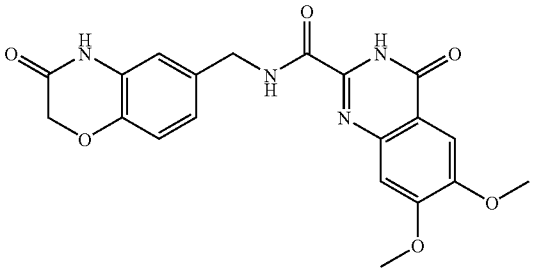 | 66%<br>$[MH]^+ = 411$ |

TABLE II.1-continued
| | | |
|---|---|---|
| 2/66 | 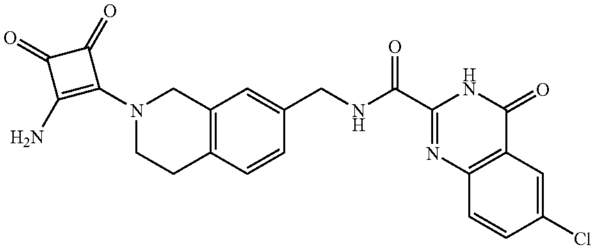 | 88%<br>$[MH]^+ = 464$ |
| 2/68 | 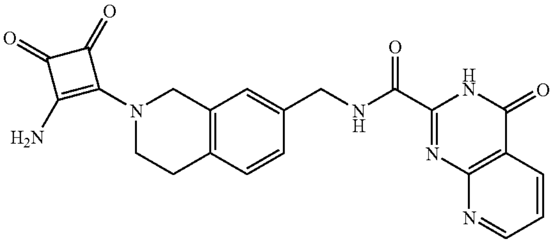 | 40%<br>$[MH]^+ = 431$ |
| 2/69 | 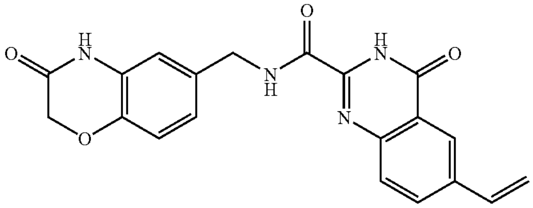 | 76%<br>$[MH]^+ = 377$ |
| 2/70 | 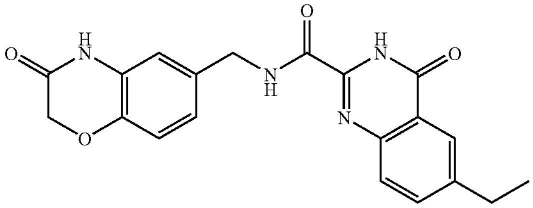 | 85%<br>$[MH]^+ = 379$ |
| 2/71 | 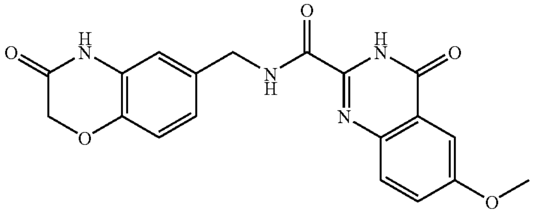 | 75%<br>$[MH]^+ = 381$ |
| 2/72 | 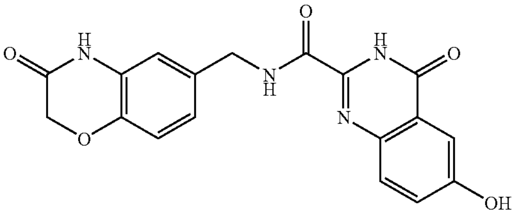 | 85%<br>$[MH]^+ = 368$ |

TABLE II.1-continued
| | | |
|---|---|---|
| 2/73 | 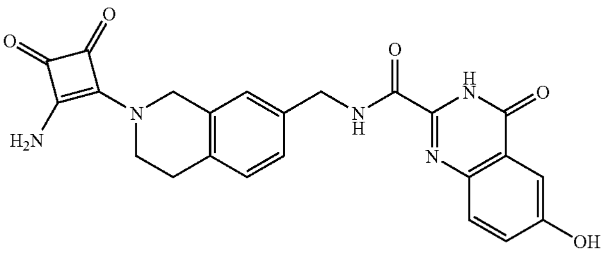 | 85%<br>$[MH]^+ = 446$ |
| 2/74 | 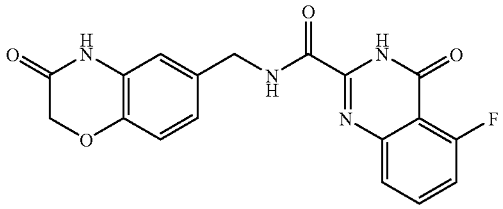 | 67%<br>$[MH]^+ = 369$ |
| 2/75 | 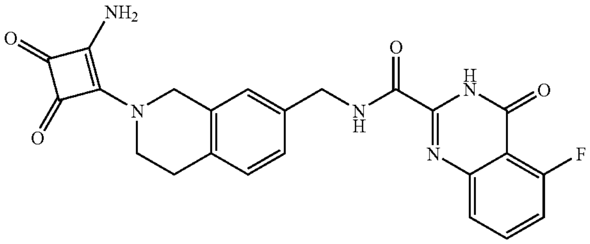 | 78%<br>$[MH]^+ = 448$ |
| 2/76 | 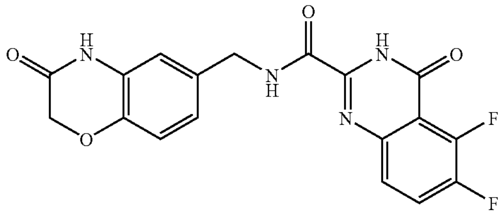 | 86%<br>$[MH]^+ = 387$ |
| 2/77 | 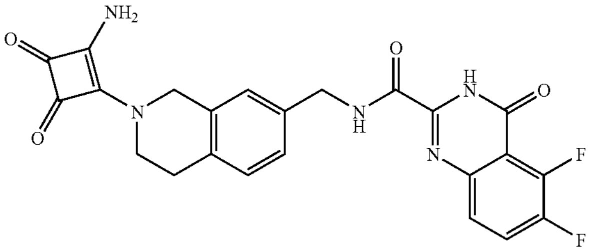 | 81%<br>$[MH]^+ = 466$ |
| 2/78 | 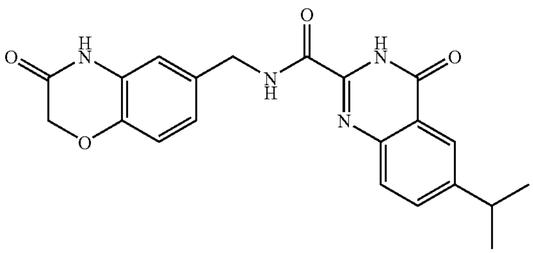 | 76%<br>$[MH]^+ = 393$ |

TABLE II.1-continued
| | | |
|---|---|---|
| 2/79 | 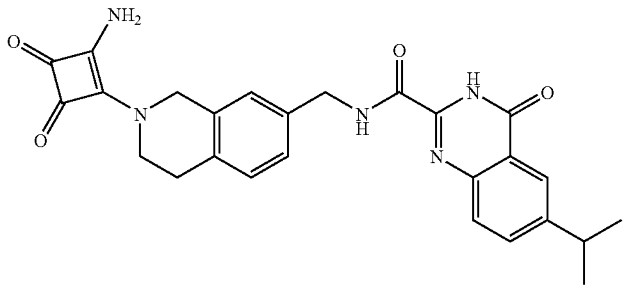 | 87% [MH]$^+$ = 472 |
| 2/80 | 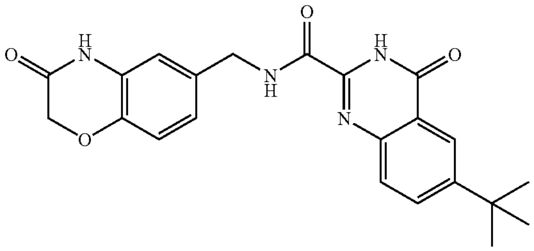 | 68% [MH]$^+$ = 407 |
| 2/81 | 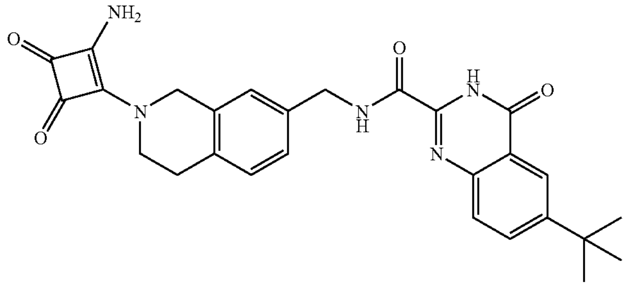 | 80% [MH]$^+$ = 486 |
| 2/82 | 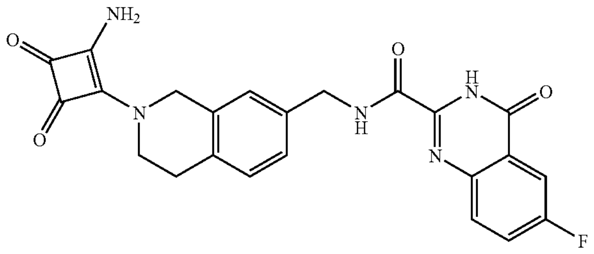 | 85% [MH]$^+$ = 448 |
| 2/83 | 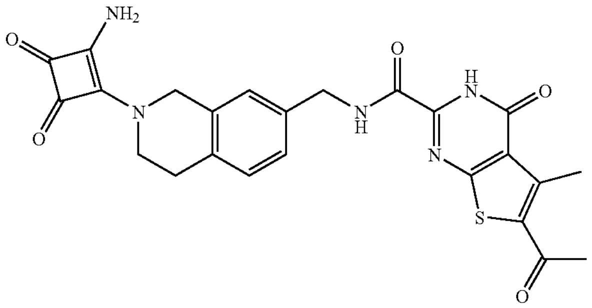 | 91% [MH]$^+$ = 492 |
| 2/84 | 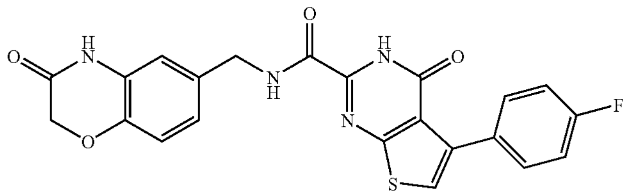 | >99% [MH]$^+$ = 451 |

TABLE II.1-continued
| | | |
|---|---|---|
| 2/85 | 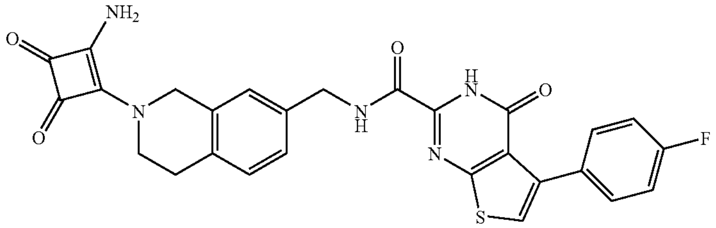 | 90%<br>$[MH]^+ = 530$ |
| 2/86 | 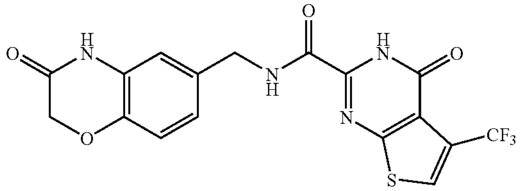 | 52%<br>$[MH]^+ = 425$ |
| 2/87 | 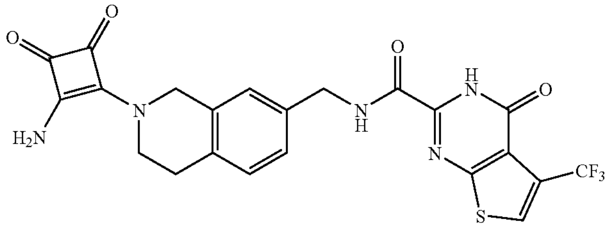 | 37%<br>$[MH]^+ = 504$ |
| 2/88 | 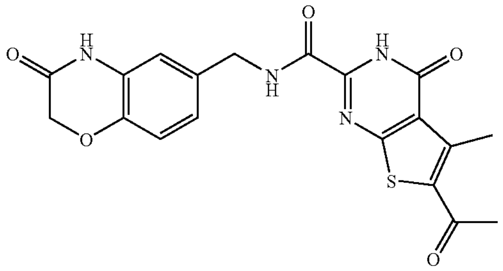 | 86%<br>$[MH]^+ = 413$ |
| 2/91 | 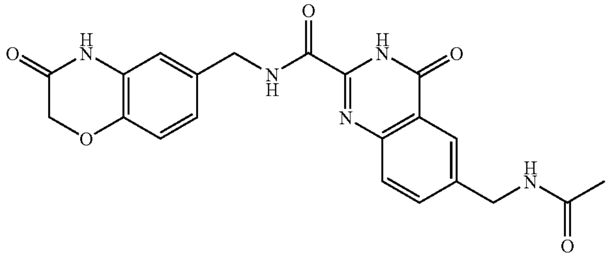 | 69%<br>$[MH]^+ = 422$ |
| 2/92 | 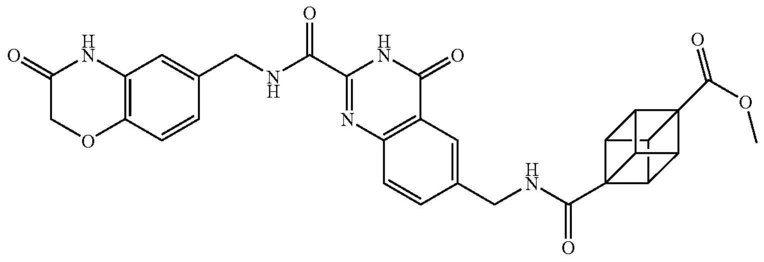 | 89%<br>$[MH]^+ = 568$ |

TABLE II.1-continued
| | | |
|---|---|---|
| 2/93 | 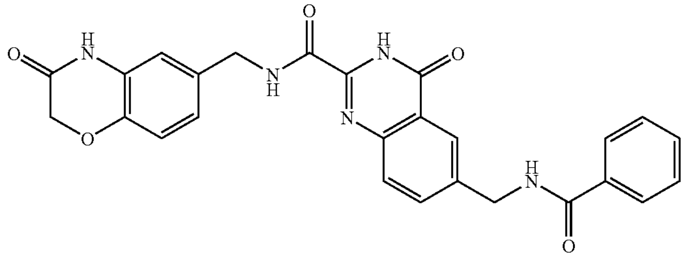 | 95%<br>$[MH]^+ = 484$ |
| 2/96 | 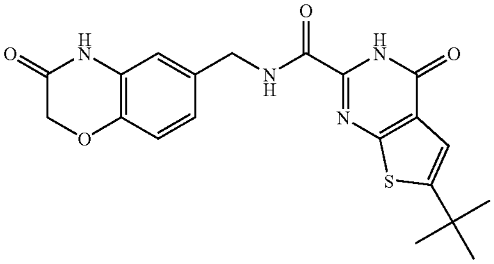 | 70%<br>$[MH]^+ = 533$ |
| 2/97 | 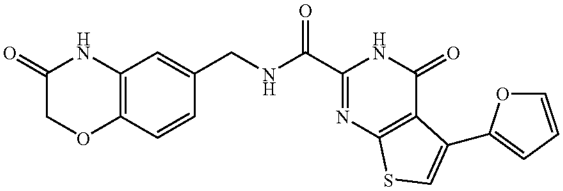 | 35%<br>$[MH]^+ = 423$ |
| 2/98 | 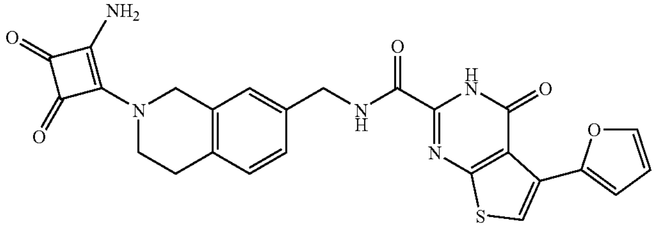 | 87%<br>$[MH]^+ = 502$ |
| 2/99 | 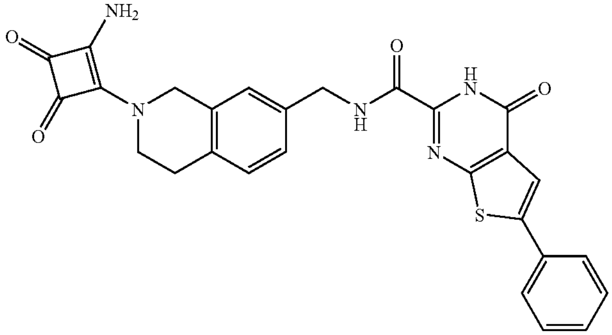 | 5%<br>$[MH]^+ = 512$ |
| 2/100 | 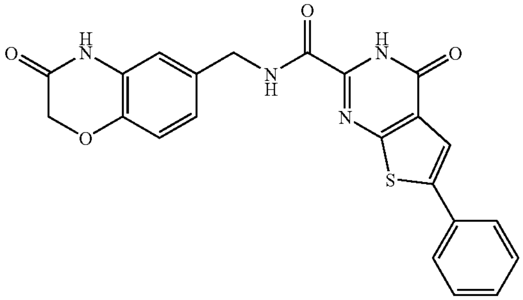 | 18%<br>$[MH]^+ = 433$ |

TABLE II.1-continued
| | | |
|---|---|---|
| 2/101 | 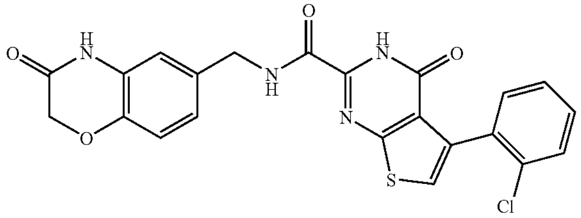 | 71% [MH]$^+$ = 467 |
| 2/102 | 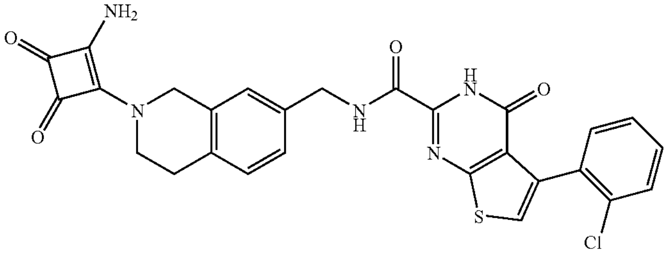 | quant. [MH]$^+$ = 547 |
| 2/105 | 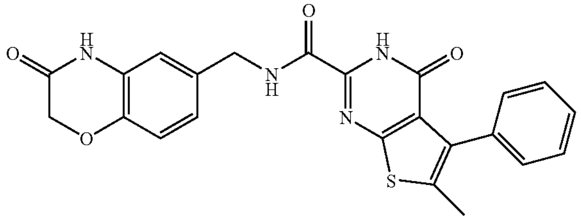 | quant. [MH]$^+$ = 447 |
| 2/106 | 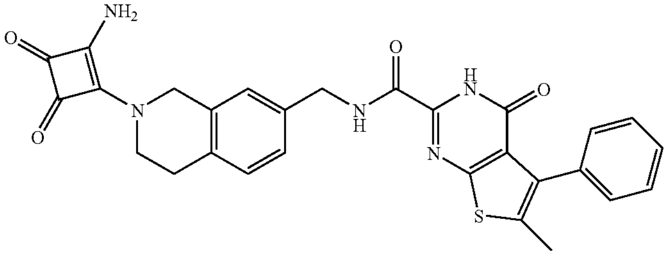 | quant. [MH]$^+$ = 526 |
| 2/109 | 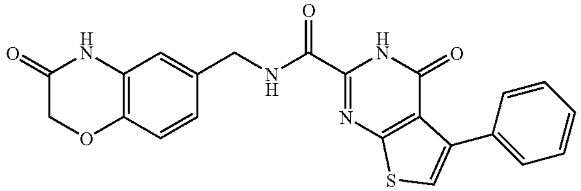 | quant. [MH]$^+$ = 463 |
| 2/110 | 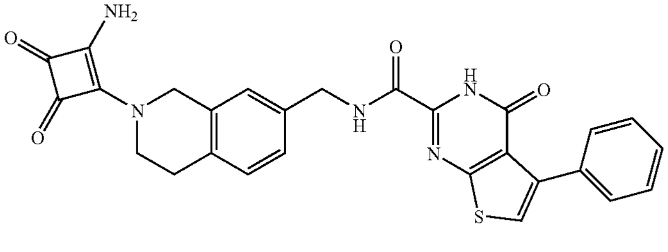 | quant. [MH]$^+$ = 542 |

TABLE II.1-continued
| | | |
|---|---|---|
| 2/111 | 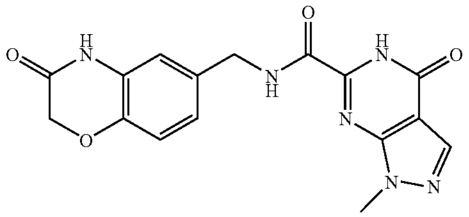 | 69%<br>$[MH]^+ = 355$ |
| 2/112 | 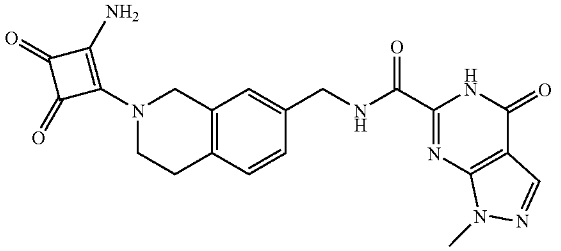 | 76%<br>$[MH]^+ = 434$ |
| 2/115 | 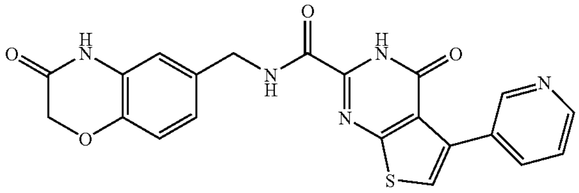 | 73%<br>$[MH]^+ = 434$ |
| 2/116 | 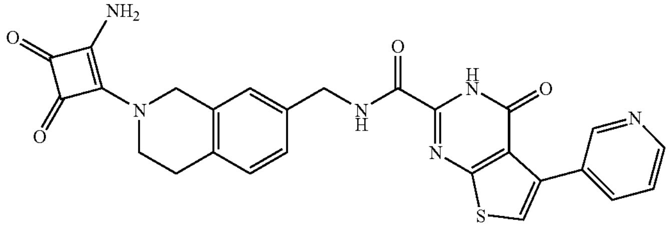 | 50%<br>$[MH]^+ = 513$ |
| 2/123 | 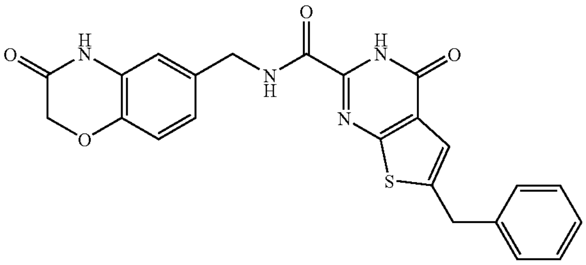 | 80%<br>$[MH]^+ = 447$ |
| 2/124 | 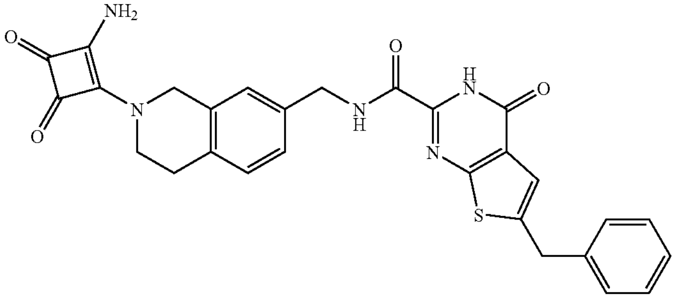 | 88%<br>$[MH]^+ = 526$ |

TABLE II.1-continued
| | | |
|---|---|---|
| 2/127 | 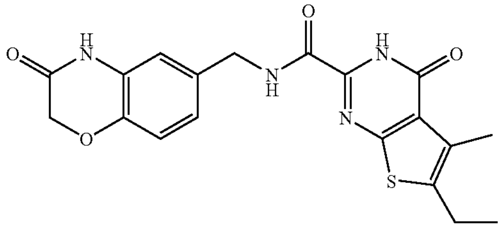 | 93%<br>$[MH]^+ = 399$ |
| 2/128 | 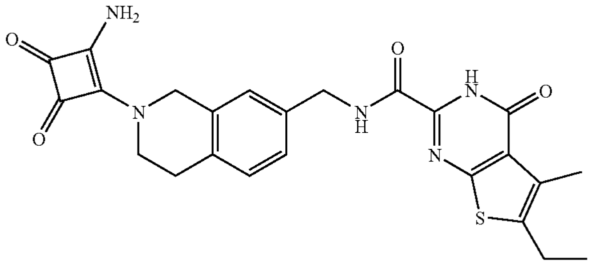 | 97%<br>$[MH]^+ = 478$ |
| 2/133 | 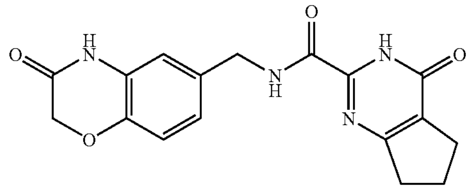 | n.d.<br>$[MH]^+ = 341$ |
| 2/134 | 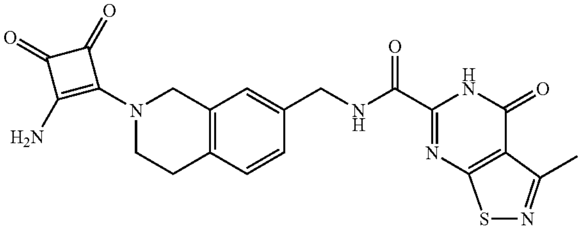 | 13%<br>$[MH]^+ = 451$ |
| 2/135 | 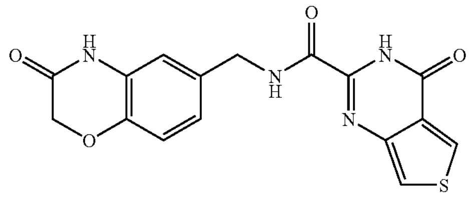 | 41%<br>$[MH]^+ = 357$ |
| 2/136 | 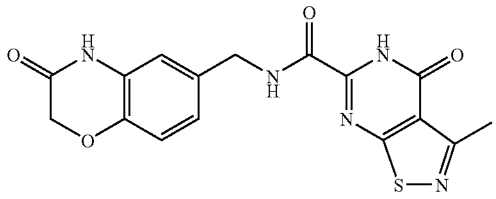 | 9%<br>$[MH]^+ = 372$ |

TABLE II.1-continued
| | | |
|---|---|---|
| 2/137 | 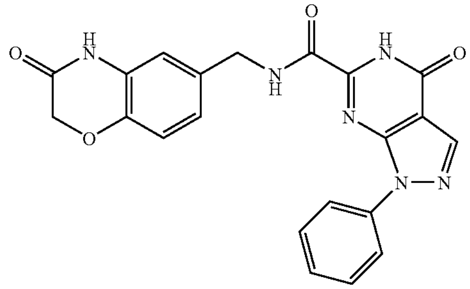 | 96%<br>$[MH]^+ = 417$ |
| 2/138 | 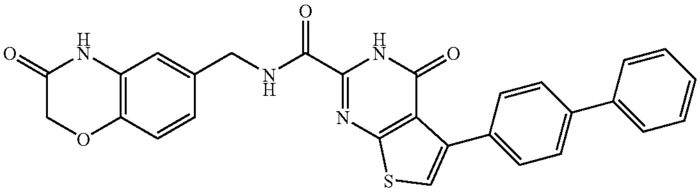 | 88%<br>$[MH]^+ = 509$ |
| 2/139 | 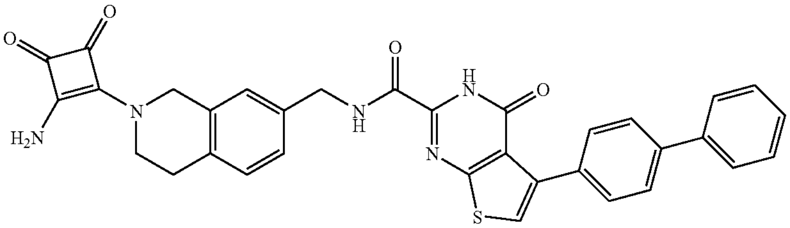 | 99%<br>$[MH]^+ = 588$ |
| 2/140 | 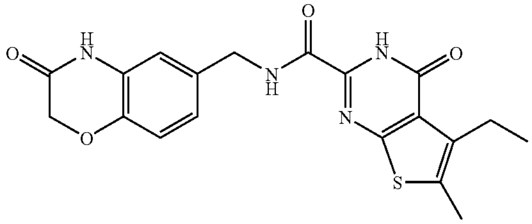 | 87%<br>$[MH]^+ = 399$ |
| 2/141 | 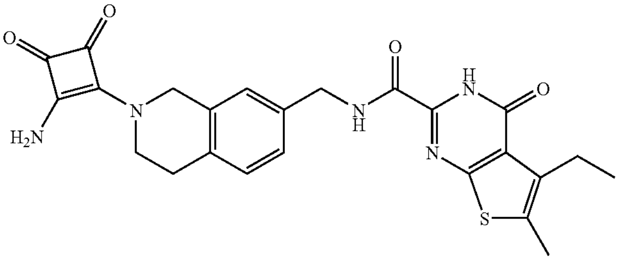 | 72%<br>$[MH]^+ = 478$ |
| 2/142 | 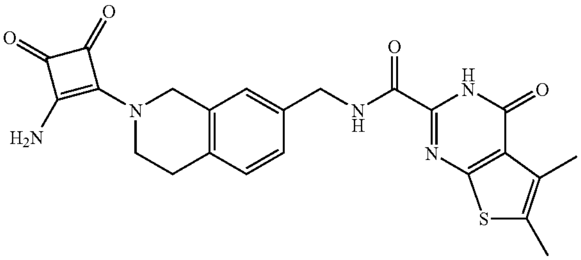 | 89%<br>$[MH]^+ = 464$ |

TABLE II.1-continued
| | | |
|---|---|---|
| 2/147 | 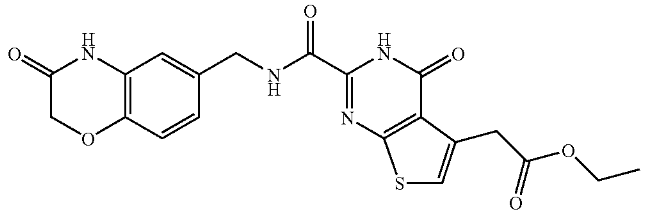 | 72%<br>$[MH]^+ = 443$ |
| 2/148 | 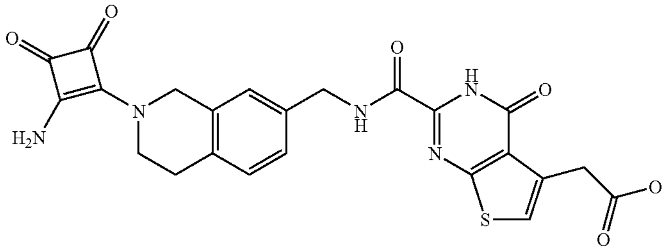 | n.d<br>$[MH]^+ = 522$ |
| 2/149 | 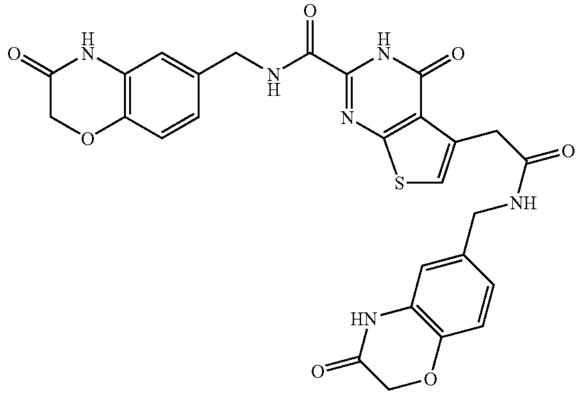 | 16%<br>$[MH]^+ = 575$ |
| 2/150 | 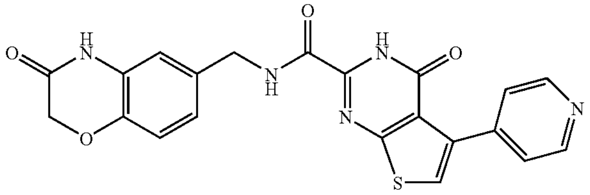 | 6%<br>$[MH]^+ = 434$ |
| 2/151 | 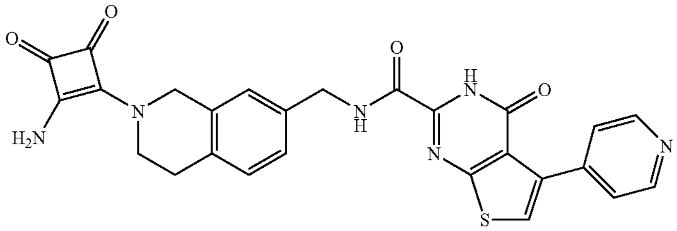 | 19%<br>$[MH]^+ = 513$ |
| 2/154 | 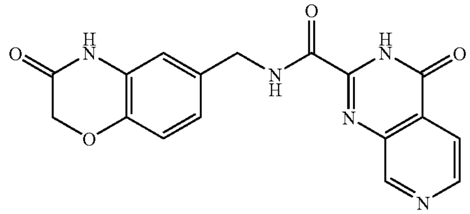 | 21%<br>$[MH]^+ = 352$ |

TABLE II.1-continued
| | | |
|---|---|---|
| 2/155 | 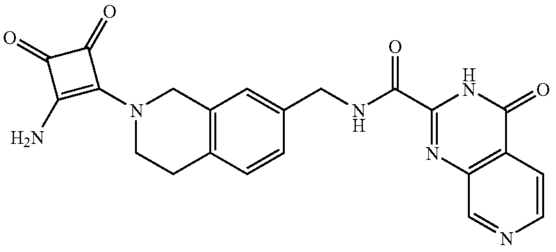 | 55%<br>$[MH]^+ = 431$ |
| 2/156 | 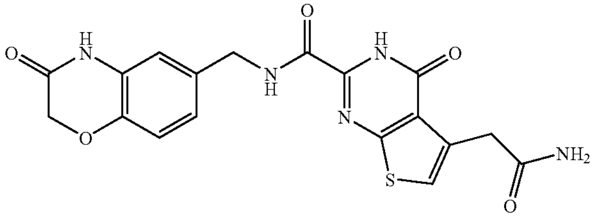 | 79%<br>$[MH]^+ = 414$ |
| 2/157 | 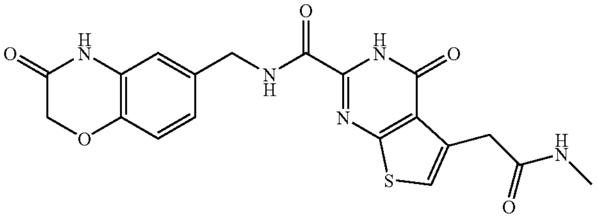 | 85%<br>$[MH]^+ = 428$ |
| 2/158 | 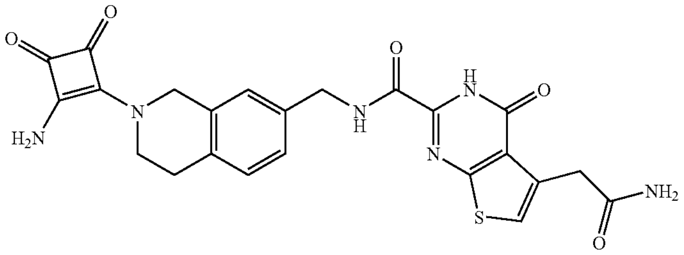 | 54%<br>$[MH]^+ = 493$ |
| 2/159 | 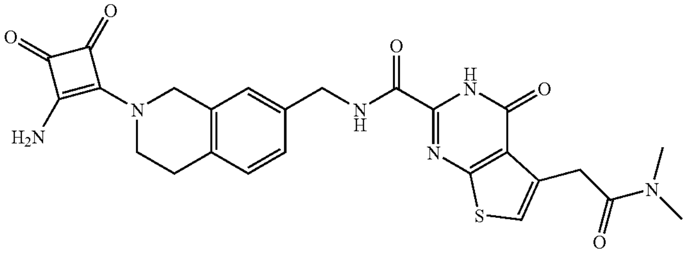 | 32%<br>$[MH]^+ = 521$ |
| 2/160 | 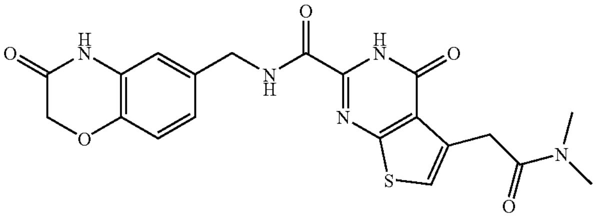 | 50%<br>$[MH]^+ = 442$ |

TABLE II.1-continued
| | | |
|---|---|---|
| 2/161 | 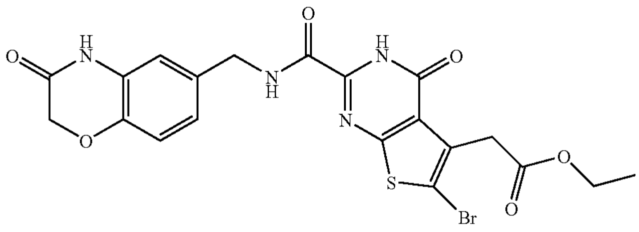 | 85%<br>$[MH]^+ = 521/523$ |
| 2/162 | 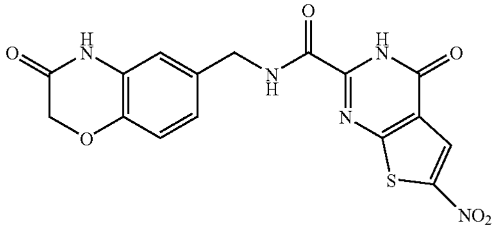 | n.d.<br>$[MH]^+$ = n.d. |
| 2/163 | 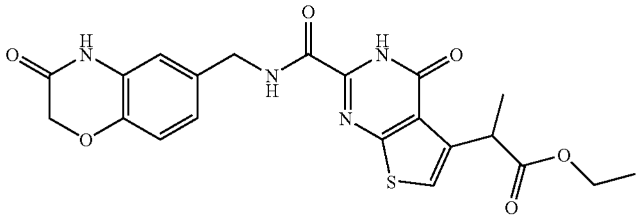 | 84%<br>$[MH]^+ = 457$ |
| 2/164 | 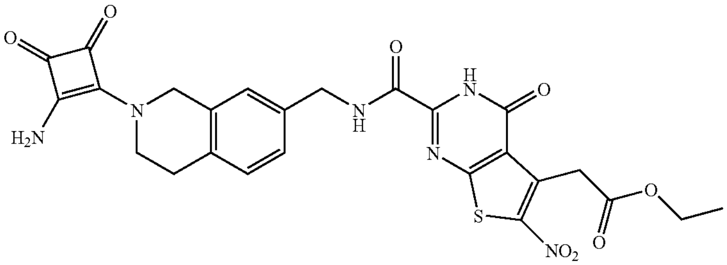 | n.d.<br>$[MH]^+ = 567$ |
| 2/165 | 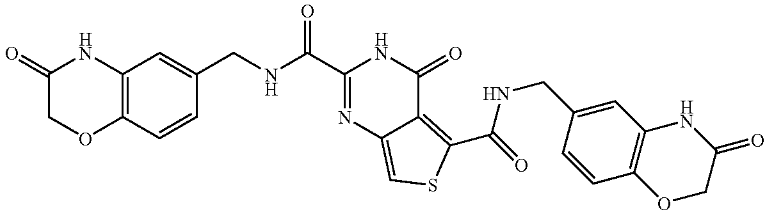 | 70%<br>$[MH]^+ = 561$ |
| 2/179 | 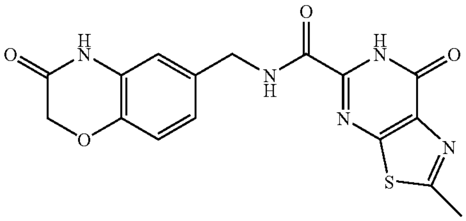 | 20%<br>$[MH]^+ = 372$ |

TABLE II.1-continued
| | | |
|---|---|---|
| 2/180 | 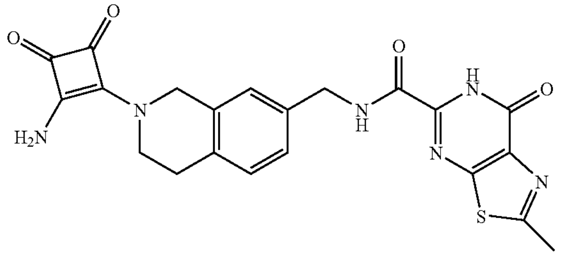 | 24%<br>$[MH]^+ = 451$ |
| 2/181 | 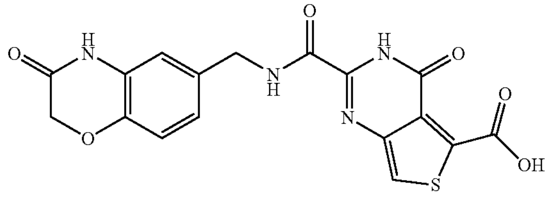 | 20%<br>$[MH]^+ = 372$ |
| 2/182 | 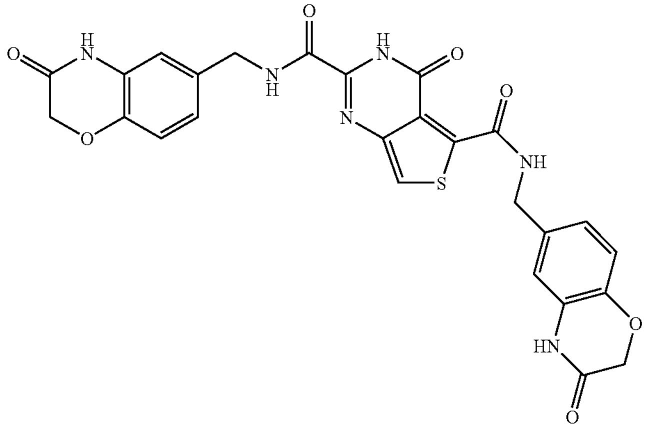 | 70%<br>$[MH]^+ = 561$ |
| 2/183 | 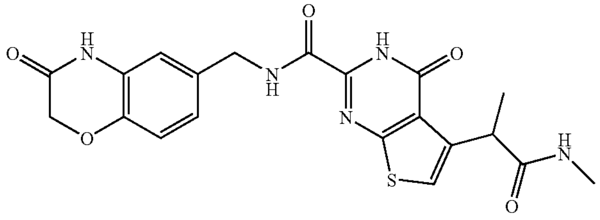 | 97%<br>$[MH]^+ = 442$ |
| 2/184 | 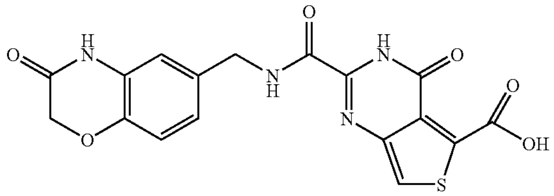 | 2%<br>$[MH]^+ = 401$ |
| 2/185 | 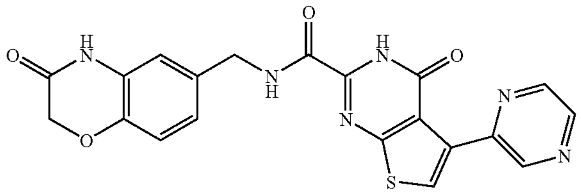 | 46%<br>$[MH]^+ = 435$ |

TABLE II.1-continued
| | | |
|---|---|---|
| 2/186 | 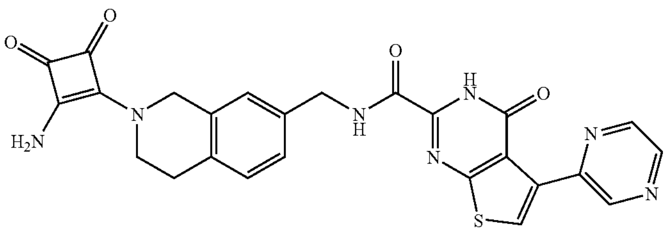 | 41%<br>$[MH]^+ = 514$ |
| 2/189 | 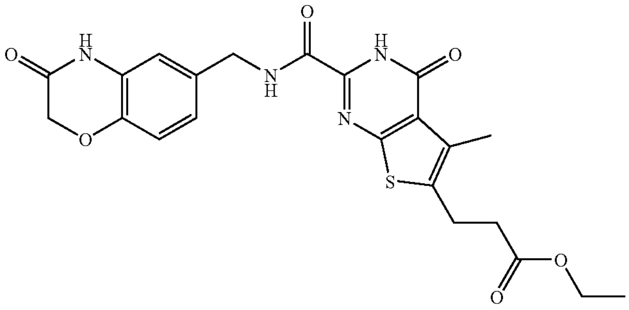 | 80%<br>$[MH]^+ = 471$ |
| 2/190 | 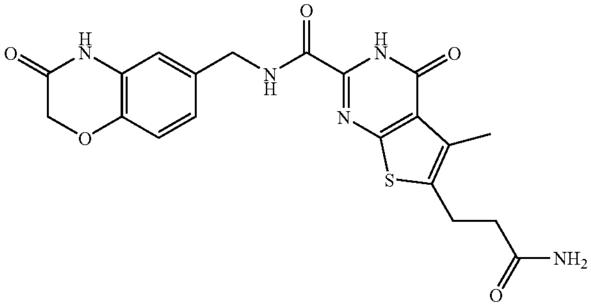 | 45%<br>$[MH]^+ = 442$ |
| 2/191 | 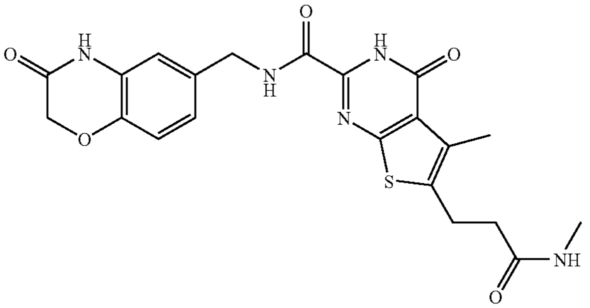 | 71%<br>$[MH]^+ = 446$ |
| 2/192 | 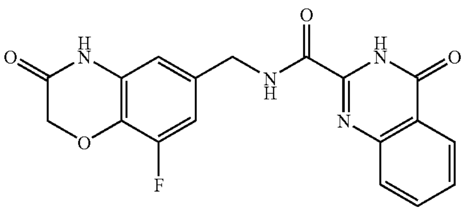 | 53%<br>$[MH]^+ = 369$ |
| 2/193 | 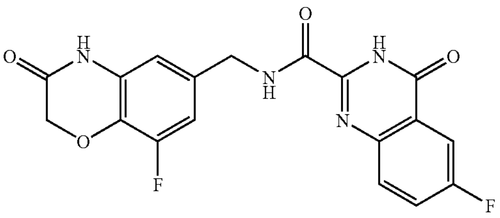 | 38%<br>$[MH]^+ = 387$ |

TABLE II.1-continued
| | | |
|---|---|---|
| 2/194 | 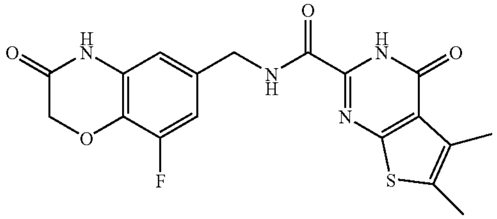 | 94%<br>$[MH]^+ = 403$ |
| 2/195 | 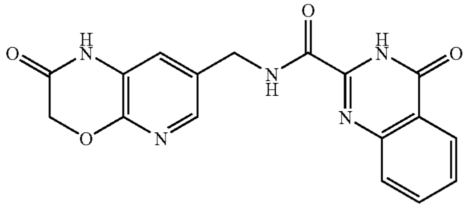 | 78%<br>$[MH]^+ = 352$ |
| 2/196 | 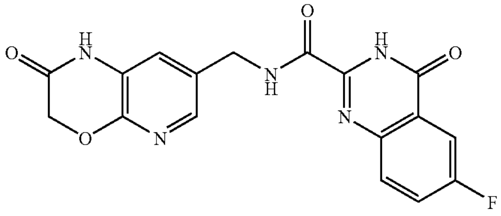 | 86%<br>$[MH]^+ = 370$ |
| 2/197 | 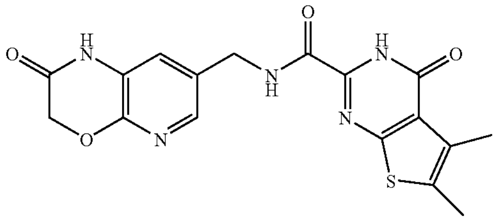 | 81%<br>$[MH]^+ = 386$ |
| 2/198 | 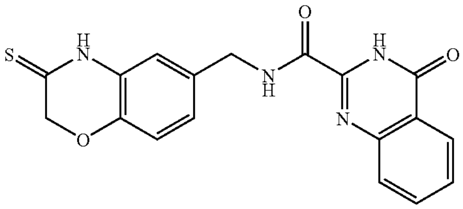 | 62%<br>$[MH]^+ = 367$ |
| 2/199 | 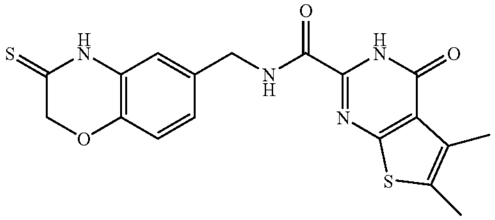 | 63%<br>$[MH]^+ = 401$ |
| 2/200 | 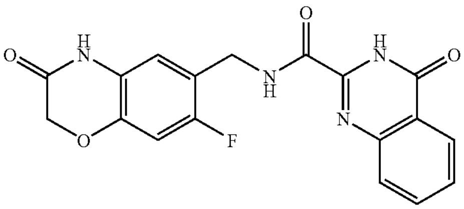 | 73%<br>$[MH]^+ = 369$ |

TABLE II.1-continued
| | | |
|---|---|---|
| 2/201 | 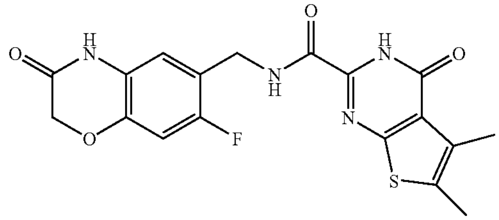 | 88%<br>$[MH]^+ = 403$ |
| 2/202 | 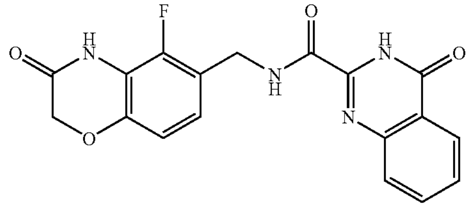 | 79%<br>$[MH]^+ = 369$ |
| 2/203 | 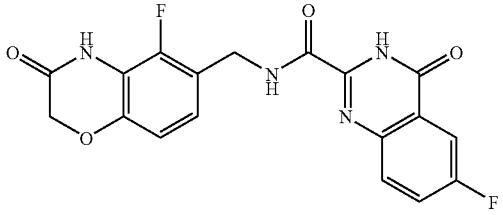 | 90%<br>$[MH]^+ = 387$ |
| 2/204 | 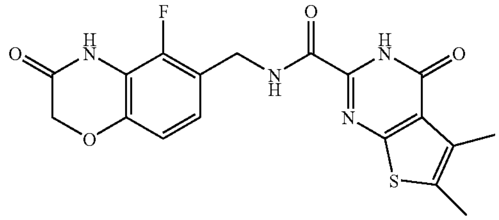 | 89%<br>$[MH]^+ = 896$ |
| 2/205 | 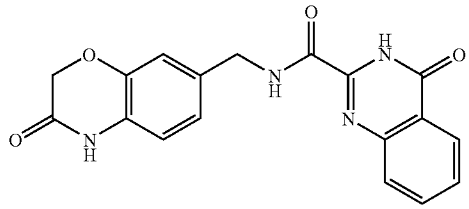 | 59%<br>$[MH]^+ = 351$ |
| 2/206 | 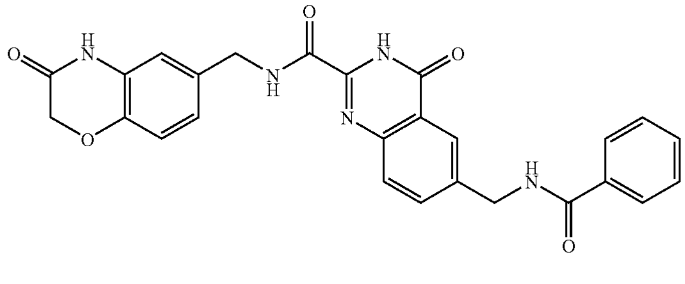 | 91%<br>$[MH]^+ = 552$ |

TABLE II.1-continued
| | | |
|---|---|---|
| 2/207 | 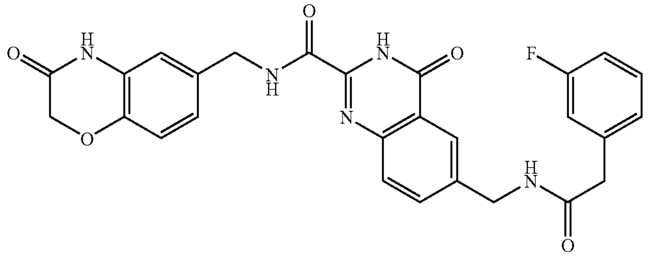 | 65%<br>$[MH]^+ = 516$ |
| 2/213 | 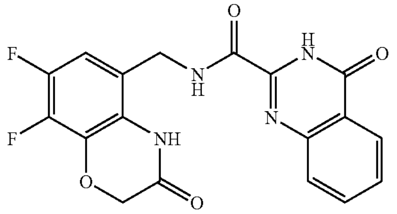 | 72%<br>$[MH]^+ = 387$ |
| 2/214 | 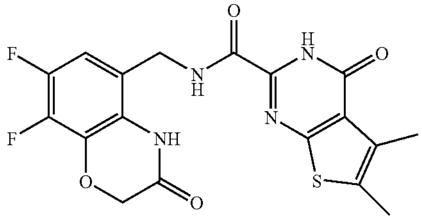 | 95%<br>$[MH]^+ = 421$ |
| 2/215 | 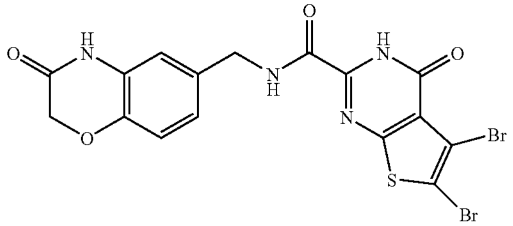 | n.d.<br>$[MH]^+ = 513/515/517$ |
| 2/216 | 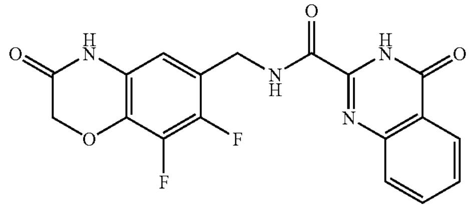 | 89%<br>$[MH]^+ = 387$ |
| 2/217 | 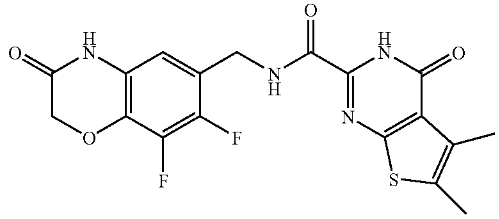 | 74%<br>$[MH]^+ = 421$ |
| 2/220 | 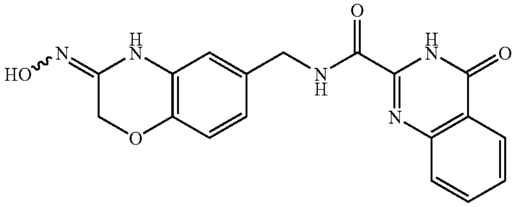 | n.d.<br>$[MH]^+ = 366$ |

TABLE II.1-continued
2/221
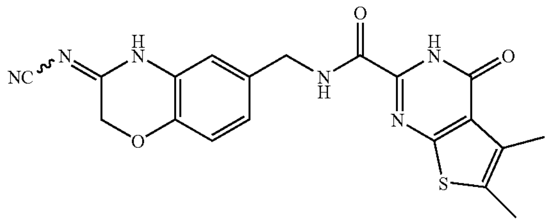
n.d.
$[MH]^+ = 409$
2/222
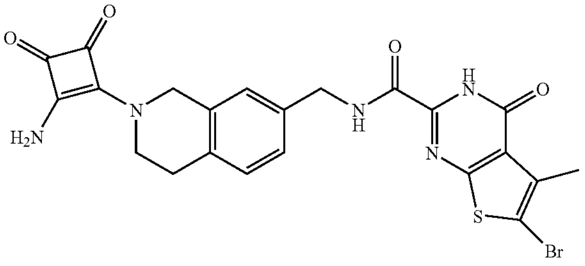
80%
$[MH]^+ = 528/530$
2/226
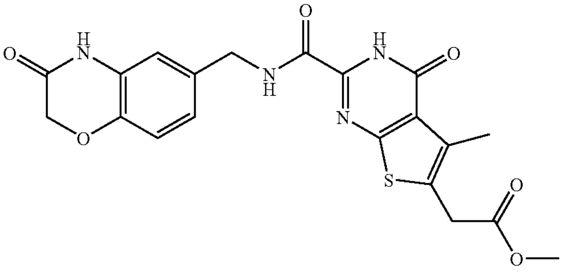
59%
$[MH]^+ = 443$
2/227
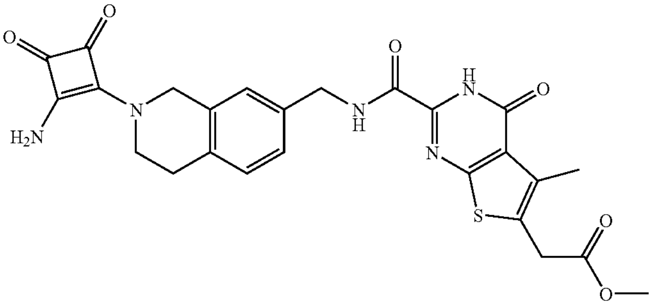
65%
$[MH]^+ = 522$
2/228
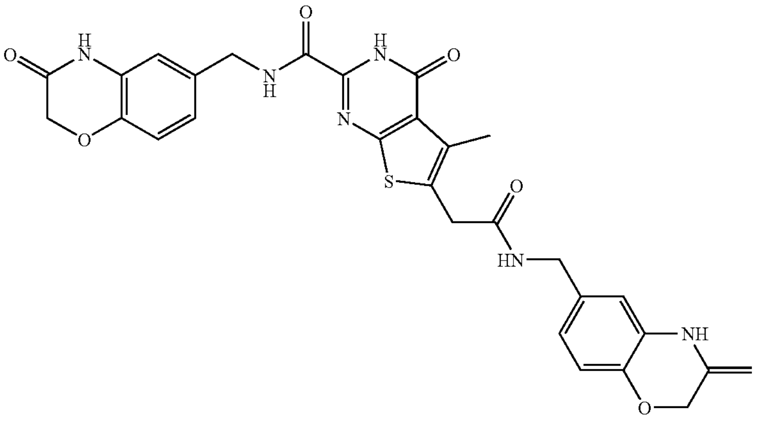
34%
$[MH]^+ = 589$ TABLE II.1-continued
| | | |
|---|---|---|
| 2/229 | 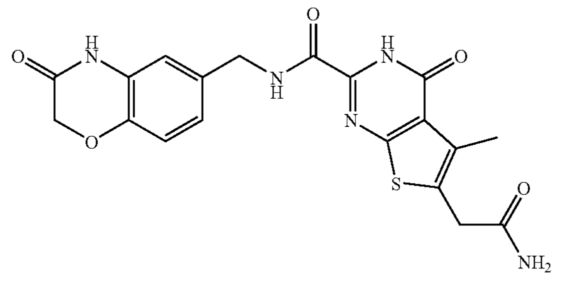 | 70%<br>$[MH]^+ = 428$ |
| 2/233 | 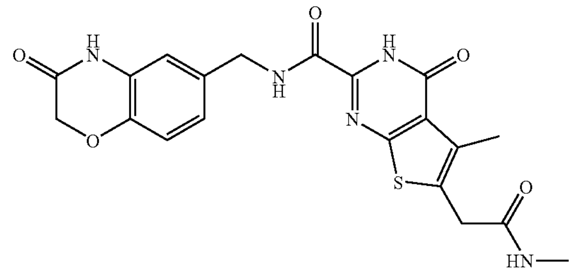 | 77%<br>$[MH]^+ = 442$ |
| 2/234 | 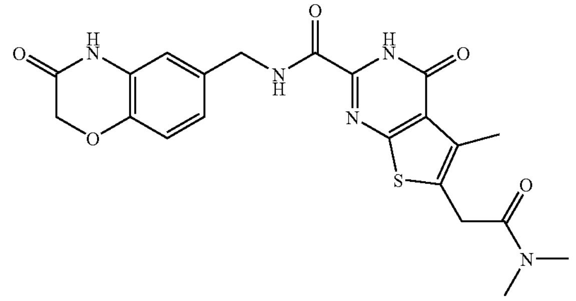 | 57%<br>$[MH]^+ = 456$ |
| 2/235 | 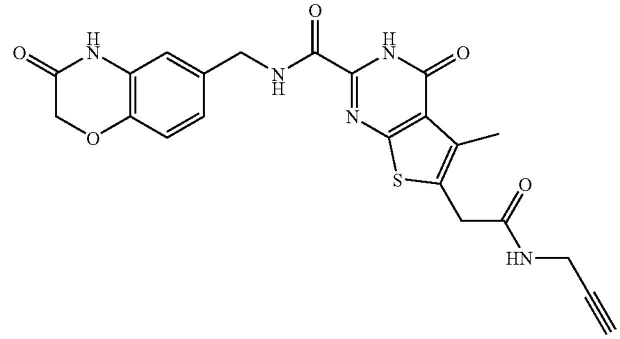 | 90%<br>$[MH]^+ = 466$ |
| 2/241 | 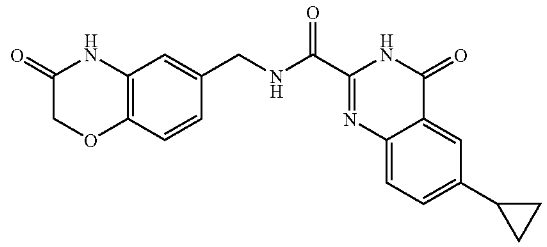 | 46%<br>$[MH]^+ = 391$ |

TABLE II.1-continued
| | | |
|---|---|---|
| 2/242 | 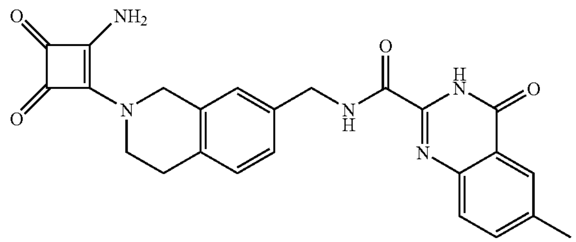 | 53%<br>$[MH]^+ = 470$ |
| 2/243 | 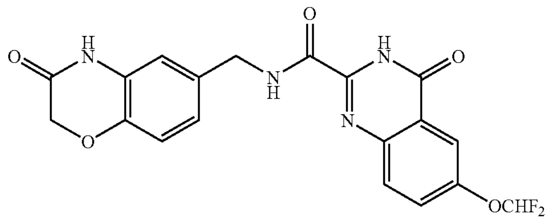 | 63%<br>$[MH]^+ = 417$ |
| 2/244 | 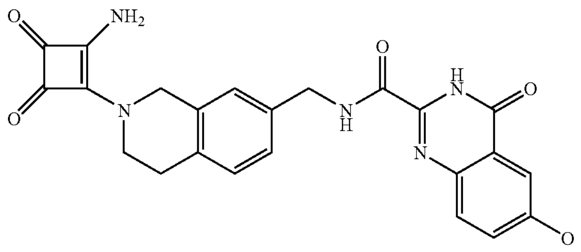 | 63%<br>$[MH]^+ = 496$ |
| 2/247 | 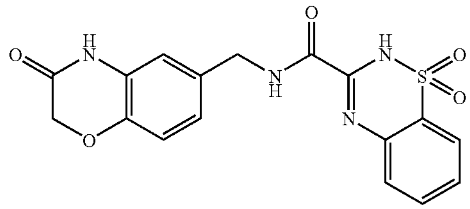 | 31%<br>$[MH]^+ = 387$ |
| 2/248 | 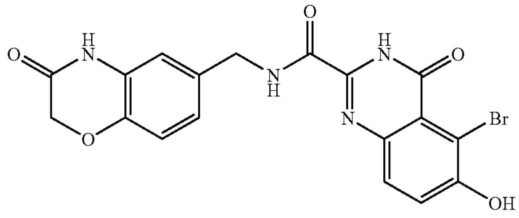 | 3%<br>$[MH]^+ = 446$ |
| 2/265 | 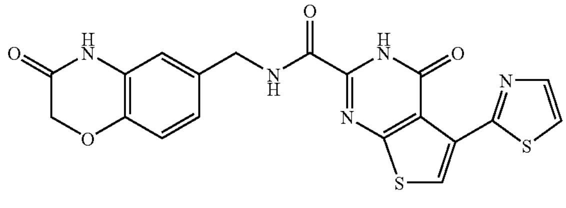 | 34%<br>(5 steps)<br>$[MH]^+ = 440$ |
| 2/271 | 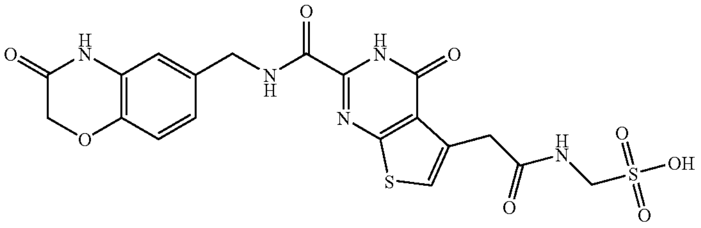 | 10%<br>$[MH]^+ = 508$ |

TABLE II.1-continued
| | | |
|---|---|---|
| 2/273 | 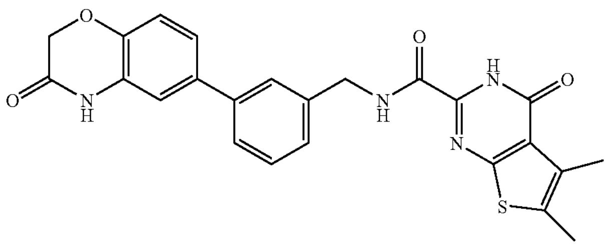 | 86%<br>$[MH]^+ = 461$ |
| 2/275 | 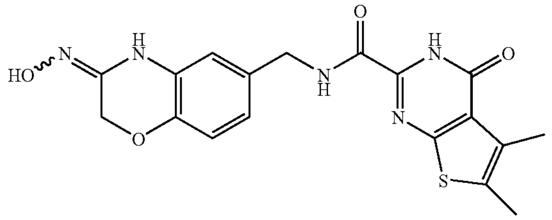 | 88%<br>$[MH]^+ = 400$ |
| 2/276 | 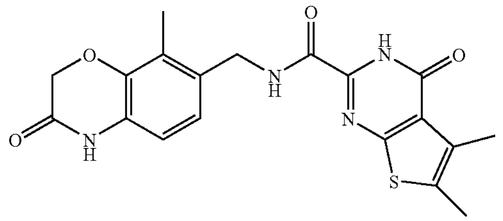 | 87%<br>$[MH]^+ = 399$ |
| 2/277 | 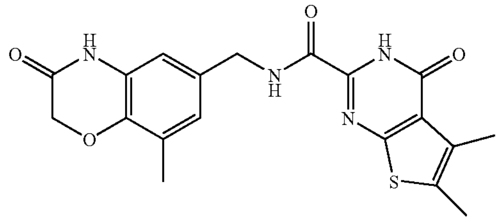 | 81%<br>$[MH]^+ = 399$ |
| 2/278 | 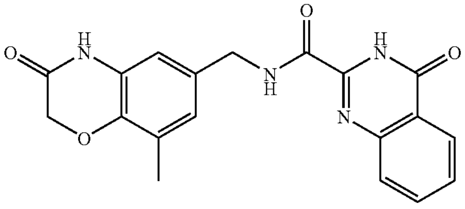 | 62%<br>$[MH]^+ = 365$ |
| 2/279 | 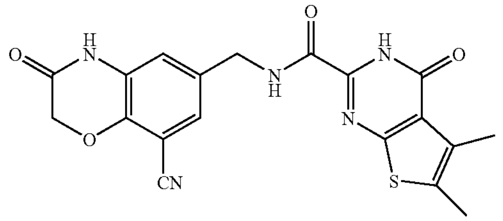 | 23%<br>$[MH]^+ = 410$ |

TABLE II.1-continued
| | | |
|---|---|---|
| 2/280 | 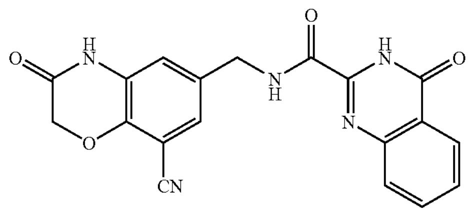 | 19%<br>$[MH]^+ = 376$ |
| 2/281 | 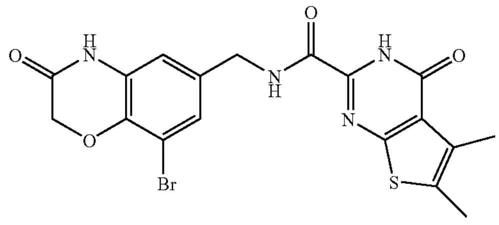 | 11%<br>$[MH]^+ = 463/465$ |
| 2/282 | 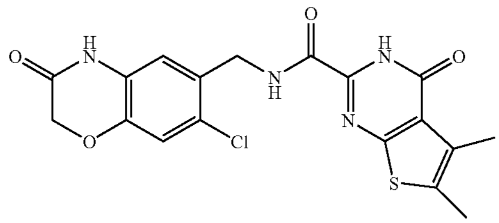 | 5%<br>$[MH]^+ = 419$ |
| 2/283 | 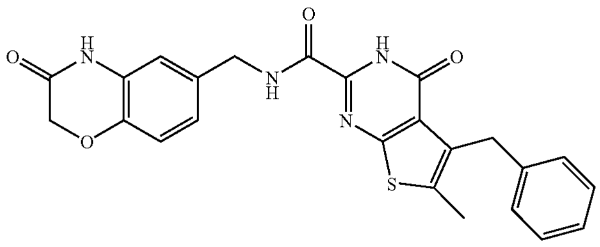 | n.d.<br>$[MH]^+ = 461$ |
| 2/284 | 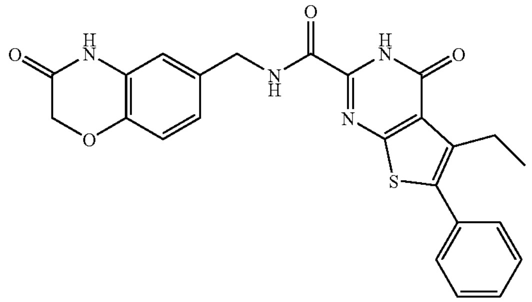 | n.d.<br>$[MH]^+ = 461$ |
| 2/285 | 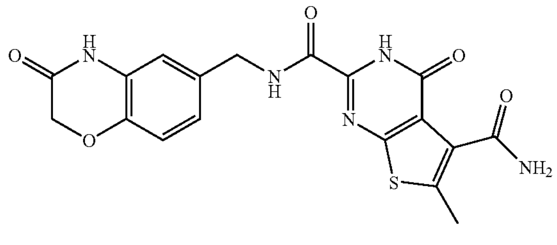 | 36%<br>$[MH]^+ = 414$ |

TABLE II.1-continued
| | | |
|---|---|---|
| 2/286 | 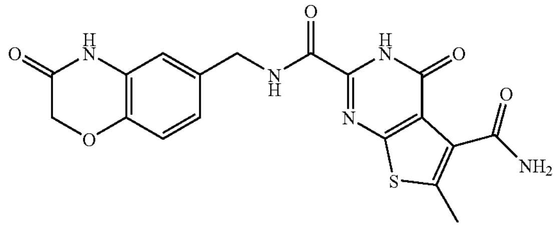 | 78%<br>$[MH]^+ = 428$ |
| 2/287 | 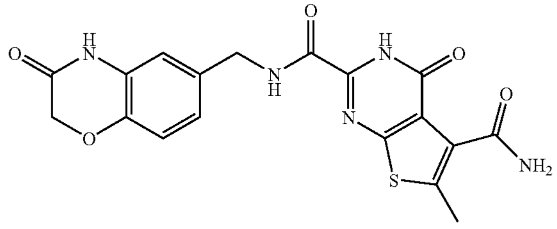 | 36%<br>$[MH]^+ = 468$ |
| 2/288 | 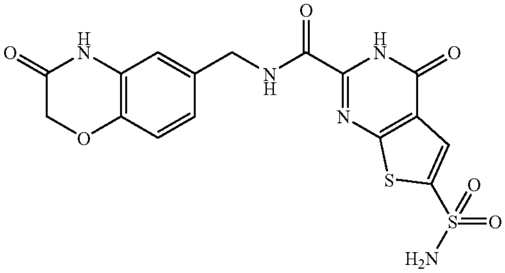 | 9%<br>$[MH]^+ = 276$ |
| 2/373 | 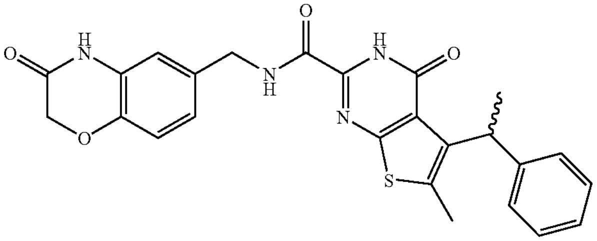 | 46%<br>$[MH]^+ = 475$ |
| 2/374 | 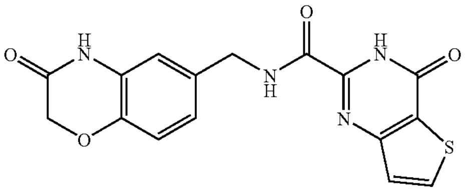 | 32%<br>$[MH]^+ = 357$ |
| 2/375 | 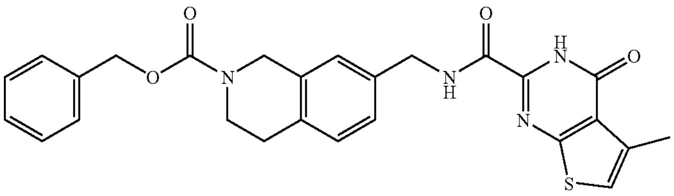 | 49%<br>$[MH]^+ = 489$ |

TABLE II.1-continued
| | | |
|---|---|---|
| 2/378 | 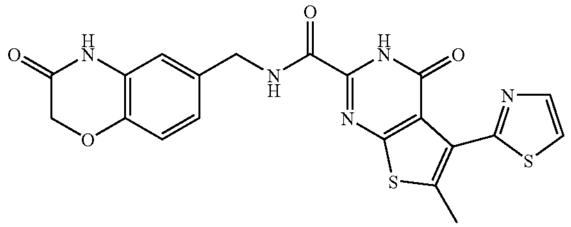 | 92%<br>$[MH]^+ = 454$ |
| 2/379 | 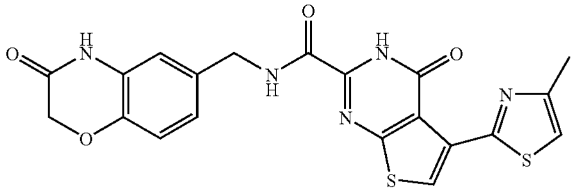 | 9%<br>$[MH]^+ = 454$ |
| 2/380 | 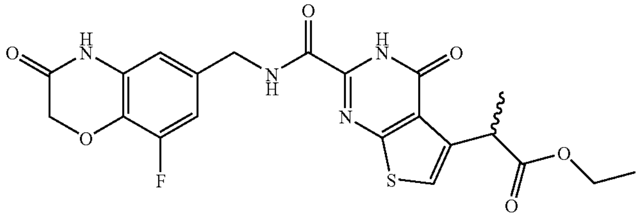 | quant.<br>$[MH]^+ = 475$ |
| 2/381 | 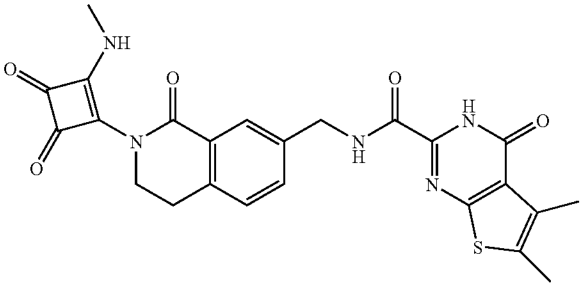 | quant.<br>$[MH]^+ = 492$ |
| 2/548 | 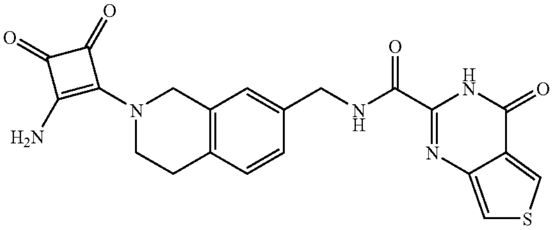 | 41%<br>$[MH]^+ = 436$ |

Example 3

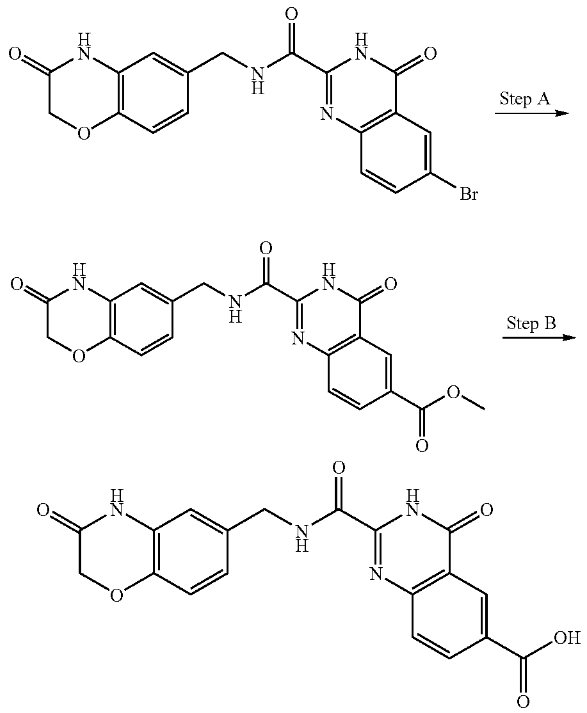

Step A

To a degassed suspension of the title compound from Example 2/21 above (100 mg) in MeOH (5 mL) were added $NEt_3$ (70 μL) palladium acetate (2 mg) and dppf (4.5 mg). The mixture was stirred overnight at 70° C. under CO atmosphere (7 bar) and then concentrated. The remaining residue was purified by chromatography (silica, chloroform/MeOH) to afford the title compound as off white solid (70 mg, 74%). $[MH]^+$=409.

Step B

To a solution of the title compound from Step A above (65 mg) in THF (3 mL) was added 1M aqueous LiOH (450 μL). The resulting mixture was stirred at room temperature overnight, concentrated and suspended in 1M aqueous HCl. The residue was filtered off and used without further purification (36 mg, 57%). $[MH]^+$=395.

Examples 4/1-4/20

Following a similar procedure as described in Example 3 step B, except using the ester indicated in Table II.2 below, the following compounds were prepared.

TABLE II.2

| Ex. # | Ester |
|---|---|
| 4/1 | 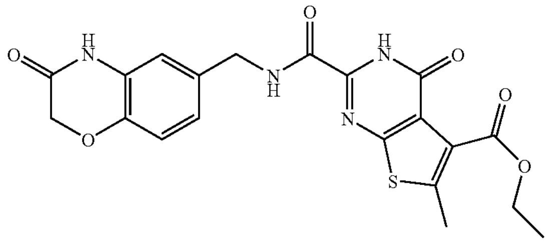 |
| 4/2 | 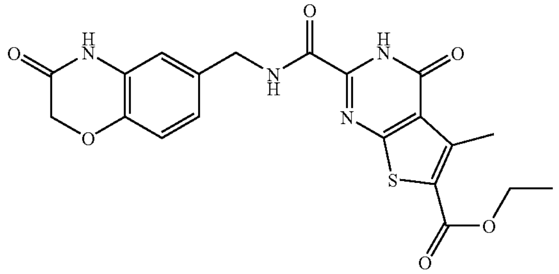 |

TABLE II.2-continued
4/3
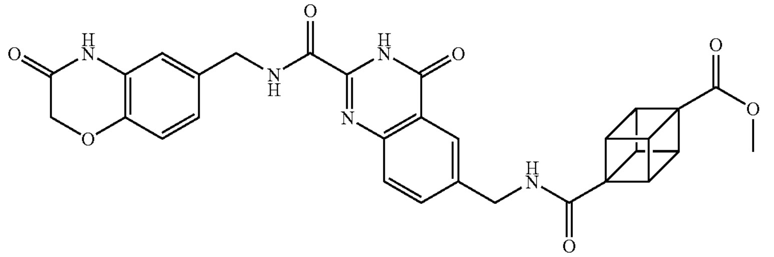
4/5
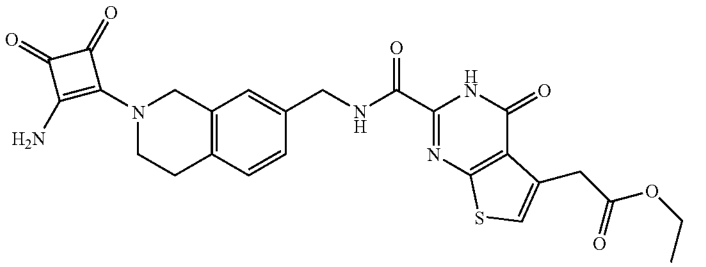
4/6
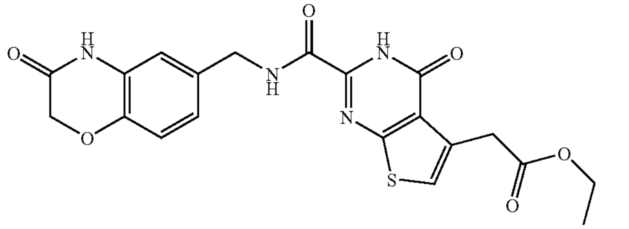
4/7
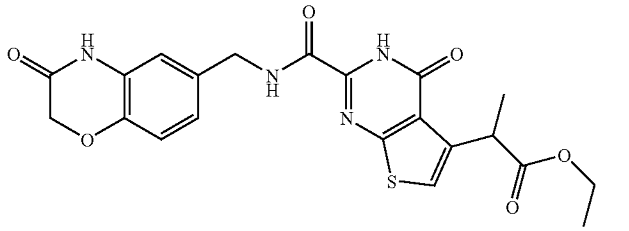
4/8
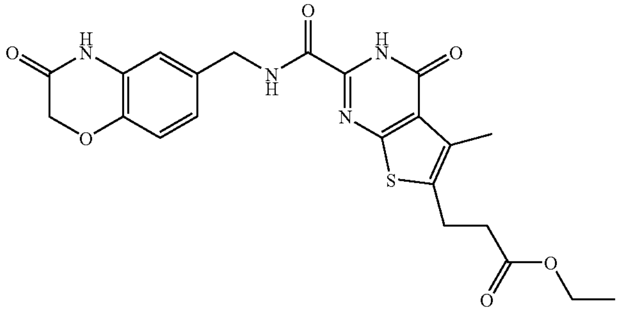
4/12
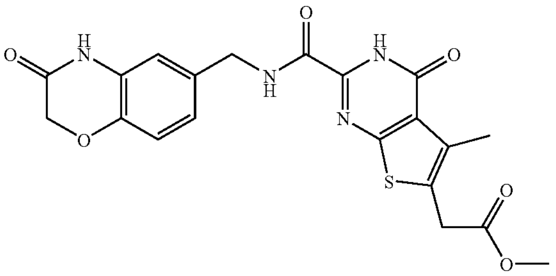

TABLE II.2-continued
| | | |
|---|---|---|
| 4/13 | 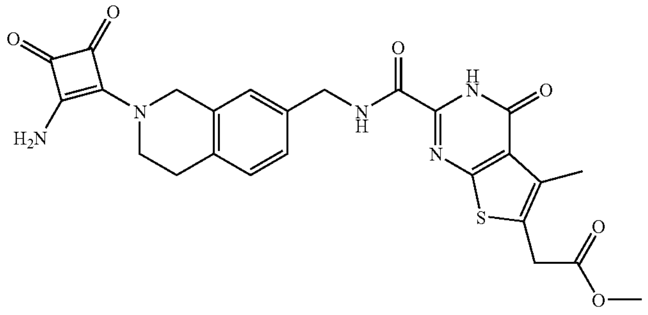 | |
| 4/20 | 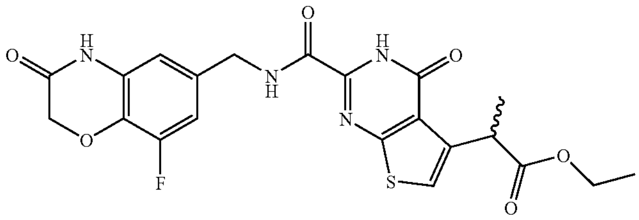 | |
| Ex. # | product | Yield |
|---|---|---|
| 4/1 | 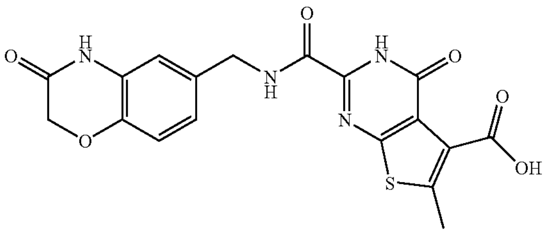 | 66% [MH]$^+$ = 415 |
| 4/2 | 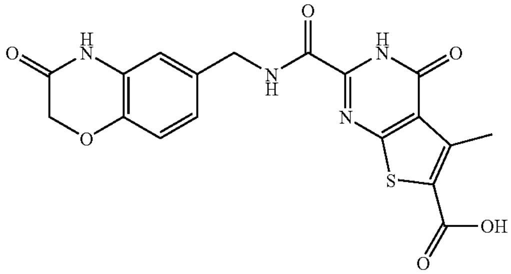 | 73% [MH]$^+$ = 415 |
| 4/3 | 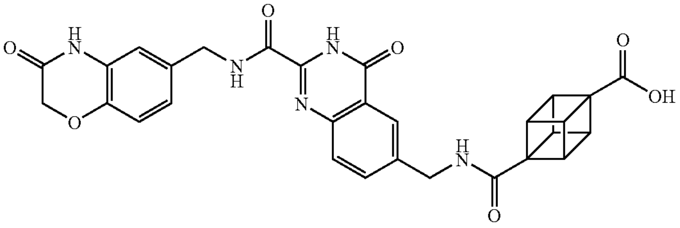 | 70% [MH]$^+$ = 554 |

TABLE II.2-continued
| | | |
|---|---|---|
| 4/5 | 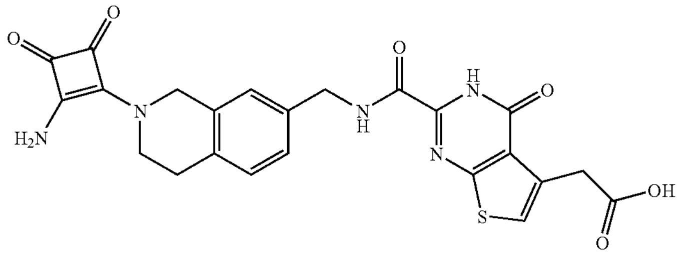 | nd.<br>$[MH]^+$ =<br>494 |
| 4/6 | 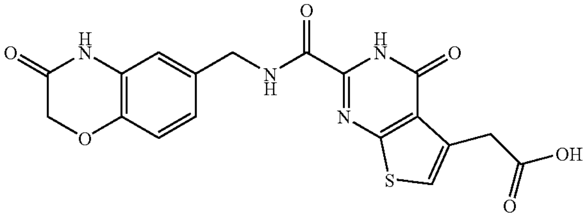 | 82%<br>$[MH]^+$ =<br>415 |
| 4/7 | 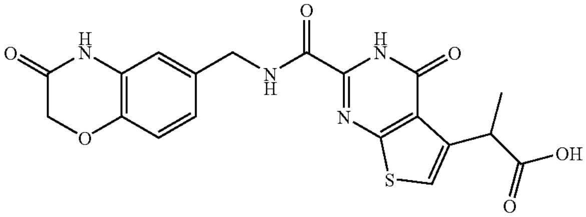 | 73%<br>$[MH]^+$ =<br>429 |
| 4/8 | 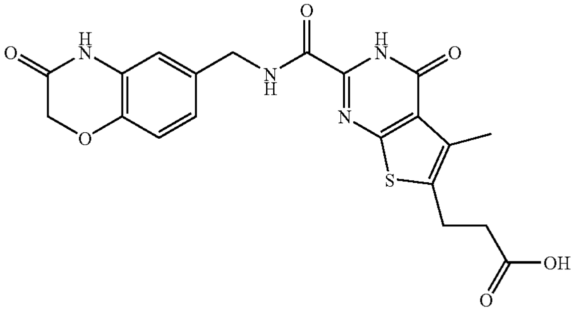 | 92%<br>$[MH]^+$ =<br>443 |
| 4/12 | 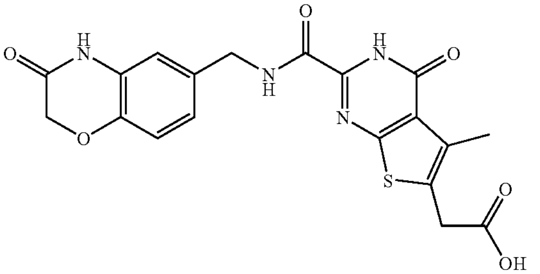 | 81%<br>$[MH]^+$ =<br>429 |

TABLE II.2-continued

| | | |
|---|---|---|
| 4/13 | 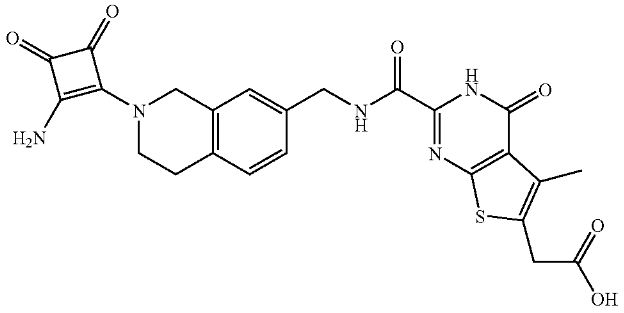 | 36% $[MH]^+$ = 429 |
| 4/20 | 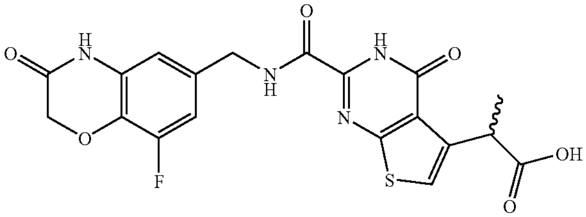 | 70% $[MH]^+$ = 447 |

Example 5

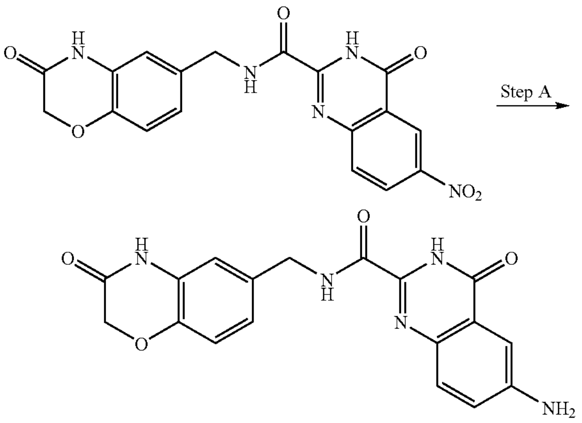

Step A

The title compound from the Example 2/57 (77 mg) and Pd/C (10%; 75 mg) were suspended in THF/MeOH and AcOH (100 μL) and hydrogenated at atmospheric pressure for 5 h, filtered over celite and evaporated to afford the title compound as a yellow solid. $[MH]^+$=366.

Example 6

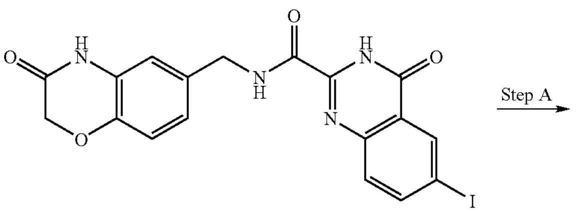

-continued

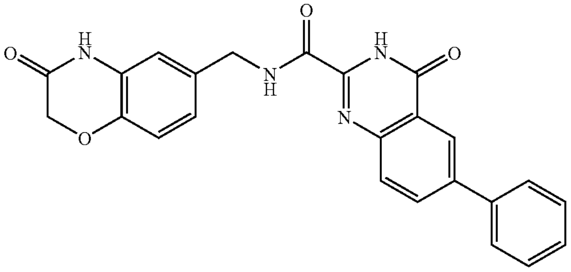

Step A

To a degassed suspension of the title compound from Example 2/42 above (120 mg) in DMF (2 mL) were added 17 mg $Pd(PPh_3)_4$, 34 mg commercially available phenylboronic acid and 2M aqueous $Na_2CO_3$ (0.5 mL). The resulting mixture was stirred at 130° C. (3 h) in a microwave oven for 30 min and than concentrated. The remaining residue was purified by chromatography (silica, chloroform/MeOH) to afford the title compound as off-white solid (11 mg, 22%). $[MH]^+$=427.

Examples 7/1

Following a similar procedure as described in the Example 6, except using the aryl halogenide and boronic acid indicated in Table II.3 below, the following compounds were prepared.

TABLE II.3

| Ex. # | aryl halogenide, boronic acid | product | yield |
|---|---|---|---|
| 7/1 | 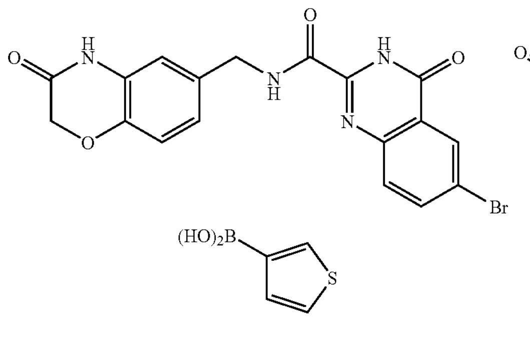 | 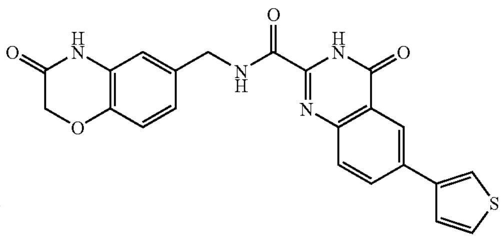 | 25%<br>$[MH]^+ = 433$ |

Example 8

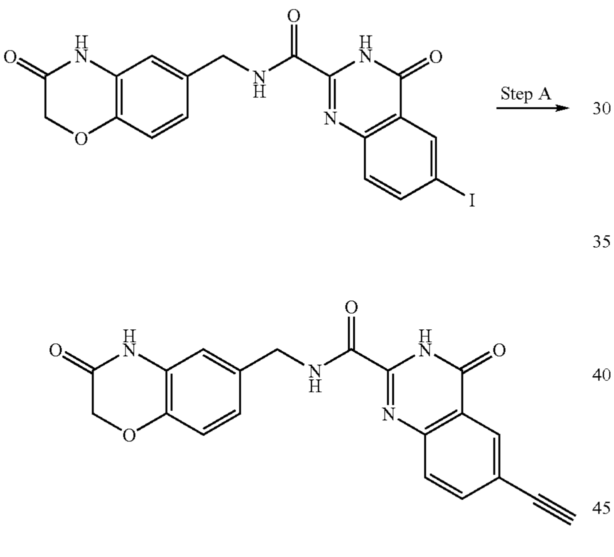

Step A

To a degassed suspension of the title compound from Example 2/42 above (70 mg) and CuI in DMF (2 mL) were added 17 mg $Pd(PPh_3)_2Cl_2$ and 16 mg commercially available trimethylsilyl acetylen. The resulting mixture was stirred at 120° C. (3 h) in a microwave oven for 20 min and than concentrated. The remaining residue was dissolved in $H_2O$/ethyl acetate, organic layer was dried ($MgSO_4$) and concentrated. The remaining residue was dissolved in MeOH $K_2CO_3$ (25 mg) was added and the mixture was stirred for 2 h, concentrated and purified by chromatography (silica, chloroform/MeOH) to afford the title compound as off white solid (2 mg, 3%). $[MH]^+$=375.

Example 8/1

Following a similar procedure as described in the Example 8, except using the aryl halogenide and acetylene indicated in Table II.4 below, the following compounds were prepared.

TABLE II.4

| Ex. # | aryl halogenide, acetylene | product | yield |
|---|---|---|---|
| 8/1 | 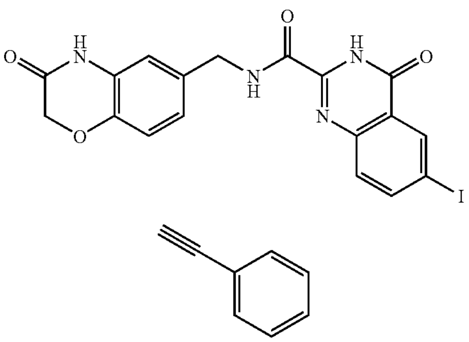 | 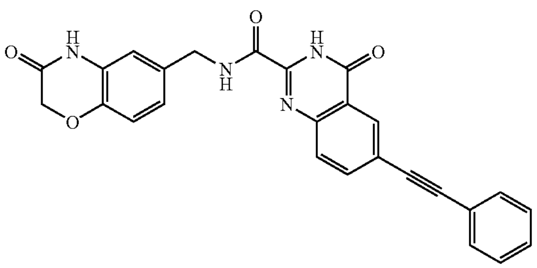 | 10%<br>$[MH]^+ = 451$ |

Example 9

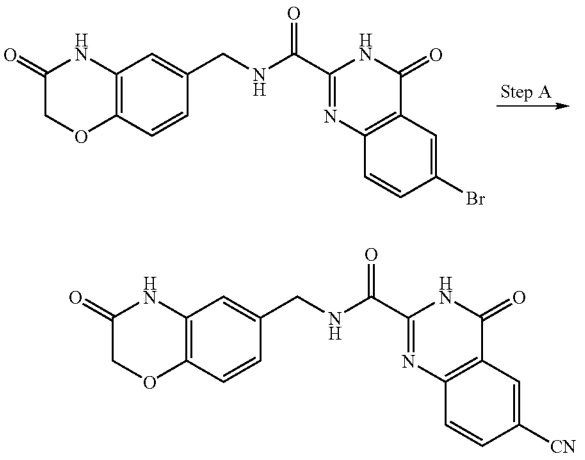

Step A

A mixture of the title compound from the Example 2/21 (150 mg), $Zn(CN)_2$ (31 mg) and $Pd(PPh_3)_4$ (20 mg) in dry DMF (3 mL) was degassed and heated at 85° C. under an argon atmosphere overnight. The mixture was concentrated, diluted with 10% aqueous citric acid, filtered and the remaining residue was slurried in methanol, filtered and dried to afford the title compound as a colorless solid (103 mg, 78%). $[MH]^+=376$.

Examples 10/1-10/2

Following a similar procedure as described in the Example 9, except using the aryl halogenide indicated in Table II.5 below, the following compounds were prepared.

TABLE II.5

| Ex. # | aryl halogenide |
|---|---|
| 10/1 | 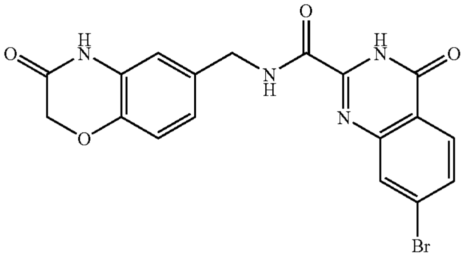 |
| 10/2 | 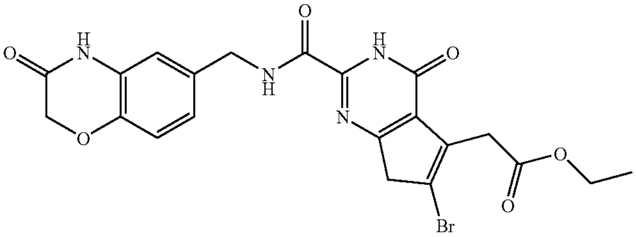 |

| Ex. # | product | yield |
|---|---|---|
| 10/1 | 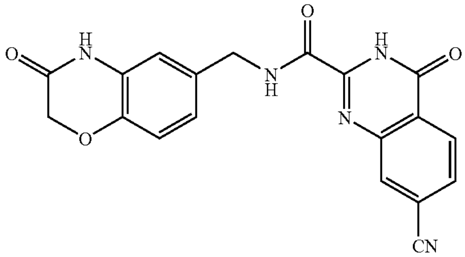 | 89% $[MH]^+$ = 376 |

TABLE II.5-continued

| | | |
|---|---|---|
| 10/2 | 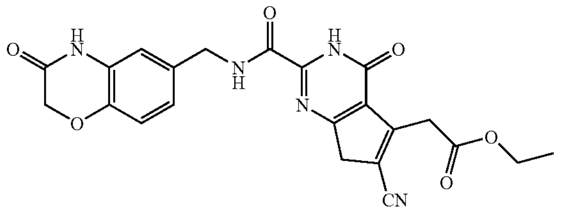 | n.d. $[MH]^+$ = 468 |

Example 11

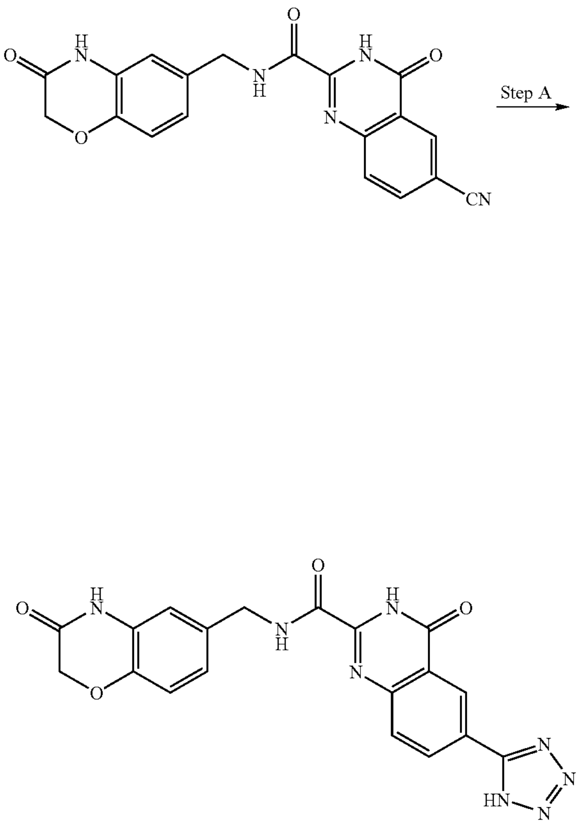

Step A

In a sealed vial was a mixture of the title compound from the Example 9 (43.3 mg), dibutyltin oxide (12 mg) and azidotrimethylsilane (400 μL) in dry toluene (10 mL) under an argon atmosphere heated at 170° C. using microwave irradiation for 13 h. The reaction mixture was absorbed on silica gel and purified by chromatography (silica, $CH_2Cl_2$/MeOH 9:1 to 4:1) and the product containing fractions further purified by thin layer chromatography ($CH_2Cl_2$/MeOH 4:1) to give the title compound as an off-white solid (6.1 mg, 14%). $[MH]^+$=419.

Example 12

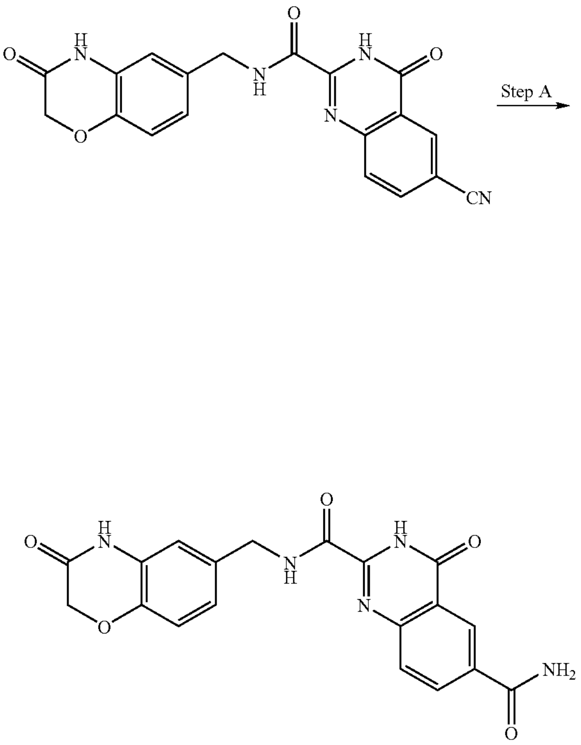

Step A

The title compound from the Example 9 (28.2 mg) and $K_2CO_3$ (21 mg) were suspended in DMSO (1 mL) and aqueous hydrogen peroxide (35%, 100 μL) was added. The reaction mixture was stirred for 3 h and diluted with 10% aqueous citric acid, filtered and dried to afford the title compound as a colorless solid (34.9 mg, quant.). $[MH]^+$=394.

Examples 13/1-13/3

Following a similar procedure as described in Example 12, except using the aryl cyanide indicated in Table II.6 below, the following compounds were prepared.

TABLE II.6
| Ex. # | aryl halogenide |
|---|---|
| 13/1 | 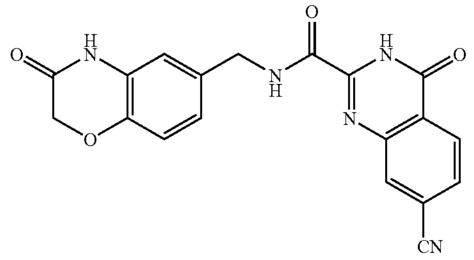 |
| 13/2 | 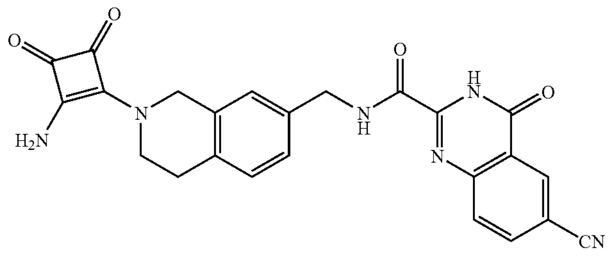 |
| 13/3 | 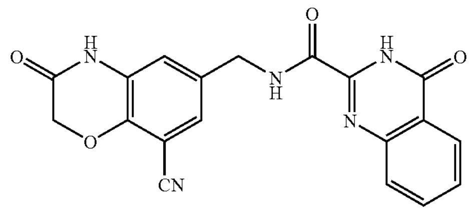 |
| Ex. # | product | yield |
|---|---|---|
| 13/1 | 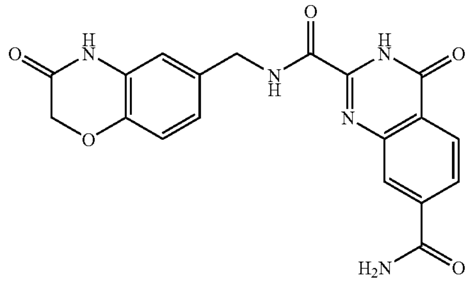 | 87% $[MH]^+$ = 394 |
| 13/2 | 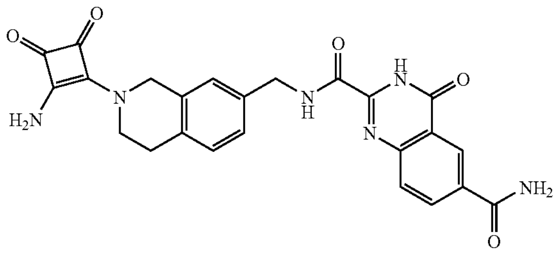 | 41% $[MH]^+$ = 473 |
| 13/3 | 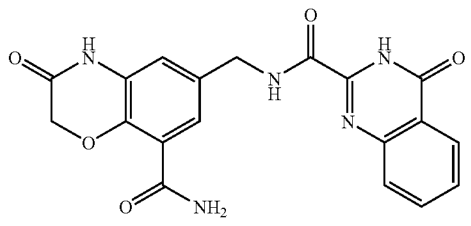 | 60% $[MH]^+$ = 394 |

Example 14

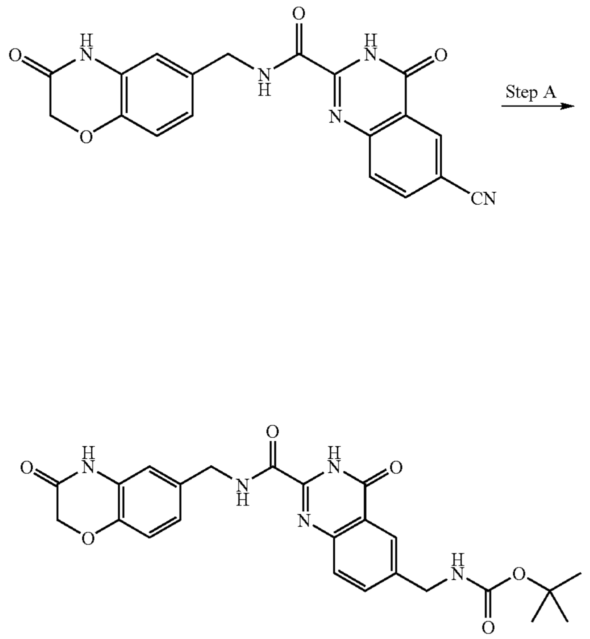

Step A

To an ice cooled solution of the title compound from the Example 9 (980 mg) in dry MeOH (20 mL) were added di-tert-butyl dicarbonate (1.5 g) and $NiCl_2.6H_2O$ (190 mg), followed by the careful portionwise addition of $NaBH_4$ (600 mg). The resulting black mixture was stirred for 20 min at 0-5° C. (ice bath), then the ice bath was removed and stirring at room temperature was continued overnight. Then diethylenetriamine was added and the mixture was concentrated to dryness. The remaining residue was suspended in EtOAc washed subsequently with 10% aqueous citric acid, saturated aqueous $NaHCO_3$ and saturated aqueous NaCl, dried ($MgSO_4$), filtered, concentrated and purified by chromatography (silica, cyclohexane/EtOAc 2:8 to 0:1) to afford the title compound as a colorless solid (262 mg, 21%). $[MH]^+=480$.

Example 15

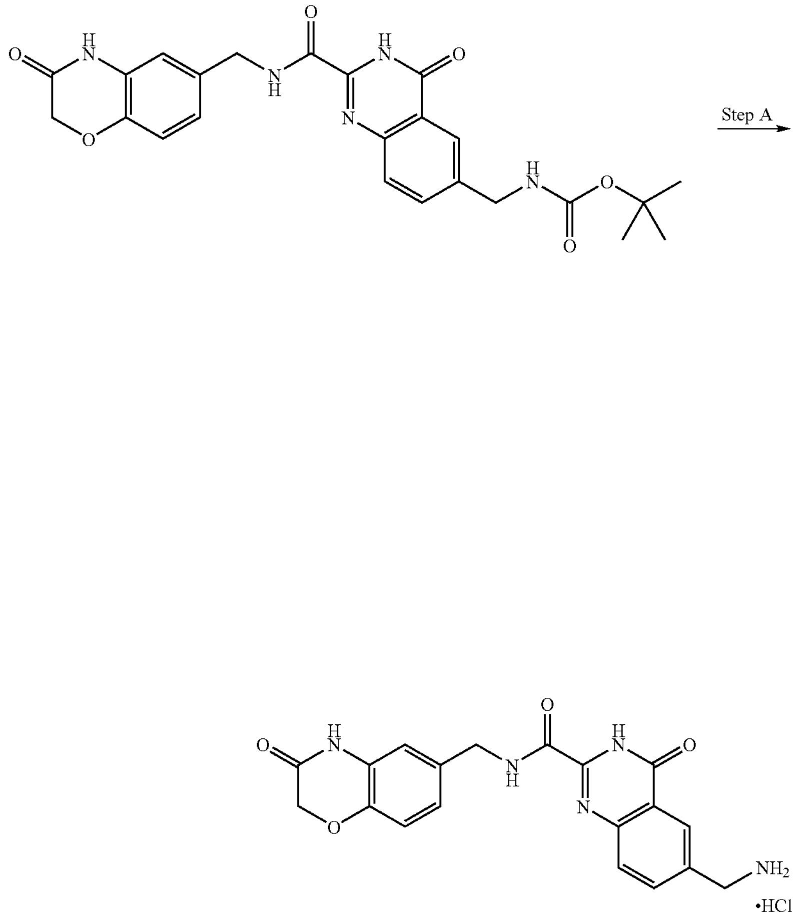

Step A

To the title compound from the Example 14 (258 mg) was added a 4M solution of HCl in 1,4-dioxane (10 mL). The reaction mixture was stirred at room temperature with temporary sonification for 5 h and concentrated to afford the title compound (240 mg, >99%). $[M-Cl]^+=380$.

Example 16

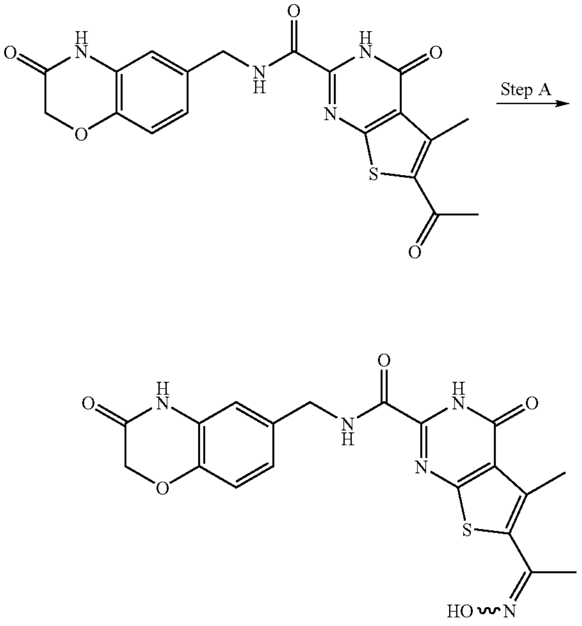

Step A

The title compound from the Example 2/88 (24.5 mg), $HONH_2$.HCl (39 mg), NaOAc (50 mg) and 3 drops aniline were stirred in $MeOH/H_2O$ (10 mL; 1:1) at 80° C. for 2 d. The reaction mixture was concentrated, diluted with water and filtered to afford the title compound (23 mg, 91%) as an off-white solid. $[MH]^+=428$.

Example 17

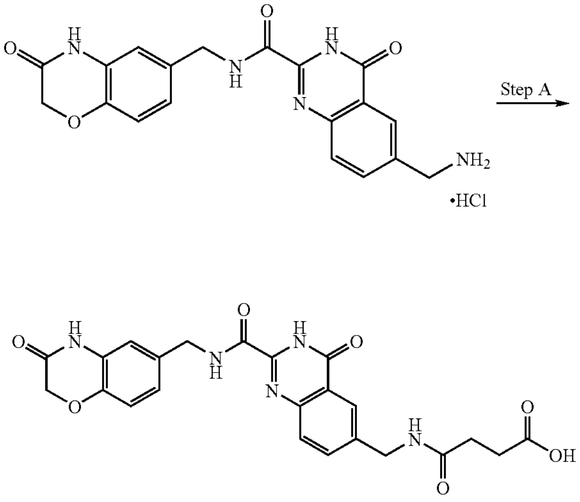

Step A

The title compound from the Example 15 (29 mg), succinic anhydride (8 mg) and pyridine (80 μL) were stirred in $CH_3CN$ at 50° C. overnight, concentrated, diluted with 10% aqueous citric acid and filtered to afford the title compound (27 mg, 81%) as an off-white solid. $[MH]^+=480$.

Example 19

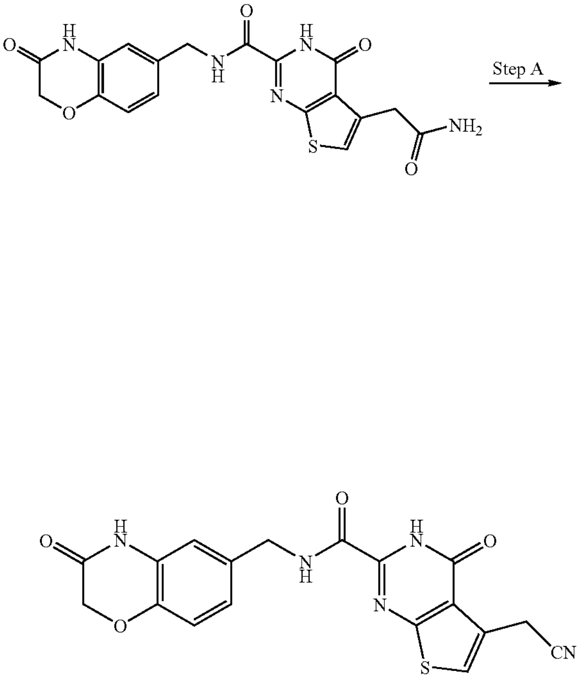

Step A

To DMF (5 mL) was added 2M oxalylchloride in dichloromethane (150 μL) at 0° C. Then a solution of the title compound from Example 2/156 (112 mg) in DMF (2 mL) was added and the mixture was stirred for 6 h at 0° C. After adding pyridine (150 μL) the mixture was stirred for additional 2 h at room temperature. The mixture was concentrated to afford the title compound after chromatography (chloroform/methanol=9:1; 19 mg, 18%). $[MH]^+=396$.

Example 20a to Example 20c

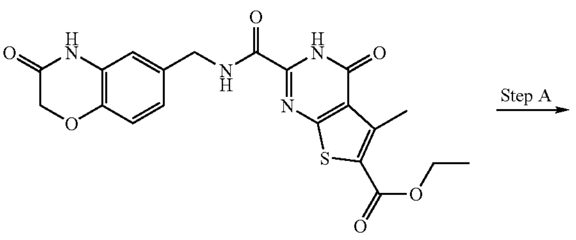

-continued

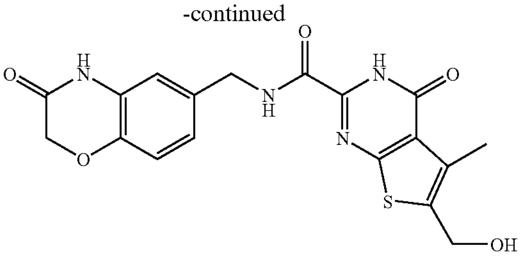

Example 20a

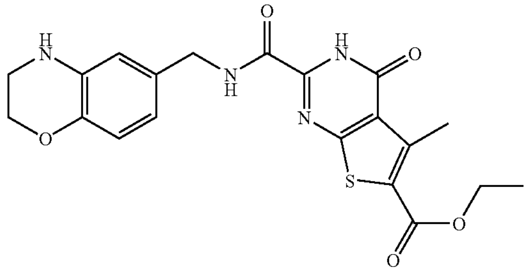

Example 20b

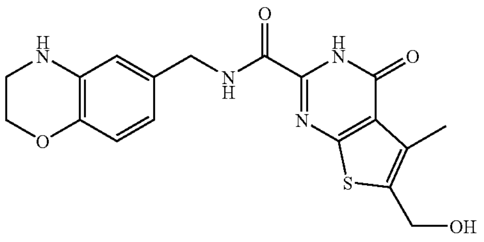

Example 20c

Step A

The title compound from example 2/28 (255 mg) was dissolved in dry THF (40 mL) and then a large excess of $LiBH_4$ was added and the mixture was stirred for 1 week with sonification for some time, evaporated, adjusted to pH ~8 with aq. $NH_4Cl$, extracted with ethyl acetate and absorbed on silica. Flash chromatography ($CH_2Cl_2$/methanol 98:2 to 85:15) afforded first the Example 20b (14.5 mg) as an off-white solid ($[MH]^+$=429), then Example 20c (31.4 mg) as a colourless solid ($[MH]^+$=387), and finally Example 20a (8.6 mg) as a colourless solid ($[MH]^+$=401).

Example 21

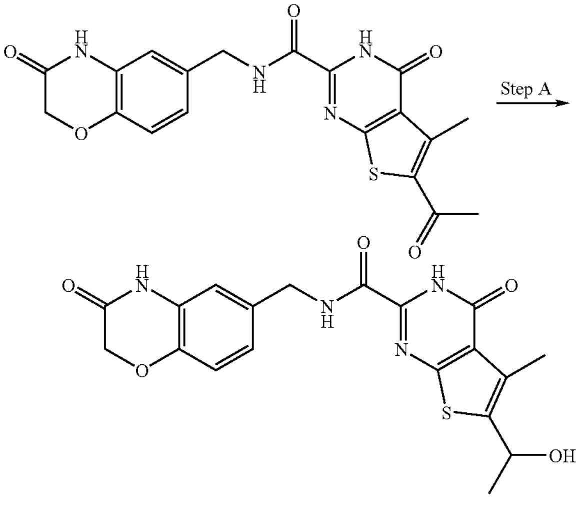

Step A

The title compound from example 2/88 (100 mg) was suspended in dry THF/MeOH (5:1) and then $NaBH_4$ (22 mg) was added and the mixture was stirred for 1.5 h, acidified with 1N HCl, filtered, washed with water and dried to afford the title compound (94 mg, 94%) as a colourless solid. $[MH]^+$= 415.

Example 23a to Example 23c

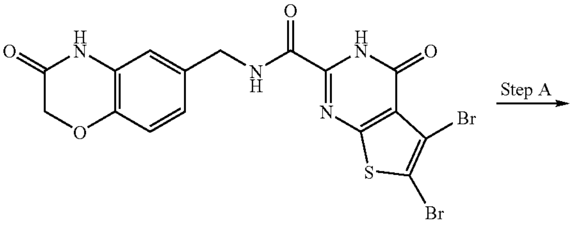

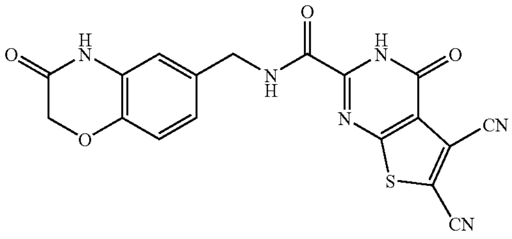

Example 23a

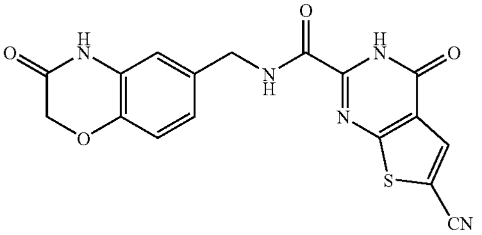

Example 23b

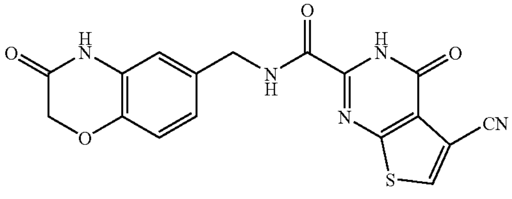

Example 23c

Step A

A suspension the title compound from Example 2/215 (170 mg) and CuCN (66 mg) in degassed DMF was stirred in a closed vial under microwave irradiation at 200° C. for 1 h, evaporated and redissolved in THF, washed with brine/1N hydrochloric acid (~1:1) and brine, dried and separated by HPLC to afford both mono-nitrile products ($[MH]^+$=382) and the di-nitrile product ($[MH]^+$=407).

Example 23/1

Following a similar procedure as described in Example 23a, except using the educt indicated in Table II.10 below, the following compounds were prepared.

TABLE II.10

| Ex. # | Educt | product | yield |
|---|---|---|---|
| 23/1 | 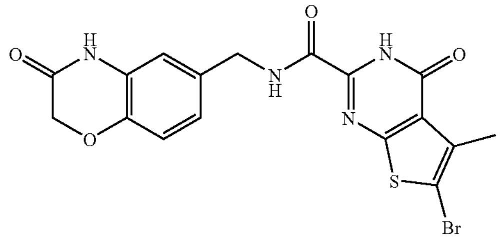 | 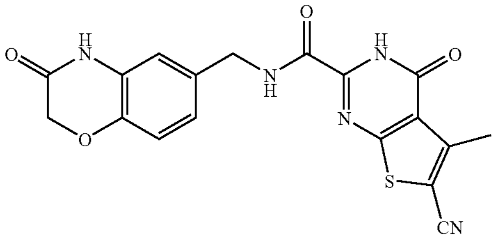 | quant. $[MH]^+$ = 396 |

Example 24

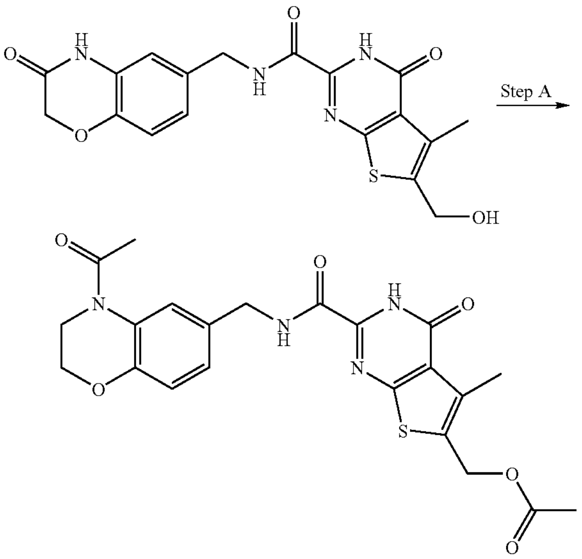

Step A

The title compound from Example 20c (29 mg) and catalytic amounts of DMAP were stirred in $Ac_2O$/pyridine (3 mL; 1:2) overnight, evaporated, coevaporated with toluene, slurried in water and filtered to afford the title compound (33 mg, 93%) as an off-white solid. $[MH]^+$=471.

Example 25

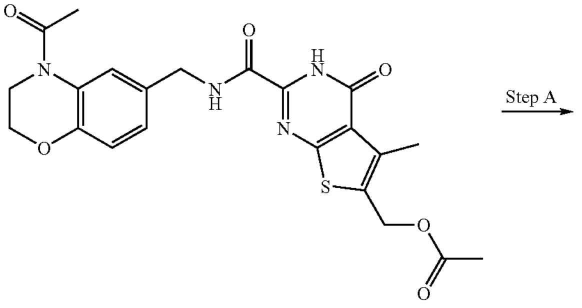

-continued

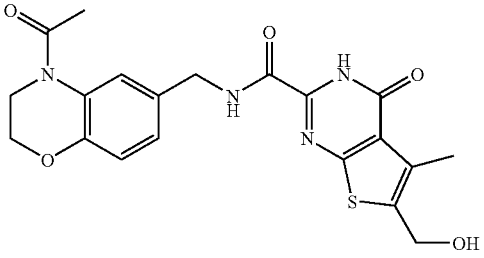

Step A

The title compound from Example 24 (14 mg) and NaOMe (13 mg) in dry MeOH were stirred for 1 h, evaporated, acidified with 1N hydrochloric acid and filtered to afford the title compound (9.1 mg, 71%) as a colourless solid. $[MH]^+$=429.

Example 27

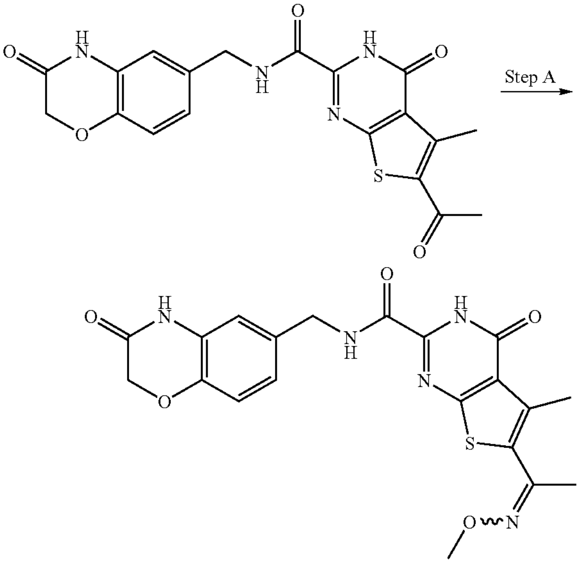

Step A

The title compound from the Example 2/88 (20 mg), $MeONH_2$.HCl (21 mg), NaOAc (30 mg) and 3 drops aniline were stirred in MeOH/$H_2O$ (10 mL; 1:1) at 80° C. for 2 d. The reaction mixture was concentrated, diluted with water and purified by HPLC to afford the title compound (7.6 mg) as a colourless solid. $[MH]^+$=442.

Example 28

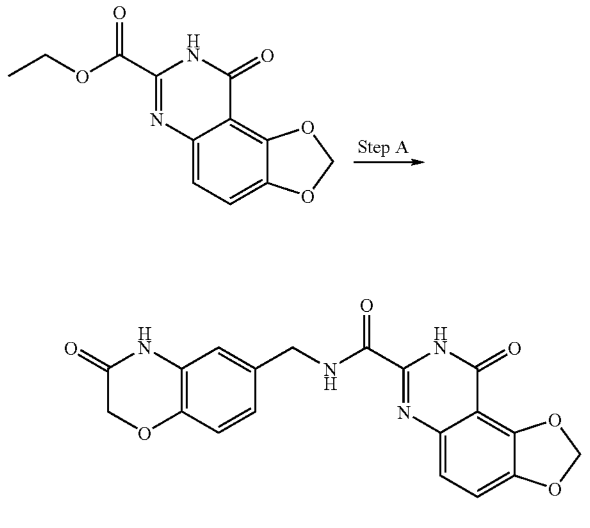

Step A

To a solution of 9-Oxo-8,9-dihydro-1,3-dioxa-6,8-diaza-cyclopenta[a]naphthalene-7-carboxylic acid ethyl ester above (32 mg) in ethanol (1 mL) were added triethyl amine (40 μL) and the title compound from the Preparative Example 13 (30 mg). The mixture was heated at 180° C. in a microwave oven for 1 h and then concentrated. The remaining residue was purified by silica gel chromatography (10% methanol in methylene chloride) to give a yellow solid (45 mg, 95%). $[MH]^+$=395.

Examples 29/1 to 29/2

Following a similar procedure as described in Example 28, except using the ester indicated in Table II.11 below, the following compounds were prepared.

TABLE II.11

| Ex. # | Ester | product | Yield |
|---|---|---|---|
| 29/1 | 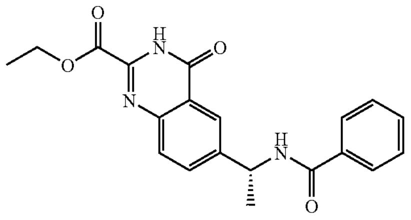 | 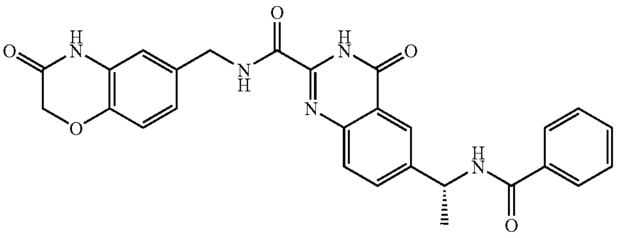 | 64% $[MH]^+$ = 498 |
| 29/2 | 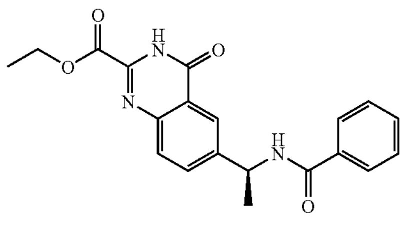 | 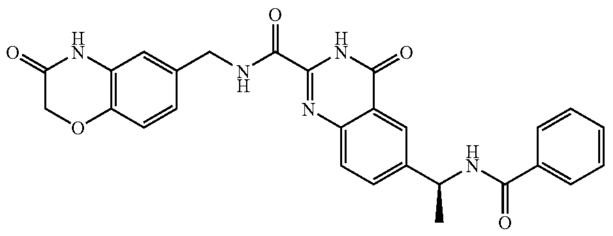 | 27% $[MH]^+$ = 498 |

Example 30

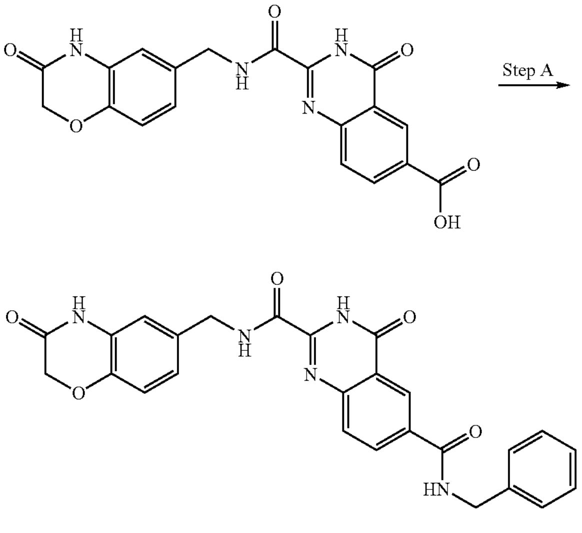

Step A

To a solution of the title compound from Example 3 above (25 mg) in DMF (2 mL) were added triethyl amine (10 μL), benzylamine (9 mg) and PyBop (38 mg). The mixture was stirred at room temperature overnight and concentrated in vaccuo. The remaining residue was purified by silica gel chromatography (10% methanol in methylene chloride) to give a yellow solid (10 mg, 41%). $[MH]^+=484$.

Examples 31/1 to 31/4

Following a similar procedure as described in Example 30, except using the amine indicated in Table II.11 below, the following compounds were prepared.

TABLE II.11

| Ex. # | Amine | product | yield |
|---|---|---|---|
| 31/1 | 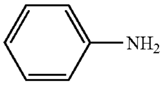 | 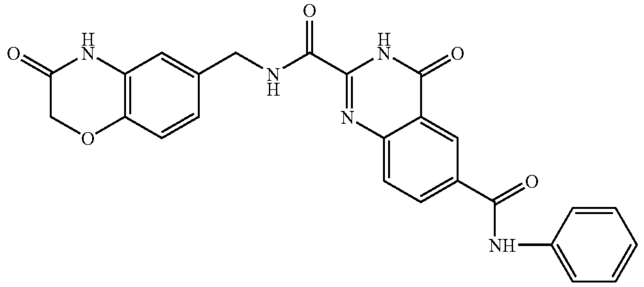 | 64% $[MH]^+$ = 470 |
| 31/2 | 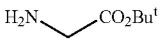 | 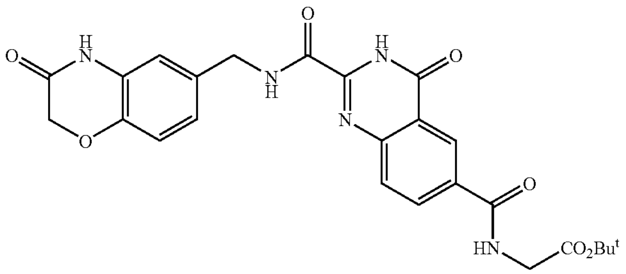 | 24% $[MH]^+$ = 508 |
| 31/3 | 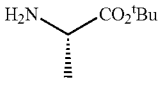 | 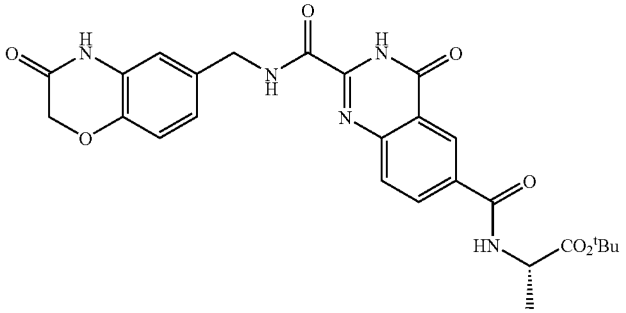 | 28% $[MH]^+$ = 522 |

TABLE II.11-continued

| Ex. # | Amine | product | yield |
|---|---|---|---|
| 31/4 | 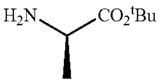 | 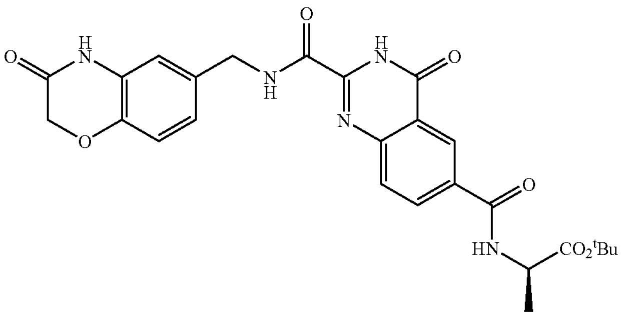 | 26% $[MH]^+$ = 466 |

Example 32

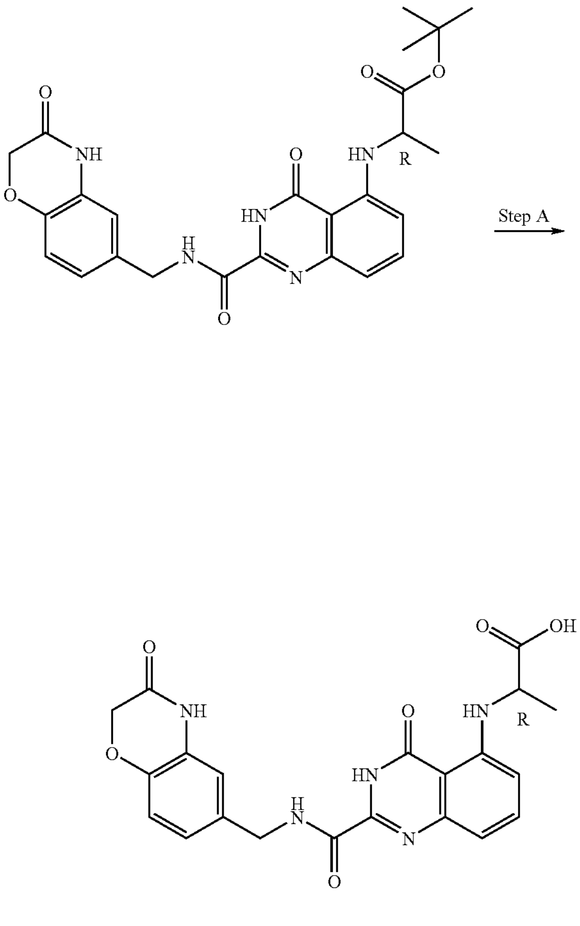

Step A

To a 10 ml round bottom flask containing a stir bar is added 20 mg of the tert.-Butyl ester above, and 2 ml of 50% trifluoroacetic acid in methylene chloride and solution stirred under closed atmosphere for 30 minutes. The volatile components of the reaction mixture was then removed under reduced pressure to give an oil which was precipitated from ether to give 8 mg (~45% crude yield) of the free acid as a white solid. $[MH]^+$=438.

Example 33

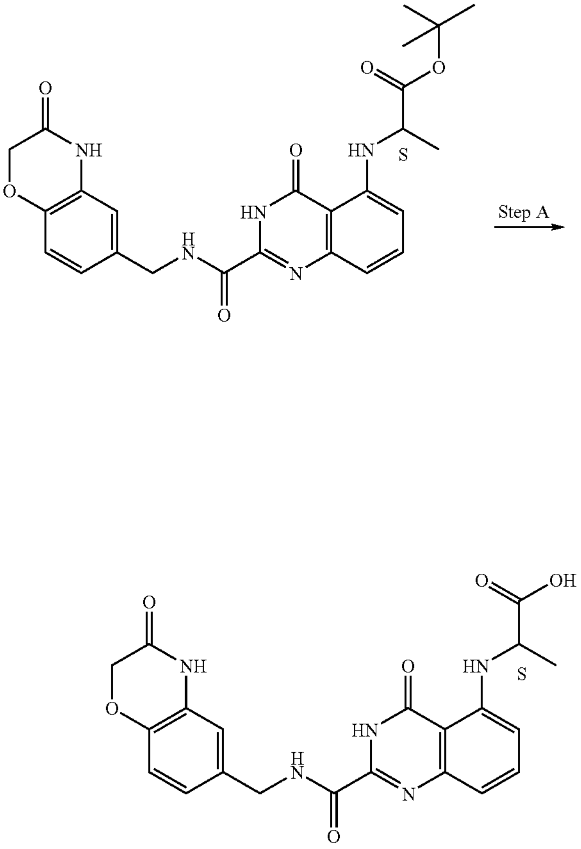

Step A

To a 10 ml round bottom flask containing a stir bar is added 10 mg of the tert.-Butyl ester above, and 2 ml of 50% trifluoroacetic acid in methylene chloride and solution stirred under closed atmosphere for 30 minutes. The volatile components of the reaction mixture was then removed under reduced pressure to give an oil which was precipitated from ether to give 5 mg (~56% crude yield) of the free acid as a white solid. $[MH]^+$=438.

Example 34

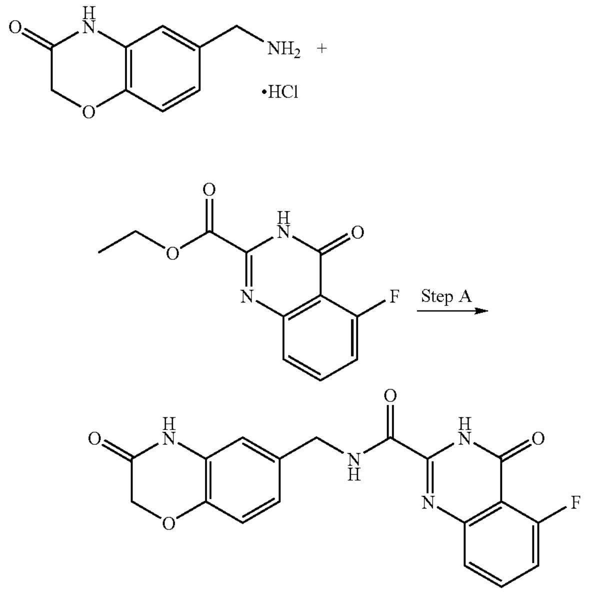

Step A

To a thick walled glass vessel containing a stir bar was added of 5-Fluoro-4-oxo-3,4-dihydro-quinazoline-2-carboxylic acid ethyl ester (100 mg), 120 mg of the hydrochloride salt of the 6-Aminomethyl-4H-benzo[1,4]oxazin-3-one, 2 ml of ethanol and 0.15 mL of triethylamine and mixture heated at 120° C. via microwave under closed atmosphere for 30 min. The mixture was then centrifuged and the solid was triturated with ethanol to give 100 mg (65%) of the desired product as a white solid. $[MH]^+$=369.

Example 35

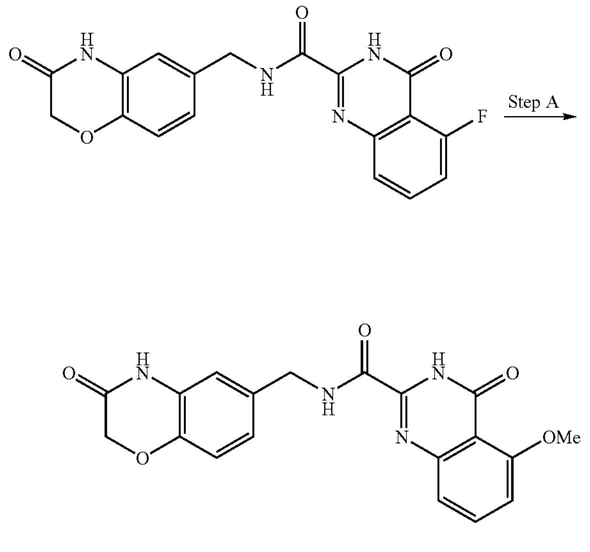

Step A

To a thick walled glass vessel containing a stir bar is added 35 mg of title compound from Example 34 above and a solution composed of 1.5 mL of a sodium methoxide solution in methanol and 2 mL of dimethylacetamide and the mixture was heated via microwave irradiation at 180° C. for 80 minutes. The volatile components of the reaction mixture were removed under reduced pressure to give crude product. The crude was triturated with ethanol to give 30 mg (83%) of the desired ether product as a white solid. $[MH]^+$=381.

Example 36

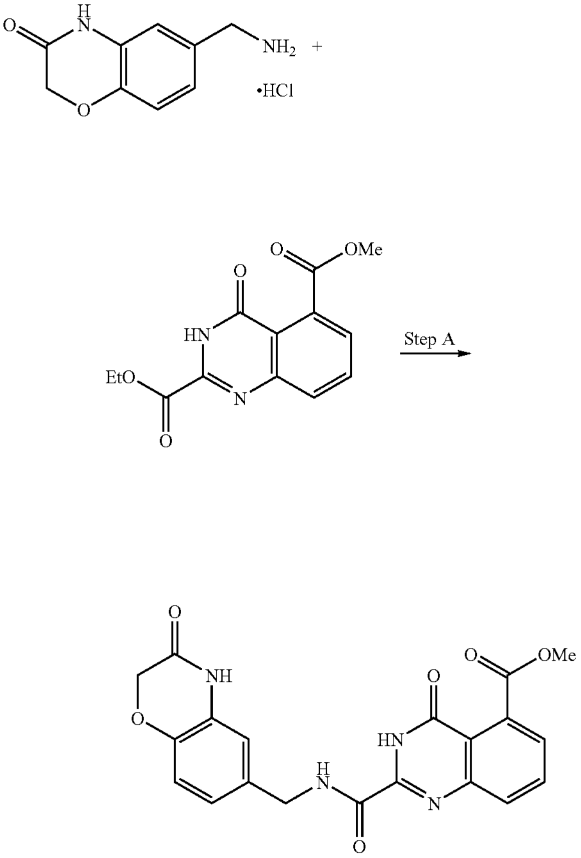

Step A

To a thick walled glass vessel containing a stir bar is added 172 mg of the diester above, 164 mg of the hydrochloride salt of the benzo[1,4]oxazinone, 3 ml of ethanol and 0.2 ml of triethylamine and mixture heated at 180° C. via microwave under closed atmosphere for 1 hour. The mixture was then centrifuged and the solid was repeatedly triturated with ethanol and then methylene chloride to give 50 mg (16% yield) of the desired amide product as a white solid. $[MH]^+$=409.

Examples 36/1-36/13

Following a similar procedure as described in Example 36, except using the amines indicated in Table II.13 below, the following compounds were prepared.

TABLE II.13
| Ex. # | Amine | product | yield |
|---|---|---|---|
| 36/1 | 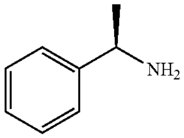 | 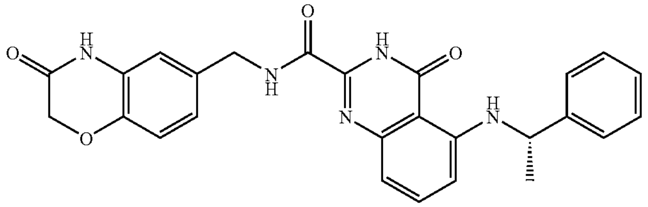 | 30% [MH]$^+$ = 470 |
| 36/2 | 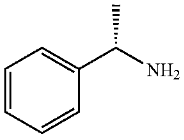 | 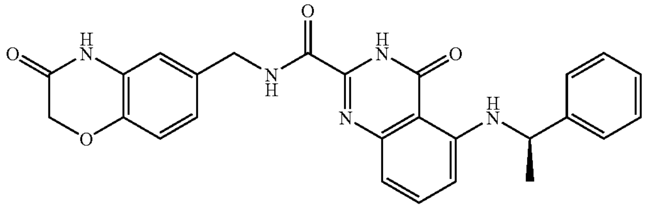 | 40% [MH]$^+$ = 470 |
| 36/3 | 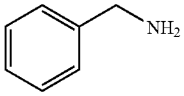 | 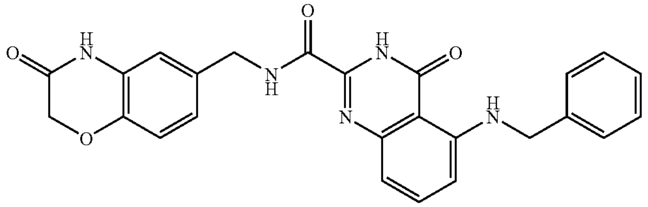 | 25% [MH]$^+$ = 456 |
| 36/4 | 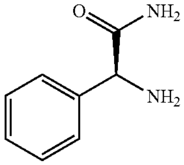 | 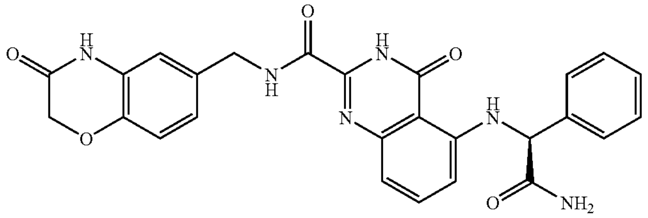 | 25% [MH]$^+$ = 499 |
| 36/5 | 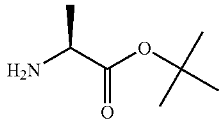 | 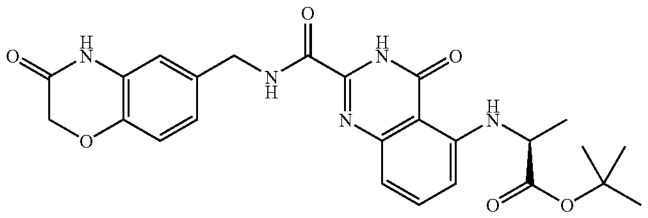 | 50% [MH]$^+$ = 494 |
| 36/6 | 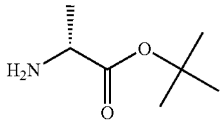 | 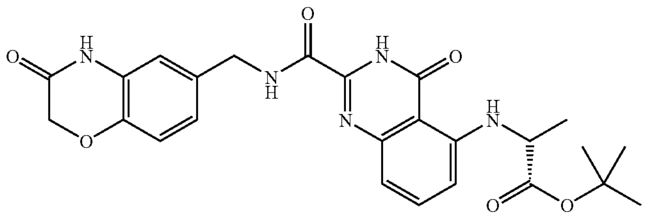 | 50% [MH]$^+$ = 494 |
| 36/7 | 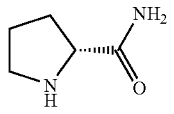 | 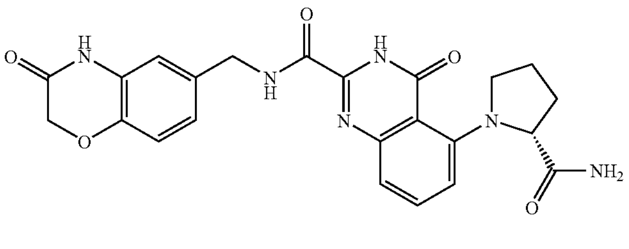 | 40% [MH]$^+$ = 463 |

TABLE II.13-continued
| Ex. # | Amine | product | yield |
|---|---|---|---|
| 36/8 | 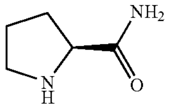 | 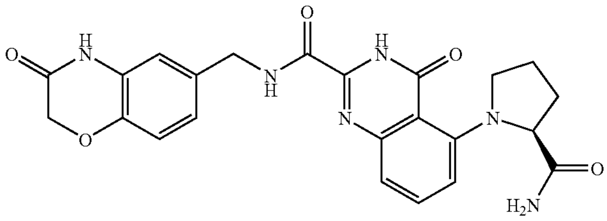 | 30%<br>$[MH]^+ = 463$ |
| 36/10 | 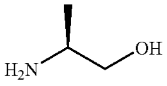 | 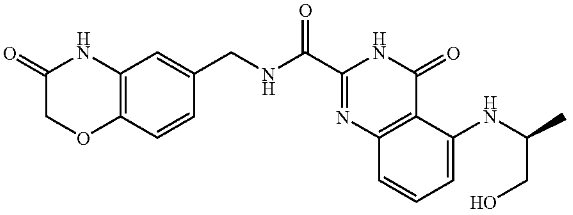 | 40%<br>$[MH]^+ = 424$ |
| 36/11 | 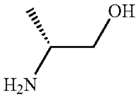 | 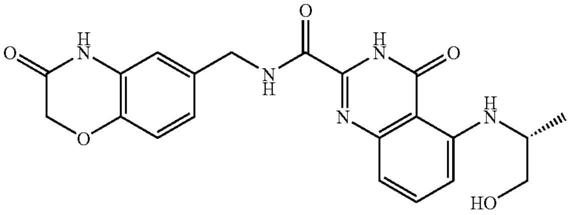 | 50%<br>$[MH]^+ = 424$ |
| 36/12 | 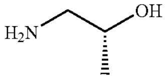 | 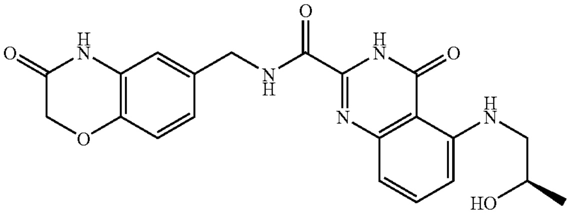 | 30%<br>$[MH]^+ = 424$ |
| 36/13 | 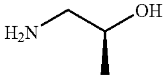 | 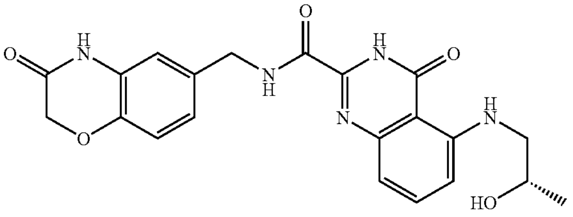 | 35%<br>$[MH]^+ = 424$ |
Example 37
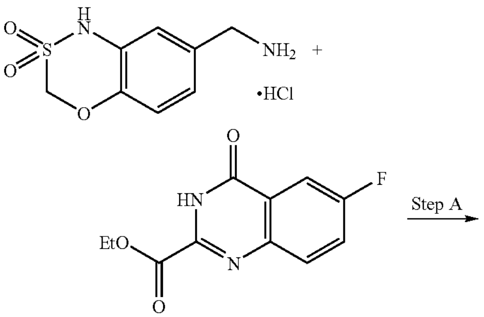
-continued
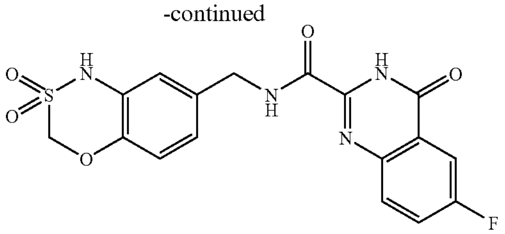
Step A
To a thick walled glass vessel containing a stir bar is added 69 mg of 6-fluoro-4-oxo-3,4-dihydro-quinazoline-2-carboxylic acid ethyl ester, 73 mg of the hydrochloride salt of the benzo[1,3,4]oxathiazine synthesized following Preparative Example 5/6, 1 mL of ethanol and 0.1 ml (0.70 mmoles) of triethylamine and mixture heated at 180° C. via microwave under closed atmosphere for 1 h. The mixture was then centrifuged and the solid was triturated with ethanol to give a white solid. The solid was purified by preparative thin layer chromatography ($SiO_2$, 10% MeOH-methylene chloride) to give 21 mg (18% yield) of the desired 6-fluoro-4-oxo-1,2,3,4-tetrahydro-quinazoline-2-carboxylic acid (2,2-dioxo-2,3-dihydro-benzo[1,3,4]oxathiazin-7-ylmethyl)-amide product as a white solid. $[MH]^+$=405.

Example 38

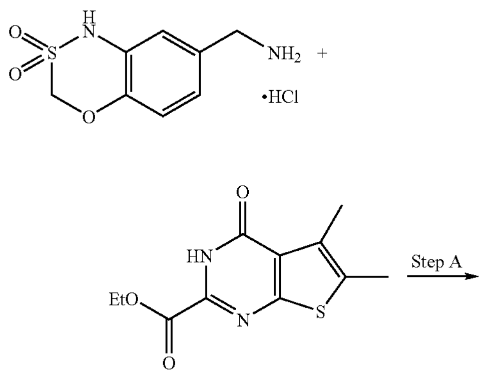

-continued

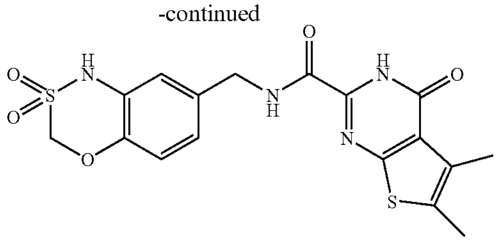

Step A

To a thick walled glass vessel containing a stir bar is added 52 mg (0.20 mmoles) of 5,6-dimethyl-4-oxo-3,4-dihydro-thieno[2,3-d]pyrimidine-2-carboxylic acid ethyl ester, 65 mg of the hydrochloride salt of the benzo[1,3,4]oxathiazine synthesized following Preparative Example 5/19, 1 mL of ethanol and 0.1 ml (0.70 mmoles) of triethylamine and mixture heated at 180° C. via microwave under closed atmosphere for 1 h. The mixture was then centrifuged and the solid was repeatedly triturated with ethanol and then methylene chloride to give 19 mg (22% yield) of the desired benzo[1,3,4]oxathiazin-7-ylmethyl)-amide product as a white solid. $[MH]^+$=421.

Examples 39/1-39/25

Following similar procedures as described in Examples 38 except using the amines and the ester indicated in Table II.14 below, the following compounds were prepared.

TABLE II.14

| Ex. # | amine; ester | product | Yield |
|---|---|---|---|
| 39/1 | 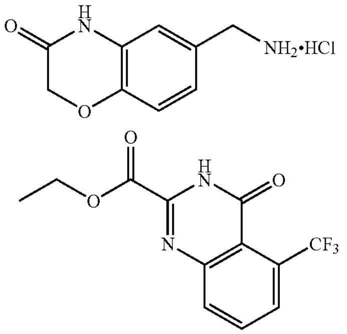 | 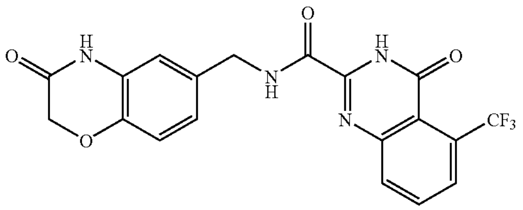 | 50% $[MH]^+$ = 419 |
| 39/2 | 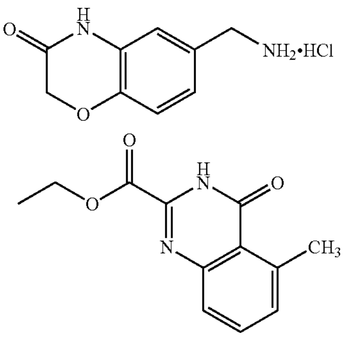 | 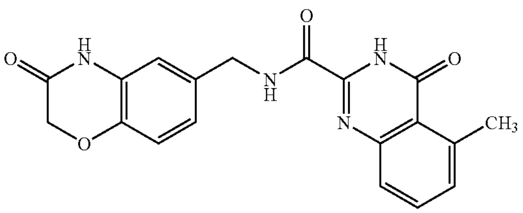 | 40% $[MH]^+$ = 365 |

TABLE II.14-continued
| Ex. # | amine; ester | product | Yield |
|---|---|---|---|
| 39/3 | 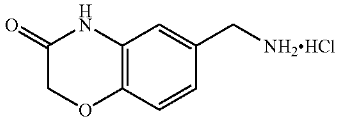 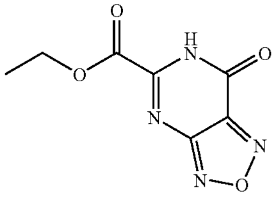 | 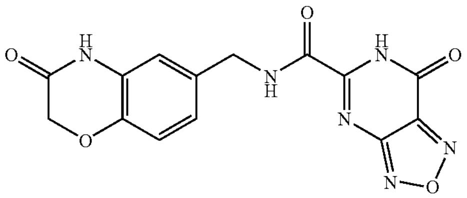 | 12% [MH]$^+$ = 343 |
| 39/4 | 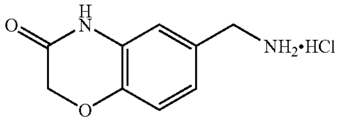 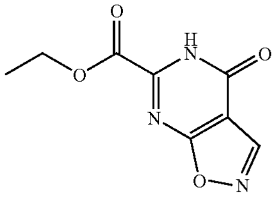 | 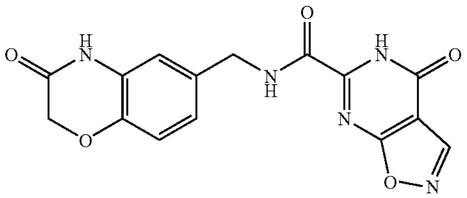 | 15% [MH]$^+$ = 342 |
| 39/5 | 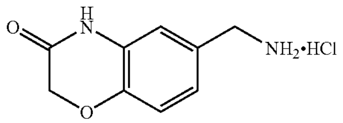 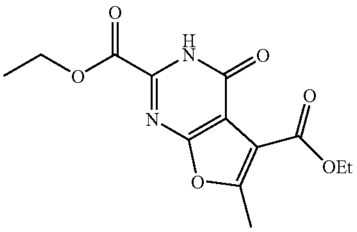 | 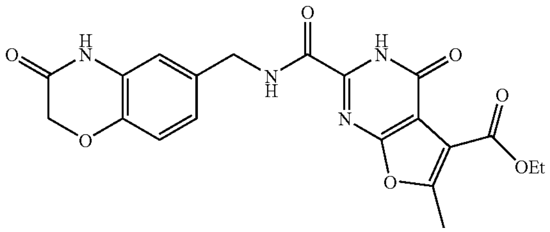 | 31% [MH]$^+$ = 427 |
| 39/6 | 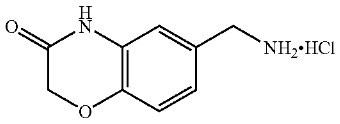 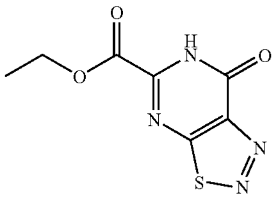 | 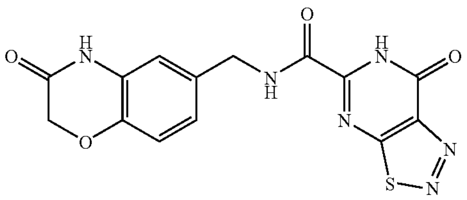 | 8% [MH]$^+$ = 359 |

TABLE II.14-continued
| Ex. # | amine; ester | product | Yield |
| --- | --- | --- | --- |
| 39/8 | 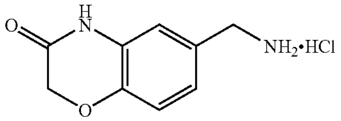 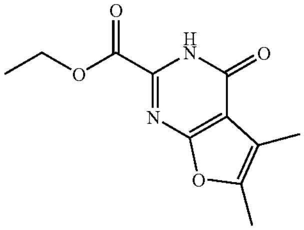 | 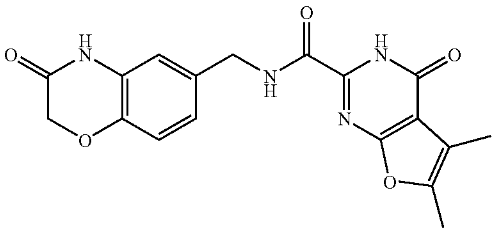 | 22% $[MH]^+$ = 369 |
| 39/9 | 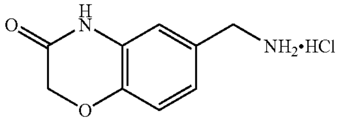 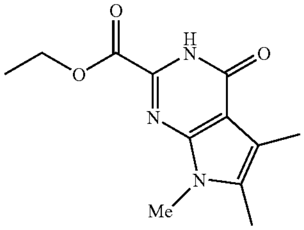 | 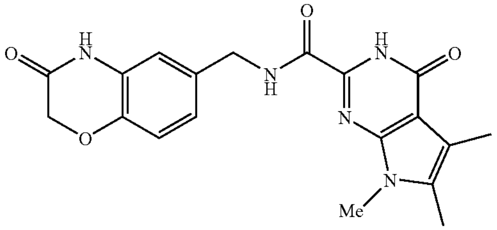 | 16% $[MH]^+$ = 382 |
| 39/10 | 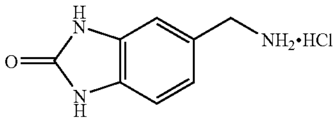 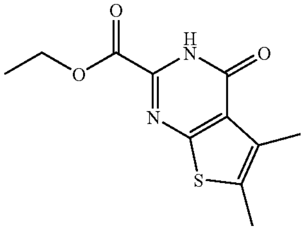 | 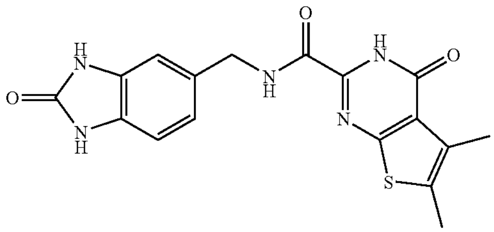 | 25% $[MH]^+$ = 370 |
| 39/11 | 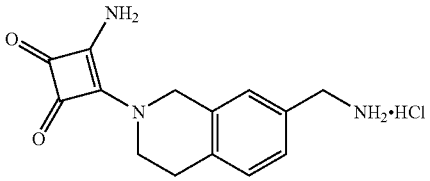 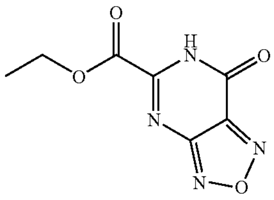 | 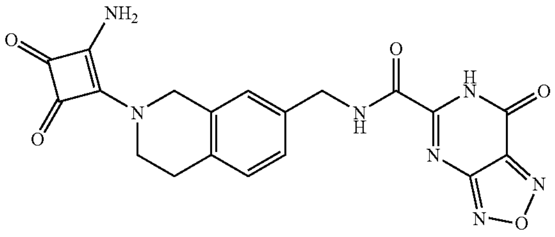 | 6% $[MH]^+$ = 422 |

TABLE II.14-continued
| Ex. # | amine; ester | product | Yield |
|---|---|---|---|
| 39/12 | 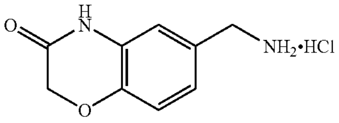 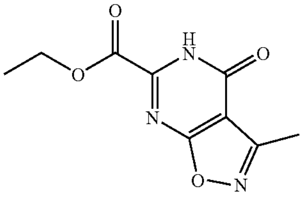 | 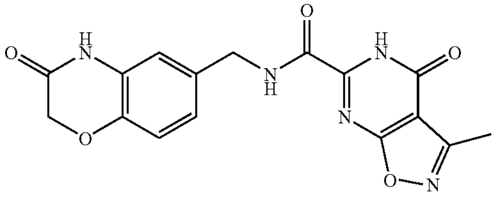 | 45% [MH]+ = 356 |
| 39/13 | 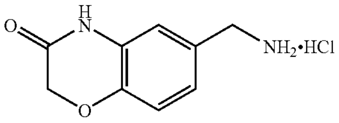 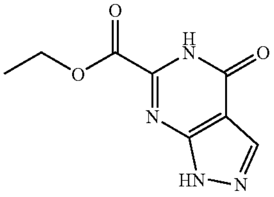 | 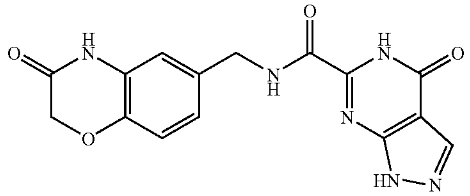 | 48% [MH]+ = 341 |
| 39/14 | 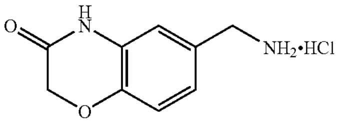 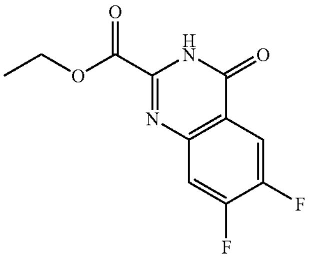 | 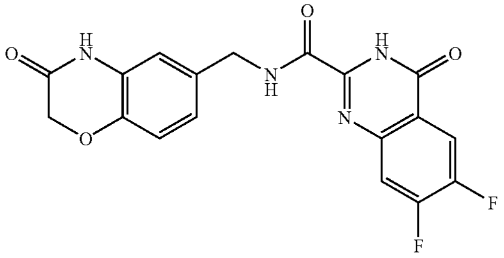 | n.d. [MH]+ = 387 |
| 39/15 | 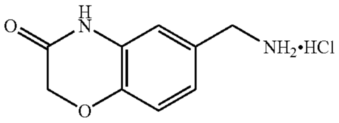 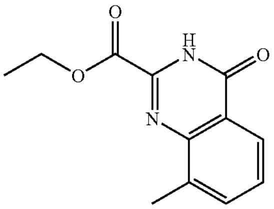 | 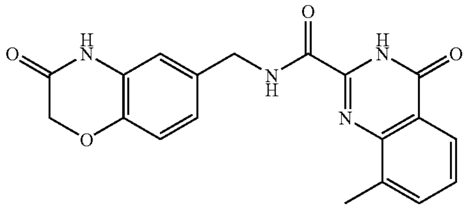 | 28% [MH]+ = 365 |

TABLE II.14-continued
| Ex. # | amine; ester | product | Yield |
| --- | --- | --- | --- |
| 39/16 | 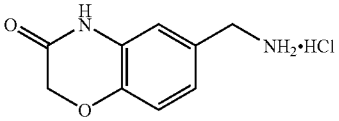 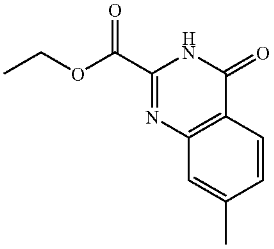 | 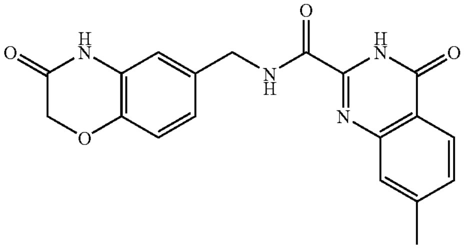 | 17% $[MH]^+$ = 365 |
| 39/17 | 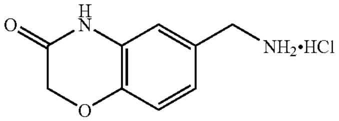 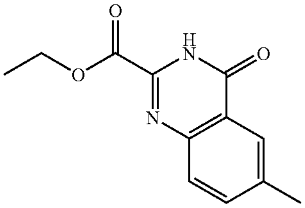 | 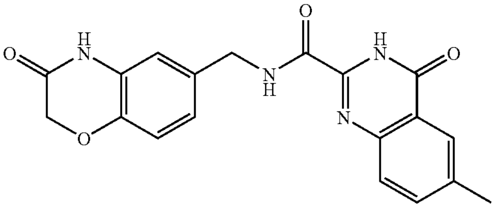 | 19% $[MH]^+$ = 365 |
| 39/18 | 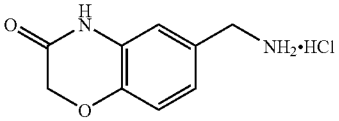 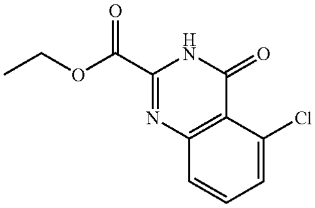 | 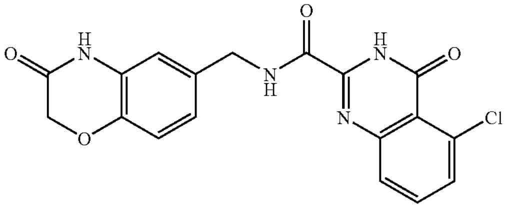 | 5% $[MH]^+$ = 385 |
| 39/19 | 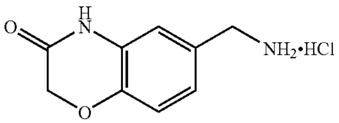 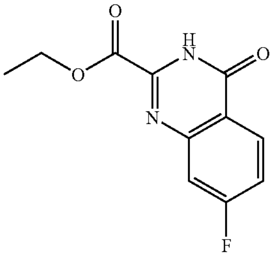 | 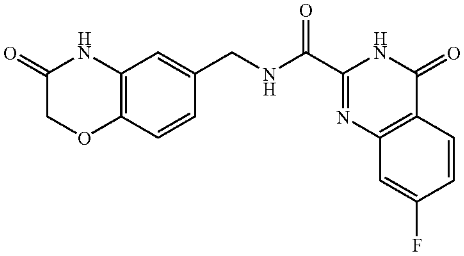 | 24% $[MH]^+$ = 369 |

TABLE II.14-continued
| Ex. # | amine; ester | product | Yield |
| --- | --- | --- | --- |
| 39/21 | 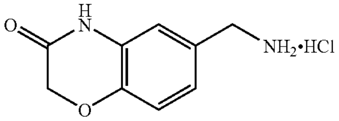 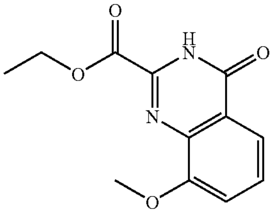 | 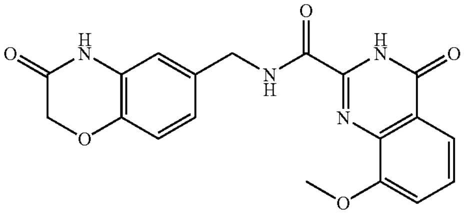 | 60% $[MH]^+$ = 381 |
| 39/22 | 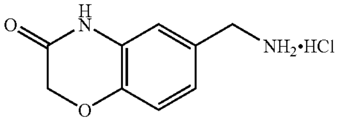 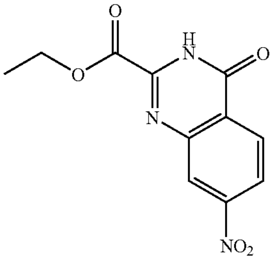 | 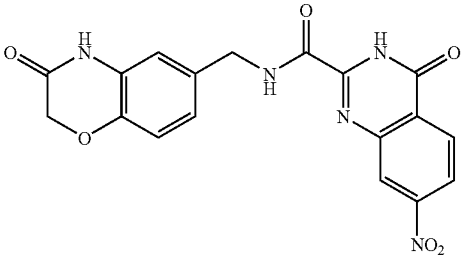 | 35% $[MH]^+$ = 396 |
| 39/23 | 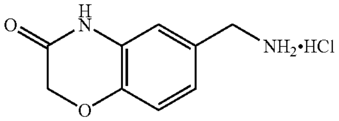 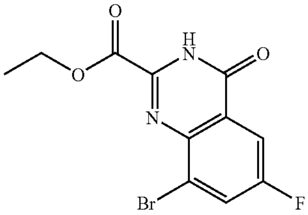 | 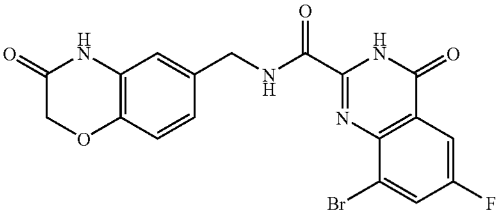 | 27% $[MH]^+$ = 448 |
| 39/24 | 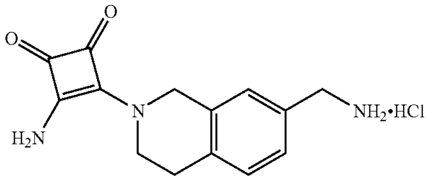 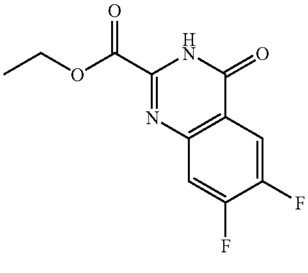 | 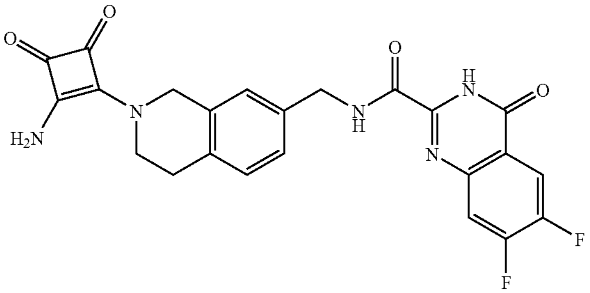 | 26% $[MH]^+$ = 466 |

TABLE II.14-continued

| Ex. # | amine; ester | product | Yield |
|---|---|---|---|
| 39/25 | 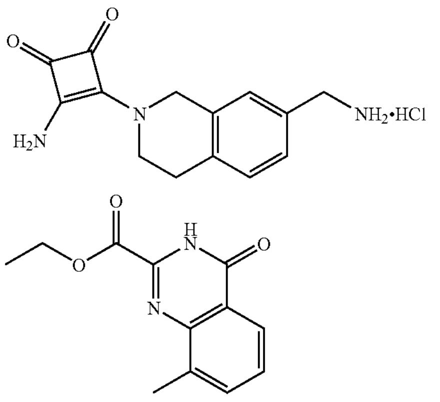 | 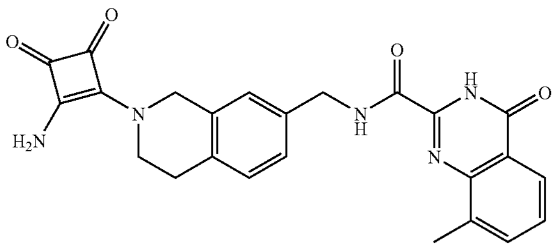 | 15% $[MH]^+$ = 444 |

Example 44

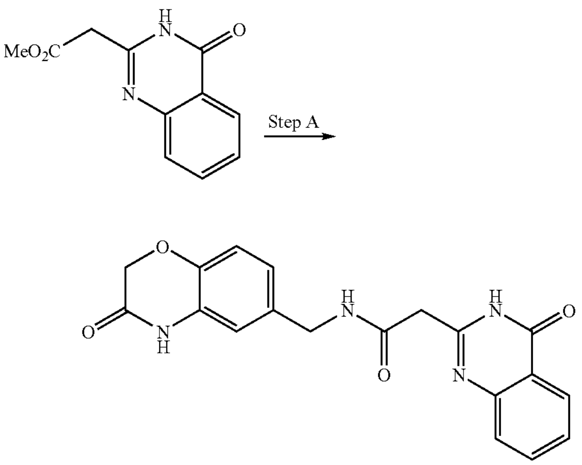

Step A

A mixture of (4-oxo-3,4-dihydro-quinazolin-2-yl)-acetic acid methyl ester (28.8 mg, 0.132 mmol), 6-(aminomethyl)-2H-benzo[b][1,4]oxazin-3(4H)-one HCl salt (34.9 mg, 0.163 mmol), and triethylamine (55 μL, 40 mg, 0.40 mmol) in DMF (1 ml) was heated in a microwave at 160° C. for 5 min, then 180° C. for 1 h. Typical aqueous workup and purification provided 7.1 mg of the desired product as a pale yellow solid. $[MH]^+$=365.

Example 45

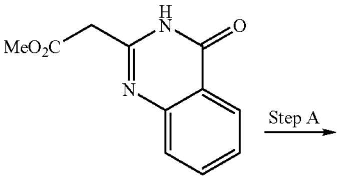

-continued

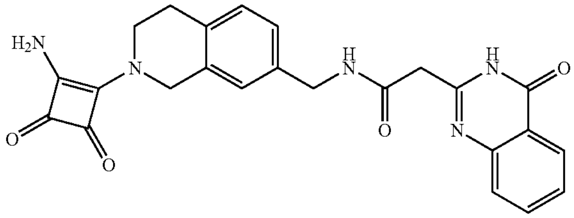

Step A

Utilizing the same procedure as indicated in Example 44 above except coupling 3-amino-4-(7-aminomethyl-3,4-dihydro-1H-isoquinolin-2-yl)-cyclobut-3-ene-1,2-dione HCl salt with 4-Oxo-3,4-dihydro-quinazoline-2-carboxylic acid ethyl ester at 120° C. for 1 h provided 23.7 mg of the desired product as a pale yellow solid. $[MH]^+$=444.

Example 1700

Assay for Determining MMP-13 Inhibition

The typical assay for MMP-13 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 μL aliquots. 10 μL of a 50 nM stock solution of catalytic domain of MMP-13 enzyme (produced by Alantos or commercially available from Invitek (Berlin), Cat. # 30100812) is added to the compound solution. The mixture of enzyme and compound in assay buffer is thoroughly mixed and incubated for 10 min at room temperature. Upon the completion of incubation, the assay is started by addition of 40 μl of a 12.5 μM stock solution of MMP-13 fluorescent substrate (Calbiochem, Cat. No. 444235). The time-dependent increase in fluorescence is measured at the 320 nm excitation and 390 nm emission by automatic plate multireader. The $IC_{50}$ values are calculated from the initial reaction rates.

Example 1701

Assay for Determining MMP-3 Inhibition

The typical assay for MMP-3 activity is carried out in assay buffer comprised of 50 mM MES, pH 6.0, 10 mM $CaCl_2$ and 0.05% Brij-35. Different concentrations of tested compounds are prepared in assay buffer in 50 μL aliquots. 10 μL of a 100 nM stock solution of the catalytic domain of MMP-3 enzyme (Biomol, Cat. No. SE-109) is added to the compound solution. The mixture of enzyme and compound in assay buffer is thoroughly mixed and incubated for 10 min at room temperature. Upon the completion of incubation, the assay is started by addition of 40 μL of a 12.5 μM stock solution of NFF-3 fluorescent substrate (Calbiochem, Cat. No. 480455). The time-dependent increase in fluorescence is measured at the 330 nm excitation and 390 nm emission by an automatic plate multireader. The $IC_{50}$ values are calculated from the initial reaction rates.

Example 1702

Assay for Determining MMP-8 Inhibition

The typical assay for MMP-8 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 μL aliquots. 10 μL of a 50 nM stock solution of activated MMP-8 enzyme (Calbiochem, Cat. No. 444229) is added to the compound solution. The mixture of enzyme and compound in assay buffer is thoroughly mixed and incubated for 10 min at 37° C. Upon the completion of incubation, the assay is started by addition of 40 μL of a 10 μM stock solution of OmniMMP fluorescent substrate (Biomol, Cat. No. P-126). The time-dependent increase in fluorescence is measured at the 320 nm excitation and 390 nm emission by an automatic plate multireader at 37° C. The $IC_{50}$ values are calculated from the initial reaction rates.

Example 1703

Assay for Determining MMP-12 Inhibition

The typical assay for MMP-12 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 μL aliquots. 10 μL of a 50 nM stock solution of the catalytic domain of MMP-12 enzyme (Biomol, Cat. No. SE-138) is added to the compound solution. The mixture of enzyme and compound in assay buffer is thoroughly mixed and incubated for 10 min at room temperature. Upon the completion of incubation, the assay is started by addition of 40 μL of a 12.5 μM stock solution of OmniMMP fluorescent substrate (Biomol, Cat. No. P-126). The time-dependent increase in fluorescence is measured at the 320 nm excitation and 390 nm emission by automatic plate multireader at 37° C. The $IC_{50}$ values are calculated from the initial reaction rates.

Example 1704

Assay for Determining Aggrecanase-1 Inhibition

The typical assay for aggrecanase-1 activity is carried out in assay buffer comprised of 50 mM Tris, pH 7.5, 150 mM NaCl, 5 mM $CaCl_2$ and 0.05% Brij-35. Different concentrations of tested compounds are prepared in assay buffer in 50 μL aliquots. 10 μl of a 75 nM stock solution of aggrecanase-1 (Invitek) is added to the compound solution. The mixture of enzyme and compound in assay buffer is thoroughly mixed. The reaction is started by addition of 40 μL of a 250 nM stock solution of aggrecan-IGD substrate (Invitek) and incubation at 37° C. for exact 15 min. The reaction is stopped by addition of EDTA and the samples are analysed by using aggrecanase ELISA (Invitek, InviLISA, Cat. No. 30510111) according to the protocol of the supplier. Shortly: 100 μL of each proteolytic reaction are incubated in a pre-coated micro plate for 90 min at room temperature. After 3 times washing, antibody-peroxidase conjugate is added for 90 min at room temperature. After 5 times washing, the plate is incubated with TMB solution for 3 min at room temperature. The peroxidase reaction is stopped with sulfurous acid and the absorbance is red at 450 nm. The $IC_{50}$ values are calculated from the absorbance signal corresponding to residual aggrecanase activity.

Example 1705

Assay for Determining Inhibition of MMP-3 Mediated Proteoglycan Degradation

The assay for MMP-3 activity is carried out in assay buffer comprised of 50 mM MES, pH 6.0, 10 mM $CaCl_2$ and 0.05% Brij-35. Articular cartilage is isolated fresh from the first phalanges of adult cows and cut into pieces (~3 mg). Bovine cartilage is incubated with 50 nM human MMP-3 (Chemikon, cat. # 25020461) in presence or absence of inhibitor for 24 h at 37° C. Sulfated glycosaminoglycan (aggrecan) degradation products (sGAG) are detected in supernatant, using a modification of the colorimetric DMMB (1,9-dimethylmethylene blue dye) assay (Billinghurst et al., 2000, Arthritis & Rheumatism, 43 (3), 664). 10 μL of the samples or standard are added to 190 μL of the dye reagent in microtiter plate wells, and the absorbance is measured at 525 nm immediately. All data points are performed in triplicates.

Example 1706

Assay for Determining Inhibition of MMP-3 Mediated Pro-Collagenase 3 Activation

The assay for MMP-3 mediated activation of pro-collagenase 3 (pro-MMP-13) is carried out in assay buffer comprised of 50 mM MES, pH 6.0, 10 mM $CaCl_2$ and 0.05% Brij-35 (Nagase; *J. Biol. Chem.* 1994 Aug. 19; 269(33):20952-7).

Different concentrations of tested compounds are prepared in assay buffer in 5 μL aliquots. 10 μl of a 100 nM stock solution of trypsin-activated (Knäuper V., et al., 1996 *J. Biol. Chem.* 271 1544-1550) human pro-MMP-3 (Chemicon; CC 1035) is added to the compound solution. To this mixture, 35 μL of a 286 nM stock solution of pro-collagenase 3 (Invitek; 30100803) is added to the mixture of enzyme and compound. The mixture is thoroughly mixed and incubated for 5 h at 37° C. Upon the completion of incubation, 10 μL of the incubation mixture is added to 50 μL assay buffer comprised of 50 mM Tris, pH 7.5, 150 mM NaCl, 5 mM $CaCl_2$ and 0.05% Brij-35 and the mixture is thoroughly mixed.

The assay to determine the MMP-13 activity is started by addition of 40 μL of a 10 μM stock solution of MMP-13 fluorogenic substrate (Calbiochem, Cat. No. 444235) in assay buffer comprised of 50 mM Tris, pH 7.5, 150 mM NaCl, 5 mM $CaCl_2$ and 0.05% Brij-35 (Knäuper, V., et al., 1996. *J. Biol. Chem.* 271, 1544-1550). The time-dependent increase in fluorescence is measured at 320 nm excitation and 390 nm emission by an automatic plate multireader at room temperature. The $IC_{50}$ values are calculated from the initial reaction rates.

The invention claimed is:

1. A compound having Formula (I):

Formula (I)

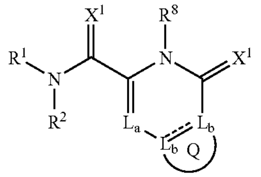

wherein:

$R^1$ is benzoxazinyl;

wherein $R^1$ is optionally substituted one or more times, or wherein $R^1$ is optionally substituted by one $R^{16}$ group and optionally substituted by one or more $R^9$ groups;

$R^2$ is selected from hydrogen and alkyl, wherein alkyl is optionally substituted one or more times or $R^1$ and $R^2$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;

$R^4$ in each occurrence is independently selected from $R^{10}$, hydrogen, alkyl, cycloalkyl, heterocycloalkyl, aryl, heteroaryl, halo, haloalkyl, $CF_3$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-CN, $(C_0\text{-}C_6)$-alkyl-$S(O)_yOR^{10}$, $(C_0\text{-}C_6)$-alkyl-$S(O)_yNR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C({=}NR^{10})NR^{10}R^{11}$, $(C_0\text{-}C_6)$-alkyl-$NR^{10}C({=}NR^{11})NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $(C_0\text{-}C_6)$-alkyl-C(O)—$NR^{11}$—CN, O—$(C_0\text{-}C_6)$-alkyl-$C(O)NR^{10}R^{11}$, $S(O)_x$—$(C_0\text{-}C_6)$-alkyl-$C(O)OR^{10}$, $S(O)_x$—$(C_0\text{-}C_6)$-alkyl-$C(O)NR^{10}R^{11}$, $(C_0\text{-}C_6)$-alkyl-$C(O)NR^{10}$—$(C_0\text{-}C_6)$-alkyl-$NR^{10}R^{11}$, $(C_0\text{-}C_6)$-alkyl-$NR^{10}$—$C(O)R^{10}$, $(C_0\text{-}C_6)$-alkyl-$NR^{10}$—$C(O)OR^{10}$, $(C_0\text{-}C_6)$-alkyl-$NR^{10}$—C(O)—$NR^{10}R^{11}$, $(C_0\text{-}C_6)$-alkyl-$NR^{10}$—$S(O)_yNR^{10}R^{11}$, $(C_0\text{-}C_6)$-alkyl-$NR^{10}$—$S(O)_yR^{10}$, O—$(C_0\text{-}C_6)$-alkyl-aryl and O—$(C_0\text{-}C_6)$-alkyl-heteroaryl, wherein each $R^4$ group is optionally substituted one or more times, or wherein each $R^4$ group is optionally substituted by one or more $R^{14}$ groups, or wherein optionally two $R^4$ groups, when taken together with the nitrogen or carbon to which they are attached complete a 3- to 8-membered saturated ring or multicyclic ring or unsaturated ring containing carbon atoms and optionally containing one or more heteroatom independently selected from O, $S(O)_x$, N, or $NR^{50}$ and which is optionally substituted one or more times, or optionally two $R^4$ groups taken together at one saturated carbon atom form ═O, ═S, ═$NR^{10}$ or ═$NOR^{10}$;

$R^5$ is independently selected from hydrogen, alkyl, $C(O)NR^{10}R^{11}$, aryl, arylalkyl, $SO_2NR^{10}R^{11}$ and $C(O)OR^{10}$ wherein alkyl, aryl and arylalkyl are optionally substituted one or more times;

$R^8$ is independently selected from hydrogen, alkyl, cycloalkyl, heterocycloalkyl, aryl, heteroaryl, $R^{10}$ and $NR^{10}R^{11}$ wherein alkyl, cycloalkyl, heterocycloalkyl, aryl, and heteroaryl is optionally substituted one or more times;

$R^9$ in each occurrence is independently selected from $R^{10}$, hydrogen, alkyl, cycloalkyl, heterocycloalkyl, aryl, heteroaryl, halo, $CHF_2$, $CF_3$, $OR^{10}$, $SR^{10}$, $COOR^{10}$, $CH(CH_3)CO_2H$, $(C_0\text{-}C_6)$-alkyl-$COR^{10}$, $(C_0\text{-}C_6)$-alkyl-$OR^{10}$, $(C_0\text{-}C_6)$-alkyl-$NR^{10}R^{11}$, $(C_0\text{-}C_6)$-alkyl-$NO_2$, $(C_0\text{-}C_6)$-alkyl-CN, $(C_0\text{-}C_6)$-alkyl-$S(O)_yR^{10}$, $(C_0\text{-}C_6)$-alkyl-$P(O)_2OH$, $(C_0\text{-}C_6)$-alkyl-$S(O)_yNR^{10}R^{11}$, $(C_0\text{-}C_6)$-alkyl-$NR^{10}CONR^{11}SO_2R^{30}$, $(C_0\text{-}C_6)$-alkyl-$S(O)_xR^{10}$, $(C_0\text{-}C_6)$-alkyl-$OC(O)R^{10}$, $(C_0\text{-}C_6)$-alkyl-$OC(O)NR^{10}R^{11}$, $(C_0\text{-}C_6)$-alkyl-$C({=}NR^{10})NR^{10}R^{11}$, $(C_0\text{-}C_6)$-alkyl-$NR^{10}C({=}NR^{11})NR^{10}R^{11}$, $(C_0\text{-}C_6)$-alkyl-$NR^{10}C$(═N—CN)$NR^{10}R^{11}$, $(C_0\text{-}C_6)$-alkyl-C(═N—CN)$NR^{10}R^{11}$, $(C_0\text{-}C_6)$-alkyl-$NR^{10}C$(═N—$NO_2$)$NR^{10}R^{11}$, $(C_0\text{-}C_6)$-alkyl-C(═N—$NO_2$)$NR^{10}R^{11}$, $(C_0\text{-}C_6)$-alkyl-$C(O)OR^{10}$, $(C_0\text{-}C_6)$-alkyl-$C(O)NR^{10}R^{11}$, $(C_0\text{-}C_6)$-alkyl-$C(O)NR^{10}SO_2R^{11}$, $C(O)NR^{10}$—$(C_0\text{-}C_6)$-alkyl-heteroaryl, $C(O)NR^{10}$—$(C_0\text{-}C_6)$-alkyl-aryl, $S(O)_2NR^{10}$—$(C_0\text{-}C_6)$-alkyl-aryl, $S(O)_2NR^{10}$—$(C_0\text{-}C_6)$-alkyl-heteroaryl, $S(O)_2NR^{10}$-alkyl, $S(O)_2$—$(C_0\text{-}C_6)$-alkyl-aryl, $S(O)_2$—$(C_0\text{-}C_6)$-alkyl-heteroaryl, $(C_0\text{-}C_6)$-alkyl-C(O)—$NR^{11}$—CN, O—$(C_0\text{-}C_6)$-alkyl-$C(O)NR^{10}R^{11}$, $S(O)_x$—$(C_0\text{-}C_6)$-alkyl-$C(O)OR^{10}$, $S(O)_x$—$(C_0\text{-}C_6)$-alkyl-$C(O)NR^{10}R^{11}$, $(C_0\text{-}C_6)$-alkyl-$C(O)NR^{10}$—$(C_0\text{-}C_6)$-alkyl-$NR^{10}R^{11}$, $(C_0\text{-}C_6)$-alkyl-$NR^{10}$—$C(O)R^{10}$, $(C_0\text{-}C_6)$-alkyl-$NR^{10}$—$C(O)OR^{10}$, $(C_0\text{-}C_6)$-alkyl-$NR^{10}$—C(O)—$NR^{10}R^{11}$, $(C_0\text{-}C_6)$-alkyl-$NR^{10}$—$S(O)_yNR^{10}R^{11}$, $(C_0\text{-}C_6)$-alkyl-$NR^{10}$—$S(O)_yR^{11}$, O—$(C_0\text{-}C_6)$-alkyl-aryl and O—$(C_0\text{-}C_6)$-alkyl-heteroaryl, wherein each $R^9$ group is optionally substituted, or wherein each $R^9$ group is optionally substituted by one or more $R^{14}$ groups;

$R^{10}$ and $R^{11}$ in each occurrence are independently selected from hydrogen, alkyl, cycloalkyl, cycloalkylalkyl, heterocycloalkyl, bicycloalkyl, heterobicycloalkyl, spiroalkyl, spiroheteroalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, bicycloalkyl, heterobicycloalkyl, spiroalkyl, spiroheteroalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted one or more times, or $R^{10}$ and $R^{11}$ when taken together with the nitrogen to which they are attached complete a 3- to 8-membered ring containing carbon atoms and optionally containing a heteroatom selected from O, $S(O)_x$, or $NR^{50}$ and which is optionally substituted one or more times;

$R^{14}$ is independently selected from hydrogen, alkyl, arylalkyl, cycloalkylalkyl, heteroarylalkyl, heterocyclylalkyl and halo, wherein alkyl, arylalkyl, cycloalkylalkyl, heteroarylalkyl and heterocyclylalkyl are optionally substituted one or more times.

$R^{16}$ is selected from cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, (i) and (ii):

(i)

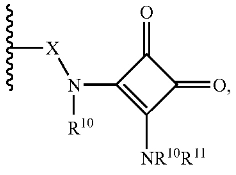

(ii)

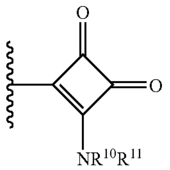

wherein cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, and heterocycloalkyl fused heteroarylalkyl are optionally substituted one or more times;

$R^{30}$ is selected from alkyl and $(C_0-C_6)$-alkyl-aryl, wherein alkyl and aryl are optionally substituted;

$R^{50}$ in each occurrence is independently selected from hydrogen, alkyl, aryl, heteroaryl, $C(O)R^{80}$, $C(O)NR^{80}R^{81}$, $SO_2R^{80}$ and $SO_2NR^{80}R^{81}$, wherein alkyl, aryl, and heteroaryl are optionally substituted one or more times;

$R^{80}$ and $R^{81}$ in each occurrence are independently selected from hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl and aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are optionally substituted, or $R^{80}$ and $R^{81}$ when taken together with the nitrogen to which they are attached complete a 3- to 8-membered ring containing carbon atoms and optionally a heteroatom selected from O, $S(O)_x$, —NH, and —N(alkyl) and which is optionally substituted one or more times;

E is selected from a bond, $CR^{10}R^{11}$, O, $NR^5$, S, S═O, $S(═O)_2$, C(═O), $N(R^{10})(C═O)$, $(C═O)N(R^{10})$, $N(R^{10})S(═O)_2$, $S(═O)_2N(R^{10})$, $C═N—OR^{11}$, $—C(R^{10}R^{11})C(R^{10}R^{11})—$, $—CH_2—W^1—$ and

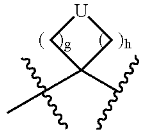

;

$L_a$ is independently selected from $CR^9$ and N;

$L_b$ is independently selected from C and N with the proviso, that both $L_b$ are not N, and that the bond between $L_b$ and $L_b$ is optionally a double bond only if both $L_b$ are C;

Q is a 4- to 8-membered ring selected from cycloalkyl, heterocycloalkyl or a 5- or 6-membered ring selected from aryl and heteroaryl, wherein Q is optionally substituted one or more times, or wherein Q is optionally substituted one or more times with $R^4$;

U is selected from $C(R^5R^{10})$, $NR^5$, O, S, S═O and $S(═O)_2$;

$W^1$ is selected from O, $NR^5$, S, S═O, $S(═O)_2$, $N(R^{10})(C═O)$, $N(R^{10})S(═O)_2$ and $S(═O)_2N(R^{10})$;

X is selected from a bond and $(CR^{10}R^{11})_wE(CR^{10}R^{11})_w$;

$X^1$ is independently selected from O, S, $NR^{10}$, N—CN, $NCOR^{10}$, $N—NO_2$, or $N—SO_2R^{10}$;

g and h are independently selected from 0-2;

w is selected from 0-4;

x is selected from 0 to 2;

y is selected from 1 and 2;

the dotted line optionally represents a double bond; and

N-oxides, pharmaceutically acceptable salts, formulations, tautomers, racemic mixtures and stereoisomers thereof.

2. A compound according to claim 1, having the structure:

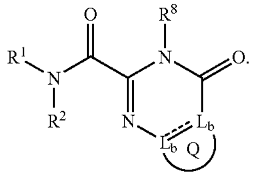

3. A compound according to claim 1, selected from:

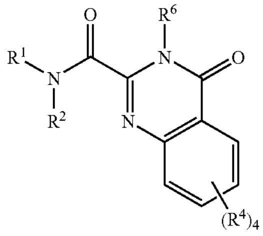

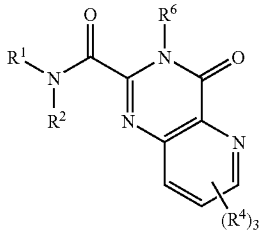

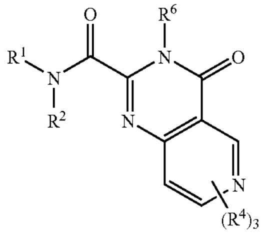

-continued
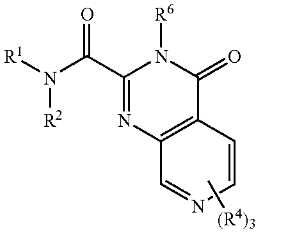
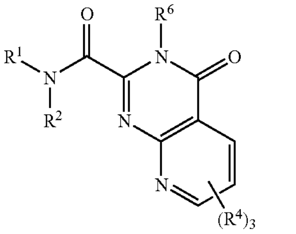
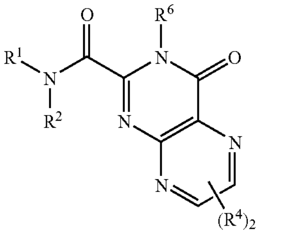
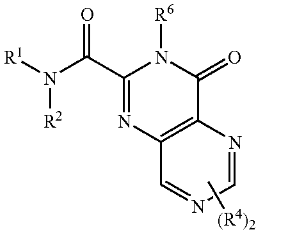
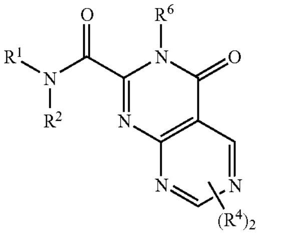
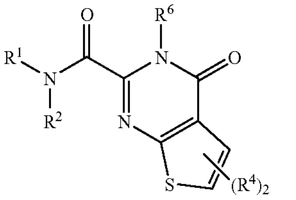
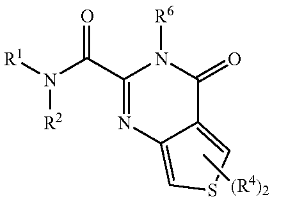
-continued
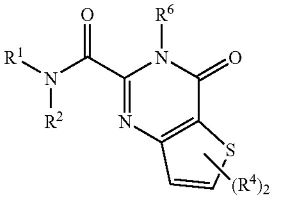
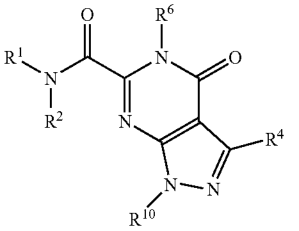
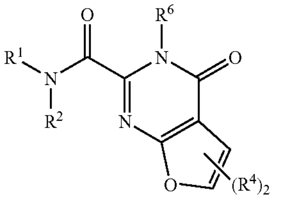
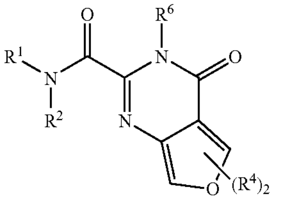
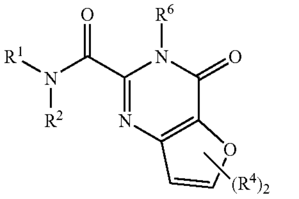
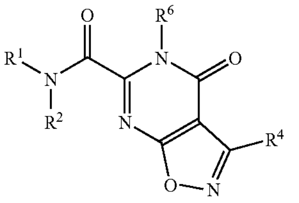
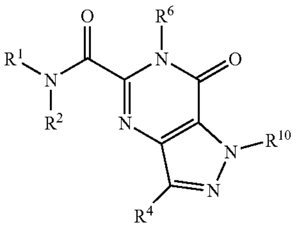
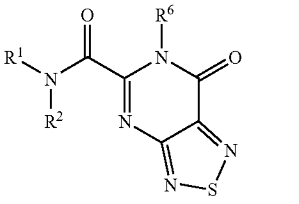

-continued
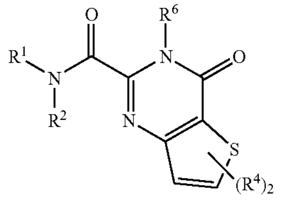
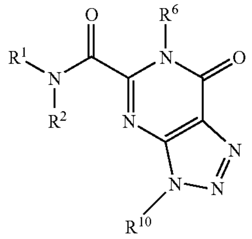
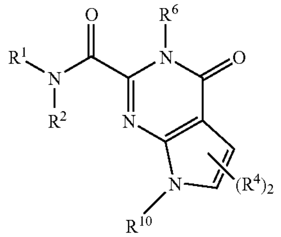
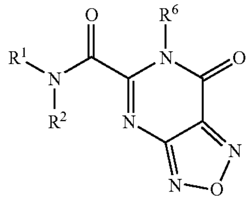
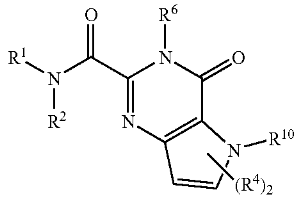
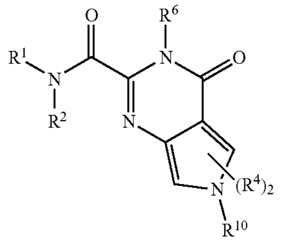
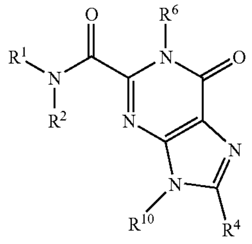
-continued
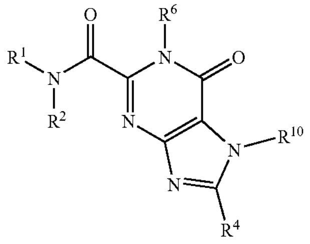
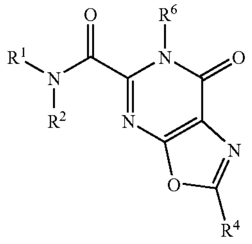
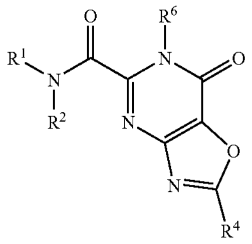
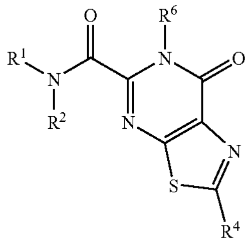
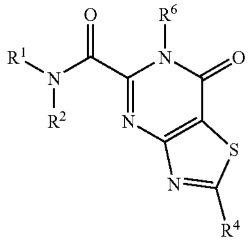
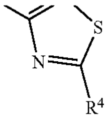
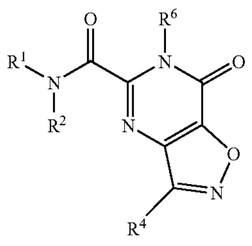

-continued
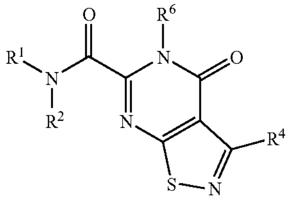
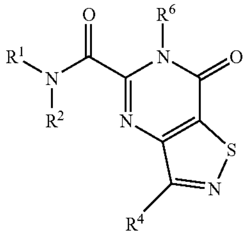
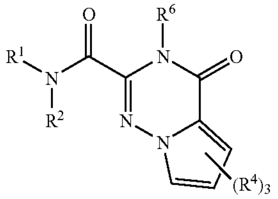
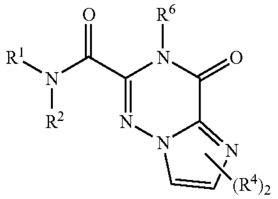
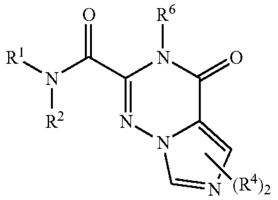
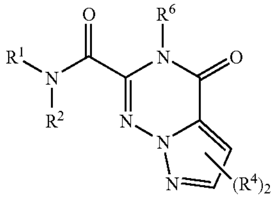
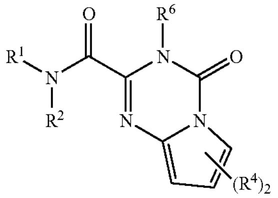
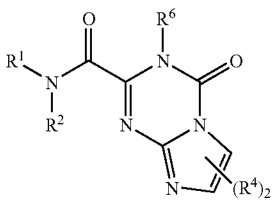
-continued
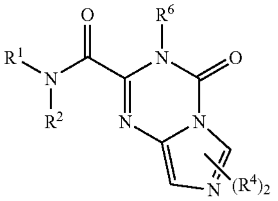
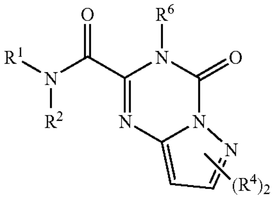
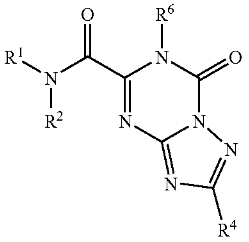
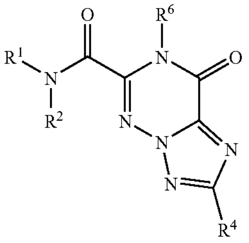
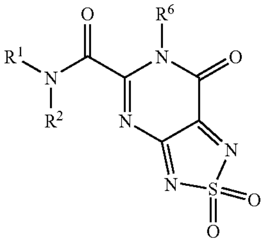
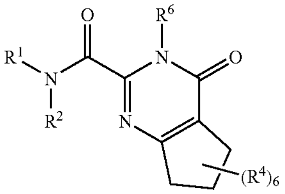
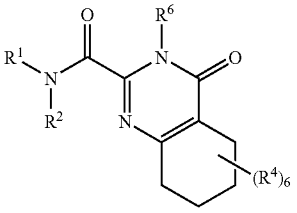

-continued
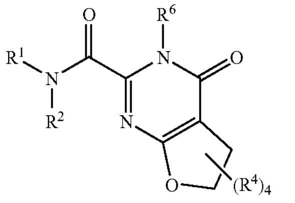
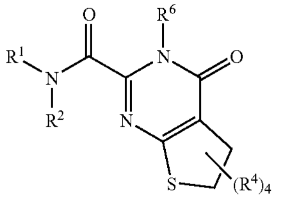
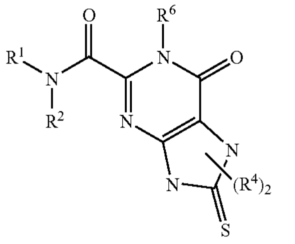
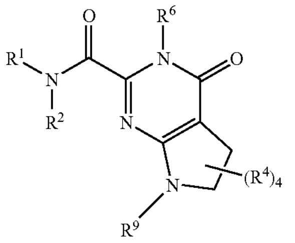
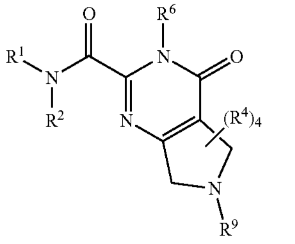
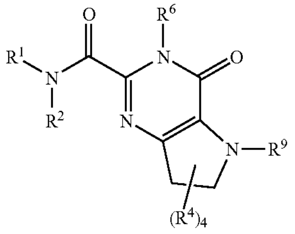
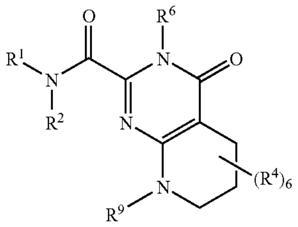
-continued
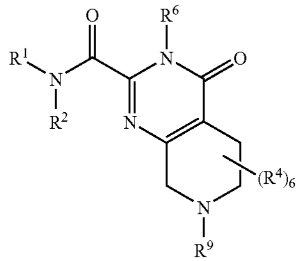
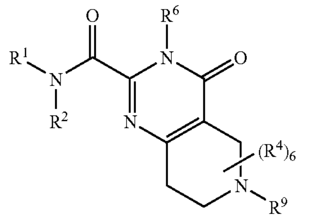
and
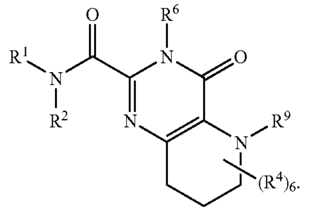
4. A compound according to claim 3, selected from:
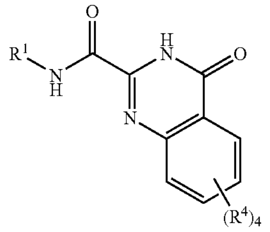
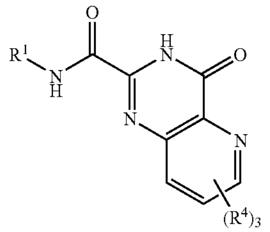
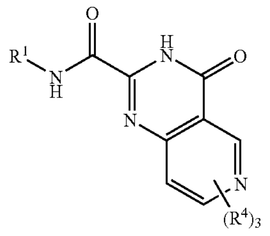

-continued
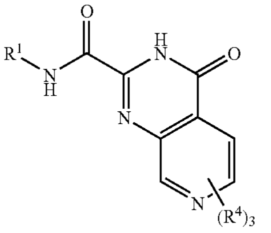
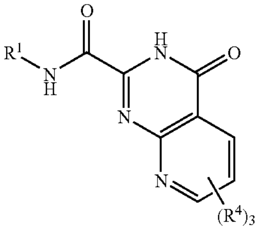
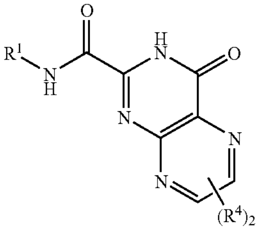
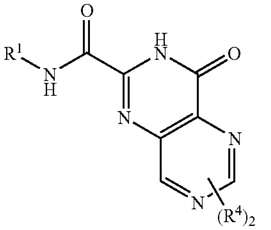
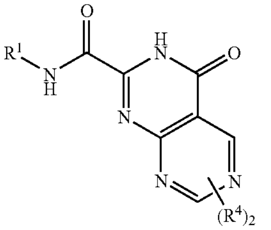
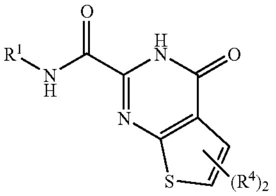
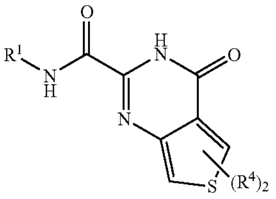
-continued
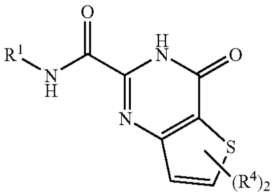
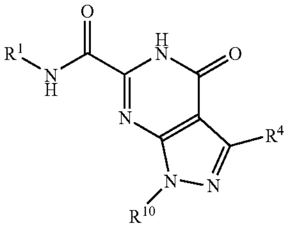
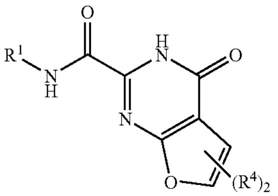
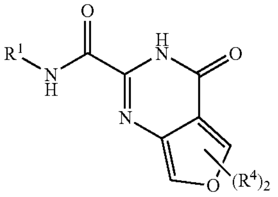
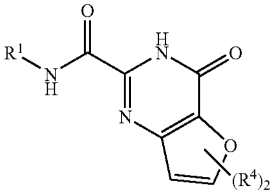
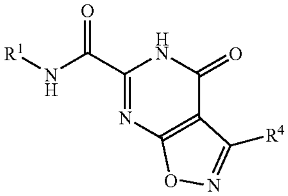
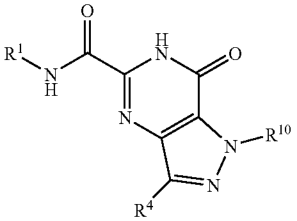
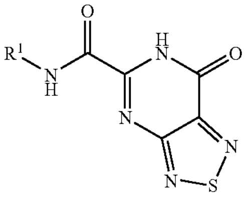

-continued
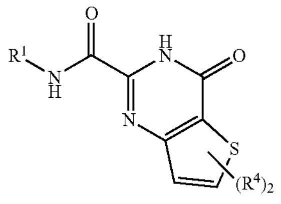
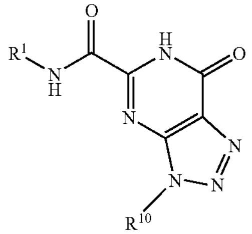
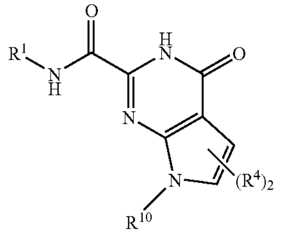
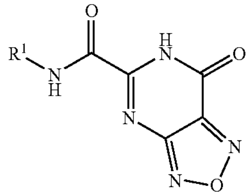
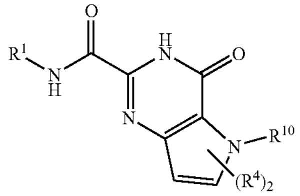
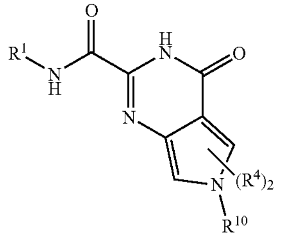
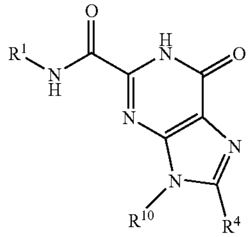
-continued
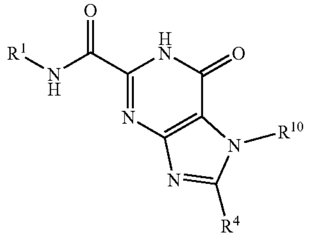
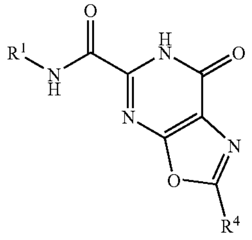
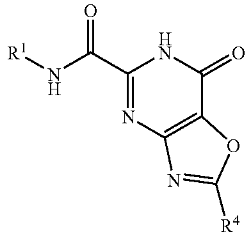
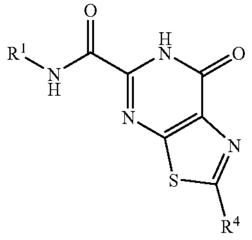
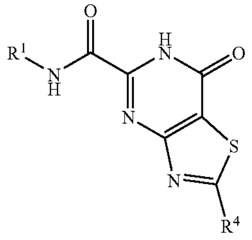
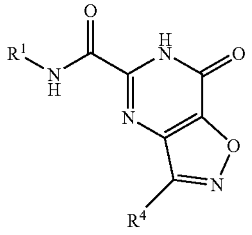
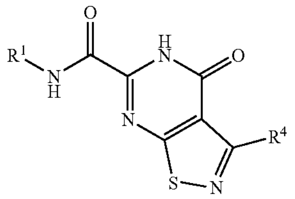

-continued
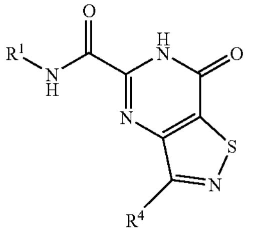
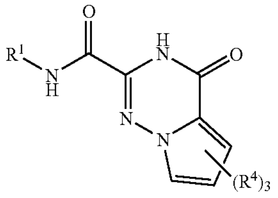
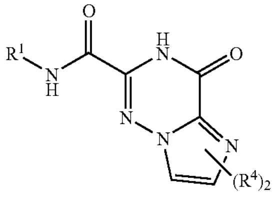
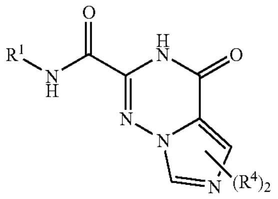
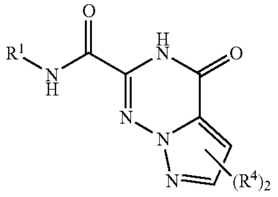
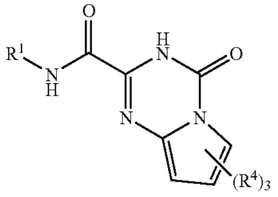
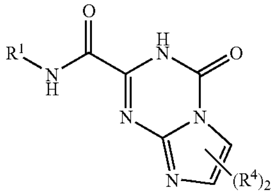
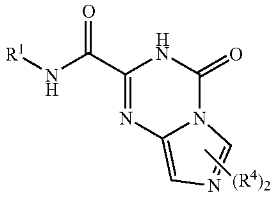
-continued
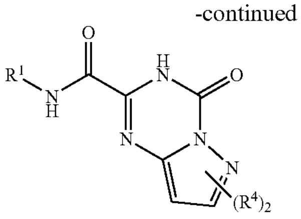
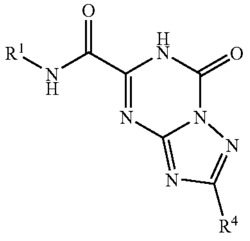
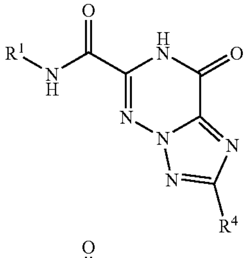
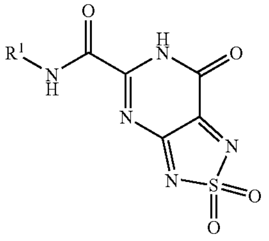
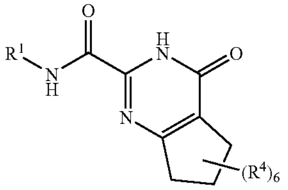
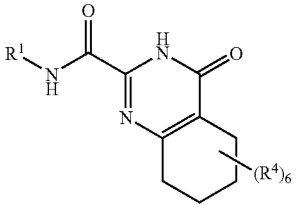
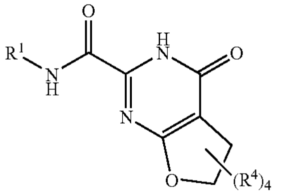
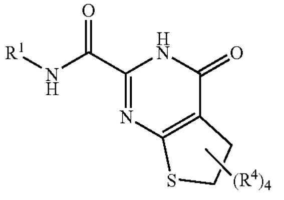

-continued
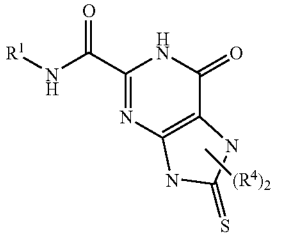
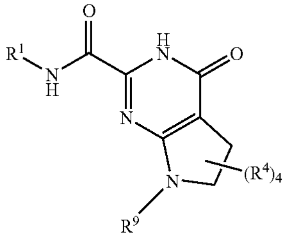
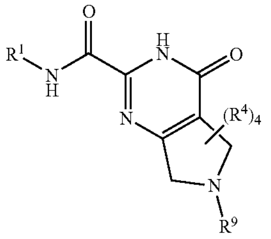
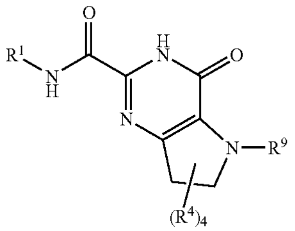
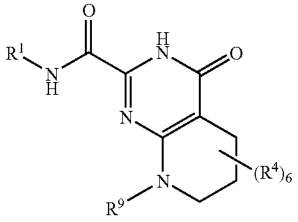
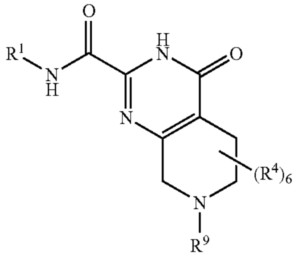
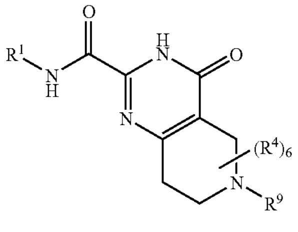
and
-continued
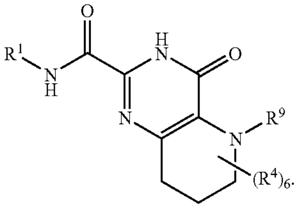
5. A compound according to claim 1, wherein $R^1$ is selected from:
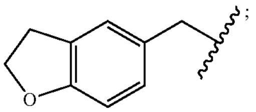
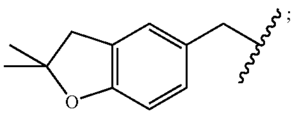
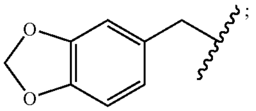
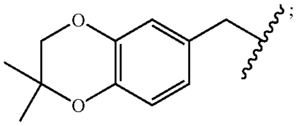
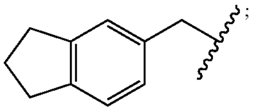
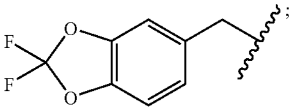
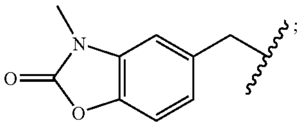
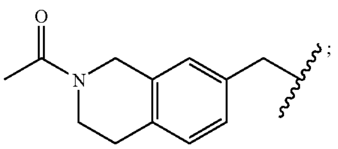
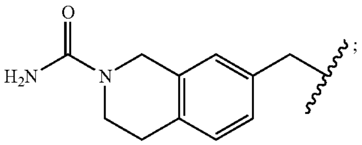
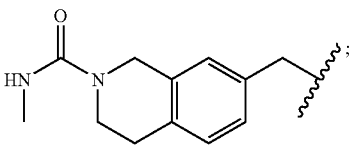

-continued
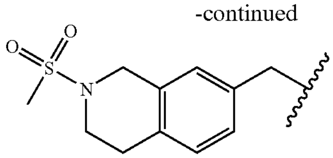
;
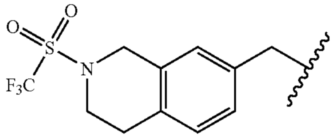
;
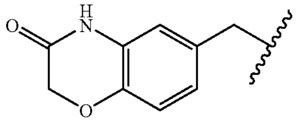
;
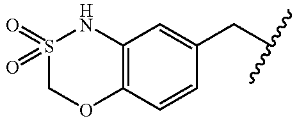
;
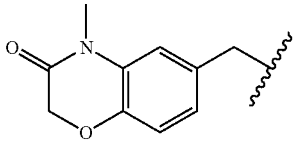
;
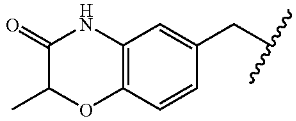
;
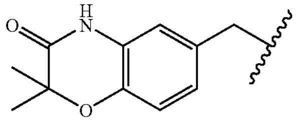
;
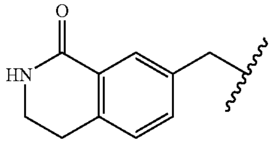
;
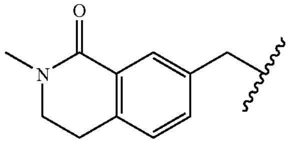
;
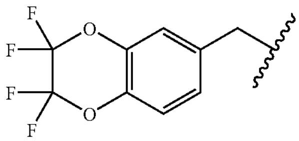
;
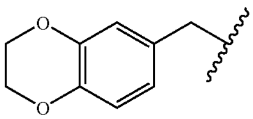
;
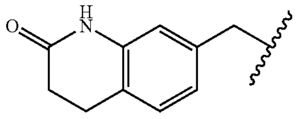
;
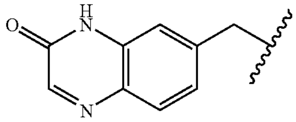
;
-continued
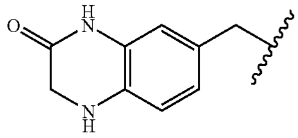
;
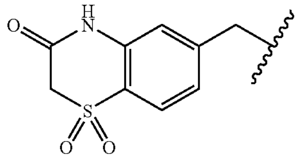
;
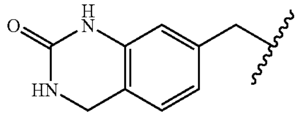
;
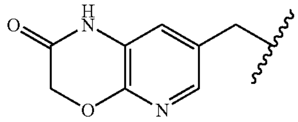
;
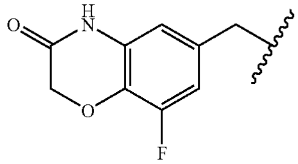
;
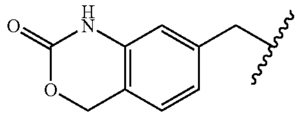
;
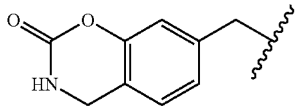
;
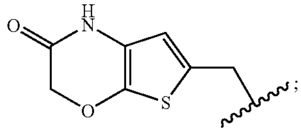
;
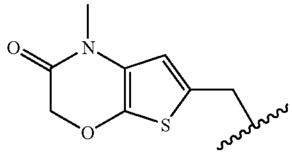
and
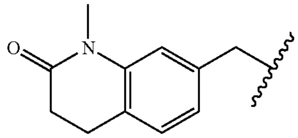
;
any of which are substituted by one or two substituents independently selected from $C_{1-2}$alkyl, $C_{1-2}$haloalkyl, halo, CN, OMe, $OCF_3$, or $OCHF_2$.

6. A compound according to claim 1, wherein $R^1$ is selected from:
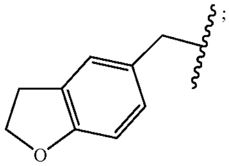
;
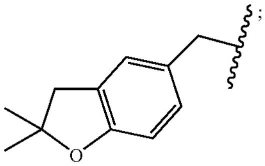
;
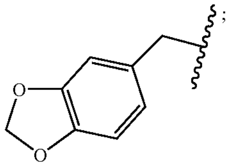
;
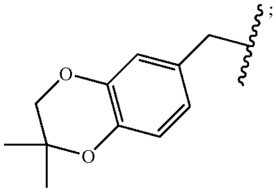
;
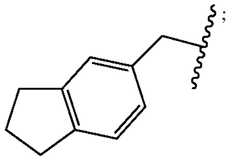
;
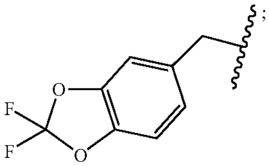
;
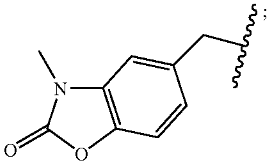
;
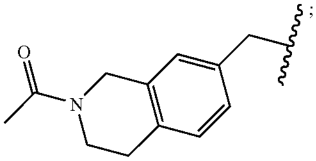
;
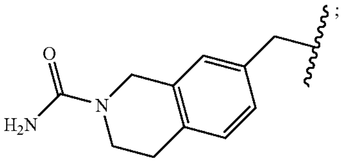
;
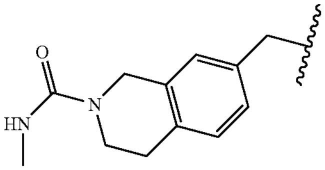
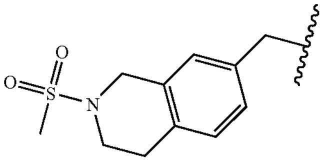
;
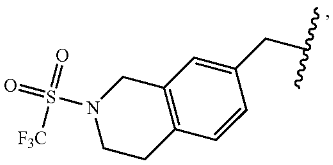
,
-continued
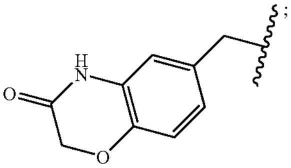
;
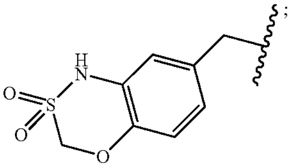
;
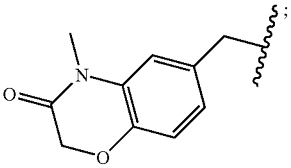
;
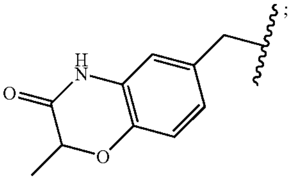
;
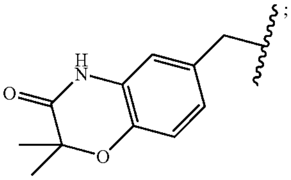
;
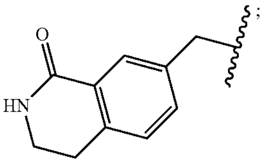
;
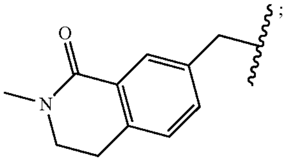
;
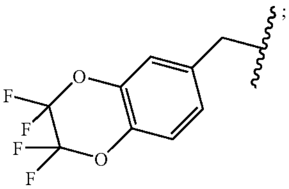
;
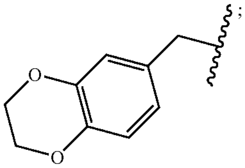
;

-continued
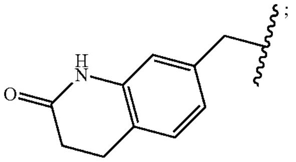
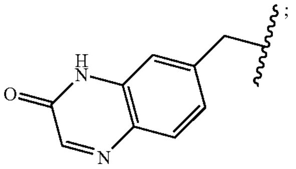
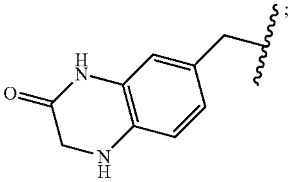
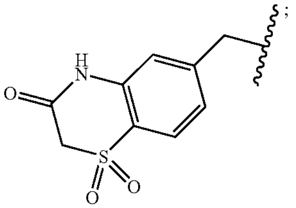
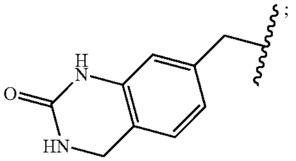
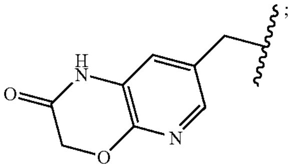
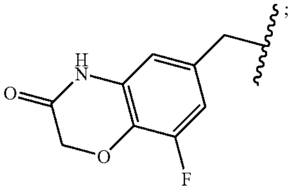
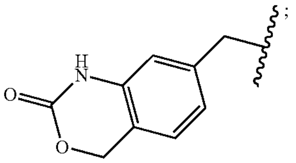
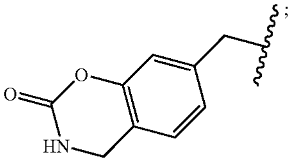
-continued
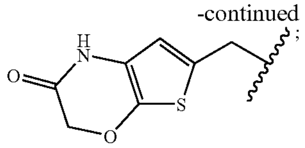
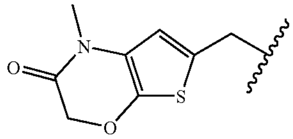
and
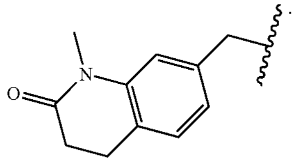
7. A compound according to claim 1, wherein $R^1$ is selected from:
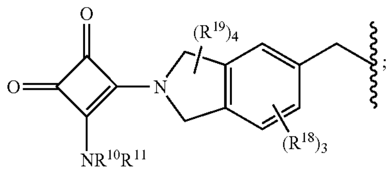
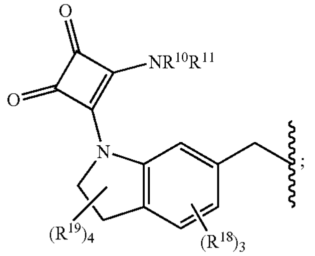
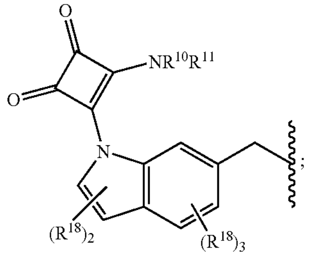
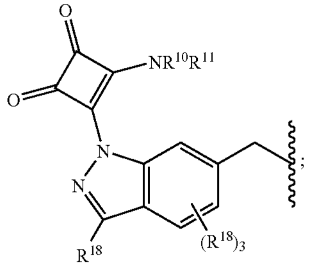
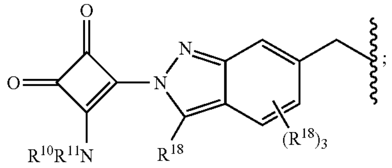

-continued
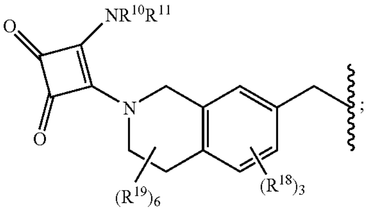
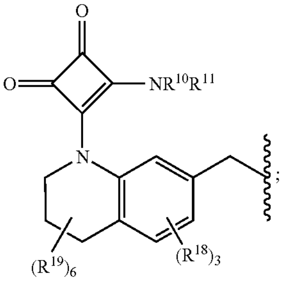
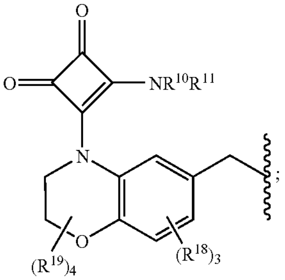
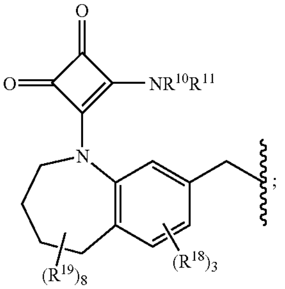
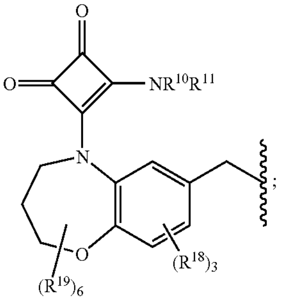
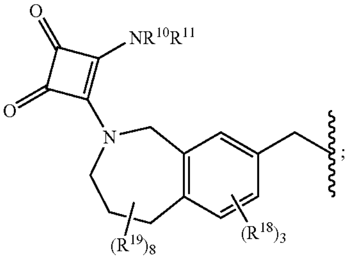
-continued
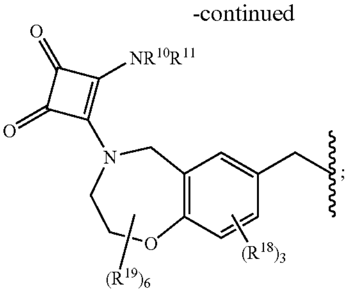
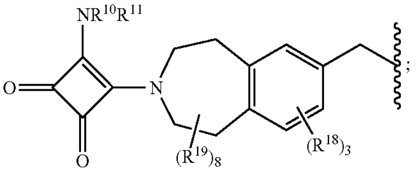
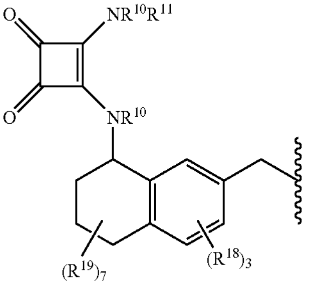
and
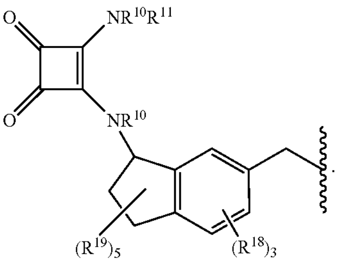
8. A compound according to claim 1, wherein $R^1$ is:
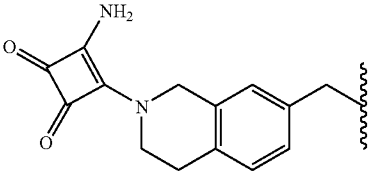
and
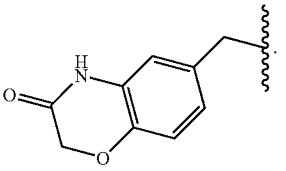

9. A compound according to claim 1, selected from:
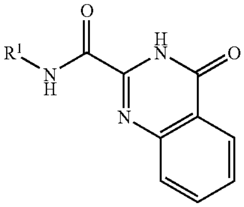
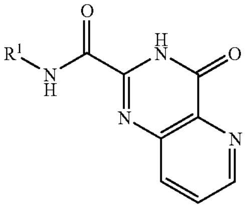
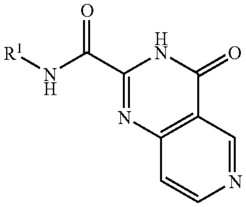
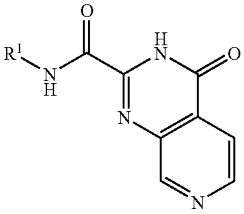
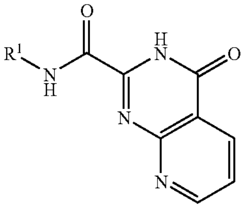
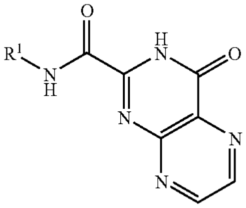
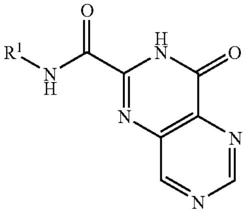
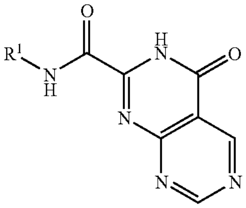
-continued
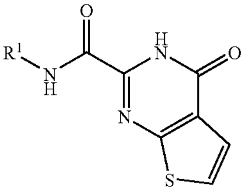
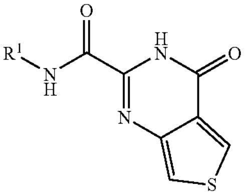
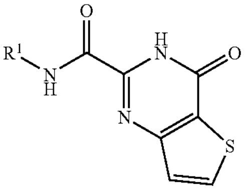
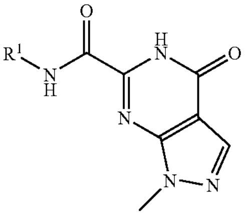
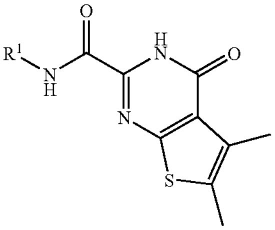
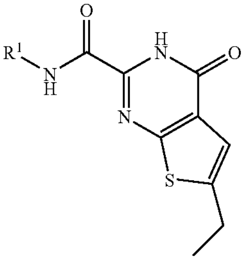
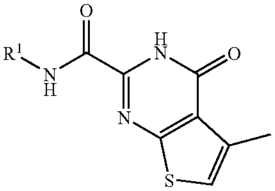
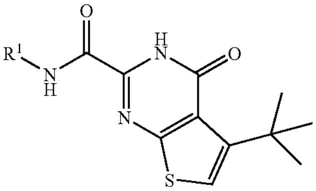

-continued
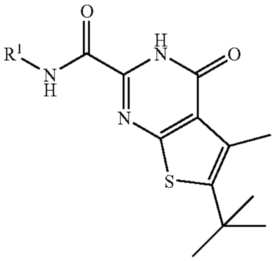
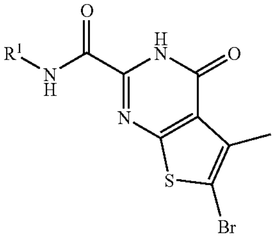
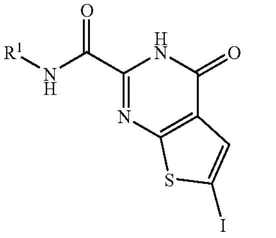
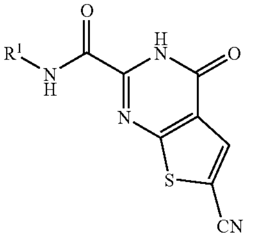
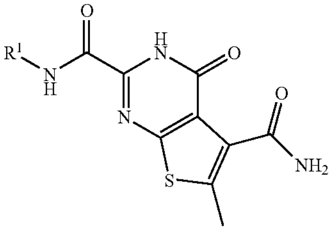
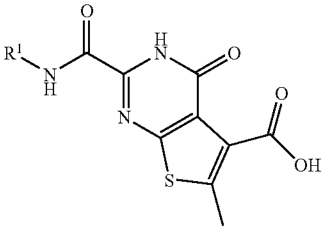
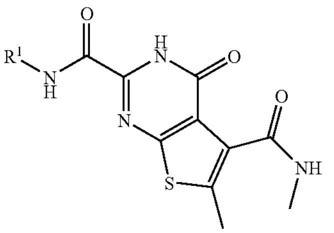
-continued
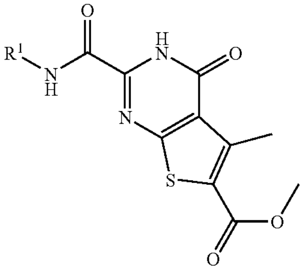
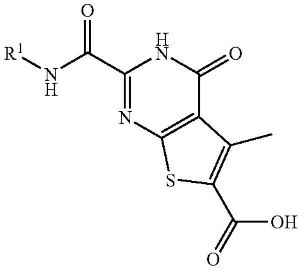
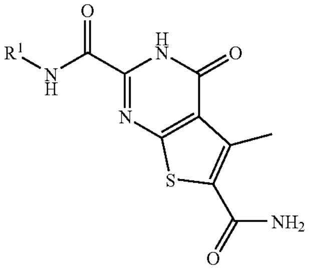
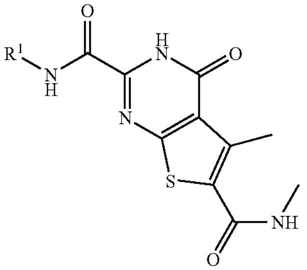
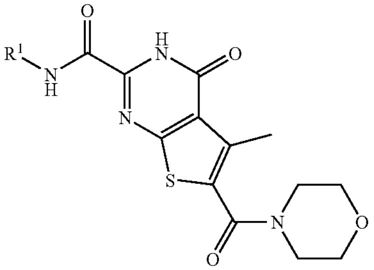
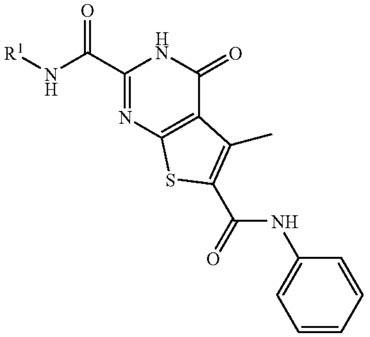

-continued
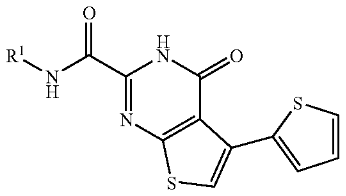
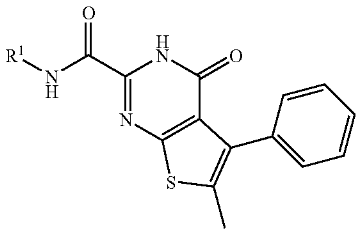
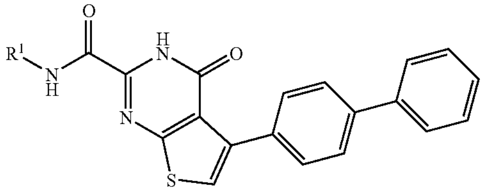
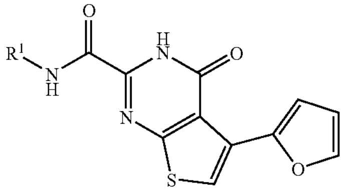
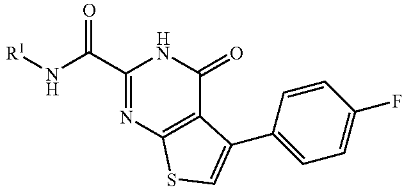
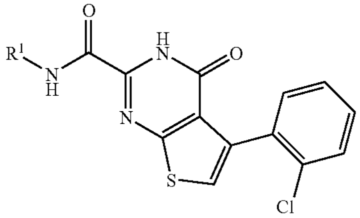
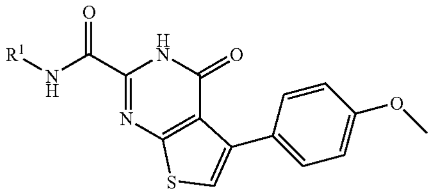
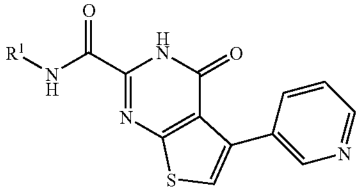
-continued
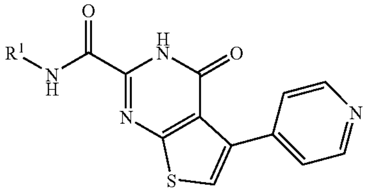
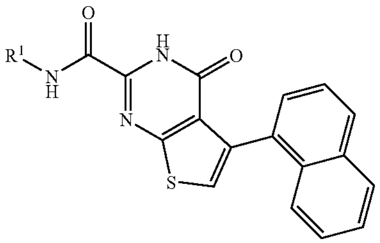
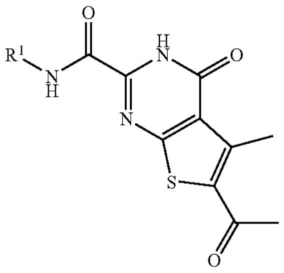
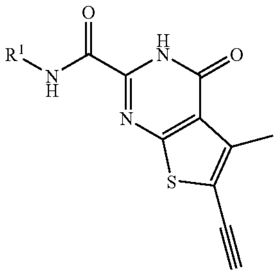
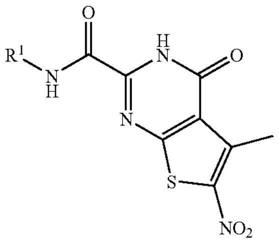
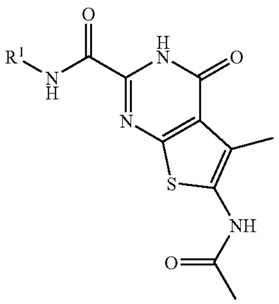

-continued
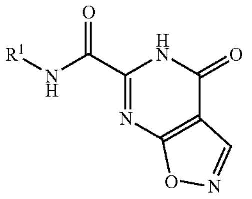
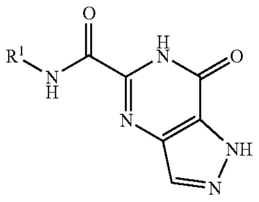
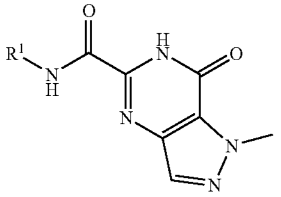
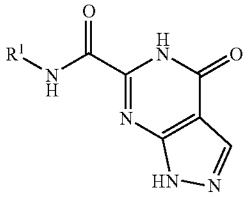
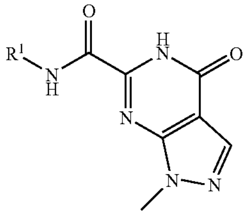
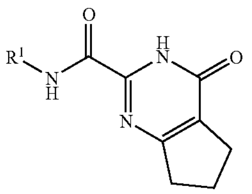
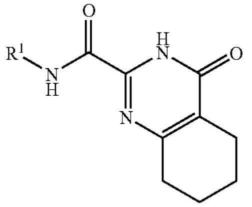
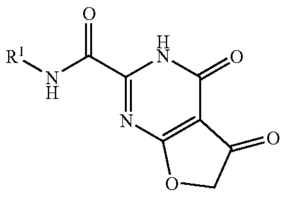
-continued
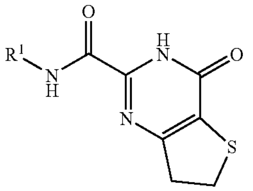
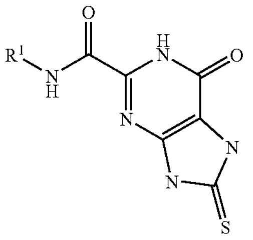
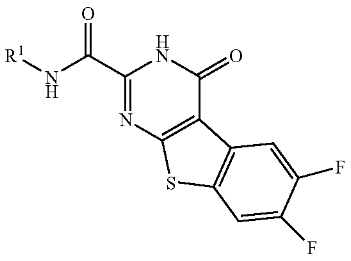
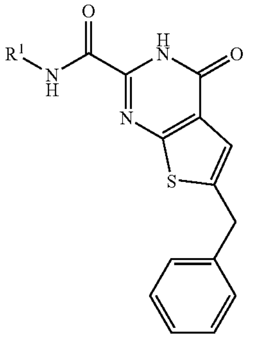
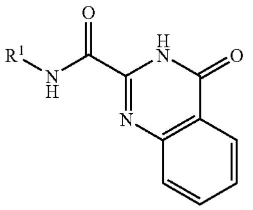
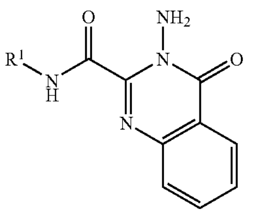
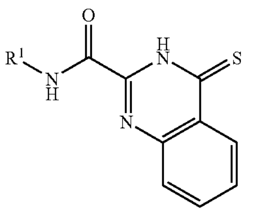

-continued
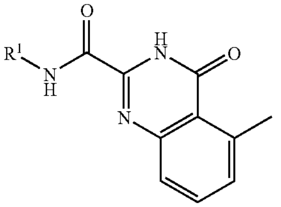
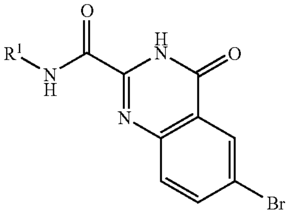
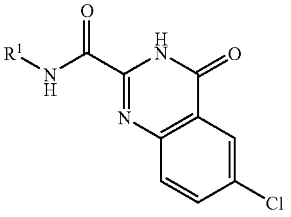
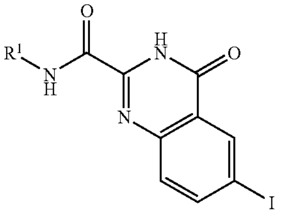
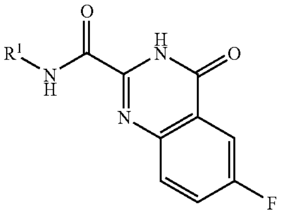
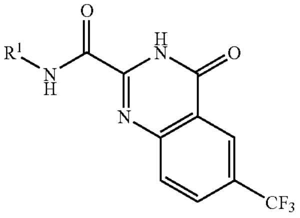
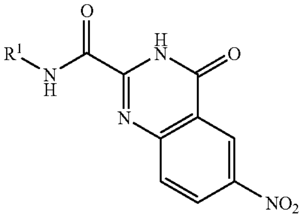
-continued
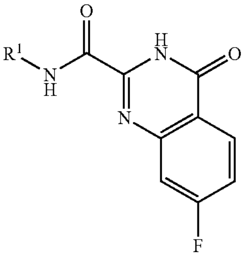
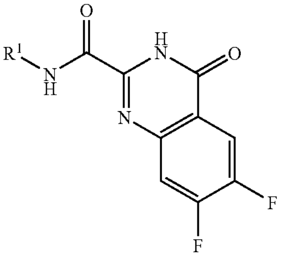
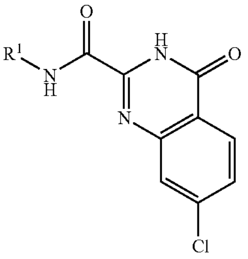
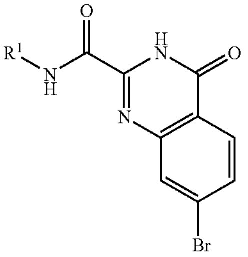
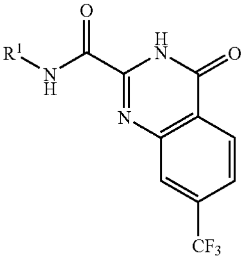
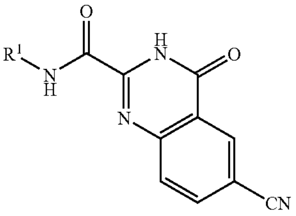

-continued
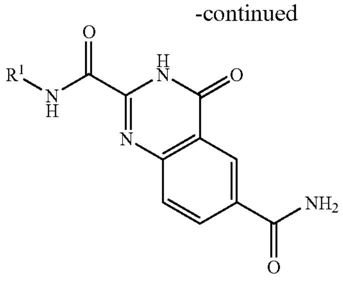
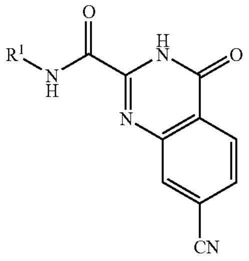
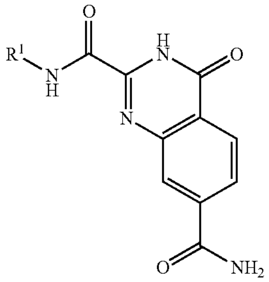
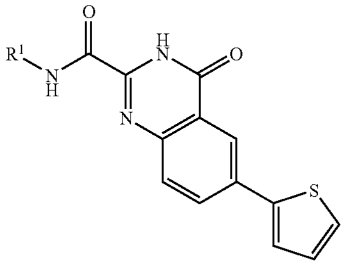
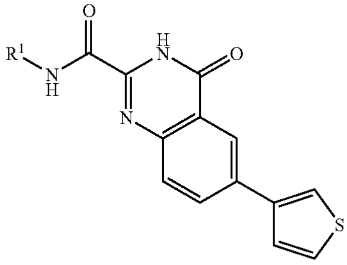
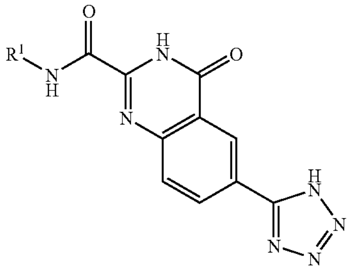
-continued
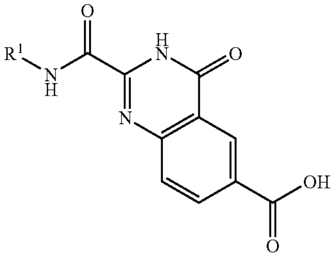
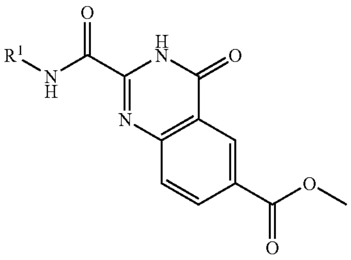
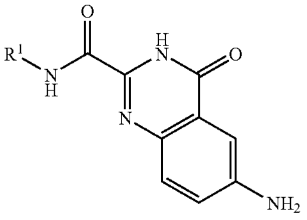
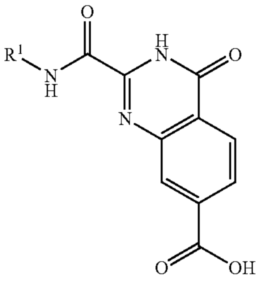
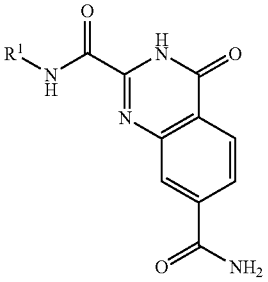
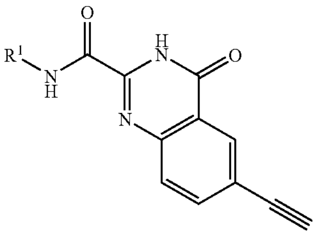

-continued
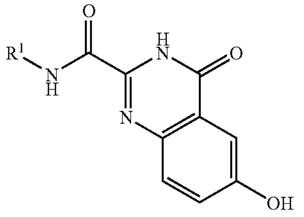
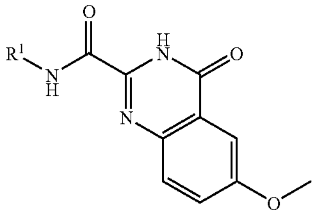
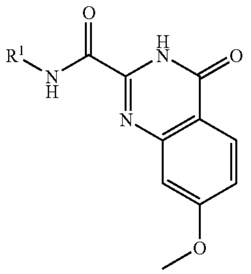
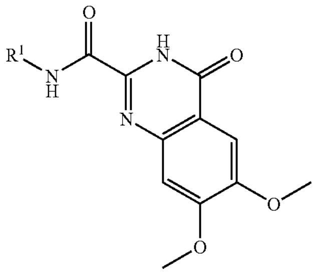
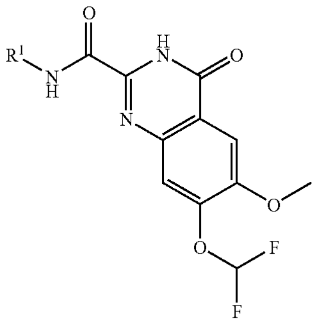
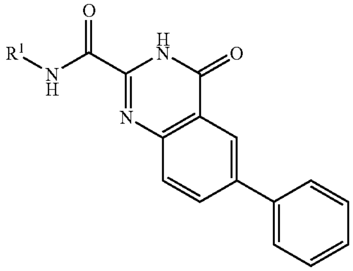
-continued
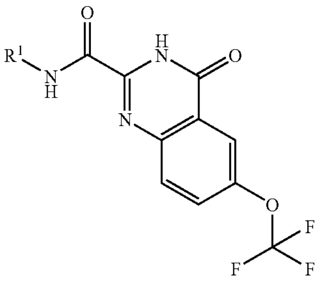
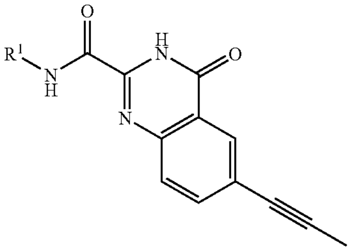
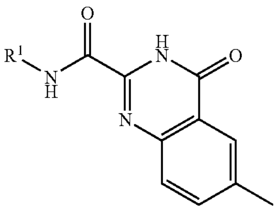
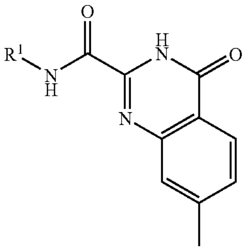
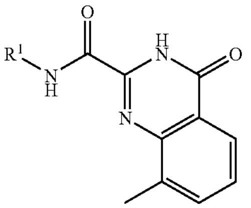
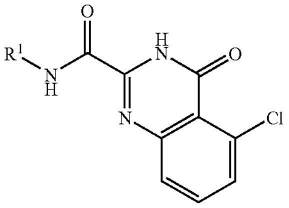
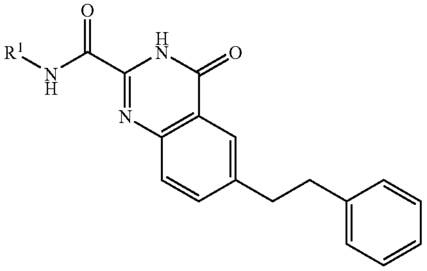

-continued
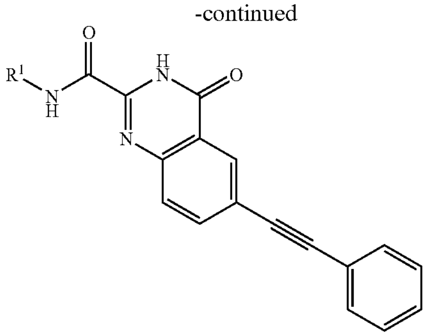
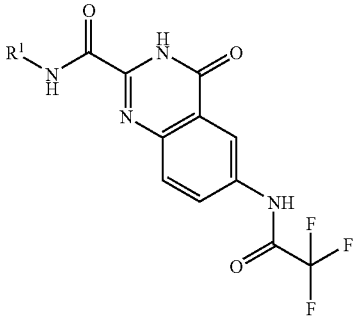
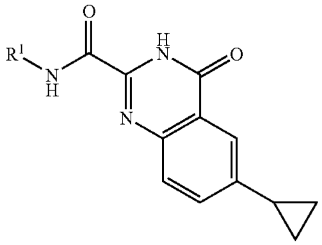
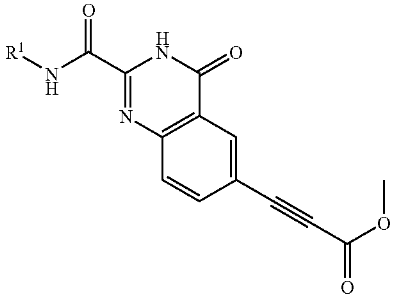
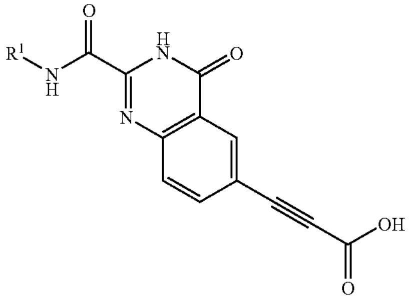
-continued
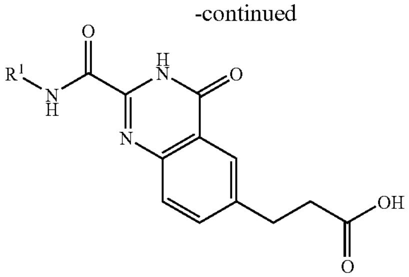
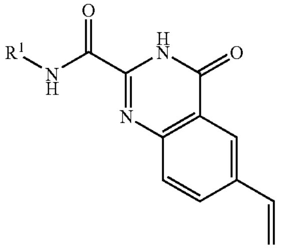
and
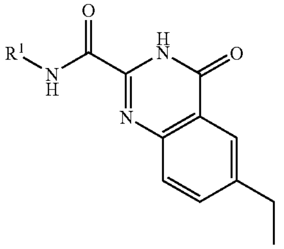
wherein $R^1$ is:
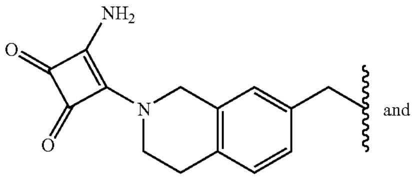
and
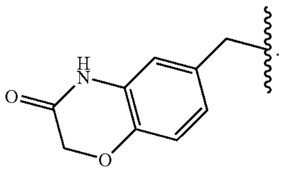

10. A compound according to claim 1, having the structure:
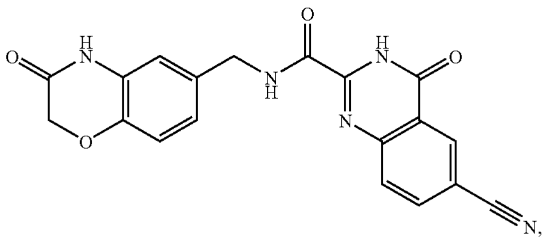
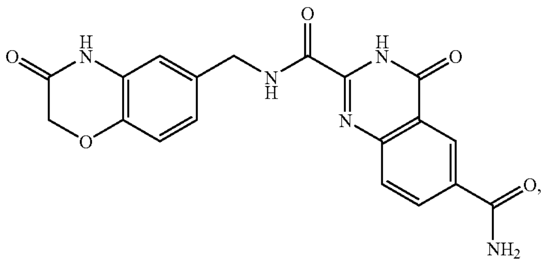
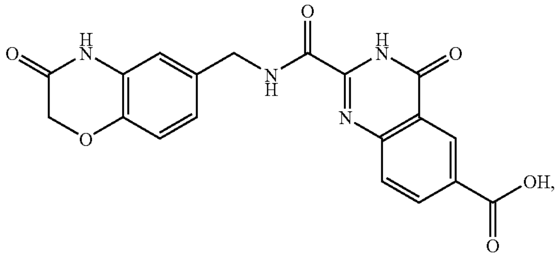
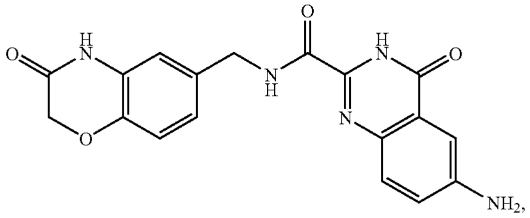
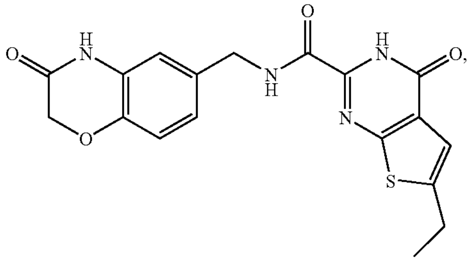
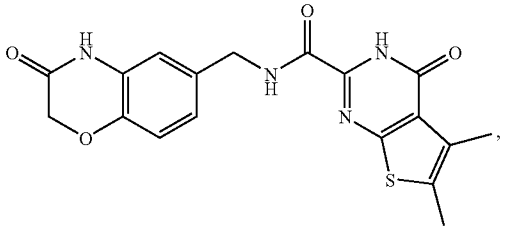

-continued
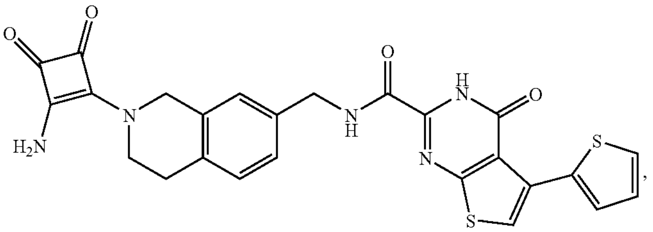
,
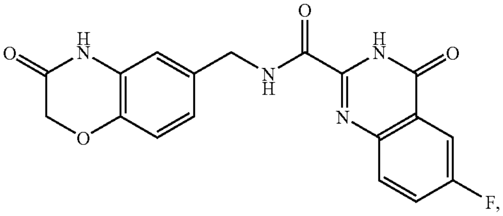
,
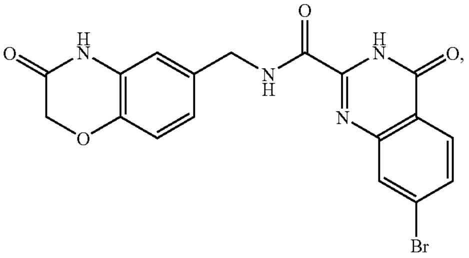
,
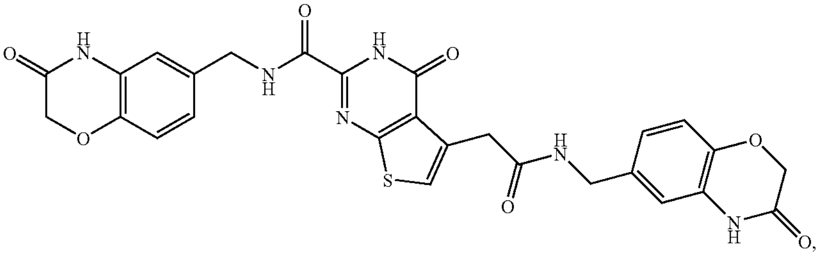
,
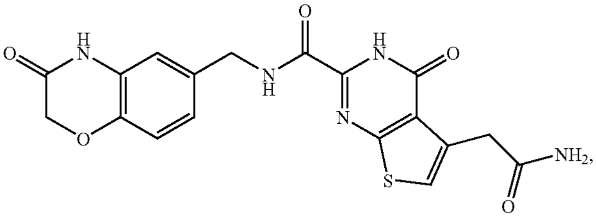
,
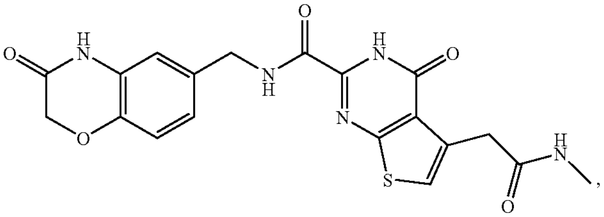
,
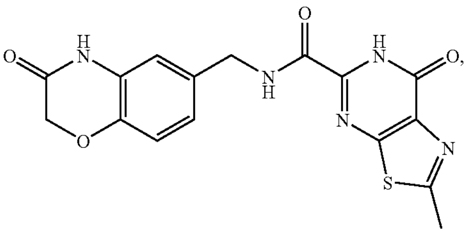

-continued
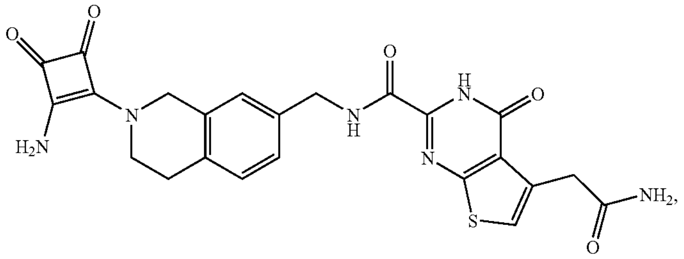
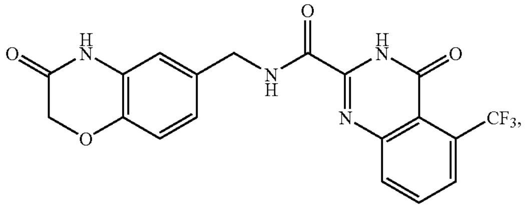
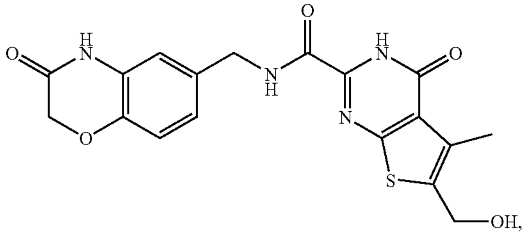
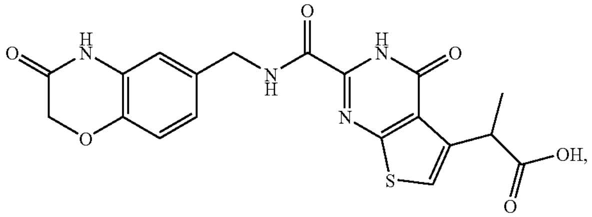
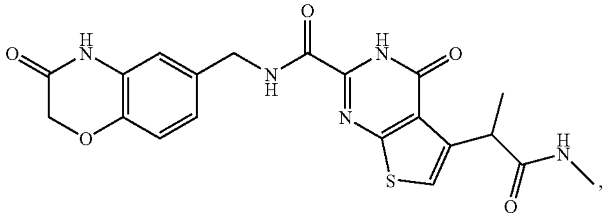
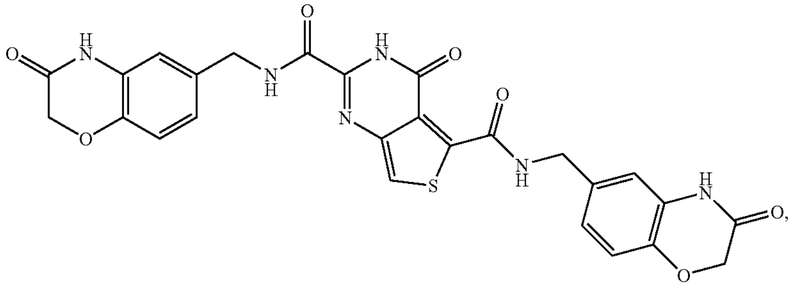
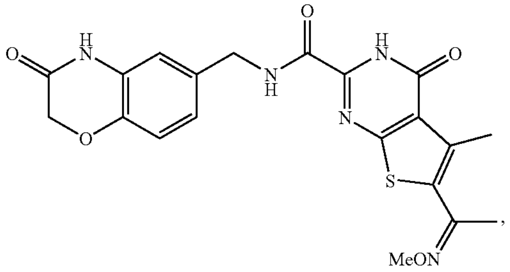

-continued
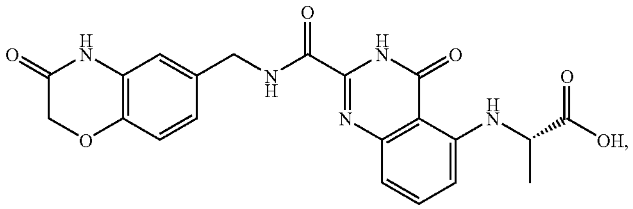
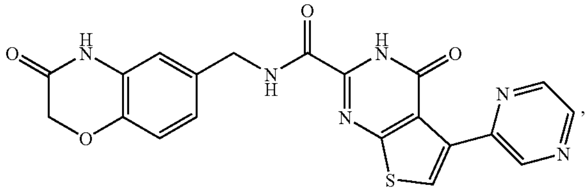
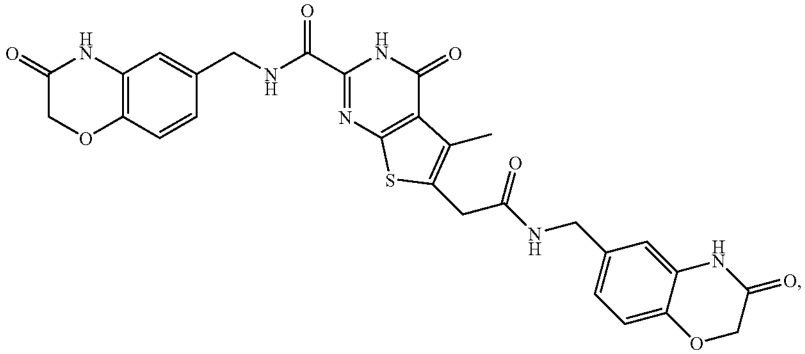
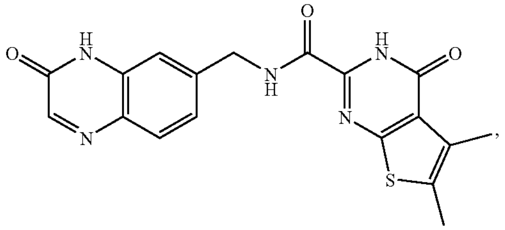
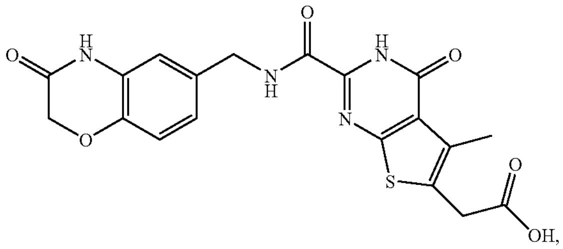
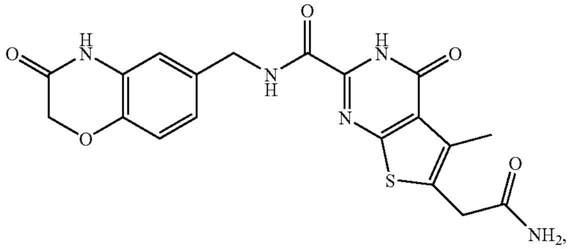

-continued
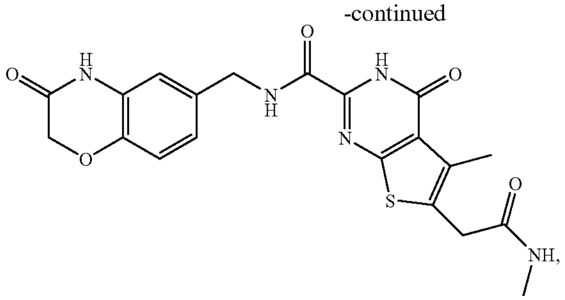
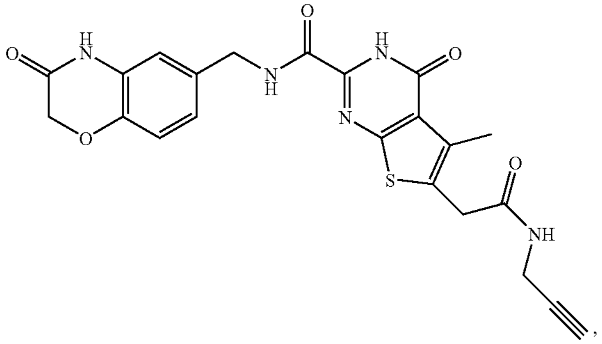
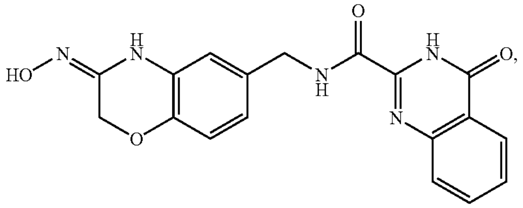
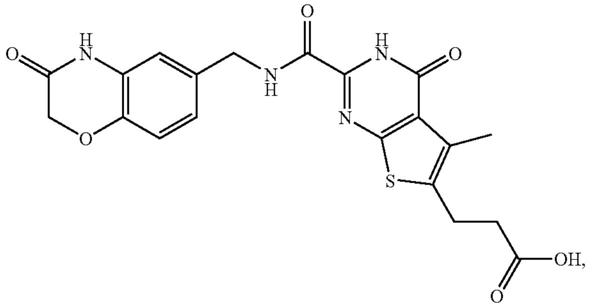
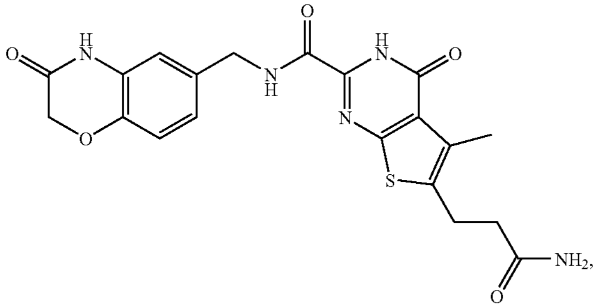

-continued
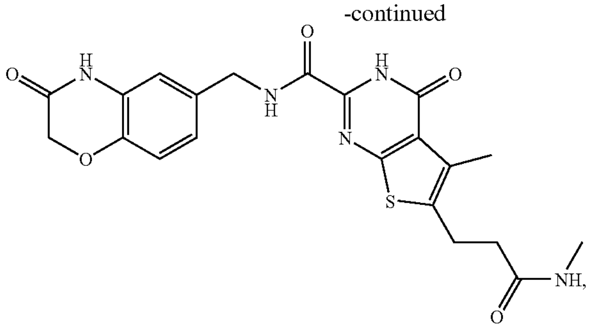
,
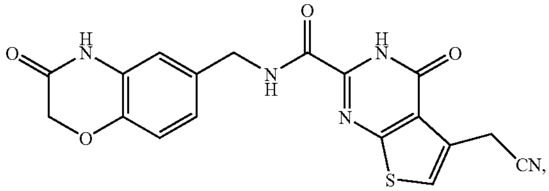
,
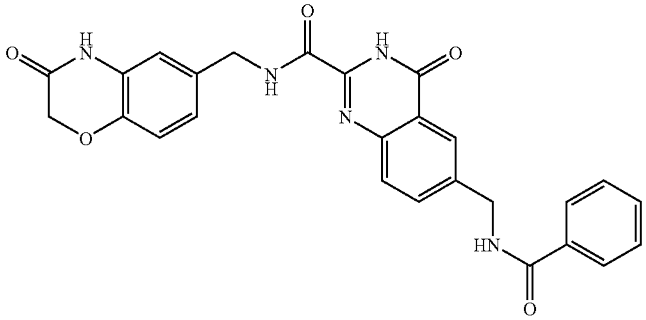
,
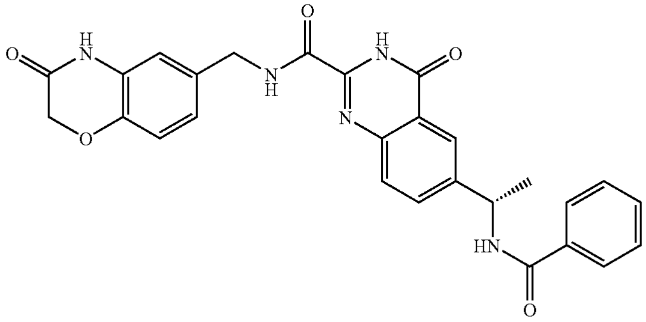
,
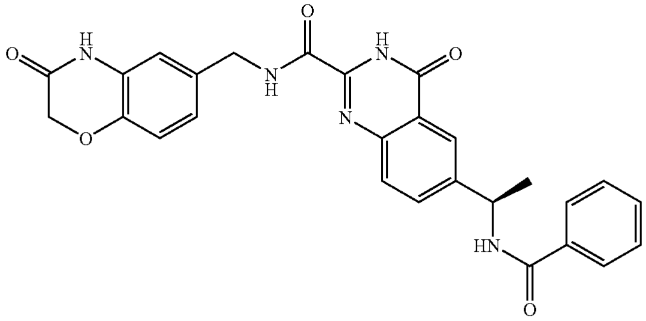
,
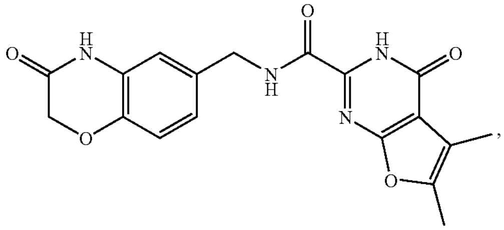
, -continued
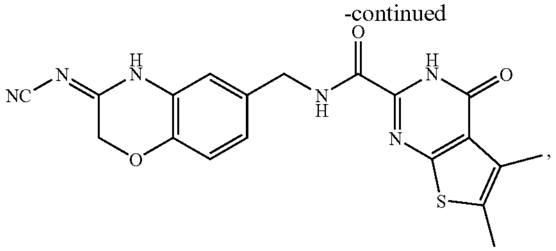
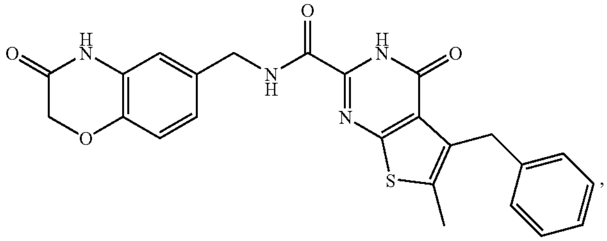
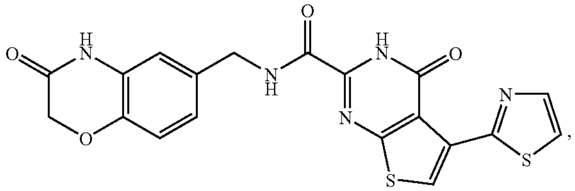
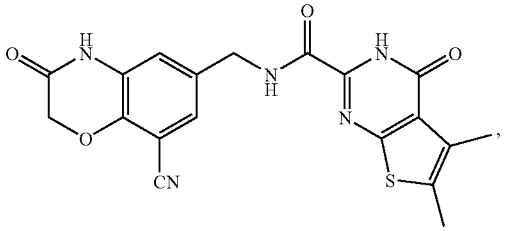
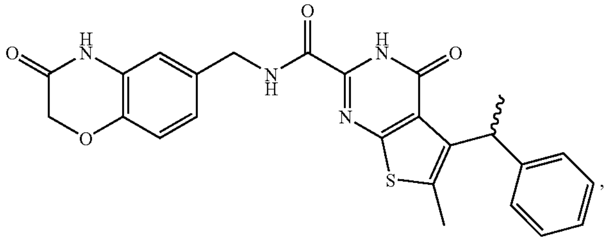
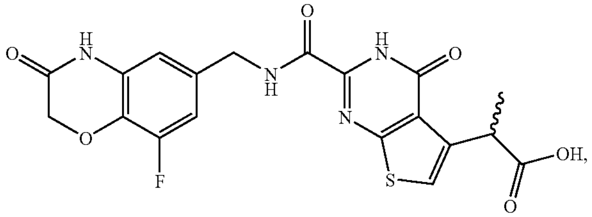
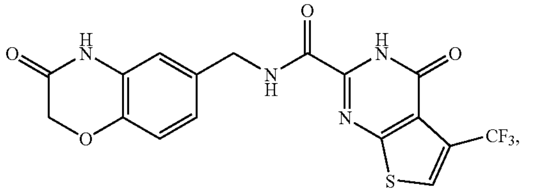

-continued
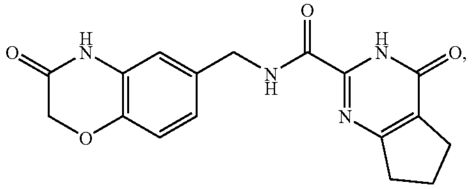
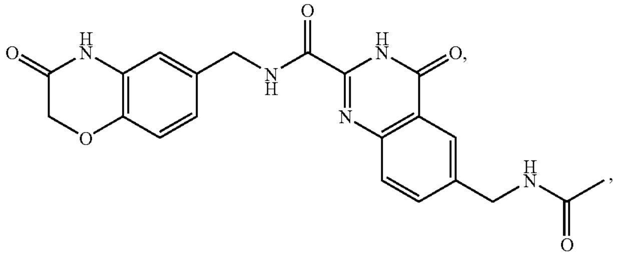
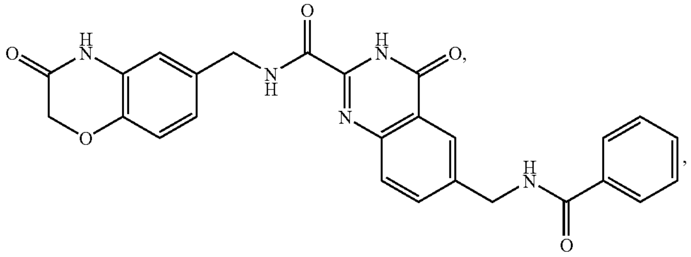
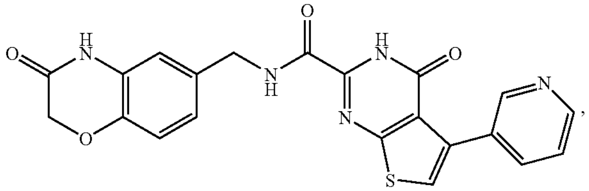
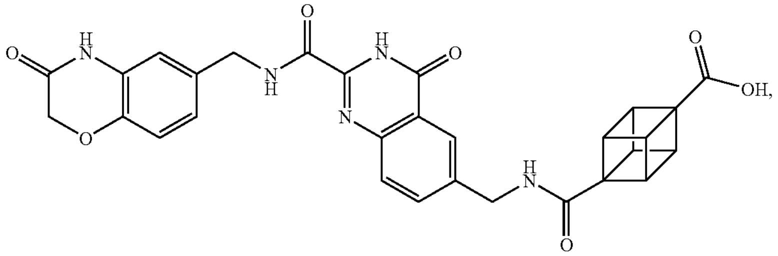
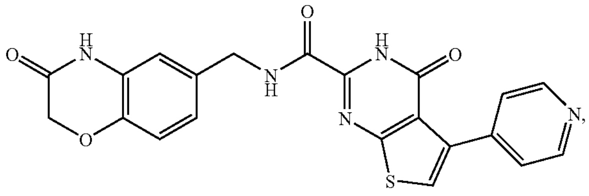
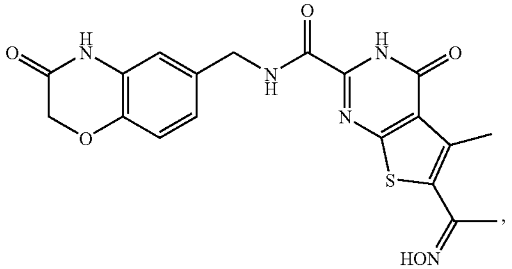

-continued

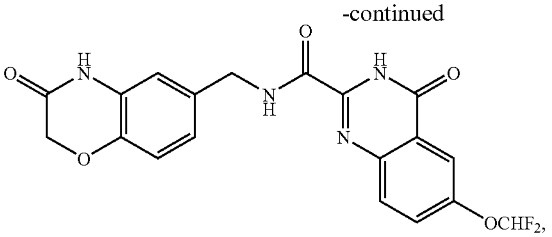

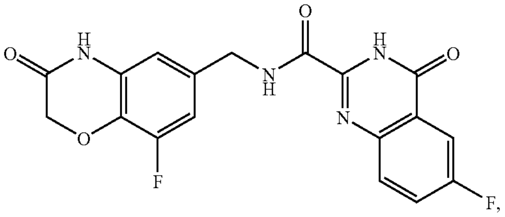

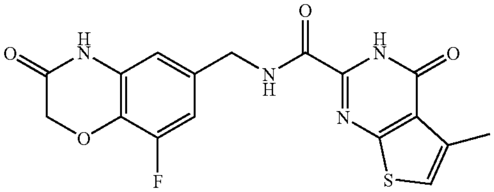

and

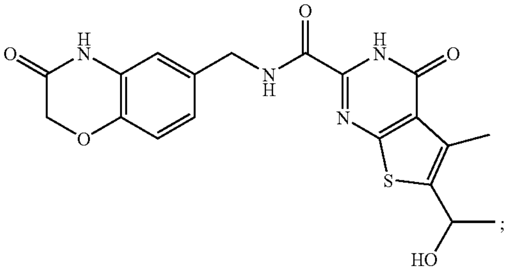

and N-oxides, pharmaceutically acceptable salts, formulations, tautomers, racemic mixtures and stereoisomers thereof.

11. A pharmaceutical composition comprising an effective amount of the compound selected from a compound according to claim 1.

12. A pharmaceutical composition comprising:

A) an effective amount of a compound according to claim 1;

B) a pharmaceutically acceptable carrier; and

C) a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; and (h) a small molecule inhibitor of pro-inflammatory cytokine production.

* * * * *